US012458674B2

(12) United States Patent
Tsedev et al.

(10) Patent No.: US 12,458,674 B2
(45) Date of Patent: Nov. 4, 2025

(54) M13 PHAGE BASED GENE THERAPY PLATFORM

(71) Applicant: Massachusetts Institute of Technology, Cambridge, MA (US)

(72) Inventors: Uyanga Tsedev, Somerville, MA (US); Angela M. Belcher, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 853 days.

(21) Appl. No.: 17/738,647

(22) Filed: May 6, 2022

(65) Prior Publication Data

US 2023/0041208 A1 Feb. 9, 2023

Related U.S. Application Data

(60) Provisional application No. 63/252,451, filed on Oct. 5, 2021, provisional application No. 63/185,076, filed on May 6, 2021.

(51) Int. Cl.

| | |
|---|---|
| ***A61K 35/76*** | (2015.01) |
| ***A61K 47/69*** | (2017.01) |
| ***A61K 48/00*** | (2006.01) |
| ***A61K 49/00*** | (2006.01) |
| ***A61P 35/00*** | (2006.01) |
| ***C07K 14/005*** | (2006.01) |
| ***C12N 1/10*** | (2006.01) |
| ***C12N 7/00*** | (2006.01) |
| ***C12P 21/02*** | (2006.01) |
| *A61K 38/00* | (2006.01) |

(52) U.S. Cl.

CPC .......... *A61K 35/76* (2013.01); *A61K 47/6901* (2017.08); *A61K 48/005* (2013.01); *A61K 49/0097* (2013.01); *A61P 35/00* (2018.01); *C07K 14/005* (2013.01); *C12N 1/105* (2021.05); *C12N 7/00* (2013.01); *C12P 21/02* (2013.01); *A61K 38/00* (2013.01); *C07K 2319/09* (2013.01); *C07K 2319/33* (2013.01); *C12N 2795/14122* (2013.01); *C12N 2795/14132* (2013.01); *C12N 2795/14152* (2013.01); *C12N 2795/14171* (2013.01)

(58) Field of Classification Search

CPC .. A61K 35/76; A61K 47/6901; A61K 48/005; A61K 49/0097; A61K 38/00; A61P 35/00; C07K 14/005; C07K 2319/09; C07K 2319/33; C12N 1/105; C12N 7/00; C12N 2795/14122; C12N 2795/14132; C12N 2795/14152; C12N 2795/14171; C12N 2795/14143; C12N 2795/14145; C12N 15/86; C12P 21/02

See application file for complete search history.

(56) References Cited

U.S. PATENT DOCUMENTS

2003/0148263 A1 8/2003 Larocca et al.
2019/0022155 A1 1/2019 Belcher et al.

FOREIGN PATENT DOCUMENTS

WO WO-2020/236982 A1 11/2020

OTHER PUBLICATIONS

Ju et al., "Drug delivery vectors based on filamentous bacteriophages and phage-mimetic nanoparticles," Drug Delivery, 2017, 24(1):1898-1908.

*Primary Examiner* — Robert S Cabral
(74) *Attorney, Agent, or Firm* — Foley & Lardner LLP

(57) ABSTRACT

An engineered phage-derived particle (PDP) for expressing a transgene in a target cell transduced with a bacteriophage, the PDP includes (i) less than about 500 bp of DNA from the bacteriophage genome, (ii) an ITR-flanked therapeutic gene up to 20 kb, (iii) an endosomal escape sequence, (iv) a nuclear localization sequence, and (v) a cell-specific targeting moiety. The PDP may escape lysosomal degradation, traffic across the nuclear envelope and expressed a therapeutic gene in a mammalian cell.

24 Claims, 87 Drawing Sheets

Specification includes a Sequence Listing.

A. inho f1 fragments f1-ori

5' TGGGCCATCGCCCTGATAGACGGTTTTTCGCCCTTTGACGTTGGCTTT^AATAGT

3' ACCCGGTAGCGGGACTATCTGCCAAAAAGCGGGAAACTGCAACCGAAA TTATCA

GGACTCTTGTTCCAAACTGGAACAA 3'

CCTGAGAACAAGGTTTGACCTTGTT 5'

PACKAGING SIGNAL (PS)

5' CGCGCCCTGTAGCGGCGCATTAAGCGCGGCGGGTGTGGTGGTTACGCGCAGCGT

3' GCGCGGGACATCGCCGCGTAATTCGCGCCGCCCACACCACCAATGCGCGTCGCA

GACCGCTACACTTGCCAGCGCCCTAGCGCCCGCTCC 3'

CTGGCGATGTGAACGGTCGCGGGATCGCGGGCGAGG 5' f1-term

5' TGGGCCATCGCCCTGATAGACGGTTTTTCGCCCTTTGACGTTGGAGTCCACGTT

3' ACCCGGTAGCGGGACTATCTGCCAAAAAGCGGGAAACTGCAACCTCAGGTGCAA

CTTT^AATAGTGGACTCTTGTTCCAAACAACACT 3'

GAAA TTATCACCTGAGAACAAGGTTTGTTGTGA 5'

Figure 9A

Figure 9B

B. cssDNA product f1-ori fragment

```
5' AATAGTGGACTCTTGTTCCAAACTGGAACAAXXXXXXXXXXXXXXXXXXXX...

3' TTATCACCTGAGAACAAGGTTTGACCTTGTTXXXXXXXXXXXXXXXXXXXX...
```

PS

```
CGCGCCCTGTAGCGGCGCATTAAGCGCGGCGGGTGTGGTGGTTACGCGCAGCGT
GCGCGGGACATCGCCGCGTAATTCGCGCCGCCCACACCACCAATGCGCGTCGCA

GACCGCTACACTTGCCAGCGCCCTAGCGCCCGCTCCXXXXXXXXXXXXXXX...
CTGGCGATGTGAACGGTCGCGGGATCGCGGGCGAGGXXXXXXXXXXXXXXX...
```

f1-term fragment

```
TGGGCCATCGCCCTGATAGACGGTTTTTCGCCCTTTGACGTTGGAGTCCACGTT
ACCCGGTAGCGGGACTATCTGCCAAAAAGCGGGAAACTGCAACCTCAGGTGCAA

CTTT 3'

GAAA 5'
```

B.
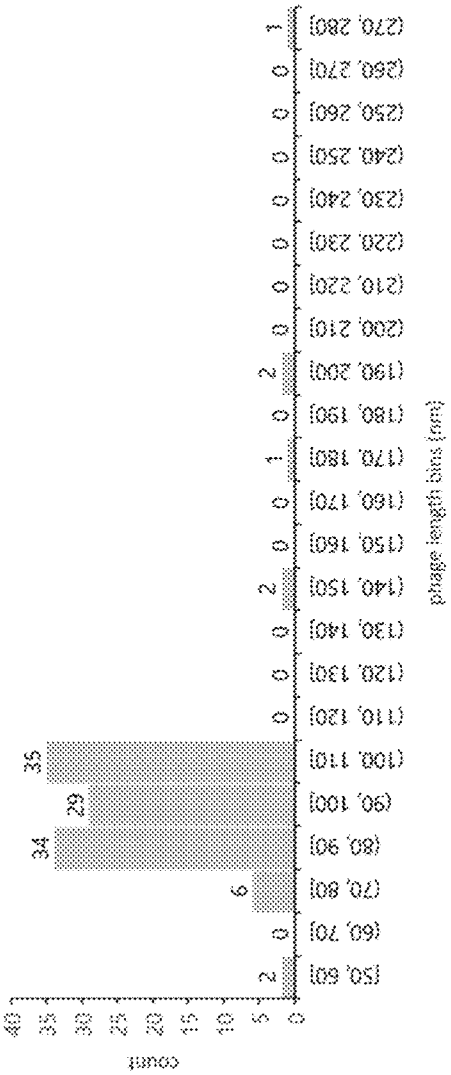
C.
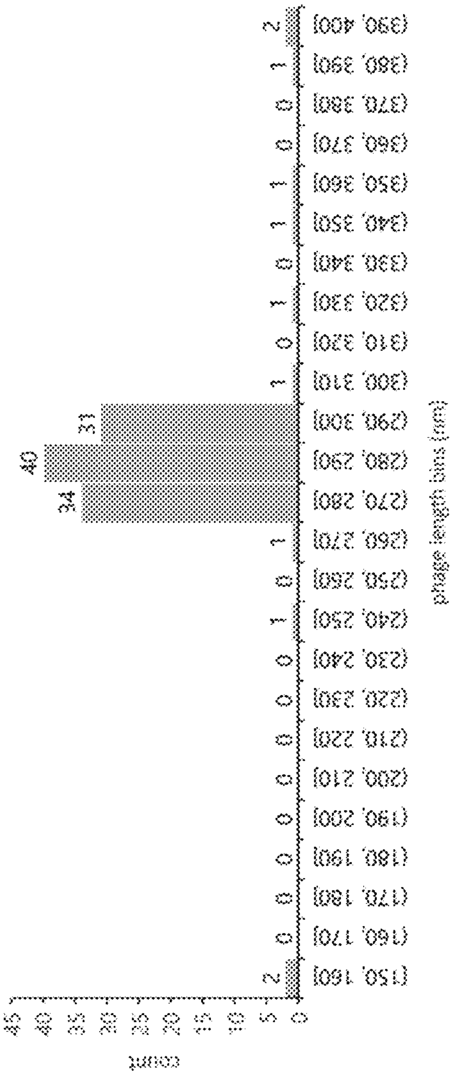
Figures 17(B) and (C)

Figure 18A-H
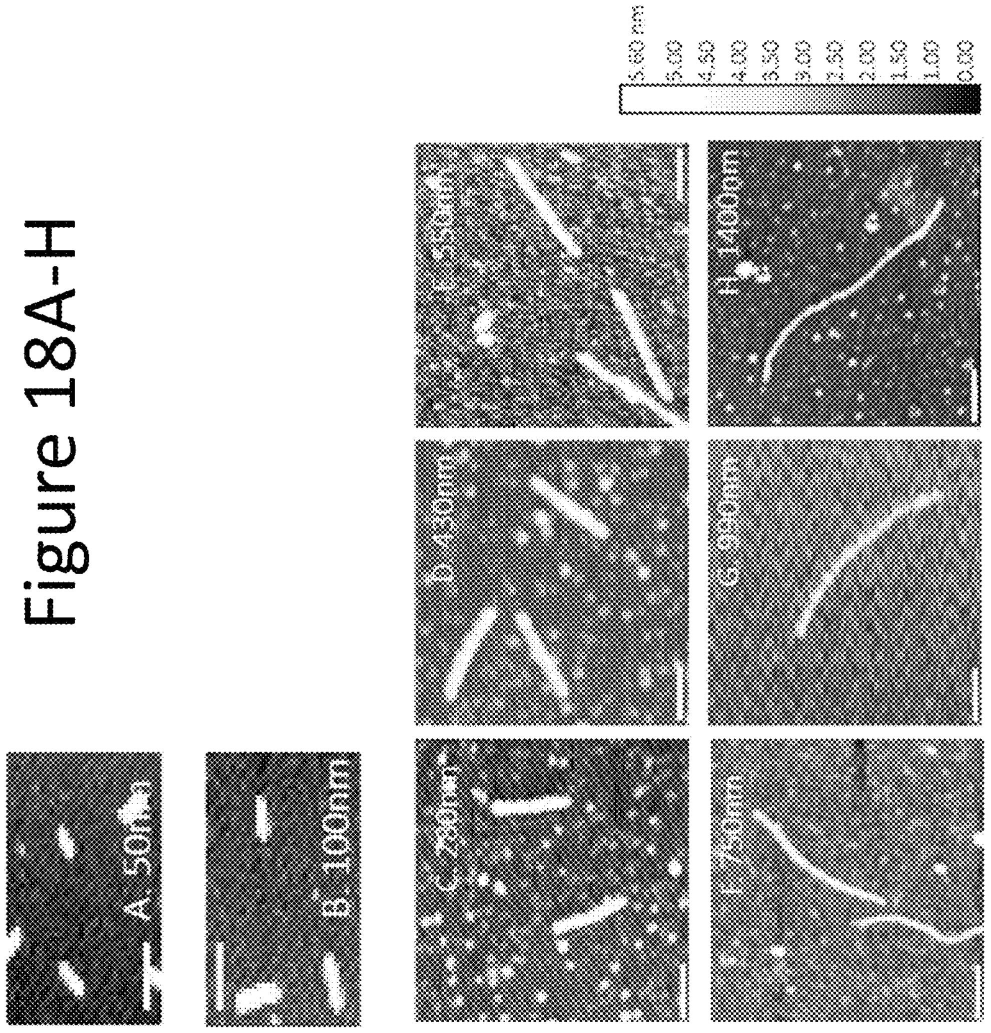

Figure 21A-B
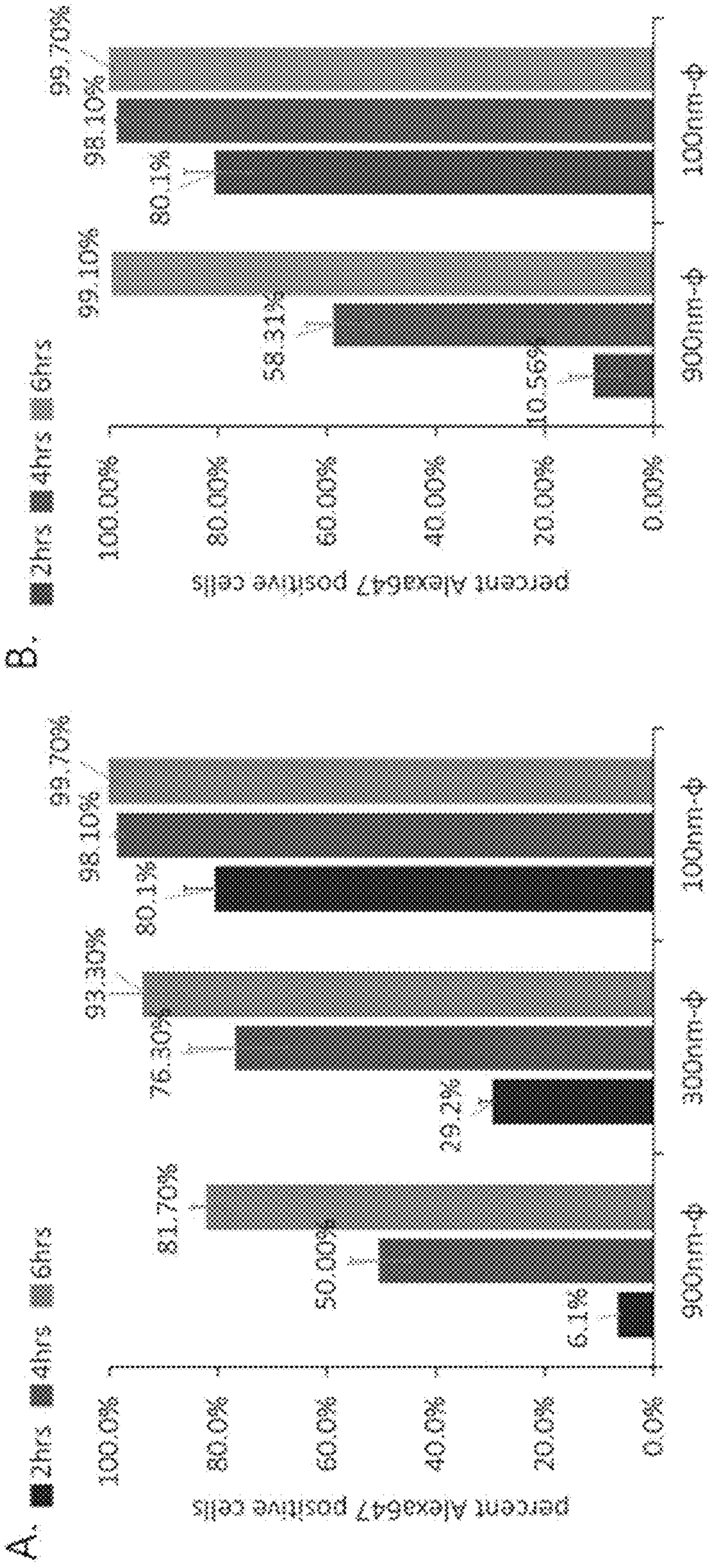

Figures 22A-B
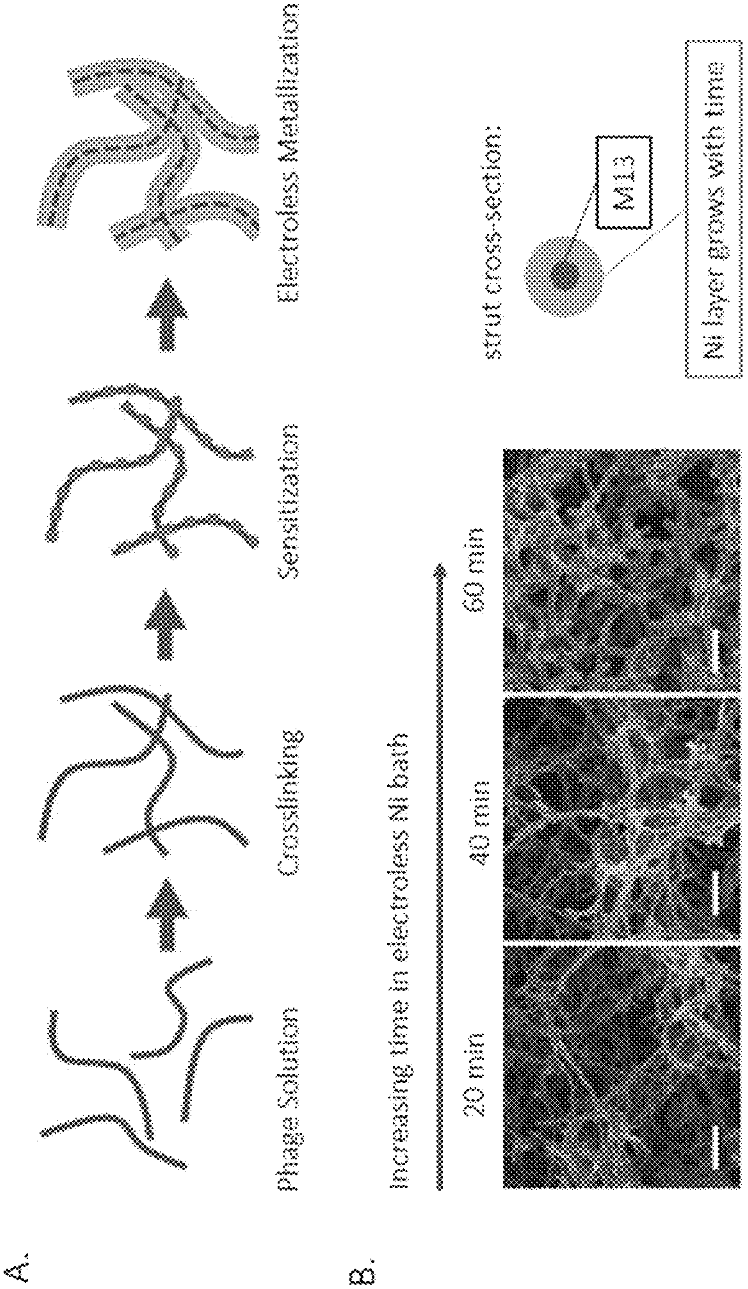

Figure 28A-C
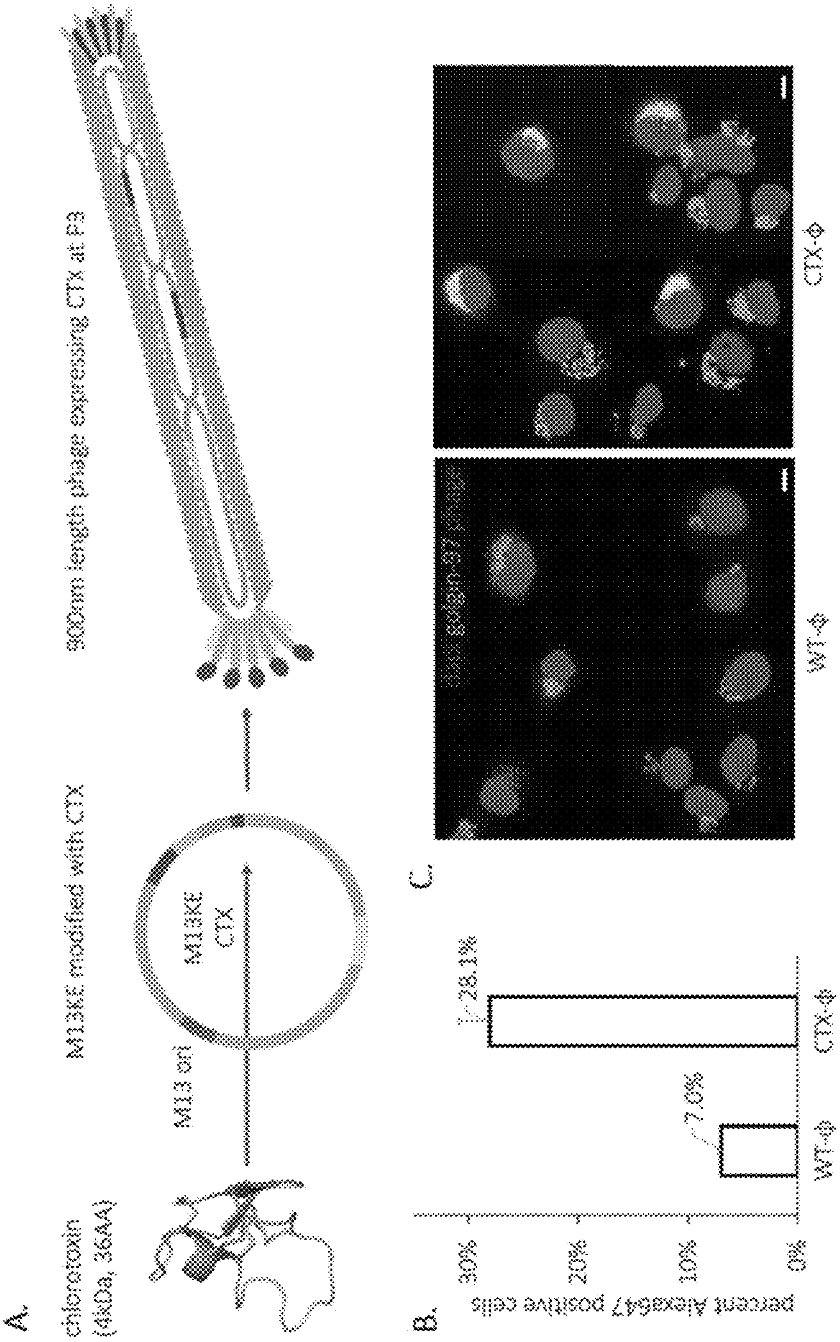

A.

f1-ori (79 bases)

5'TGGGCCATCGCCCTGATAGACGGTTTTTCGCCCTTTG
ACGTTGGCTTT^AATAGTGGACTCTTGTTCCAAACTGG
AACAA3'

PS (90 bases)

5'CGCGCCCTGTAGCGGCGCATTAAGCGCGGCGGGTG
TGGTGGTTACGCGCAGCGTGACCGCTACACTTGCCAG
CGCCCTAGCGCCCGCTCC3' f1-ori (87 bases)

5'TGGGCCATCGCCCTGATAGACGGTTTTTCGCCCTTTG
ACGTTGGAGTCCACGTTCTTT^AATAGTGGACTCTTGTT
CCAAACAACACT3'

Figures 36A-36C

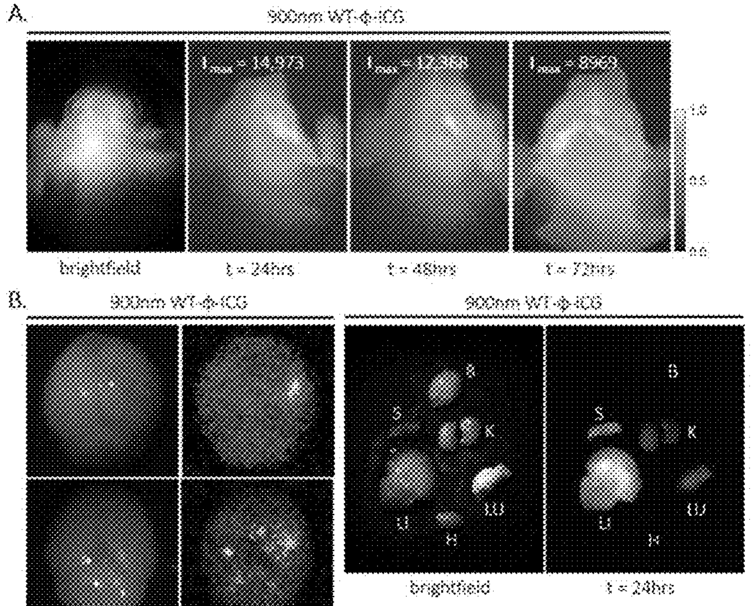

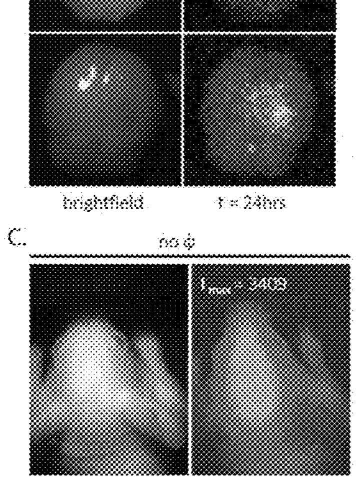

Figure 9| Tumor accumulation of control wildtype phage. A) 2e13 particles of ICG loaded wildtype phage injected in tumor bearing mice is tracked for tumor localization signal over 72 hrs. B) Extraction of brain 24 hrs post dosing of mice with ICG-loaded wildtype phages reveal limited tumor signal in the SWIR. Typical distribution of phage is observed for clearance by the spleen, liver, kidneys, and lung macrophages. C) Mouse with no phage or ICG exposure is imaged, showing low intensity skin/bone autofluorescence for comparison at the 808nm (5V) excitation and 1150nm long pass filter setting used throughout experimentation.

Figure 37
p3
5' TTAGTGGTACCTTTCTATTCTCACTCT
3' AATCACCATGGAAAGATAAGAGTGAGA
p3→
TCGGCCGAAACT 3'
AGCCGGCTTTGA 5'
p3
5' TCTCACTCT
GGTGGAGGT
3' AGAGTGAGA
CCACCTCCA
p3→
TCGGCCGAAACT 3'
AGCCGGCTTTGA 5'

AFM sample preparation of phage particles

B.

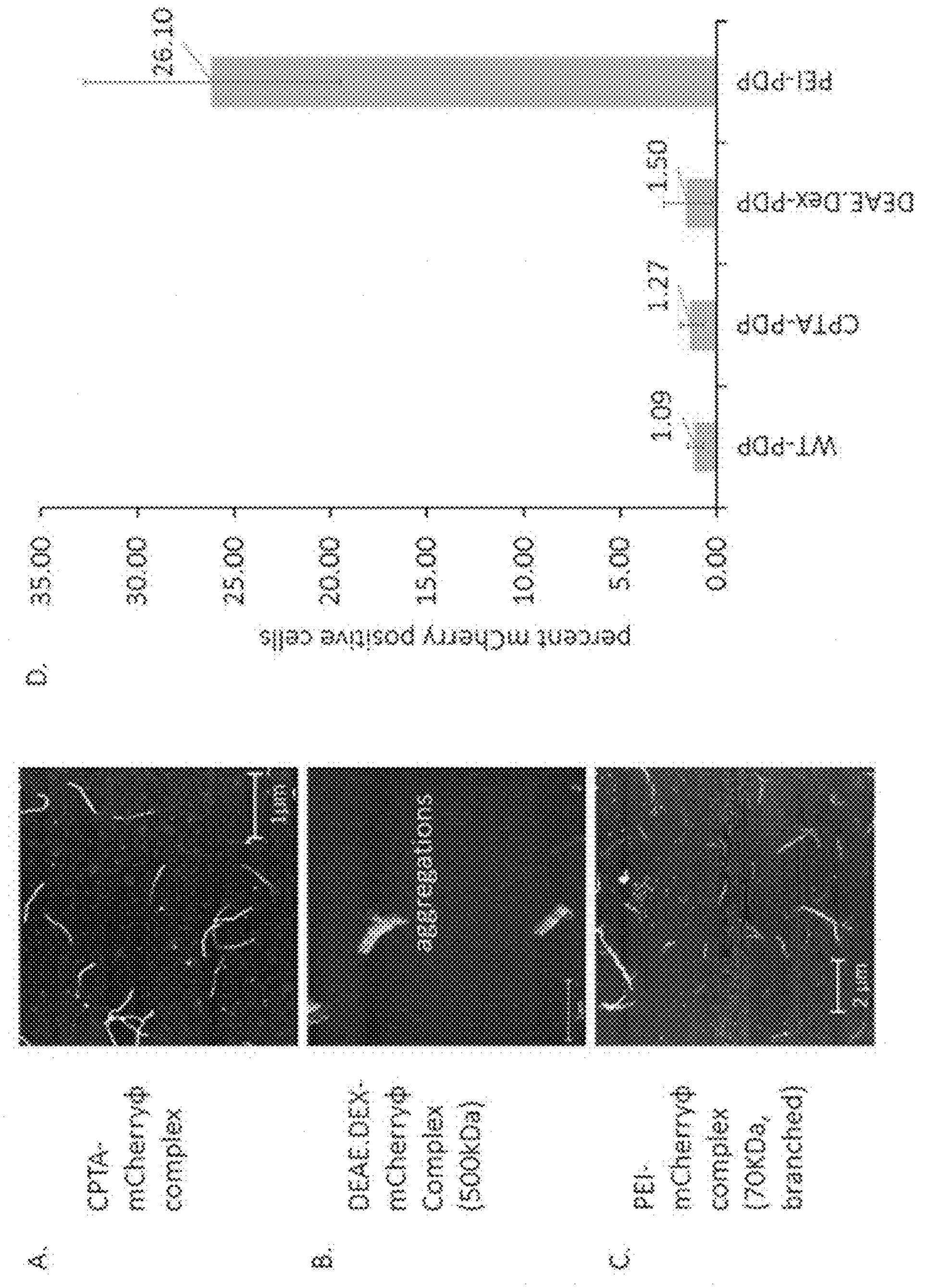
Figure 45A-D

Figure 53A-B
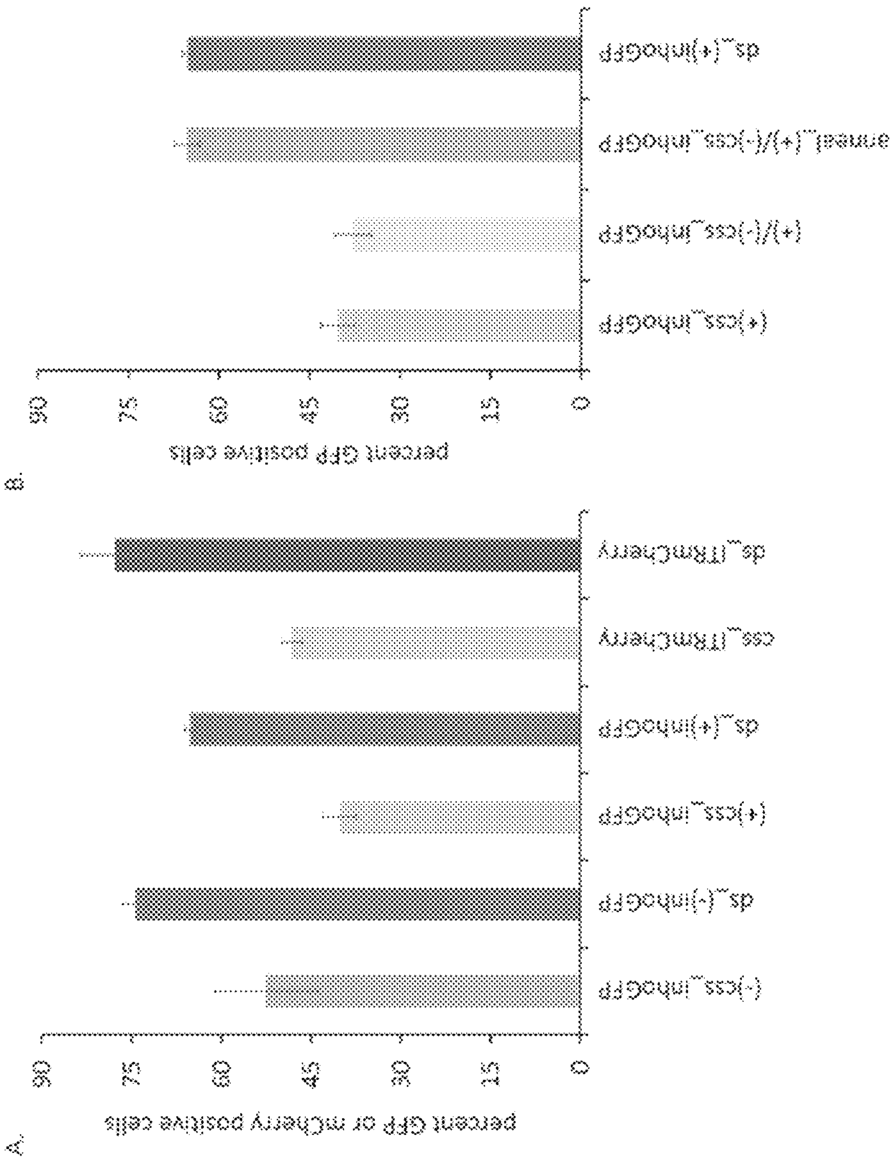

inho19800
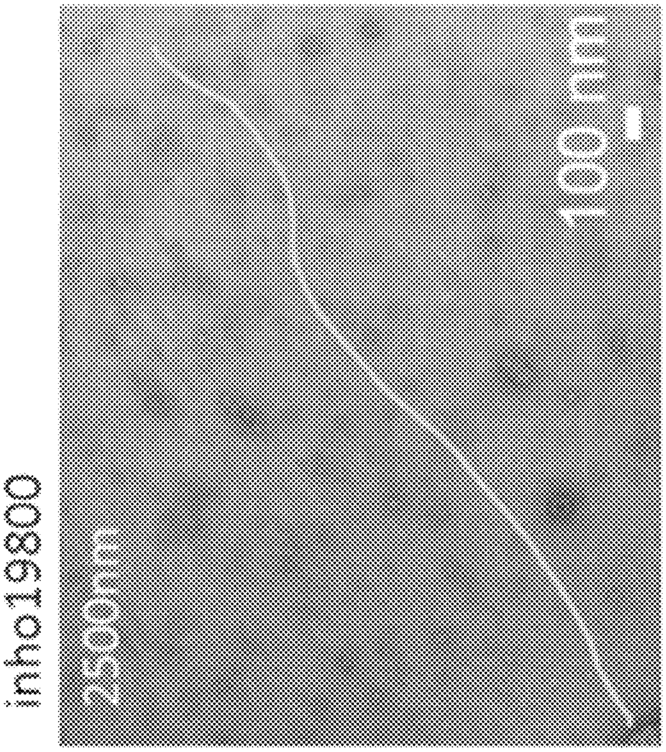
inho135
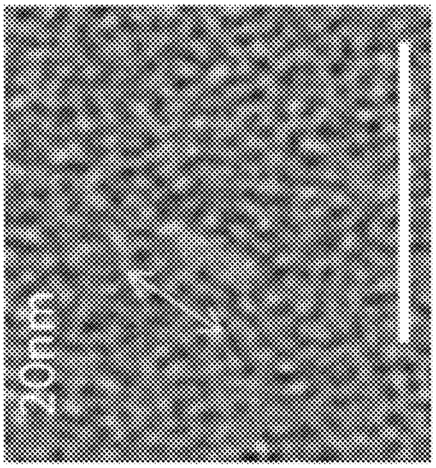
Figure 56

A.

B.

A.

ICG-Phage Cleaning by 60% Ethanol

Figure A - | Li r lati f phage 24hrs to 72hrs. Alexa647 immunostaining for p8 capsid of phage on liver histology slides from mice treated with CTX-phage. Degradation of

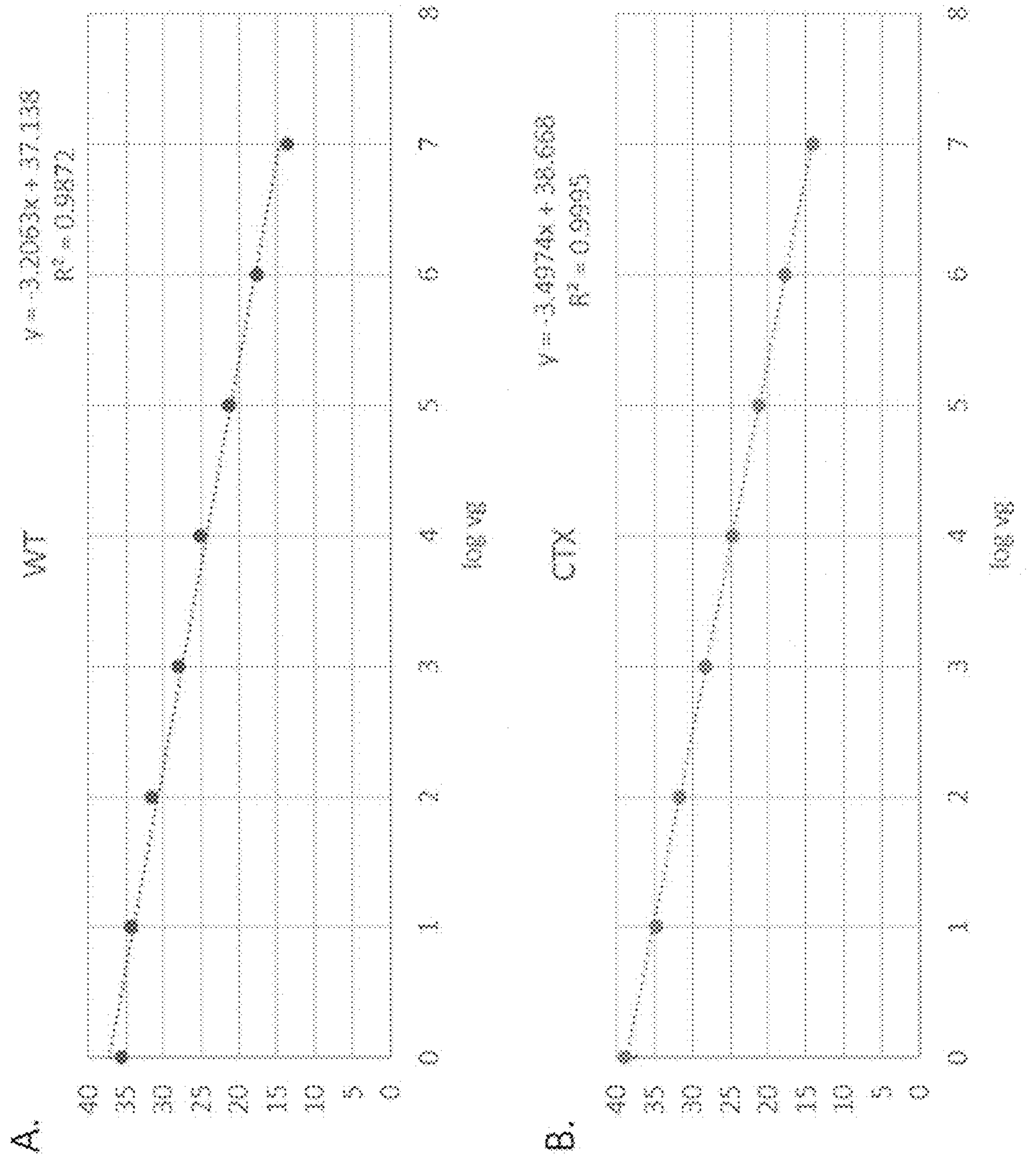
Figure 73A-B

SEQUENCE LISTING

```
<160> NUMBER OF SEQ ID NOS: 140

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5


<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Glu Ala Glu
1


<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Glu Glu Glu
1


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ser Pro His Thr Glu Leu Pro
1               5


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 5

Ile Lys Val Ala Val
1 5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Asp Gly Glu Ala
1

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
agtccacgtt 10

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
tttttggggc tttt 14

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Asp Asp Ala His Val His Trp Glu
1 5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Cys Thr Ser Thr Ser Ala Pro Tyr Cys
1 5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Thr Gly Asn Tyr Lys Ala Leu His Pro His Asn Gly
1 5 10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Ala Cys Ser Tyr Thr Ser Ser Thr Met Cys Gly Gly Gly Ser
1 5 10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Cys Arg Thr Ile Gly Pro Ser Val Cys
1 5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 14

Cys Ser Xaa Thr Ser Ser Thr Xaa Cys
1 5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Cys Ser Tyr Thr Ser Ser Thr Met Cys
1 5

<210> SEQ ID NO 16
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 16
atgtgcatgc cgtgctttac c 21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcactcggc cgaaactgtt ga 22

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcgtcgac attcctgaga ttcc 24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taagggattt tgccgatttc ggc 23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctatctcgg gctattcttt tgat 24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctcctctg acttcaacag cg 22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
catcactgcc acccagaaga ctg 23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
aagttttgtc gtctttccag acgt 24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
cagggatagc aagcccaata gg 22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
tgtccacctg gccctggatc ttg 23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gtgccgtaaa gcactaaatc gga 23

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
cccactacgt gaaccatcac cc 22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
accaccctgt tgctgtagcc aa 22

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
atgccagtga gcttcccgtt cag 23

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic 10xHis tag

<400> SEQUENCE: 30

His His His His His His His His His His
1 5 10

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic 20xHis tag

<400> SEQUENCE: 31

His His His His His His His His His His His His His His His His
1 5 10 15

His His His His
20

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gly Leu Phe His Ala Ile Ala His Phe Ile His Gly Gly Trp His Gly
1 5 10 15

Leu Ile His Gly Trp Tyr Gly
20

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tctttcgctg ctgaggagga ggatcccgca aaagcg 36

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cgcttttgcg ggatcctcct cctcagcagc gaaaga 36

<210> SEQ ID NO 35
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gctgtttaag aaattcacct cggcagcaag ctgataaacc gataca 46

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
tgtatcggtt tatcagcttg ctgccgaggt gaatttctta aacagc 46

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aagcctcagc gaccgaagct atcggttatg cgtggg 36

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cccacgcata accgatagct tcggtcgctg aggctt 36

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gcaagcctca gcgaccgaat gtatcggtta tgc 33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
gcataaccga tacattcggt cgctgaggct tgc 33

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
agcctcagcg accgaagata tcggttatgc gtg 33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
cacgcataac cgatatcttc ggtcgctgag gct 33

<210> SEQ ID NO 43
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
cctgcaagcc tcagcgaccg aagagatcgg ttatgcg 37

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
cgcataaccg atctcttcgg tcgctgaggc ttgcagg 37

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
gcaagcctca gcgaccgaat ttatcggtta tgc 33

<210> SEQ ID NO 46

<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
gcataaccga taaattcggt cgctgaggct tgc 33

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
aagcctcagc gaccgaaggt atcggttatg cgtggg 36

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
cccacgcata accgatacct tcggtcgctg aggctt 36

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
agcctcagcg accgaacata tcggttatgc gtg 33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
cacgcataac cgatatgttc ggtcgctgag gct 33

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
aagcctcagc gaccgaaatt atcggttatg cgtggg 36

<210> SEQ ID NO 52
<211> LENGTH: 36

<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
cccacgcata accgataatt tcggtcgctg aggctt 36

<210> SEQ ID NO 53
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
cctgcaagcc tcagcgaccg aaaagatcgg ttatgcg 37

<210> SEQ ID NO 54
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
cgcataaccg atcttttcgg tcgctgaggc ttgcagg 37

<210> SEQ ID NO 55
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
caagcctcag cgaccgaatt aatcggttat gcgtgg 36

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
ccacgcataa ccgattaatt cggtcgctga ggcttg 36

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
tccctgcaag cctcagcgac cgaaatgatc ggttatgcgt 40

<210> SEQ ID NO 58
<211> LENGTH: 40
<212> TYPE: DNA

<213> ORGANISM: Artificial Sequence
<220> FEATURE:
<223> OTHER INFORMATION: Description of Artificial Sequence: Synthetic primer

<400> SEQUENCE: 58
acgcataacc gatcatttcg gtcgctgagg cttgcaggga 40

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
agcctcagcg accgaaaata tcggttatgc gtg 33

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
cacgcataac cgatattttc ggtcgctgag gct 33

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
aagcctcagc gaccgaacct atcggttatg cgtggg 36

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
cccacgcata accgataggt tcggtcgctg aggctt 36

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
cctgcaagcc tcagcgaccg aacagatcgg ttatgcg 37

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 64
cgcataaccg atctgttcgg tcgctgaggc ttgcagg 37

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
aagcctcagc gaccgaacgt atcggttatg cgtggg 36

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
cccacgcata accgatacgt tcggtcgctg aggctt 36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
aagcctcagc gaccgaaagt atcggttatg cgtggg 36

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
cccacgcata accgatactt tcggtcgctg aggctt 36

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
aagcctcagc gaccgaaact atcggttatg cgtggg 36

<210> SEQ ID NO 70
<211> LENGTH: 36
<212> TYPE: DNA
<213> ORGANISM: Artificial Sequence
<220> FEATURE:

<223> OTHER INFORMATION: Description of Artificial Sequence: Synthetic primer

<400> SEQUENCE: 70
cccacgcata accgatagtt tcggtcgctg aggctt 36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
aagcctcagc gaccgaagtt atcggttatg cgtggg 36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cccacgcata accgataact tcggtcgctg aggctt 36

<210> SEQ ID NO 73
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
caagcctcag cgaccgaatg gatcggttat gcgtgg 36

<210> SEQ ID NO 74
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ccacgcataa ccgatccatt cggtcgctga ggcttg 36

<210> SEQ ID NO 75
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
gcaattcctt tagtggtacc tttctattct cactcggccg aaactgttga aagt 54

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
cttcctggca tcttccagga aatctccg 28

<210> SEQ ID NO 77
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
actttcaaca gtttcggccg agtgagaata gaaaggtacc actaaaggaa ttgc 54

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
cggagatttc ctggaagatg ccaggaag 28

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
tgtctttcgc tgcagagggt gaggatcccg caaaag 36

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
cttttgcggg atcctcaccc tctgcagcga aagaca 36

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
gtgtcggggt cgtcgccgga ttcg 24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 82
cgaatccggc gacgaccccg acac 24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
gatgatgcgc acgtgcactg ggag 24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
ctcccagtgc acgtgcgcat catc 24

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gattcgccgc atactgagtt gccg 24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
cggcaactca gtatgcggcg aatc 24

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ccggcatgaa tttatcagct agaacggttg 30

<210> SEQ ID NO 88
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
cttctgtaaa tcgtcgctat taattaattt tcccttagaa 40

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
aaattcatgc cggagagggt agctattttt 30

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
ttctaaggga aaattaatta atagcgacga tttacagaag 40

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
gttctggtgt ttcttgtcag ggcaagcct 29

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
acggctttgc cgcggccctc tcact 25

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
aggcttgccc tgacaagaaa caccagaac 29

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
agtgagaggg ccgcggcaaa gccgt 25

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
aacgctacta ctattagtag aa 22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gccagcctat gcgcctggtc tg 22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
ttctcttgag gagtctcagc ct 22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
ggcttaactc aattcttgtg gg 22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
atataaccca acctaagccg ga 22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
taaagactaa tagccattca aa 22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
aaaagcacca ctggcagcag cc 22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
aatcaccatg agtgacgact ga 22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
tctcaccctt ttgaatcttt ac 22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
atctgcatta gttgaatgtg 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
cgatcccgca aaagcggcct 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
tttatacggg cactgttact 20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tcttttatat gttgccacct 20

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
tacccgttct tggaatgata a 21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
ttgatttatg tactgtttcc 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
ctcagcgtgg cactgttgca 20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
tcgctttctt cccttccttt 20

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
tacctcggtt caaagagttg g 21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cccatataaa tcagcatcca t 21

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
atttccccga aaagtgccac ctgacgtc 28

<210> SEQ ID NO 115
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
tttttacggt tcctggcctt ttgctgg 27

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccgcacgcga aagcttcaaa atat 24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acatgaagca aatatttaaa ttgt 24

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ccctttcgtc ttcaagaatt ctgggc 26

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
tgtgataaac taccgcatta aagct 25

<210> SEQ ID NO 120
<211> LENGTH: 8380
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (7783)..(7783)
<223> OTHER INFORMATION: a, c, t, g, unknown or other

<400> SEQUENCE: 120
aacgctacta ctattagtag aattgatgcc accttttcag ctcgcgcccc aaatgaaaat 60
atagctaaac aggttattga ccatttgcga aatgtatcta atggtcaaac taaatctact 120
cgttcgcaga attgggaatc aactgttaca tggaatgaaa cttccagaca ccgtacttta 180
gttgcatatt taaaacatgt tgagctacag caccagatcc agcaattaag ctctaagcca 240
tccgcaaaaa tgacctctta tcaaaaggag caattaaagg tactctctaa tcctgacctg 300
ttggagtttg cttccggtct ggttcgcttt gaagctcgaa ttaaaacgcg atatttgaag 360
tctttcgggc ttcctcttaa tctttttgat gcaatccgct ttgcttctga ctataatagt 420
cagggtaaag acctgatttt tgatttatgg tcattctcgt tttctgaact gtttaaagca 480
tttgaggggg attcaatgaa tatttatgac gattccgcag tattggacgc tatccagtct 540
aaacatttta ctattacccc ctctggcaaa acttcttttg caaaagcctc tcgctatttt 600
tgtttttatc gtcgtctggt aaacgagggt tatgatagtg ttgctcttac tatgcctcgt 660
aattcctttt ggcgttatgt atctgcatta gttgaatgtg gtattcctaa atctcaactg 720
atgaatcttt ctacctgtaa taatgttgtt ccgttagttc gttttattaa cgtagatttt 780
tcttcccaac gtcctgactg gtataatgag ccagttctta aaatcgcata aggtaattca 840
caatgattaa agttgaaatt aaaccatctc aagcgcaatt cactacccgt tctggtgttt 900
ctcgtcaggg caagccttat tcactgaatg agcagctttg ttacgttgat ttgggtaatg 960
aatatccggt gcttgtcaag attactcttg atgacggtca gccagcctat gcgcctggtc 1020
tgtacaccgt tcatctgtcc tcgttcaaag ttggtcagtt cggttccctt atgattgacc 1080
gtctgcgcct cgttccggct aagtaacatg gagcaggtcg cggatttcga cacaatttat 1140
caggcgatga tacaaatctc cgttgtactt tgtttcgcgc ttggtataat cgctgggggt 1200
caaagatgag tgttttagtg tattctttcg cctctttcgt tttaggttgg tgccttcgta 1260
gtggcattac gtattttacc cgtttaatgg aagcttcctc atgaaaaagt ctttagtcct 1320
caaagcctct gtagccgttg ctaccctcgt tccgatgctg tctttcgctg ctgagggtga 1380
cgatcccgca aaagcggcct ttgactccct gcaagcctca gcgaccgaat atatcggtta 1440
tgcgtgggcg atggttgttg tcattgtcgg cgcaactatc ggtatcaagc tgtttaagaa 1500
attcacctcg aaagcaagct gataaaccga tacaattaaa ggctcctttt ggagcctttt 1560

-continued

```
tttttggaga ttttcaacgt gaaaaaatta ttattcgcaa ttcctttagt tgttcctttc   1620
tattctcact ccgctgaaac tgttgaaagt tgtttagcaa aaccccatac agaaaattca   1680
tttactaacg tctggaaaga cgacaaaact ttagatcgtt acgctaacta tgagggctgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggctctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt tccattctgg ctttaatgag   2220
gatccattcg tttgtgaata tcaaggccaa tcgtctgacc tgcctcaacc tcctgttaat   2280
gctggcggcg gctctggtgg tggttctggt ggcggctctg agggtggtgg ctctgagggt   2340
ggcggttctg agggtggcgg ctctgagggt ggcggttccg gtggtggctc tggttccggt   2400
gattttgatt atgaaaagat ggcaaacgct aataaggggg ctatgaccga aaatgccgat   2460
gaaaacgcgc tacagtctga cgctaaaggc aaacttgatt ctgtcgctac tgattacggt   2520
gctgctatcg acggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtctttg gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaaaggg cttcggtaag atagctattg ctatttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcatttttg acgttaaaca aaaaatcgtt tcttatttgg   3180
attgggataa ataatatggc tgtttatttt gtaactggca aattaggctc tggaaagacg   3240
ctcgttagcg ttggtaagat tcaggataaa attgtagctg ggtgcaaaat agcaactaat   3300
cttgatttaa ggcttcaaaa cctcccgcaa gtcgggaggt tcgctaaaac gcctcgcgtt   3360
cttagaatac cggataagcc ttctatatct gatttgcttg ctattgggcg cggtaatgat   3420
tcctacgatg aaaataaaaa cggcttgctt gttctcgatg agtgcggtac ttggtttaat   3480
acccgttctt ggaatgataa ggaaagacag ccgattattg attggtttct acatgctcgt   3540
aaattaggat gggatattat ttttcttgtt caggacttat ctattgttga taaacaggcg   3600
cgttctgcat tagctgaaca tgttgtttat tgtcgtcgtc tggacagaat tactttacct   3660
tttgtcggta ctttatattc tcttattact ggctcgaaaa tgcctctgcc taaattacat   3720
gttggcgttg ttaaatatgg cgattctcaa ttaagcccta ctgttgagcg ttggctttat   3780
actggtaaga atttgtataa cgcatatgat actaaacagg ctttttctag taattatgat   3840
tccggtgttt attcttattt aacgccttat ttatcacacg gtcggtattt caaaccatta   3900
aatttaggtc agaagatgaa attaactaaa atatatttga aaaagttttc tcgcgttctt   3960
```

```
tgtcttgcga ttggatttgc atcagcattt acatatagtt atataaccca acctaagccg   4020
gaggttaaaa aggtagtctc tcagacctat gattttgata aattcactat tgactcttct   4080
cagcgtctta atctaagcta tcgctatgtt ttcaaggatt ctaagggaaa attaattaat   4140
agcgacgatt tacagaagca aggttattca ctcacatata ttgatttatg tactgtttcc   4200
attaaaaaag gtaattcaaa tgaaattgtt aaatgtaatt aattttgttt tcttgatgtt   4260
tgtttcatca tcttcttttg ctcaggtaat tgaaatgaat aattcgcctc tgcgcgattt   4320
tgtaacttgg tattcaaagc aatcaggcga atccgttatt gtttctcccg atgtaaaagg   4380
tactgttact gtatattcat ctgacgttaa acctgaaaat ctacgcaatt tctttatttc   4440
tgttttacgt gcaaataatt ttgatatggt aggttctaac ccttccatta ttcagaagta   4500
taatccaaac aatcaggatt atattgatga attgccatca tctgataatc aggaatatga   4560
tgataattcc gctccttctg gtggtttctt tgttccgcaa aatgataatg ttactcaaac   4620
ttttaaaatt aataacgttc gggcaaagga tttaatacga gttgtcgaat tgtttgtaaa   4680
gtctaatact tctaaatcct caaatgtatt atctattgac ggctctaatc tattagttgt   4740
tagtgctcct aaagatattt tagataacct tcctcaattc ctttcaactg ttgatttgcc   4800
aactgaccag atattgattg agggtttgat atttgaggtt cagcaaggtg atgctttaga   4860
tttttcattt gctgctggct ctcagcgtgg cactgttgca ggcggtgtta atactgaccg   4920
cctcacctct gttttatctt ctgctggtgg ttcgttcggt atttttaatg gcgatgtttt   4980
agggctatca gttcgcgcat taaagactaa tagccattca aaaatattgt ctgtgccacg   5040
tattcttacg ctttcaggtc agaagggttc tatctctgtt ggccagaatg tccctttat    5100
tactggtcgt gtgactggtg aatctgccaa tgtaaataat ccatttcaga cgattgagcg   5160
tcaaaatgta ggtatttcca tgagcgtttt tcctgttgca atggctggcg gtaatattgt   5220
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaggattct ggcgtaccgt tcctgtctaa   5400
aatcccttta atcggcctcc tgtttagctc ccgctctgat tctaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttccttt ctcgccacgt tcgccggctt tctgcagaga acatggcttc   5640
atgtggcagg agaaaaaagg ctgcaccggt gcgtcagcag aatatgtgat acaggatata   5700
ttccgcttcc tcgctcactg actcgctacg ctcggtcgtt cgactgcggc gagcggaaat   5760
ggcttacgaa cggggcggag atttcctgga agatgccagg aagatactta acagggaagt   5820
gagagggccg cggcaaagcc gtttttccat aggctccgcc cccctgacaa gcatcacgaa   5880
atctgacgct caaatcagtg gtggcgaaac ccgacaggac tataaagata ccaggcgttt   5940
ccccctggcg gctccctcgt gcgctctcct gttcctgcct ttcggtttac cggtgtcatt   6000
ccgctgttat ggccgcgttt gtctcattcc acgcctgaca ctcagttccg ggtaggcagt   6060
tcgctccaag ctggactgta tgcacgaacc ccccgttcag tccgaccgct gcgccttatc   6120
cggtaactat cgtcttgagt ccaacccgga aagacatgca aaagcaccac tggcagcagc   6180
cactggtaat tgatttagag gagttagtct tgaagtcatg cgccggttaa ggctaaactg   6240
aaaggacaag ttttggtgac tgcgctcctc caagccagtt acctcggttc aaagagttgg   6300
```

```
tagctcagag aaccttcgaa aaaccgccct gcaaggcggt tttttcgttt tcagagcaag   6360
agattacgcg cagaccaaaa cgatctcaag aagatcatct tattaagggg tctgacgctc   6420
agtggaacga aaactcacgt taagggattt tggtcatgag attatcaaaa aggatcttca   6480
cctagatcct tttaaattaa aaatgaagtt ttaaatcaat ctaaagtata tatgagtaaa   6540
cttggtctga cagttaccaa tgcttaatca gtgaggcacc tatctcagcg atctgtctat   6600
ttcgttcatc catagttgcc tgactccccg tcgtgtagat aactacgata cgggagggct   6660
taccatctgg ccccagtgct gcaatgatac cgcgagaccc acgctcaccg gctccagatt   6720
tatcagcaat aaaccagcca gccgattcga gctcgcccgg ggatcgacca gttggtgatt   6780
ttgaactttt gctttgccac ggaacggtct gcgttgtcgg gaagatgcgt gatctgatcc   6840
ttcaactcag caaaagttcg atttattcaa caaagccgcc gtcccgtcaa gtcagcgtaa   6900
tgctctgcca gtgttacaac caattaacca attctgatta gaaaaactca tcgagcatca   6960
aatgaaactg caatttattc atatcaggat tatcaatacc atatttttga aaaagccgtt   7020
tctgtaatga aggagaaaac tcaccgaggc agttccatag gatggcaaga tcctggtatc   7080
ggtctgcgat tccgactcgt ccaacatcaa tacaacctat taatttcccc tcgtcaaaaa   7140
taaggttatc aagtgagaaa tcaccatgag tgacgactga atccggtgag aatggcaaaa   7200
gcttatgcat ttctttccag acttgttcaa caggccagcc attacgctcg tcatcaaaat   7260
cactcgcatc aaccaaaccg ttattcattc gtgattgcgc ctgagcgaga cgaaatacgc   7320
gatcgctgtt aaaaggacaa ttacaaacag gaatcgaatg caaccggcgc aggaacactg   7380
ccagcgcatc aacaatattt tcacctgaat caggatattc ttctaatacc tggaatgctg   7440
ttttcccggg gatcgcagtg gtgagtaacc atgcatcatc aggagtacgg ataaaatgct   7500
tgatggtcgg aagaggcata aattccgtca gccagtttag tctgaccatc tcatctgtaa   7560
catcattggc aacgctacct ttgccatgtt tcagaaacaa ctctggcgca tcgggcttcc   7620
catacaatcg atagattgtc gcacctgatt gcccgacatt atcgcgagcc catttatacc   7680
catataaatc agcatccatg ttggaattta atcgcggcct cgagcaagac gtttcccgtt   7740
gaatatggct cataacaccc cttgtattac tgtttatgta agnagacagt tttattgttc   7800
atgatgatat atttttatct tgtgcaatgt aacatcagag acctattggt taaaaaatga   7860
gctgatttaa caaaaattta acgcgaattt taacaaaata ttaacgttta caatttaaat   7920
atttgcttat acaatcttcc tgtttttggg gcttttctga ttatcaaccg gggtacatat   7980
gattgacatg ctagttttac gattaccgtt catcgattct cttgtttgct ccagactctc   8040
aggcaatgac ctgatagcct ttgtagacct ctcaaaaata gctaccctct ccggcatgaa   8100
tttatcagct agaacggttg aatatcatat tgatggtgat ttgactgtct ccggcctttc   8160
tcacccgttt gaatctttac ctacacatta ctcaggcatt gcatttaaaa tatatgaggg   8220
ttctaaaaat ttttatcctt gcgttgaaat aaaggcttct cccgcaaaag tattacaggg   8280
tcataatgtt tttggtacaa ccgatttagc tttatgctct gaggctttat tgcttaattt   8340
tgctaattct ttgccttgcc tgtatgattt attggatgtt                         8380
```

<210> SEQ ID NO 121
<211> LENGTH: 8506
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<221> NAME/KEY: modified_base
<222> LOCATION: (7909)..(7909)
<223> OTHER INFORMATION: a, c, t, g, unknown or other

<400> SEQUENCE: 121
aacgctacta ctattagtag aattgatgcc accttttcag ctcgcgcccc aaatgaaaat 60
atagctaaac aggttattga ccatttgcga aatgtatcta atggtcaaac taaatctact 120
cgttcgcaga attgggaatc aactgttaca tggaatgaaa cttccagaca ccgtacttta 180
gttgcatatt taaaacatgt tgagctacag caccagatcc agcaattaag ctctaagcca 240
tccgcaaaaa tgacctctta tcaaaaggag caattaaagg tactctctaa tcctgacctg 300
ttggagtttg cttccggtct ggttcgcttt gaagctcgaa ttaaaacgcg atatttgaag 360
tctttcgggc ttcctcttaa tctttttgat gcaatccgct ttgcttctga ctataatagt 420
cagggtaaag acctgatttt tgatttatgg tcattctcgt tttctgaact gtttaaagca 480
tttgaggggg attcaatgaa tatttatgac gattccgcag tattggacgc tatccagtct 540
aaacatttta ctattacccc ctctggcaaa acttcttttg caaaagcctc tcgctatttt 600
tgtttttatc gtcgtctggt aaacgagggt tatgatagtg ttgctcttac tatgcctcgt 660
aattcctttt ggcgttatgt atctgcatta gttgaatgtg gtattcctaa atctcaactg 720
atgaatcttt ctacctgtaa taatgttgtt ccgttagttc gttttattaa cgtagatttt 780
tcttcccaac gtcctgactg gtataatgag ccagttctta aaatcgcata aggtaattca 840
caatgattaa agttgaaatt aaaccatctc aagcgcaatt cactacccgt tctggtgttt 900
ctcgtcaggg caagccttat tcactgaatg agcagctttg ttacgttgat ttgggtaatg 960
aatatccggt gcttgtcaag attactcttg atgacggtca gccagcctat gcgcctggtc 1020
tgtacaccgt tcatctgtcc tcgttcaaag ttggtcagtt cggttccctt atgattgacc 1080
gtctgcgcct cgttccggct aagtaacatg gagcaggtcg cggatttcga cacaatttat 1140
caggcgatga tacaaatctc cgttgtactt tgtttcgcgc ttggtataat cgctgggggt 1200
caaagatgag tgttttagtg tattctttcg cctctttcgt tttaggttgg tgccttcgta 1260
gtggcattac gtattttacc cgtttaatgg aagcttcctc atgaaaaagt ctttagtcct 1320
caaagcctct gtagccgttg ctaccctcgt tccgatgctg tctttcgctg cagattcgcc 1380
gcatactgag ttgccggatc ccgcaaaagc ggcctttgac tccctgcaag cctcagcgac 1440
cgaatatatc ggttatgcgt gggcgatggt tgttgtcatt gtcggcgcaa ctatcggtat 1500
caagctgttt aagaaattca cctcgaaagc aagctgataa accgatacaa ttaaaggctc 1560
cttttggagc cttttttttt ggagattttc aacgtgaaaa aattattatt cgcaattcct 1620
ttagtggtac ctttctattc tcactctatg tgcatgccgt gctttaccac cgatcatcag 1680
atggcgcgca aatgcgatga ttgctgcggc ggcaaaggcc gcggcaaatg ctatggcccg 1740
cagtgcctgt gccgctcggc cgaaactgtt gaaagttgtt tagcaaaacc ccatacagaa 1800
aattcattta ctaacgtctg gaaagacgac aaaactttag atcgttacgc taactatgag 1860
ggctgtctgt ggaatgctac aggcgttgta gtttgtactg gtgacgaaac tcagtgttac 1920
ggtacatggg ttcctattgg gcttgctatc cctgaaaatg agggtggtgg ctctgagggt 1980
ggcggttctg agggtggcgg ctctgagggt ggcggtacta aacctcctga gtacggtgat 2040
acacctattc cgggctatac ttatatcaac cctctcgacg gcacttatcc gcctggtact 2100
gagcaaaacc ccgctaatcc taatccttct cttgaggagt ctcagcctct taatactttc 2160
atgtttcaga ataataggtt ccgaaatagg cagggggcat taactgttta tacgggcact 2220

```
gttactcaag gcactgaccc cgttaaaact tattaccagt acactcctgt atcatcaaaa   2280
gccatgtatg acgcttactg gaacggtaaa ttcagagact gcgctttcca ttctggcttt   2340
aatgaggatc cattcgtttg tgaatatcaa ggccaatcgt ctgacctgcc tcaacctcct   2400
gttaatgctg gcggcggctc tggtggtggt tctggtggcg gctctgaggg tggtggctct   2460
gagggtggcg gttctgaggg tggcggctct gagggtggcg gttccggtgg tggctctggt   2520
tccggtgatt ttgattatga aaagatggca aacgctaata agggggctat gaccgaaaat   2580
gccgatgaaa acgcgctaca gtctgacgct aaaggcaaac ttgattctgt cgctactgat   2640
tacggtgctg ctatcgacgg tttcattggt gacgtttccg gccttgctaa tggtaatggt   2700
gctactggtg attttgctgg ctctaattcc caaatggctc aagtcggtga cggtgataat   2760
tcacctttaa tgaataattt ccgtcaatat ttaccttccc tccctcaatc ggttgaatgt   2820
cgcccttttg tctttggcgc tggtaaacca tatgaatttt ctattgattg tgacaaaata   2880
aacttattcc gtggtgtctt tgcgtttctt ttatatgttg ccacctttat gtatgtattt   2940
tctacgtttg ctaacatact gcgtaataag gagtcttaat catgccagtt cttttgggta   3000
ttccgttatt attgcgtttc ctcggtttcc ttctggtaac tttgttcggc tatctgctta   3060
cttttcttaa aaagggcttc ggtaagatag ctattgctat ttcattgttt cttgctctta   3120
ttattgggct taactcaatt cttgtgggtt atctctctga tattagcgct caattaccct   3180
ctgactttgt tcagggtgtt cagttaattc tcccgtctaa tgcgcttccc tgtttttatg   3240
ttattctctc tgtaaaggct gctattttca tttttgacgt taaacaaaaa atcgtttctt   3300
atttggattg ggataaataa tatggctgtt tattttgtaa ctggcaaatt aggctctgga   3360
aagacgctcg ttagcgttgg taagattcag gataaaattg tagctgggtg caaaatagca   3420
actaatcttg atttaaggct tcaaaacctc ccgcaagtcg ggaggttcgc taaaacgcct   3480
cgcgttctta gaataccgga taagccttct atatctgatt tgcttgctat tgggcgcggt   3540
aatgattcct acgatgaaaa taaaaacggc ttgcttgttc tcgatgagtg cggtacttgg   3600
tttaataccc gttcttggaa tgataaggaa agacagccga ttattgattg gtttctacat   3660
gctcgtaaat taggatggga tattattttt cttgttcagg acttatctat tgttgataaa   3720
caggcgcgtt ctgcattagc tgaacatgtt gtttattgtc gtcgtctgga cagaattact   3780
ttaccttttg tcggtacttt atattctctt attactggct cgaaaatgcc tctgcctaaa   3840
ttacatgttg gcgttgttaa atatggcgat tctcaattaa gccctactgt tgagcgttgg   3900
ctttatactg gtaagaattt gtataacgca tatgatacta aacaggcttt ttctagtaat   3960
tatgattccg gtgtttattc ttatttaacg ccttatttat cacacggtcg gtatttcaaa   4020
ccattaaatt taggtcagaa gatgaaatta actaaaatat atttgaaaaa gttttctcgc   4080
gttctttgtc ttgcgattgg atttgcatca gcatttacat atagttatat aacccaacct   4140
aagccggagg ttaaaaaggt agtctctcag acctatgatt ttgataaatt cactattgac   4200
tcttctcagc gtcttaatct aagctatcgc tatgttttca aggattctaa gggaaaatta   4260
attaatagcg acgatttaca gaagcaaggt tattcactca catatattga tttatgtact   4320
gtttccatta aaaaaggtaa ttcaaatgaa attgttaaat gtaattaatt ttgttttctt   4380
gatgtttgtt tcatcatctt cttttgctca ggtaattgaa atgaataatt cgcctctgcg   4440
cgattttgta acttggtatt caaagcaatc aggcgaatcc gttattgttt ctcccgatgt   4500
aaaaggtact gttactgtat attcatctga cgttaaacct gaaaatctac gcaatttctt   4560
```

```
tatttctgtt ttacgtgcaa ataattttga tatggtaggt tctaaccctt ccattattca   4620
gaagtataat ccaaacaatc aggattatat tgatgaattg ccatcatctg ataatcagga   4680
atatgatgat aattccgctc cttctggtgg tttctttgtt ccgcaaaatg ataatgttac   4740
tcaaactttt aaaattaata acgttcgggc aaaggattta atacgagttg tcgaattgtt   4800
tgtaaagtct aatacttcta aatcctcaaa tgtattatct attgacggct ctaatctatt   4860
agttgttagt gctcctaaag atattttaga taaccttcct caattccttt caactgttga   4920
tttgccaact gaccagatat tgattgaggg tttgatattt gaggttcagc aaggtgatgc   4980
tttagatttt tcatttgctg ctggctctca gcgtggcact gttgcaggcg gtgttaatac   5040
tgaccgcctc acctctgttt tatcttctgc tggtggttcg ttcggtattt ttaatggcga   5100
tgttttaggg ctatcagttc gcgcattaaa gactaatagc cattcaaaaa tattgtctgt   5160
gccacgtatt cttacgcttt caggtcagaa gggttctatc tctgttggcc agaatgtccc   5220
ttttattact ggtcgtgtga ctggtgaatc tgccaatgta aataatccat ttcagacgat   5280
tgagcgtcaa aatgtaggta tttccatgag cgtttttcct gttgcaatgg ctggcggtaa   5340
tattgttctg gatattacca gcaaggccga tagtttgagt tcttctactc aggcaagtga   5400
tgttattact aatcaaagaa gtattgctac aacggttaat ttgcgtgatg gacagactct   5460
tttactcggt ggcctcactg attataaaaa cacttctcag gattctggcg taccgttcct   5520
gtctaaaatc cctttaatcg gcctcctgtt tagctcccgc tctgattcta acgaggaaag   5580
cacgttatac gtgctcgtca aagcaaccat agtacgcgcc ctgtagcggc gcattaagcg   5640
cggcgggtgt ggtggttacg cgcagcgtga ccgctacact tgccagcgcc ctagcgcccg   5700
ctcctttcgc tttcttccct tcctttctcg ccacgttcgc cggctttctg cagagaacat   5760
ggcttcatgt ggcaggagaa aaaaggctgc accggtgcgt cagcagaata tgtgatacag   5820
gatatattcc gcttcctcgc tcactgactc gctacgctcg gtcgttcgac tgcggcgagc   5880
ggaaatggct tacgaacggg gcggagattt cctggaagat gccaggaaga tacttaacag   5940
ggaagtgaga gggccgcggc aaagccgttt ttccataggc tccgcccccc tgacaagcat   6000
cacgaaatct gacgctcaaa tcagtggtgg cgaaacccga caggactata aagataccag   6060
gcgtttcccc ctggcggctc cctcgtgcgc tctcctgttc ctgcctttcg gtttaccggt   6120
gtcattccgc tgttatggcc gcgtttgtct cattccacgc ctgacactca gttccgggta   6180
ggcagttcgc tccaagctgg actgtatgca cgaacccccc gttcagtccg accgctgcgc   6240
cttatccggt aactatcgtc ttgagtccaa cccggaaaga catgcaaaag caccactggc   6300
agcagccact ggtaattgat ttagaggagt tagtcttgaa gtcatgcgcc ggttaaggct   6360
aaactgaaag gacaagtttt ggtgactgcg ctcctccaag ccagttacct cggttcaaag   6420
agttggtagc tcagagaacc ttcgaaaaac cgccctgcaa ggcggttttt tcgttttcag   6480
agcaagagat tacgcgcaga ccaaaacgat ctcaagaaga tcatcttatt aaggggtctg   6540
acgctcagtg gaacgaaaac tcacgttaag ggattttggt catgagatta tcaaaaagga   6600
tcttcaccta gatcctttta aattaaaaat gaagttttaa atcaatctaa agtatatatg   6660
agtaaacttg gtctgacagt taccaatgct taatcagtga ggcacctatc tcagcgatct   6720
gtctatttcg ttcatccata gttgcctgac tccccgtcgt gtagataact acgatacggg   6780
agggcttacc atctggcccc agtgctgcaa tgataccgcg agacccacgc tcaccggctc   6840
cagatttatc agcaataaac cagccagccg attcgagctc gcccggggat cgaccagttg   6900
gtgattttga acttttgctt tgccacggaa cggtctgcgt tgtcgggaag atgcgtgatc   6960
```

tgatccttca actcagcaaa agttcgattt attcaacaaa gccgccgtcc cgtcaagtca 7020
gcgtaatgct ctgccagtgt tacaaccaat taaccaattc tgattagaaa aactcatcga 7080
gcatcaaatg aaactgcaat ttattcatat caggattatc aataccatat ttttgaaaaa 7140
gccgtttctg taatgaagga gaaaactcac cgaggcagtt ccataggatg gcaagatcct 7200
ggtatcggtc tgcgattccg actcgtccaa catcaataca acctattaat ttcccctcgt 7260
caaaaataag gttatcaagt gagaaatcac catgagtgac gactgaatcc ggtgagaatg 7320
gcaaaagctt atgcatttct ttccagactt gttcaacagg ccagccatta cgctcgtcat 7380
caaaatcact cgcatcaacc aaaccgttat tcattcgtga ttgcgcctga gcgagacgaa 7440
atacgcgatc gctgttaaaa ggacaattac aaacaggaat cgaatgcaac cggcgcagga 7500
acactgccag cgcatcaaca atattttcac ctgaatcagg atattcttct aatacctgga 7560
atgctgtttt cccggggatc gcagtggtga gtaaccatgc atcatcagga gtacggataa 7620
aatgcttgat ggtcggaaga ggcataaatt ccgtcagcca gtttagtctg accatctcat 7680
ctgtaacatc attggcaacg ctacctttgc catgtttcag aaacaactct ggcgcatcgg 7740
gcttcccata caatcgatag attgtcgcac ctgattgccc gacattatcg cgagcccatt 7800
tatacccata taaatcagca tccatgttgg aatttaatcg cggcctcgag caagacgttt 7860
cccgttgaat atggctcata acaccccttg tattactgtt tatgtaagna gacagtttta 7920
ttgttcatga tgatatattt ttatcttgtg caatgtaaca tcagagacct attggttaaa 7980
aaatgagctg atttaacaaa aatttaacgc gaattttaac aaaatattaa cgtttacaat 8040
ttaaatattt gcttatacaa tcttcctgtt tttggggctt ttctgattat caaccggggt 8100
acatatgatt gacatgctag ttttacgatt accgttcatc gattctcttg tttgctccag 8160
actctcaggc aatgacctga tagcctttgt agacctctca aaaatagcta ccctctccgg 8220
catgaattta tcagctagaa cggttgaata tcatattgat ggtgatttga ctgtctccgg 8280
cctttctcac ccgtttgaat ctttacctac acattactca ggcattgcat ttaaaatata 8340
tgagggttct aaaaattttt atccttgcgt tgaaataaag gcttctcccg caaaagtatt 8400
acagggtcat aatgtttttg gtacaaccga tttagcttta tgctctgagg ctttattgct 8460
taattttgct aattctttgc cttgcctgta tgatttattg gatgtt 8506

<210> SEQ ID NO 122
<211> LENGTH: 9047
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (2589)..(2589)
<223> OTHER INFORMATION: a, c, t, g, unknown or other

<400> SEQUENCE: 122
gccggctttc tgcagagaac atggcttcat gtggcaggag aaaaaaggct gcagctcgag 60
cttactcccc atccccctgt tgacaattaa tcatcggctc gtataatgtg tggaattgtg 120
agcggataac aatttcttaa tggaaacttc ctcatgaaaa agtctttagt tcttaaagca 180
tctgttgctg ttgcgactct tgttcctatg ctaagctttg cccaccacca ccaccatcat 240
catcaccacc acggtggagg tcctgcagaa ggtgatgacc cggctaaagc tgcttttgac 300
tctcttcagg cttctgctac tgaatacatc ggctacgctt gggctatggt ggttgttatc 360

```
gttggtgcta ctattggcat caaacttttc aaaaaattca cttctaaagc gtcttaatga    420
actcagatac ccagcccgcc taatgagcgg gctttttttt aagctagctt accggtgcgt    480
cagcagaata tgtgatacag gatatattcc gcttcctcgc tcactgactc gctacgctcg    540
gtcgttcgac tgcggcgagc ggaaatggct tacgaacggg gcggagattt cctggaagat    600
gccaggaaga tacttaacag ggaagtgaga gggccgcggc aaagccgttt ttccataggc    660
tccgcccccc tgacaagcat cacgaaatct gacgctcaaa tcagtggtgg cgaaacccga    720
caggactata aagataccag gcgtttcccc ctggcggctc cctcgtgcgc tctcctgttc    780
ctgcctttcg gtttaccggt gtcattccgc tgttatggcc gcgtttgtct cattccacgc    840
ctgacactca gttccgggta ggcagttcgc tccaagctgg actgtatgca cgaacccccc    900
gttcagtccg accgctgcgc cttatccggt aactatcgtc ttgagtccaa cccggaaaga    960
catgcaaaag caccactggc agcagccact ggtaattgat ttagaggagt tagtcttgaa   1020
gtcatgcgcc ggttaaggct aaactgaaag gacaagtttt ggtgactgcg ctcctccaag   1080
ccagttacct cggttcaaag agttggtagc tcagagaacc ttcgaaaaac cgccctgcaa   1140
ggcggttttt tcgttttcag agcaagagat tacgcgcaga ccaaaacgat ctcaagaaga   1200
tcatcttatt aaggggtctg acgctcagtg gaacgaaaac tcacgttaag ggattttggt   1260
catgagatta tcaaaaagga tcttcaccta gatcctttta aattaaaaat gaagttttaa   1320
atcaatctaa agtatatatg agtaaacttg gtctgacagt taccaatgct taatcagtga   1380
ggcacctatc tcagcgatct gtctatttcg ttcatccata gttgcctgac tccccgtcgt   1440
gtagataact acgatacggg agggcttacc atctggcccc agtgctgcaa tgataccgcg   1500
agacccacgc tcaccggctc cagatttatc agcaataaac cagccagccg attcgagctc   1560
gcccggggat cgaccagttg gtgattttga acttttgctt tgccacggaa cggtctgcgt   1620
tgtcgggaag atgcgtgatc tgatccttca actcagcaaa agttcgattt attcaacaaa   1680
gccgccgtcc cgtcaagtca gcgtaatgct ctgccagtgt tacaaccaat taaccaattc   1740
tgattagaaa aactcatcga gcatcaaatg aaactgcaat ttattcatat caggattatc   1800
aataccatat ttttgaaaaa gccgtttctg taatgaagga gaaaactcac cgaggcagtt   1860
ccataggatg gcaagatcct ggtatcggtc tgcgattccg actcgtccaa catcaataca   1920
acctattaat ttcccctcgt caaaaataag gttatcaagt gagaaatcac catgagtgac   1980
gactgaatcc ggtgagaatg gcaaaagctt atgcatttct ttccagactt gttcaacagg   2040
ccagccatta cgctcgtcat caaaatcact cgcatcaacc aaaccgttat tcattcgtga   2100
ttgcgcctga gcgagacgaa atacgcgatc gctgttaaaa ggacaattac aaacaggaat   2160
cgaatgcaac cggcgcagga acactgccag cgcatcaaca atattttcac ctgaatcagg   2220
atattcttct aatacctgga atgctgtttt cccggggatc gcagtggtga gtaaccatgc   2280
atcatcagga gtacggataa aatgcttgat ggtcggaaga ggcataaatt ccgtcagcca   2340
gtttagtctg accatctcat ctgtaacatc attggcaacg ctacctttgc catgtttcag   2400
aaacaactct ggcgcatcgg gcttcccata caatcgatag attgtcgcac ctgattgccc   2460
gacattatcg cgagcccatt tatacccata taaatcagca tccatgttgg aatttaatcg   2520
cggcctcgag caagacgttt cccgttgaat atggctcata acaccccttg tattactgtt   2580
tatgtaagna gacagtttta ttgttcatga tgatatattt ttatcttgtg caatgtaaca   2640
tcagagacct attggttaaa aaatgagctg atttaacaaa aatttaacgc gaattttaac   2700
```

```
aaaatattaa cgtttacaat ttaaatattt gcttatacaa tcttcctgtt tttggggctt   2760
ttctgattat caaccggggt acatatgatt gacatgctag ttttacgatt accgttcatc   2820
gattctcttg tttgctccag actctcaggc aatgacctga tagcctttgt agacctctca   2880
aaaatagcta ccctctccgg catgaattta tcagctagaa cggttgaata tcatattgat   2940
ggtgatttga ctgtctccgg cctttctcac ccgtttgaat ctttacctac acattactca   3000
ggcattgcat ttaaaatata tgagggttct aaaaattttt atccttgcgt tgaaataaag   3060
gcttctcccg caaaagtatt acagggtcat aatgtttttg gtacaaccga tttagcttta   3120
tgctctgagg ctttattgct taattttgct aattctttgc cttgcctgta tgatttattg   3180
gatgttaacg ctactactat tagtagaatt gatgccacct tttcagctcg cgccccaaat   3240
gaaaatatag ctaaacaggt tattgaccat ttgcgaaatg tatctaatgg tcaaactaaa   3300
tctactcgtt cgcagaattg ggaatcaact gttacatgga atgaaacttc cagacaccgt   3360
actttagttg catatttaaa acatgttgag ctacagcacc agatccagca attaagctct   3420
aagccatccg caaaaatgac ctcttatcaa aaggagcaat taaaggtact ctctaatcct   3480
gacctgttgg agtttgcttc cggtctggtt cgctttgaag ctcgaattaa aacgcgatat   3540
ttgaagtctt tcgggcttcc tcttaatctt tttgatgcaa tccgctttgc ttctgactat   3600
aatagtcagg gtaaagacct gatttttgat ttatggtcat tctcgttttc tgaactgttt   3660
aaagcatttg agggggattc aatgaatatt tatgacgatt ccgcagtatt ggacgctatc   3720
cagtctaaac attttactat taccccctct ggcaaaactt cttttgcaaa agcctctcgc   3780
tatttttgtt tttatcgtcg tctggtaaac gagggttatg atagtgttgc tcttactatg   3840
cctcgtaatt ccttttggcg ttatgtatct gcattagttg aatgtggtat tcctaaatct   3900
caactgatga atctttctac ctgtaataat gttgttccgt tagttcgttt tattaacgta   3960
gatttttctt cccaacgtcc tgactggtat aatgagccag ttcttaaaat cgcataaggt   4020
aattcacaat gattaaagtt gaaattaaac catctcaagc gcaattcact acccgttctg   4080
gtgtttctcg tcagggcaag ccttattcac tgaatgagca gctttgttac gttgatttgg   4140
gtaatgaata tccggtgctt gtcaagatta ctcttgatga cggtcagcca gcctatgcgc   4200
ctggtctgta caccgttcat ctgtcctcgt tcaaagttgg tcagttcggt tcccttatga   4260
ttgaccgtct gcgcctcgtt ccggctaagt aacatggagc aggtcgcgga tttcgacaca   4320
atttatcagg cgatgataca aatctccgtt gtactttgtt tcgcgcttgg tataatcgca   4380
ggcggccaga ggtgagacgt gctgacggcc agctgataaa ccgattactg ttcgctgggg   4440
gtcaaagaat gaaatcccta ttgcctacgg cagccgctgg attgttatta ctcgcggccc   4500
agccggccat ggcgaaaagg acagctgatg gatcagaatt tgagagcccg aaaaagaaac   4560
gtaaggtggg ccagggcggc cagggtgtcg acatgagtgt tttagtgtat tctttcgcta   4620
gcttcgtttt aggttggtgc cttcgtagtg gcattacgta ttttacccgt ttaatggaaa   4680
cttcctcatg aaaaagtctt tagtcctcaa agcctctgta gccgttgcta ccctcgttcc   4740
gatgctgtct ttcgctgctg agggtgacga tcccgcaaaa gcggcctttg actccctgca   4800
agcctcagcg accgaatata tcggttatgc gtgggcgatg gttgttgtca ttgtcggcgc   4860
aactatcggt atcaagctgt ttaagaaatt cacctcgaaa gcaagctgat aaaccgatac   4920
aattaaaggc tccttttgga gccttttttt ttggagattt tcaacgtgaa aaaattatta   4980
ttcgcaattc ctttagtggt acctttctat tctcactctg gcctgaacga catcttcgag   5040
gctcagaaaa tcgaatggca cgagtcggcc gaaactgttg aaagttgttt agcaaaaccc   5100
```

```
catacagaaa attcatttac taacgtctgg aaagacgaca aaactttaga tcgttacgct   5160
aactatgagg gctgtctgtg gaatgctaca ggcgttgtag tttgtactgg tgacgaaact   5220
cagtgttacg gtacatgggt tcctattggg cttgctatcc ctgaaaatga gggtggtggc   5280
tctgagggtg gcggttctga gggtggcggc tctgagggtg gcggtactaa acctcctgag   5340
tacggtgata cacctattcc gggctatact tatatcaacc ctctcgacgg cacttatccg   5400
cctggtactg agcaaaaccc cgctaatcct aatccttctc ttgaggagtc tcagcctctt   5460
aatactttca tgtttcagaa taataggttc cgaaataggc agggggcatt aactgtttat   5520
acgggcactg ttactcaagg cactgacccc gttaaaactt attaccagta cactcctgta   5580
tcatcaaaag ccatgtatga cgcttactgg aacggtaaat tcagagactg cgctttccat   5640
tctggcttta atgaggatcc attcgtttgt gaatatcaag gccaatcgtc tgacctgcct   5700
caacctcctg ttaatgctgg cggcggctct ggtggtggtt ctggtggcgg ctctgagggt   5760
ggtggctctg agggtggcgg ttctgagggt ggcggctctg agggtggcgg ttccggtggt   5820
ggctctggtt ccggtgattt tgattatgaa aagatggcaa acgctaataa gggggctatg   5880
accgaaaatg ccgatgaaaa cgcgctacag tctgacgcta aaggcaaact tgattctgtc   5940
gctactgatt acggtgctgc tatcgacggt ttcattggtg acgtttccgg ccttgctaat   6000
ggtaatggtg ctactggtga ttttgctggc tctaattccc aaatggctca agtcggtgac   6060
ggtgataatt cacctttaat gaataatttc cgtcaatatt taccttccct ccctcaatcg   6120
gttgaatgtc gcccttttgt ctttggcgct ggtaaaccat atgaattttc tattgattgt   6180
gacaaaataa acttattccg tggtgtcttt gcgtttcttt tatatgttgc cacctttatg   6240
tatgtatttt ctacgtttgc taacatactg cgtaataagg agtcttaatc atgccagttc   6300
ttttgggtat tccgttatta ttgcgtttcc tcggtttcct tctggtaact ttgttcggct   6360
atctgcttac ttttcttaaa aagggcttcg gtaagatagc tattgctatt tcattgtttc   6420
ttgctcttat tattgggctt aactcaattc ttgtgggtta tctctctgat attagcgctc   6480
aattaccctc tgactttgtt cagggtgttc agttaattct cccgtctaat gcgcttccct   6540
gtttttatgt tattctctct gtaaaggctg ctattttcat ttttgacgtt aaacaaaaaa   6600
tcgtttctta tttggattgg gataaataat atggctgttt attttgtaac tggcaaatta   6660
ggctctggaa agacgctcgt tagcgttggt aagattcagg ataaaattgt agctgggtgc   6720
aaaatagcaa ctaatcttga tttaaggctt caaaacctcc cgcaagtcgg gaggttcgct   6780
aaaacgcctc gcgttcttag aataccggat aagccttcta tatctgattt gcttgctatt   6840
gggcgcggta atgattccta cgatgaaaat aaaaacggct tgcttgttct cgatgagtgc   6900
ggtacttggt ttaatacccg ttcttggaat gataaggaaa gacagccgat tattgattgg   6960
tttctacatg ctcgtaaatt aggatgggat attatttttc ttgttcagga cttatctatt   7020
gttgataaac aggcgcgttc tgcattagct gaacatgttg tttattgtcg tcgtctggac   7080
agaattactt taccttttgt cggtacttta tattctctta ttactggctc gaaaatgcct   7140
ctgcctaaat tacatgttgg cgttgttaaa tatggcgatt ctcaattaag ccctactgtt   7200
gagcgttggc tttatactgg taagaatttg tataacgcat atgatactaa acaggctttt   7260
tctagtaatt atgattccgg tgtttattct tatttaacgc cttatttatc acacggtcgg   7320
tatttcaaac cattaaattt aggtcagaag atgaaattaa ctaaaatata tttgaaaaag   7380
ttttctcgcg ttctttgtct tgcgattgga tttgcatcag catttacata tagttatata   7440
```

acccaaccta agccggaggt taaaaaggta gtctctcaga cctatgattt tgataaattc 7500
actattgact cttctcagcg tcttaatcta agctatcgct atgttttcaa ggattctaag 7560
ggaaaattaa ttaatagcga cgatttacag aagcaaggtt attcactcac atatattgat 7620
ttatgtactg tttccattaa aaaaggtaat tcaaatgaaa ttgttaaatg taattaattt 7680
tgttttcttg atgtttgttt catcatcttc ttttgctcag gtaattgaaa tgaataattc 7740
gcctctgcgc gattttgtaa cttggtattc aaagcaatca ggcgaatccg ttattgtttc 7800
tcccgatgta aaaggtactg ttactgtata ttcatctgac gttaaacctg aaaatctacg 7860
caatttcttt atttctgttt tacgtgcaaa taattttgat atggtaggtt ctaacccttc 7920
cattattcag aagtataatc caaacaatca ggattatatt gatgaattgc catcatctga 7980
taatcaggaa tatgatgata attccgctcc ttctggtggt ttctttgttc cgcaaaatga 8040
taatgttact caaactttta aaattaataa cgttcgggca aaggatttaa tacgagttgt 8100
cgaattgttt gtaaagtcta atacttctaa atcctcaaat gtattatcta ttgacggctc 8160
taatctatta gttgttagtg ctcctaaaga tattttagat aaccttcctc aattcctttc 8220
aactgttgat ttgccaactg accagatatt gattgagggt ttgatatttg aggttcagca 8280
aggtgatgct ttagattttt catttgctgc tggctctcag cgtggcactg ttgcaggcgg 8340
tgttaatact gaccgcctca cctctgtttt atcttctgct ggtggttcgt tcggtatttt 8400
taatggcgat gttttagggc tatcagttcg cgcattaaag actaatagcc attcaaaaat 8460
attgtctgtg ccacgtattc ttacgctttc aggtcagaag ggttctatct ctgttggcca 8520
gaatgtccct tttattactg gtcgtgtgac tggtgaatct gccaatgtaa ataatccatt 8580
tcagacgatt gagcgtcaaa atgtaggtat ttccatgagc gtttttcctg ttgcaatggc 8640
tggcggtaat attgttctgg atattaccag caaggccgat agtttgagtt cttctactca 8700
ggcaagtgat gttattacta atcaaagaag tattgctaca acggttaatt tgcgtgatgg 8760
acagactctt ttactcggtg gcctcactga ttataaaaac acttctcagg attctggcgt 8820
accgttcctg tctaaaatcc ctttaatcgg cctcctgttt agctcccgct ctgattctaa 8880
cgaggaaagc acgttatacg tgctcgtcaa agcaaccata gtacgcgccc tgtagcggcg 8940
cattaagcgc ggcgggtgtg gtggttacgc gcagcgtgac cgctacactt gccagcgccc 9000
tagcgcccgc tcctttcgct ttcttccctt cctttctcgc cacgttc 9047

<210> SEQ ID NO 123
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123
atgtgcatgc cgtgctttac caccgatcat cagatggcgc gcaaatgcga tgattgctgc 60
ggcggcaaag gccgcggcaa atgctatggc ccgcagtgcc tgtgccgc 108

<210> SEQ ID NO 124
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 124
ggcctgaacg acatcttcga ggctcagaaa atcgaatggc acgag 45

<210> SEQ ID NO 125
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 125
aaaaggacag ctgatggatc agaatttgag agcccgaaaa agaaacgtaa ggtgggccag 60
ggcggccagg gtgtcgac 78

<210> SEQ ID NO 126
<211> LENGTH: 4888
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126
ttctgggcca tcgccctgat agacggtttt tcgccctttg acgttggctt taatagtgga 60
ctcttgttcc aaactggaac aacactcaac cctatctcgg gctattcttt tgatttataa 120
gggattttgc cgatttcggc ctattggtta aaaaatgagc tgatttaaca aaaatttaac 180
gcgaatttta acaaaatatt aacgtttaca atttaaatat ttgcttatac aatccgcgcc 240
ctgtagcggc gcattaagcg cggcgggtgt ggtggttacg cgcagcgtga ccgctacact 300
tgccagcgcc ctagcgcccg ctcctttcgc tttcttccct tcctttctcg ccacgttcgc 360
cggctttccc cgtcaagctc taaatcgggg gctcccttta gggttccgat ttagtgcttt 420
acggcacctc gaccccaaaa aacttgattt gggtgatggt tcacgtagtg ggccatcgcc 480
ctgatagacg gtttttcgcc ctttgacgtt ggagtccacg ttctttaata gtggactctt 540
gttccaaaca acactaagct ttaatgcggt agtttatcac agttaaattg ctaacgcagt 600
caggcaccgt gtatgaaatc taacaatgcg ctcatcgtca tcctcggcac cgtcaccctg 660
gatgctgtag gcataggctt ggttatgccg gtactgccgg gcctcttgcg ggatatcgtc 720
cattccgaca gcatcgccag tcactatggc gtgctgctag cgctatatgc gttgatgcaa 780
tttctatgcg cacccgttct cggagcactg tccgaccgct ttggccgccg cccagtcctg 840
ctcgcttcgc tacttggagc cactatcgac tacgcgatca tggcgaccac acccgtcctg 900
tggatcctct acgccggacg catcgtggcc ggcatcaccg gcgccacagg tgcggttgct 960
ggcgcctata tcgccgacat caccgatggg gaagatcggg ctcgccactt cgggctcatg 1020
agcgcttgtt tcggcgtggg tatggtggca ggccccgtgg ccgggggact gttgggcgcc 1080
atctccttgc atgcaccatt ccttgcggcg gcggtgctca acggcctcaa cctactactg 1140
ggctgcttcc taatgcagga gtcgcataag ggagagcgtc gaccgatgcc cttgagagcc 1200
ttcaacccag tcagctcctt ccggtgggcg cggggcatga ctatcgtcgc cgcacttatg 1260
actgtcttct ttatcatgca actcgtagga caggtgccgg cagcgctctg ggtcattttc 1320
ggcgaggacc gctttcgctg gagcgcgacg atgatcggcc tgtcgcttgc ggtattcgga 1380
atcttgcacg ccctcgctca agccttcgtc actggtcccg ccaccaaacg tttcggcgag 1440
aagcaggcca ttatcgccgg catggcggcc gacgcgctgg gctacgtctt gctggcgttc 1500

-continued

```
gcgacgcgag gctggatggc cttccccatt atgattcttc tcgcttccgg cggcatcggg   1560
atgcccgcgt tgcaggccat gctgtccagg caggtagatg acgaccatca gggacagctt   1620
caaggatcgc tcgcggctct taccagccta acttcgatca ttggaccgct gatcgtcacg   1680
gcgatttatg ccgcctcggc gagcacatgg aacgggttgg catggattgt aggcgccgcc   1740
ctataccttg tctgcctccc cgcgttgcgt cgcggtgcat ggagccgggc cacctcgacc   1800
tgaatggaag ccggcggcac ctcgctaacg gattcaccac tccaagaatt ggagccaatc   1860
aattcttgcg gagaactgtg aatgcgcaaa ccaacccttg gcagaacata tccatcgcgt   1920
ccgccatctc cagcagccgc acgcggcgca tctcgggcag cgttgggtcc tggccacggg   1980
tgcgcatgat cgtgctcctg tcgttgagga cccggctagg ctggcggggt tgccttactg   2040
gttagcagaa tgaatcaccg atacgcgagc gaacgtgaag cgactgctgc tgcaaaacgt   2100
ctgcgacctg agcaacaaca tgaatggtct tcggtttccg tgtttcgtaa agtctggaaa   2160
cgcggaagtc agcgccctgc accattatgt tccggatctg catcgcagga tgctgctggc   2220
taccctgtgg aacacctaca tctgtattaa cgaagcgctg gcattgaccc tgagtgattt   2280
ttctctggtc ccgccgcatc cataccgcca gttgtttacc ctcacaacgt tccagtaacc   2340
gggcatgttc atcatcagta acccgtatcg tgagcatcct ctctcgtttc atcggtatca   2400
ttacccccat gaacagaaat cccccttaca cggaggcatc agtgaccaaa caggaaaaaa   2460
ccgcccttaa catggcccgc tttatcagaa gccagacatt aacgcttctg gagaaactca   2520
acgagctgga cgcggatgaa caggcagaca tctgtgaatc gcttcacgac cacgctgatg   2580
agctttaccg cagctgcctc gcgcgtttcg gtgatgacgg tgaaaacctc tgacacatgc   2640
agctcccgga gacggtcaca gcttgtctgt aagcggatgc cgggagcaga caagcccgtc   2700
agggcgcgtc agcgggtgtt ggcgggtgtc ggggcgcagc catgacccag tcacgtagcg   2760
atagcggagt gtatactggc ttaactatgc ggcatcagag cagattgtac tgagagtgca   2820
ccatatgcgg tgtgaaatac cgcacagatg cgtaaggaga aaataccgca tcaggcgctc   2880
ttccgcttcc tcgctcactg actcgctgcg ctcggtcgtt cggctgcggc gagcggtatc   2940
agctcactca aaggcggtaa tacggttatc cacagaatca ggggataacg caggaaagaa   3000
catgtgagca aaaggccagc aaaaggccag gaaccgtaaa aaggccgcgt tgctggcgtt   3060
tttccatagg ctccgccccc ctgacgagca tcacaaaaat cgacgctcaa gtcagaggtg   3120
gcgaaacccg acaggactat aaagatacca ggcgtttccc cctggaagct ccctcgtgcg   3180
ctctcctgtt ccgaccctgc cgcttaccgg atacctgtcc gcctttctcc cttcgggaag   3240
cgtggcgctt tctcatagct cacgctgtag gtatctcagt tcggtgtagg tcgttcgctc   3300
caagctgggc tgtgtgcacg aaccccccgt tcagcccgac cgctgcgcct tatccggtaa   3360
ctatcgtctt gagtccaacc cggtaagaca cgacttatcg ccactggcag cagccactgg   3420
taacaggatt agcagagcga ggtatgtagg cggtgctaca gagttcttga agtggtggcc   3480
taactacggc tacactagaa ggacagtatt tggtatctgc gctctgctga agccagttac   3540
cttcggaaaa agagttggta gctcttgatc cggcaaacaa accaccgctg gtagcggtgg   3600
tttttttgtt tgcaagcagc agattacgcg cagaaaaaaa ggatctcaag aagatccttt   3660
gatcttttct acggggtctg acgctcagtg gaacgaaaac tcacgttaag ggattttggt   3720
catgagatta tcaaaaagga tcttcaccta gatcctttta aattaaaaat gaagttttaa   3780
atcaatctaa agtatatatg agtaaacttg gtctgacagt taccaatgct taatcagtga   3840
ggcacctatc tcagcgatct gtctatttcg ttcatccata gttgcctgac tccccgtcgt   3900
```

```
gtagataact acgatacggg agggcttacc atctggcccc agtgctgcaa tgataccgcg   3960

agacccacgc tcaccggctc cagatttatc agcaataaac cagccagccg gaagggccga   4020

gcgcagaagt ggtcctgcaa ctttatccgc ctccatccag tctattaatt gttgccggga   4080

agctagagta agtagttcgc cagttaatag tttgcgcaac gttgttgcca ttgctgcagg   4140

catcgtggtg tcacgctcgt cgtttggtat ggcttcattc agctccggtt cccaacgatc   4200

aaggcgagtt acatgatccc ccatgttgtg caaaaaagcg gttagctcct tcggtcctcc   4260

gatcgttgtc agaagtaagt tggccgcagt gttatcactc atggttatgg cagcactgca   4320

taattctctt actgtcatgc catccgtaag atgcttttct gtgactggtg agtactcaac   4380

caagtcattc tgagaatagt gtatgcggcg accgagttgc tcttgcccgg cgtcaacacg   4440

ggataatacc gcgccacata gcagaacttt aaaagtgctc atcattggaa aacgttcttc   4500

ggggcgaaaa ctctcaagga tcttaccgct gttgagatcc agttcgatgt aacccactcg   4560

tgcacccaac tgatcttcag catcttttac tttcaccagc gtttctgggt gagcaaaaac   4620

aggaaggcaa aatgccgcaa aaaagggaat aagggcgaca cggaaatgtt gaatactcat   4680

actcttcctt tttcaatatt attgaagcat ttatcagggt tattgtctca tgagcggata   4740

catatttgaa tgtatttaga aaaataaaca aataggggtt ccgcgcacat ttccccgaaa   4800

agtgccacct gacgtctaag aaaccattat tatcatgaca ttaacctata aaaataggcg   4860

tatcacgagg ccctttcgtc ttcaagaa                                      4888
```

<210> SEQ ID NO 127
<211> LENGTH: 6373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
ttctgggcca tcgccctgat agacggtttt tcgccctttg acgttggctt taatagtgga     60

ctcttgttcc aaactggaac aacactcaac cctatctcgg gctattcttt tgatttataa    120

gggattttgc cgatttcggc ctattggtta aaaaatgagc tgatttaaca aaaatttaac    180

gcgaatttta acaaaatatt aacgtttaca atttgatgta cgggccagat atacgcgttg    240

acattgatta ttgactagtt attaatagta atcaattacg gggtcattag ttcatagccc    300

atatatggag ttccgcgtta cataacttac ggtaaatggc ccgcctggct gaccgcccaa    360

cgacccccgc ccattgacgt caataatgac gtatgttccc atagtaacgc caatagggac    420

tttccattga cgtcaatggg tggactattt acggtaaact gcccacttgg cagtacatca    480

agtgtatcat atgccaagta cgccccctat tgacgtcaat gacggtaaat ggcccgcctg    540

gcattatgcc cagtacatga ccttatggga ctttcctact tggcagtaca tctacgtatt    600

agtcatcgct attaccatgg tgatgcggtt ttggcagtac atcaatgggc gtggatagcg    660

gtttgactca cggggatttc caagtctcca ccccattgac gtcaatggga gtttgttttg    720

gcaccaaaat caacgggact ttccaaaatg tcgtaacaac tccgccccat tgacgcaaat    780

gggcggtagg cgtgtacggt gggaggtcta tataagcaga gctctctggc taactagaga    840

acccactgct tactggctta tcgaaattaa tacgactcac tatagggaga cccaagcttg    900

gtaccgagct cggatccagc caccatggga gtcaaagttc tgtttgccct gatctgcatc    960

gctgtggccg aggccaagcc caccgagaac aacgaagact tcaacatcgt ggccgtggcc   1020
```

-continued

```
agcaacttcg cgaccacgga tctcgatgct gaccgcggga agttgcccgg caagaagctg   1080
ccgctggagg tgctcaaaga gatggaagcc aatgcccgga aagctggctg caccaggggc   1140
tgtctgatct gcctgtccca catcaagtgc acgcccaaga tgaagaagtt catcccagga   1200
cgctgccaca cctacgaagg cgacaaagag tccgcacagg gcggcatagg cgaggcgatc   1260
gtcgacattc ctgagattcc tgggttcaag gacttggagc ccatggagca gttcatcgca   1320
caggtcgatc tgtgtgtgga ctgcacaact ggctgcctca aagggcttgc caacgtgcag   1380
tgttctgacc tgctcaagaa gtggctgccg caacgctgtg cgacctttgc cagcaagatc   1440
cagggccagg tggacaagat caagggggcc ggtggtgact aagcggccgc aataaaatat   1500
ctttattttc attacatctg tgtgttggtt ttttgtgtgt ctagaaataa ttcttactgt   1560
catatcccgc ccctaactcc gcccagttcc gcccattctc cgccccatgg ctgactaatt   1620
tttttattt atgcagaggc cgaggccgcc tctgcctctg agctattcca gaagtagtga   1680
ggaggctttt ttggaggcca aatatttgct tatacaatcc gcgccctgta gcggcgcatt   1740
aagcgcggcg ggtgtggtgg ttacgcgcag cgtgaccgct acacttgcca gcgccctagc   1800
gcccgctcct ttcgctttct tcccttcctt tctcgccacg ttcgccggct ttccccgtca   1860
agctctaaat cgggggctcc ctttagggtt ccgatttagt gctttacggc acctcgaccc   1920
caaaaaactt gatttgggtg atggttcacg tagtgggcca tcgccctgat agacggtttt   1980
tcgccctttg acgttggagt ccacgttctt taatagtgga ctcttgttcc aaacaacact   2040
aagctttaat gcggtagttt atcacagtta aattgctaac gcagtcaggc accgtgtatg   2100
aaatctaaca atgcgctcat cgtcatcctc ggcaccgtca ccctggatgc tgtaggcata   2160
ggcttggtta tgccggtact gccgggcctc ttgcgggata tcgtccattc cgacagcatc   2220
gccagtcact atggcgtgct gctagcgcta tatgcgttga tgcaatttct atgcgcaccc   2280
gttctcggag cactgtccga ccgctttggc cgccgcccag tcctgctcgc ttcgctactt   2340
ggagccacta tcgactacgc gatcatggcg accacacccg tcctgtggat cctctacgcc   2400
ggacgcatcg tggccggcat caccggcgcc acaggtgcgg ttgctggcgc ctatatcgcc   2460
gacatcaccg atggggaaga tcgggctcgc cacttcgggc tcatgagcgc ttgtttcggc   2520
gtgggtatgg tggcaggccc cgtggccggg ggactgttgg gcgccatctc cttgcatgca   2580
ccattccttg cggcggcggt gctcaacggc ctcaacctac tactgggctg cttcctaatg   2640
caggagtcgc ataagggaga gcgtcgaccg atgcccttga gagccttcaa cccagtcagc   2700
tccttccggt gggcgcgggg catgactatc gtcgccgcac ttatgactgt cttctttatc   2760
atgcaactcg taggacaggt gccggcagcg ctctgggtca ttttcggcga ggaccgcttt   2820
cgctggagcg cgacgatgat cggcctgtcg cttgcggtat tcggaatctt gcacgccctc   2880
gctcaagcct tcgtcactgg tcccgccacc aaacgtttcg gcgagaagca ggccattatc   2940
gccggcatgg cggccgacgc gctgggctac gtcttgctgg cgttcgcgac gcgaggctgg   3000
atggccttcc ccattatgat tcttctcgct tccggcggca tcgggatgcc cgcgttgcag   3060
gccatgctgt ccaggcaggt agatgacgac catcagggac agcttcaagg atcgctcgcg   3120
gctcttacca gcctaacttc gatcattgga ccgctgatcg tcacggcgat ttatgccgcc   3180
tcggcgagca catggaacgg gttggcatgg attgtaggcg ccgccctata ccttgtctgc   3240
ctccccgcgt tgcgtcgcgg tgcatggagc cgggccacct cgacctgaat ggaagccggc   3300
ggcacctcgc taacggattc accactccaa gaattggagc caatcaattc ttgcggagaa   3360
```

```
ctgtgaatgc gcaaaccaac ccttggcaga acatatccat cgcgtccgcc atctccagca   3420
gccgcacgcg gcgcatctcg ggcagcgttg ggtcctggcc acgggtgcgc atgatcgtgc   3480
tcctgtcgtt gaggacccgg ctaggctggc ggggttgcct tactggttag cagaatgaat   3540
caccgatacg cgagcgaacg tgaagcgact gctgctgcaa aacgtctgcg acctgagcaa   3600
caacatgaat ggtcttcggt ttccgtgttt cgtaaagtct ggaaacgcgg aagtcagcgc   3660
cctgcaccat tatgttccgg atctgcatcg caggatgctg ctggctaccc tgtggaacac   3720
ctacatctgt attaacgaag cgctggcatt gaccctgagt gatttttctc tggtcccgcc   3780
gcatccatac cgccagttgt ttaccctcac aacgttccag taaccgggca tgttcatcat   3840
cagtaacccg tatcgtgagc atcctctctc gtttcatcgg tatcattacc cccatgaaca   3900
gaaatccccc ttacacggag gcatcagtga ccaaacagga aaaaaccgcc cttaacatgg   3960
cccgctttat cagaagccag acattaacgc ttctggagaa actcaacgag ctggacgcgg   4020
atgaacaggc agacatctgt gaatcgcttc acgaccacgc tgatgagctt taccgcagct   4080
gcctcgcgcg tttcggtgat gacggtgaaa acctctgaca catgcagctc ccggagacgg   4140
tcacagcttg tctgtaagcg gatgccggga gcagacaagc ccgtcagggc gcgtcagcgg   4200
gtgttggcgg gtgtcggggc gcagccatga cccagtcacg tagcgatagc ggagtgtata   4260
ctggcttaac tatgcggcat cagagcagat tgtactgaga gtgcaccata tgcggtgtga   4320
aataccgcac agatgcgtaa ggagaaaata ccgcatcagg cgctcttccg cttcctcgct   4380
cactgactcg ctgcgctcgg tcgttcggct gcggcgagcg gtatcagctc actcaaaggc   4440
ggtaatacgg ttatccacag aatcagggga taacgcagga aagaacatgt gagcaaaagg   4500
ccagcaaaag gccaggaacc gtaaaaaggc cgcgttgctg gcgtttttcc ataggctccg   4560
cccccctgac gagcatcaca aaaatcgacg ctcaagtcag aggtggcgaa acccgacagg   4620
actataaaga taccaggcgt ttccccctgg aagctccctc gtgcgctctc ctgttccgac   4680
cctgccgctt accggatacc tgtccgcctt tctcccttcg ggaagcgtgg cgctttctca   4740
tagctcacgc tgtaggtatc tcagttcggt gtaggtcgtt cgctccaagc tgggctgtgt   4800
gcacgaaccc cccgttcagc ccgaccgctg cgccttatcc ggtaactatc gtcttgagtc   4860
caacccggta agacacgact tatcgccact ggcagcagcc actggtaaca ggattagcag   4920
agcgaggtat gtaggcggtg ctacagagtt cttgaagtgg tggcctaact acggctacac   4980
tagaaggaca gtatttggta tctgcgctct gctgaagcca gttaccttcg gaaaaagagt   5040
tggtagctct tgatccggca aacaaaccac cgctggtagc ggtggttttt ttgtttgcaa   5100
gcagcagatt acgcgcagaa aaaaaggatc tcaagaagat cctttgatct tttctacggg   5160
gtctgacgct cagtggaacg aaaactcacg ttaagggatt ttggtcatga gattatcaaa   5220
aaggatcttc acctagatcc ttttaaatta aaaatgaagt tttaaatcaa tctaaagtat   5280
atatgagtaa acttggtctg acagttacca atgcttaatc agtgaggcac ctatctcagc   5340
gatctgtcta tttcgttcat ccatagttgc ctgactcccc gtcgtgtaga taactacgat   5400
acgggagggc ttaccatctg gccccagtgc tgcaatgata ccgcgagacc cacgctcacc   5460
ggctccagat ttatcagcaa taaaccagcc agccggaagg gccgagcgca gaagtggtcc   5520
tgcaacttta tccgcctcca tccagtctat taattgttgc cgggaagcta gagtaagtag   5580
ttcgccagtt aatagtttgc gcaacgttgt tgccattgct gcaggcatcg tggtgtcacg   5640
ctcgtcgttt ggtatggctt cattcagctc cggttcccaa cgatcaaggc gagttacatg   5700
atcccccatg ttgtgcaaaa aagcggttag ctccttcggt cctccgatcg ttgtcagaag   5760
```

taagttggcc gcagtgttat cactcatggt tatggcagca ctgcataatt ctcttactgt 5820
catgccatcc gtaagatgct tttctgtgac tggtgagtac tcaaccaagt cattctgaga 5880
atagtgtatg cggcgaccga gttgctcttg cccggcgtca acacgggata ataccgcgcc 5940
acatagcaga actttaaaag tgctcatcat tggaaaacgt tcttcggggc gaaaactctc 6000
aaggatctta ccgctgttga gatccagttc gatgtaaccc actcgtgcac ccaactgatc 6060
ttcagcatct tttactttca ccagcgtttc tgggtgagca aaaacaggaa ggcaaaatgc 6120
cgcaaaaaag ggaataaggg cgacacggaa atgttgaata ctcatactct tcctttttca 6180
atattattga agcatttatc agggttattg tctcatgagc ggatacatat ttgaatgtat 6240
ttagaaaaat aaacaaatag gggttccgcg cacatttccc cgaaaagtgc cacctgacgt 6300
ctaagaaacc attattatca tgacattaac ctataaaaat aggcgtatca cgaggccctt 6360
tcgtcttcaa gaa 6373

<210> SEQ ID NO 128
<211> LENGTH: 2711
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 128
ccaatgattg ggccatcgcc ctgatagacg gtttttcgcc ctttgacgtt ggctttaata 60
gtggactctt gttccaaact ggaacaacac tcaaccctat ctcgggctat tcttttgatt 120
tataagggat tttgccgatt tcggcctatt ggttaaaaaa tgagctgatt taacaaaaat 180
ttaacgcgac atgtcctgca ggcagctgcg cgctcgctcg ctcactgagg ccgcccgggc 240
aaagcccggg cgtcgggcga cctttggtcg cccggcctca gtgagcgagc gagcgcgcag 300
agagggagtg gccaactcca tcactagggg ttcctgcggc cgcacgcgaa agcttcaaaa 360
tattagaatt cacgtttaca atttaaatat ttgcttcatg tcctgcaggc agctgcgcgc 420
tcgctcgctc actgaggccg cccgggcaaa gcccgggcgt cgggcgacct ttggtcgccc 480
ggcctcagtg agcgagcgag cgcgcagaga gggagtggcc aactccatca ctaggggttc 540
ctgcggccgc acgcgataca atccgcgccc tgtagcggcg cattaagcgc ggcgggtgtg 600
gtggttacgc gcagcgtgac cgctacactt gccagcgccc tagcgcccgc tcctttcgct 660
ttcttccctt cctttctcgc cacgttcgcc ggctttcccc gtcaagctct aaatcggggg 720
ctccctttag ggttccgatt tagtgcttta cggcacctcg accccaaaaa acttgatttg 780
ggtgatggtt cacgtagtgg gccatcgccc tgatagacgg tttttcgccc tttgacgttg 840
gagtccacgt tctttaatag tggactcttg ttccaaacaa cactatcgga aagaacatgt 900
gagcaaaagg ccagcaaaag gccaggaacc gtaaaaaggc cgcgttgctg gcgtttttcc 960
ataggctccg cccccctgac gagcatcaca aaaatcgacg ctcaagtcag aggtggcgaa 1020
acccgacagg actataaaga taccaggcgt ttccccctgg aagctccctc gtgcgctctc 1080
ctgttccgac cctgccgctt accggatacc tgtccgcctt tctcccttcg ggaagcgtgg 1140
cgctttctca tagctcacgc tgtaggtatc tcagttcggt gtaggtcgtt cgctccaagc 1200
tgggctgtgt gcacgaaccc cccgttcagc ccgaccgctg cgccttatcc ggtaactatc 1260
gtcttgagtc caacccggta agacacgact tatcgccact ggcagcagcc actggtaaca 1320
ggattagcag agcgaggtat gtaggcggtg ctacagagtt cttgaagtgg tggcctaact 1380

```
acggctacac tagaagaaca gtatttggta tctgcgctct gctgaagcca gttaccttcg   1440

gaaaaagagt tggtagctct tgatccggca aacaaaccac cgctggtagc ggtggttttt   1500

ttgtttgcaa gcagcagatt acgcgcagaa aaaaaggatc tcaagaagat cctttgatct   1560

tttctacggg gtctgacgct cagtggaacg aaaactcacg ttaagggatt ttggtcatga   1620

gattatcaaa aaggatcttc acctagatcc ttttaaatta aaaatgaagt tttaaatcaa   1680

tctaaagtat atatgagtaa acttggtctg acagttacca atgcttaatc agtgaggcac   1740

ctatctcagc gatctgtcta tttcgttcat ccatagttgc ctgactcccc gtcgtgtaga   1800

taactacgat acgggagggc ttaccatctg gccccagtgc tgcaatgata ccgcgagacc   1860

cacgctcacc ggctccagat ttatcagcaa taaaccagcc agccggaagg gccgagcgca   1920

gaagtggtcc tgcaacttta tccgcctcca tccagtctat taattgttgc cgggaagcta   1980

gagtaagtag ttcgccagtt aatagtttgc gcaacgttgt tgccattgct acaggcatcg   2040

tggtgtcacg ctcgtcgttt ggtatggctt cattcagctc cggttcccaa cgatcaaggc   2100

gagttacatg atcccccatg ttgtgcaaaa aagcggttag ctccttcggt cctccgatcg   2160

ttgtcagaag taagttggcc gcagtgttat cactcatggt tatggcagca ctgcataatt   2220

ctcttactgt catgccatcc gtaagatgct tttctgtgac tggtgagtac tcaaccaagt   2280

cattctgaga atagtgtatg cggcgaccga gttgctcttg cccggcgtca atacgggata   2340

ataccgcgcc acatagcaga actttaaaag tgctcatcat tggaaaacgt tcttcggggc   2400

gaaaactctc aaggatctta ccgctgttga gatccagttc gatgtaaccc actcgtgcac   2460

ccaactgatc ttcagcatct tttactttca ccagcgtttc tgggtgagca aaaacaggaa   2520

ggcaaaatgc cgcaaaaaag ggaataaggg cgacacggaa atgttgaata ctcatactct   2580

tcctttttca atattattga agcatttatc agggttattg tctcatgagc ggatacatat   2640

ttgaatgtat ttagaaaaat aaacaaatag gggttccgcg cacatttccc cgaaaagtgc   2700

cacctgacgt c                                                        2711
```

<210> SEQ ID NO 129
<211> LENGTH: 4694
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
ccaatgattg ggccatcgcc ctgatagacg gtttttcgcc ctttgacgtt ggctttaata     60

gtggactctt gttccaaact ggaacaacac tcaaccctat ctcgggctat tcttttgatt    120

tataagggat tttgccgatt tcggcctatt ggttaaaaaa tgagctgatt taacaaaaat    180

ttaacgcgac atgtcctgca ggcagctgcg cgctcgctcg ctcactgagg ccgcccgggc    240

aaagcccggg cgtcgggcga cctttggtcg cccggcctca gtgagcgagc gagcgcgcag    300

agagggagtg gccaactcca tcactagggg ttcctgcggc cgcacgcgaa agcttcaaaa    360

tattagaatt cacgtttaca atttgataat acgactcact atagggggat ccacgtatgt    420

cgaggtaggc gtgtacggtg ggaggcctat ataagcagag ctcgtttagt gaaccgtcag    480

atcgcctgga ggtaccgcca ccatggtgag caagggcgag gaggataaca tggccatcat    540

caaggagttc atgcgcttca aggtgcacat ggagggctcc gtgaacggcc acgagttcga    600

gatcgagggc gagggcgagg gccgccccta cgagggcacc cagaccgcca agctgaaggt    660
```

gaccaagggt ggccccctgc ccttcgcctg ggacatcctg tcccctcagt tcatgtacgg 720
ctccaaggcc tacgtgaagc accccgccga catccccgac tacttgaagc tgtccttccc 780
cgagggcttc aagtgggagc gcgtgatgaa cttcgaggac ggcggcgtgg tgaccgtgac 840
ccaggactcc tccctgcagg acggcgagtt catctacaag gtgaagctgc gcggcaccaa 900
cttcccctcc gacggccccg taatgcagaa gaagaccatg ggctgggagg cctcctccga 960
gcggatgtac cccgaggacg gcgccctgaa gggcgagatc aagcagaggc tgaagctgaa 1020
ggacggcggc cactacgacg ctgaggtcaa gaccacctac aaggccaaga agcccgtgca 1080
gctgcccggc gcctacaacg tcaacatcaa gttggacatc acctcccaca acgaggacta 1140
caccatcgtg gaacagtacg aacgcgccga gggccgccac tccaccggcg gcatggacga 1200
gctgtacaag taagaattcg atatcaagct tatcgataat caacctctgg attacaaaat 1260
ttgtgaaaga ttgactggta ttcttaacta tgttgctcct tttacgctat gtggatacgc 1320
tgctttaatg cctttgtatc atgctattgc ttcccgtatg gctttcattt tctcctcctt 1380
gtataaatcc tggttgctgt ctctttatga ggagttgtgg cccgttgtca ggcaacgtgg 1440
cgtggtgtgc actgtgtttg ctgacgcaac ccccactggt tggggcattg ccaccacctg 1500
tcagctcctt tccgggactt tcgctttccc cctccctatt gccacggcgg aactcatcgc 1560
cgcctgcctt gcccgctgct ggacaggggc tcggctgttg ggcactgaca attccgtggt 1620
gttgtcgggg aaatcatcgt cctttccttg gctgctcgcc tatgttgcca cctggattct 1680
gcgcgggacg tccttctgct acgtcccttc ggccctcaat ccagcggacc ttccttcccg 1740
cggcctgctg ccggctctgc ggcctcttcc gcgtcttcgc cttcgccctc agacgagtcg 1800
gatctccctt tgggccgcct ccccgcatcg ataccgagcg ctgctcgaga gatctacggg 1860
tggcatccct gtgacccctc cccagtgcct ctcctggccc tggaagttgc cactccagtg 1920
cccaccagcc ttgtcctaat aaaattaagt tgcatcattt tgtctgacta ggtgtccttc 1980
tataatatta tggggtggag gggggtggta tggagcaagg ggcaagttgg gaagacaacc 2040
tgtagggcct gcggggtcta ttgggaacca agctggagtg cagtggcaca atcttggctc 2100
actgcaatct ccgcctcctg ggttcaagcg attctcctgc ctcagcctcc cgagttgttg 2160
ggattccagg catgcatgac caggctcagc taatttttgt ttttttggta gagacggggt 2220
ttcaccatat tggccaggct ggtctccaac tcctaatctc aggtgatcta cccaccttgg 2280
cctcccaaat tgctgggatt acaggcgtga accactgctc ccttccctgt ccttctgatt 2340
ttgtaggtaa ccacgtgcgg accgagcaaa tatttgcttc atgtcctgca ggcagctgcg 2400
cgctcgctcg ctcactgagg ccgcccgggc aaagcccggg cgtcgggcga cctttggtcg 2460
cccggcctca gtgagcgagc gagcgcgcag agagggagtg gccaactcca tcactagggg 2520
ttcctgcggc cgcacgcgat acaatccgcg ccctgtagcg gcgcattaag cgcggcgggt 2580
gtggtggtta cgcgcagcgt gaccgctaca cttgccagcg ccctagcgcc cgctcctttc 2640
gctttcttcc cttcctttct cgccacgttc gccggctttc cccgtcaagc tctaaatcgg 2700
gggctccctt tagggttccg atttagtgct ttacggcacc tcgaccccaa aaaacttgat 2760
ttgggtgatg gttcacgtag tgggccatcg ccctgataga cggtttttcg ccctttgacg 2820
ttggagtcca cgttctttaa tagtggactc ttgttccaaa caacactatc ggaaagaaca 2880
tgtgagcaaa aggccagcaa aaggccagga accgtaaaaa ggccgcgttg ctggcgtttt 2940
tccataggct ccgcccccct gacgagcatc acaaaaatcg acgctcaagt cagaggtggc 3000
gaaacccgac aggactataa agataccagg cgtttccccc tggaagctcc ctcgtgcgct 3060
ctcctgttcc gaccctgccg cttaccggat acctgtccgc ctttctccct tcgggaagcg 3120
tggcgctttc tcatagctca cgctgtaggt atctcagttc ggtgtaggtc gttcgctcca 3180
agctgggctg tgtgcacgaa ccccccgttc agcccgaccg ctgcgcctta tccggtaact 3240
atcgtcttga gtccaacccg gtaagacacg acttatcgcc actggcagca gccactggta 3300
acaggattag cagagcgagg tatgtaggcg gtgctacaga gttcttgaag tggtggccta 3360
actacggcta cactagaaga acagtatttg gtatctgcgc tctgctgaag ccagttacct 3420
tcggaaaaag agttggtagc tcttgatccg gcaaacaaac caccgctggt agcggtggtt 3480
tttttgtttg caagcagcag attacgcgca gaaaaaaagg atctcaagaa gatcctttga 3540
tcttttctac ggggtctgac gctcagtgga acgaaaactc acgttaaggg attttggtca 3600
tgagattatc aaaaaggatc ttcacctaga tccttttaaa ttaaaaatga agttttaaat 3660
caatctaaag tatatatgag taaacttggt ctgacagtta ccaatgctta atcagtgagg 3720
cacctatctc agcgatctgt ctatttcgtt catccatagt tgcctgactc cccgtcgtgt 3780
agataactac gatacgggag ggcttaccat ctggccccag tgctgcaatg ataccgcgag 3840
acccacgctc accggctcca gatttatcag caataaacca gccagccgga agggccgagc 3900
gcagaagtgg tcctgcaact ttatccgcct ccatccagtc tattaattgt tgccgggaag 3960
ctagagtaag tagttcgcca gttaatagtt tgcgcaacgt tgttgccatt gctacaggca 4020
tcgtggtgtc acgctcgtcg tttggtatgg cttcattcag ctccggttcc caacgatcaa 4080
ggcgagttac atgatccccc atgttgtgca aaaaagcggt tagctccttc ggtcctccga 4140
tcgttgtcag aagtaagttg gccgcagtgt tatcactcat ggttatggca gcactgcata 4200
attctcttac tgtcatgcca tccgtaagat gcttttctgt gactggtgag tactcaacca 4260
agtcattctg agaatagtgt atgcggcgac cgagttgctc ttgcccggcg tcaatacggg 4320
ataataccgc gccacatagc agaactttaa aagtgctcat cattggaaaa cgttcttcgg 4380
ggcgaaaact ctcaaggatc ttaccgctgt tgagatccag ttcgatgtaa cccactcgtg 4440
cacccaactg atcttcagca tcttttactt tcaccagcgt ttctgggtga gcaaaaacag 4500
gaaggcaaaa tgccgcaaaa aagggaataa gggcgacacg gaaatgttga atactcatac 4560
tcttcctttt tcaatattat tgaagcattt atcagggtta ttgtctcatg agcggataca 4620
tatttgaatg tatttagaaa aataaacaaa taggggttcc gcgcacattt ccccgaaaag 4680
tgccacctga cgtc 4694

<210> SEQ ID NO 130
<211> LENGTH: 101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130
cactcaaccc tatctcgggc tattcttttg atttataagg gattttgccg atttcggcct 60
attggttaaa aaatgagctg atttaacaaa aatttaacgc g 101

<210> SEQ ID NO 131
<211> LENGTH: 90
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 131
cgcgccctgt agcggcgcat taagcgcggc gggtgtggtg gttacgcgca gcgtgaccgc     60
tacacttgcc agcgccctag cgcccgctcc                                      90

<210> SEQ ID NO 132
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tgggccatcg ccctgataga cggtttttcg ccctttgacg ttggctttaa tagtggactc     60
ttgttccaaa ctggaacaa                                                  79

<210> SEQ ID NO 133
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgggccatcg ccctgataga cggtttttcg ccctttgacg ttggagtcca cgttctttaa     60
tagtggactc ttgttccaaa caacact                                         87

<210> SEQ ID NO 134
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc t                                              141

<210> SEQ ID NO 135
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tgggccatcg ccctgataga cggtttttcg ccctttgacg ttggctttaa tagtggactc     60
ttgttccaaa ctggaacaa                                                  79

<210> SEQ ID NO 136
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tgggccatcg ccctgataga cggtttttcg ccctttgacg ttggagtcca cgttctttaa 60
tagtggactc ttgttccaaa caacact 87

<210> SEQ ID NO 137
<211> LENGTH: 214
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (32)..(51)
<223> OTHER INFORMATION: a, c, t, g, unknown or other
<220> FEATURE:
<221> NAME/KEY: modified_base
<222> LOCATION: (142)..(156)
<223> OTHER INFORMATION: a, c, t, g, unknown or other

<400> SEQUENCE: 137
aatagtggac tcttgttcca aactggaaca annnnnnnnn nnnnnnnnnn ncgcgccctg 60
tagcggcgca ttaagcgcgg cgggtgtggt ggttacgcgc agcgtgaccg ctacacttgc 120
cagcgcccta gcgcccgctc cnnnnnnnnn nnnnnntggg ccatcgccct gatagacggt 180
ttttcgccct ttgacgttgg agtccacgtt cttt 214

<210> SEQ ID NO 138
<211> LENGTH: 147
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 138
ttagtggtac ctttctattc tcactctatg tgcatgccgt gctttaccac cgatcatcag 60
atggcgcgca aatgcgatga ttgctgcggc ggcaaaggcc gcggcaaatg ctatggcccg 120
cagtgcctgt gccgctcggc cgaaact 147

<210> SEQ ID NO 139
<211> LENGTH: 156
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
tctcactctc atcatcacca ccaccatggt ggaggtatgt gcatgccgtg ctttaccacc 60
gatcatcaga tggcgcgcaa atgcgatgat tgctgcggcg gcaaaggccg cggcaaatgc 120
tatggcccgc agtgcctgtg ccgctcggcc gaaact 156

```
<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Lys Ala Ser
1
```

M13 PHAGE BASED GENE THERAPY PLATFORM

CROSS-REFERENCE TO RELATED APPLICATIONS

This application claims priority to U.S. Provisional Application No. 63/185,076, filed May 6, 2021 and U.S. Provisional Application No. 63/252,451, filed Oct. 5, 2021, the entire contents of which are incorporated herein by reference.

STATEMENT REGARDING FEDERALLY SPONSORED RESEARCH OR DEVELOPMENT

This invention was made with Government support under Grant No. HR0011-15-C-0084 awarded by the Defense Advanced Research Projects Agency (DARPA). The Government has certain rights in the invention.

SEQUENCE LISTING

The instant application contains a Sequence Listing which has been submitted electronically in ASCII format and is hereby incorporated by reference in its entirety. Said ASCII copy, created on Jun. 30, 2022, is named 038436-0189_SL.txt and is 91,969 bytes in size.

SUMMARY

This Summary introduces a selection of embodiments in simplified form that are described further below in the Detailed Description. This Summary neither identifies key or essential features, nor limits the scope, of the claimed subject matter.

M13 bacteriophage, a naturally monodisperse multifunctional nanostructure, consists of thousands of distinct protein subunits organized in a filamentous viral capsid; 900 nm in length and 6 nm in diameter. All M13 capsids are amenable to mutation and can be tuned for the binding and nucleation of inorganics and nanoparticles, and for the expression of ligands, functional moieties, and even enzymes. These capabilities for medical imaging and therapy have been harnessed by (i) tailoring the assembly of M13 into ultra-short, 'inho', phage derived particles, (ii) developing a chlorotoxin (CTX) motif on the M13 p3 capsid to enable phage particle crossing of the blood-brain-barrier and homing to glioblastoma cancer cells, and (iii) building 'inho' phage derived transgene cassettes for phage gene delivery in mammalian cells. Tight control over the genetic sequence provided by 'inho' phagemids allow production of phage particles ranging in length from 25 nm to over 2500 nm, as dictated by the length of the packaged DNA. This length control over the phage filament is used to demonstrate the impact of the particle length on the morphology of phage templated metal nanofoams and on the in-vitro and in-vivo tissue trafficking of targeted phage nanocarrriers. An optimal length for enhancing ion transport and active material access in MnOx cathodes is described. Chlorotoxin-phages, conjugate with indocyanine green dye (ICG), are visualized in-vivo in the second window near infrared (SWIR) and home effectively to mouse brain tumor. Ultra-short, 50 nm chlorotoxin-phage particles are shown to vastly improve this localization specificity. Additionally, the 'inho' phagemid system is engineered to produce ITR-flanked transgene cassettes. Such reporter genes packaged within targeted, cationically modified, 'inho' phages are able to transduce liver and brain cancer cells. The closed-ended, single-stranded 'inho' phage-derived cassettes have capacity up to 20 kilobases and can be delivered within phage particles as well as non-viral delivery vehicles. Ultimately, therapy or imaging agent carrying, miniaturized, chlorotoxin-targeted, M13 phage is considered here as a complete nanotheranostic platform that could augment the therapeutic efficacy of combination drugs shuttled to the site of glioma. The described multimodal, nanoplatform is re-designable for applications in nanomaterials, diagnostics, and across disease types.

The following Detailed Description references the accompanying drawings which form a part this application, and which show, by way of illustration, specific example implementations. Other implementations may be made without departing from the scope of the disclosure.

BRIEF DESCRIPTION OF THE FIGURES

FIG. 3A shows size control of phage length and cssDNA, including picturing the inho phage aerogel and nickel nanofoam. FIG. 3B shows targeted phage delivery of materials to mouse GBM22 glioma xenograft, trafficking profile modulated by size of phage nanocarrier. FIG. 3C shows the Inho cssDNA transgene design and surface manipulation of phage particles for cell transduction.

FIG. 9A-9B show embodiments of Inho construct sequence elements. FIG. 9A depicts f1-ori, f1-term, and packaging signal sequences of inho constructs (nick sites ^ designed). FIG. 9A discloses SEQ ID NOS 135, 131, and 136, respectively, in order of appearance. FIG. 9B shows an expected sequence of final cssDNA produced by inho construct. FIG. 9B discloses SEQ ID NO: 137.

FIG. 14A provides a TBE-PAGE gel of the inho 285, 311, 344, 475, 1310, and 1960 constructs, stained with SYBR-Gold. Inho cssDNA run higher than the reference ruler (designed for dsDNA).

MES running buffer. FIG. 15A Gel proteins are transferred for anti-p3 western blotting. FIG. 15A Alexa488 emission from fluorophor labeled p8.

FIG. 17A-17C provide histogram distributions of phage sizes. AFM imaging of FIG. 17A inho285, FIG. 17B, inho475, and FIG. 17C inho1960 were analyzed for phage length with about 90% of all measured lengths falling within 10 nm of the predicted base size bin (50 nm, 100 nm, and 280 nm respectively).

FIG. 18A-18H provide atomic force microscopy images of new small phages. FIG. 18A: inho285, 50 nm; FIG. 18B: inho475, 100 nm; FIG. 18C: inho1960, 280 nm; FIG. 18D: inho3000, 430 nm; FIG. 18E: inho3504, 550 nm; FIG. 18F: inho4888, 750 nm; FIG. 18G: M13KE, 900 nm, and FIG. 18H: K48A, 1400m, (200 nm scale). AFM cross-sectional height was ~5 nm for phages.

FIG. 21A-21B describe the surface binding and uptake dynamic of short chlorotoxin targeted phage doses. Flow cytometry sorting of CTX-phage-Alex647 positive GBM22 cells post serum free incubation. FIG. 21A: 2.7 pg per cell doses of 100 nm, 300 nm, 900 nm phage variants or with FIG. 21B: 1e6 phage particles per cell of 100 nm and 900 nm phage variants. Series shown over 2, 4, or 6 hours, all phage samples conjugate with Alexa dye prior to incubation (n=3 per group).

FIG. 22A-22B depict a synthesis process for producing bio-templated Ni nanofoam material. FIG. 22A schematically shows phage in solution that is crosslinked and sensitized by palladium solution prior to electroless nickel deposition. FIG. 22B shows that the thickness of the nickel layer is determined by exposure time to the electroless deposition solution.

FIG. 24A) Schematic showing gel formation determined by concentration dependent uniform crosslinking or aggregation and separation. FIG. 24 B) Effective volume occupied by a phage particle. FIG. 24 C) Critical concentration model where N defines the degree of phage overlap (i.e. measured from SEM, the average width of gel strut given in phage diameters is approx. 4 to 8).

FIG. 26A shows C/20 discharge curves for the Ni—$MnO_x$ cathodes half cells cycled between 2.0V and 4.5V using a BioLogic tester. FIG. 26B shows Ragone plots for cathodes measuring specific capacities of the cathode variants at varying rates.

FIG. 27A) Battery testing schematic and nominal capacity defined. FIG. 27B) Discharge capacity averages for varying length phage cathodes as measured from 4.4V to 2V at varying rates (n=3 per group).

FIG. 28A-28C relate to P3 expression of chlorotoxin. Peptide. FIG. 28A provides a schematic of CTX-phage. FIG. 28B shows flow cytometry percent GBM22 cell uptake of Alexa647 conjugate CTX-phage and WT-phage. FIG. 28C depicts nuclear (DAPI/blue) and golgi (anti-golgin-97 detected using Alexa488/green secondary) immunofluorescent staining of GBM22 cells incubated with Alexa555/red conjugate CTX-phage and WT-phage for 4 hours (5 μm).

FIG. 29A provides a cranial imaging schematic. Intracranial fluorescent imaging of 29B) BL6 tumor (GL261) breaing mouse 29C) NCR-NU tumor (U87) bearing mice injected with 1e13 pft CTX-phage Alexa555 or WT-phage-Alexa555.

FIG. 30A discloses SEQ ID NOS 135, 131, and 136, respectively, in order of appearance.

µm scale) and immunofluorescent imaging (50 µm scale) of 33C) brain and 33D) liver slices of mice dosed with 900 nm CTX-phage-ICG 24 hrs prior (nuclear DAPI/cyan staining and anti-p8 antibody stained with Alexa647/magenta secondary).

Figures 34A, 34B:
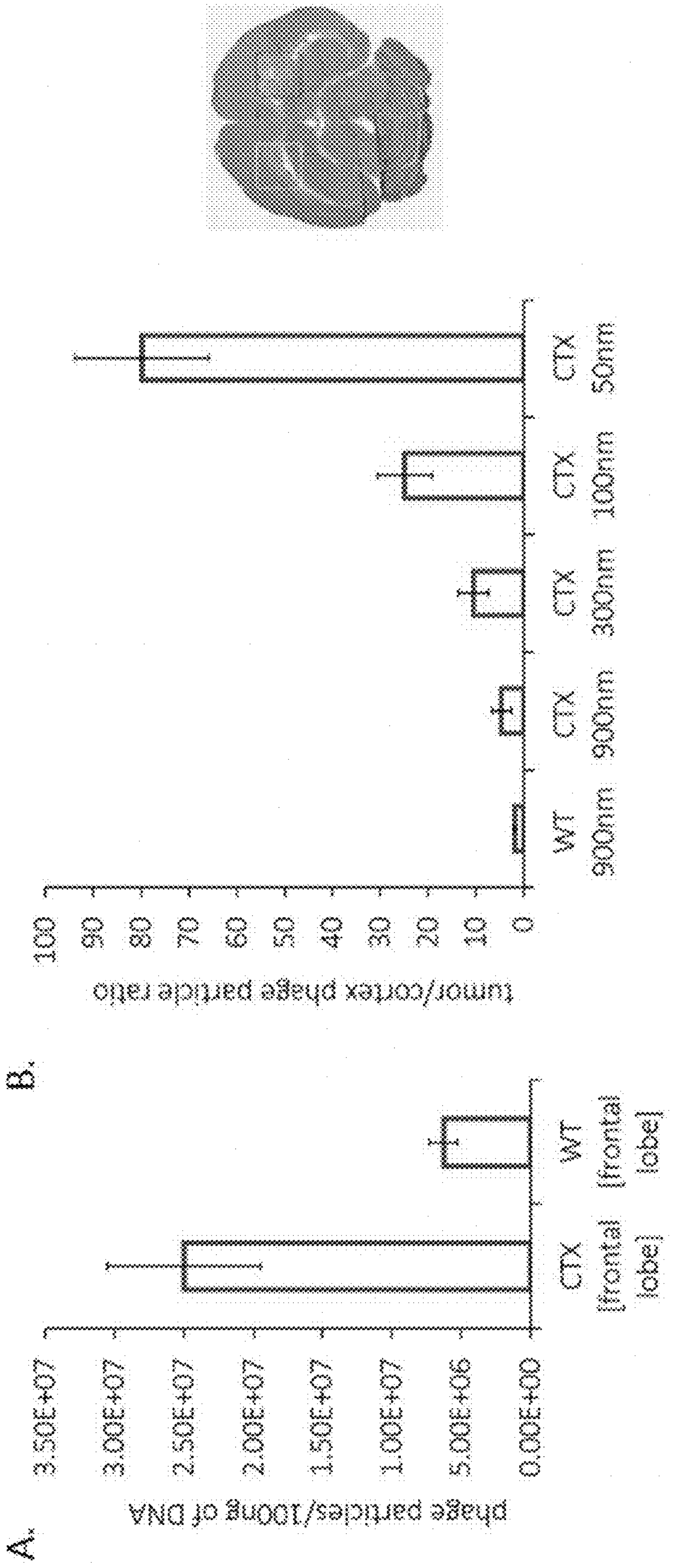

FIG. 34A-34B depict specificity of tumor accumulation of chlorotoxin-phages. 34A) Wildtype and CTX phage quantification in brain tissue in healthy NCR-NU mice (n=3) 24 hrs post tail vein administration of 2e12 phage per mouse. Greater localization observed by the CTX-phage (t(18)=−14.19, p<1.6e−11, one-tail). 34B) Ratios of phage qPCR count in tumorous brain section (representative red box) over left frontal cortex sectioning (representative white box) from GBM22 tumor bearing NCR-NU mice (n=4), (f(1)=201, p<7.6e−16, ANOVA).

Figures 35A, 35B, 35C:
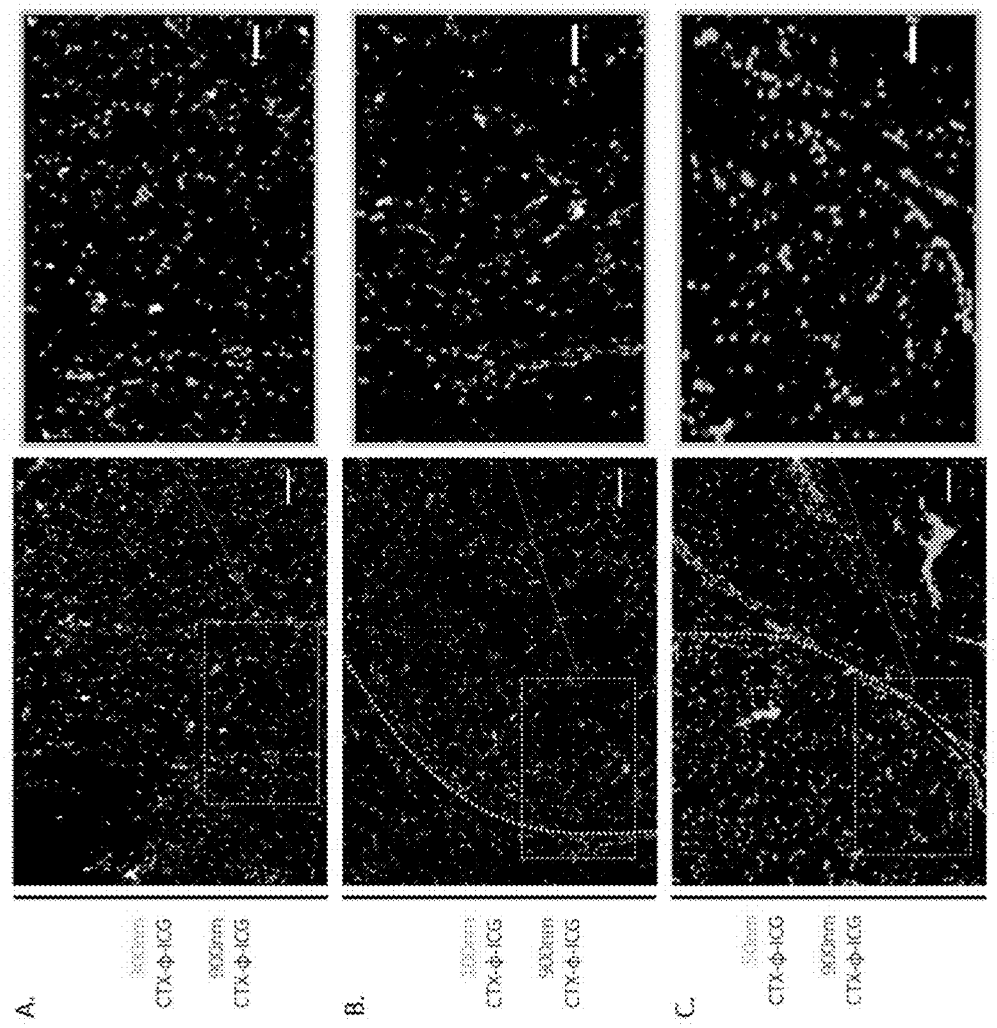

FIG. 35A-35C show tumor accumulation of phage particles by size. Phage size mixtures of 35A) 1e12 units 300 nm CTX-phage-Alexa555 with 1e12 units 900 nm CTX-phage-Alexa647, 35B) 1e12 units 100 nm CTX-phage-Alexa555 with 1e12 units 900 nm CTX-phage-Alexa647, and 35C) 1e12 units 50 nm CTX-phage-Alexa555 with 1e12 units 900 nm CTX-phage-Alexa647, were dosed to mice bearing GBM22 tumor. 48 hrs histology brain sections show nuclear DAPI staining (cyan) and the Alexa555 (yellow) and Alexa647 (magenta) dye bearing phages (100 µm, 50 µm scales). Tumor region delineated by white dashed border.

FIG. 36A-36C show tumor accumulation of control wildtype phage. 36A) 2e13 particles of ICG loaded wildtype phage injected in tumor bearing mice is tracked for tumor localization signal over 72 hrs. 36B) Extraction of brain 24 hrs post dosing of mice with ICG-loaded wildtype phages reveal limited tumor signal in the SWIR. Typical distribution of phage is observed for clearance by the spleen, liver, kidneys, and lung macrophages. 36C) Mouse with no phage or ICG exposure is imaged, showing low intensity skin/bone autofluorescence for comparison at the 808 nm (5V) excitation and 1150 nm long pass filter setting used throughout experimentation.

Figure 37:

FIG. 37 depicts the M13 phage p3 capsid modified with chlorotoxin and chlorotoxin his tag sequence at the N-terminus. FIG. 37 discloses SEQ ID NOS 138, 1, and 139, respectively, in order of appearance.

Figure 38:
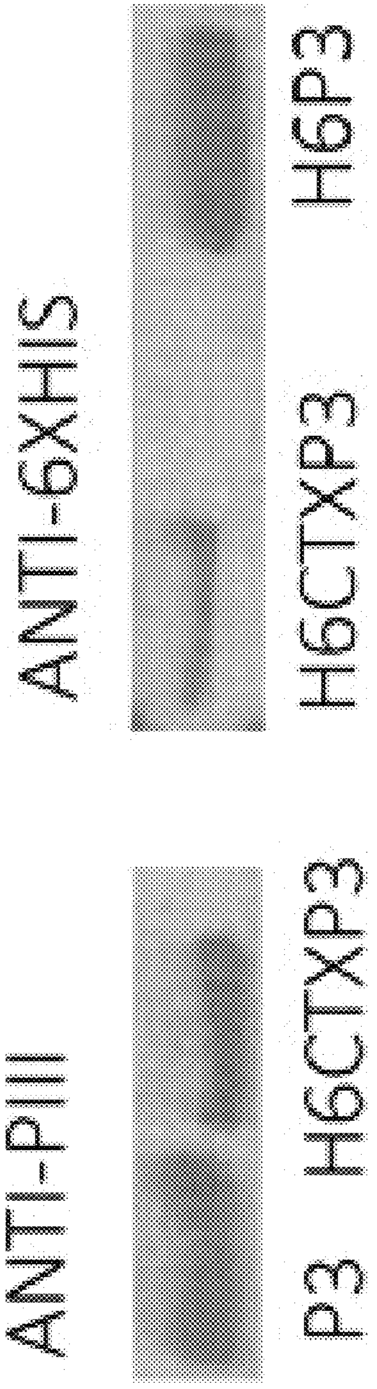

FIG. 38 shows phage variant with CTX expression with His6 tag (SEQ ID NO: 1). Anti-p3 and anti-his6 western blots of H6CTX phage show labeling of p3 c-terminal end and n-terminal HIS6 (SEQ ID NO: 1). Full CTX sequence present on phage products.

Figure 39:
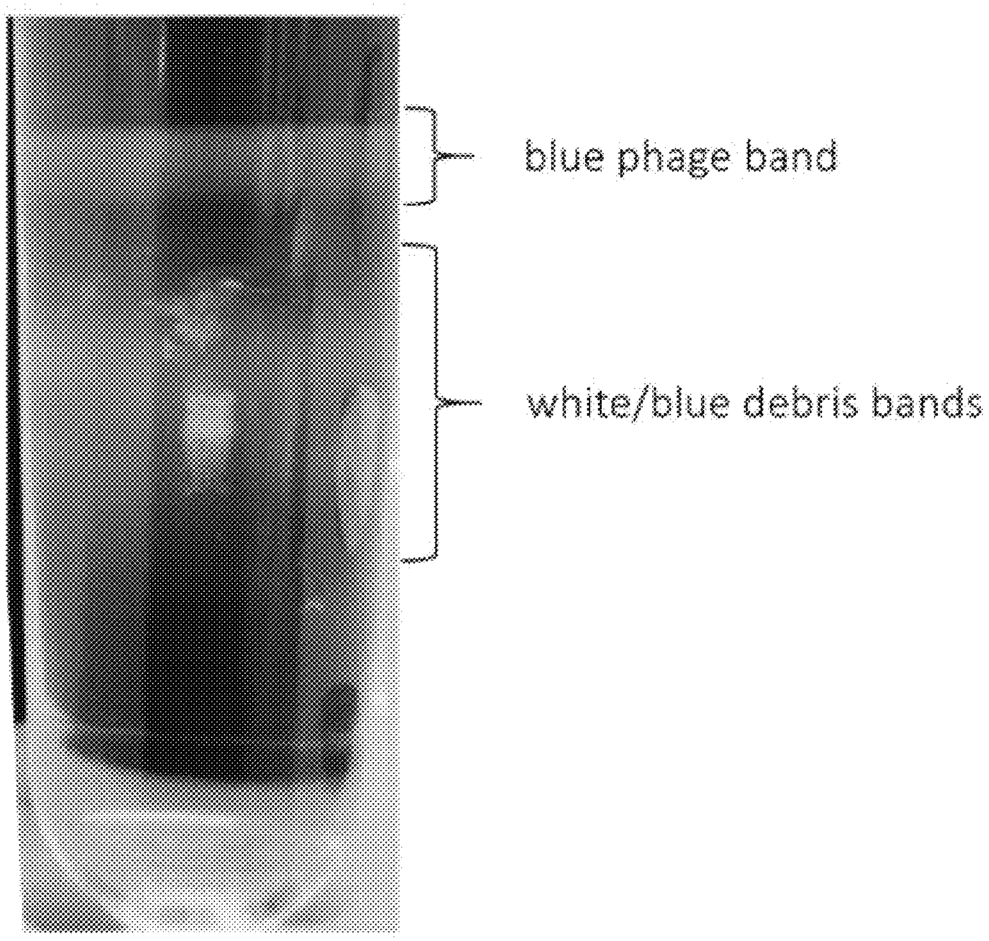

FIG. 39 shows phage ultracentrifugation. Phage run in CsCl density gradient setup from 1.6 g/mL to 1.2 g/mL (tubes for SW32 ultracentrifugation at 30,000 rmp, 4° C. for 4 hours). Blue-ish band above the 1.3 g/mL density line is collected and further processed. White, gray, and blue bands below the 1.3 g/mL density cut-off are discarded (bacterial and DNA debris).

Figure 40A:
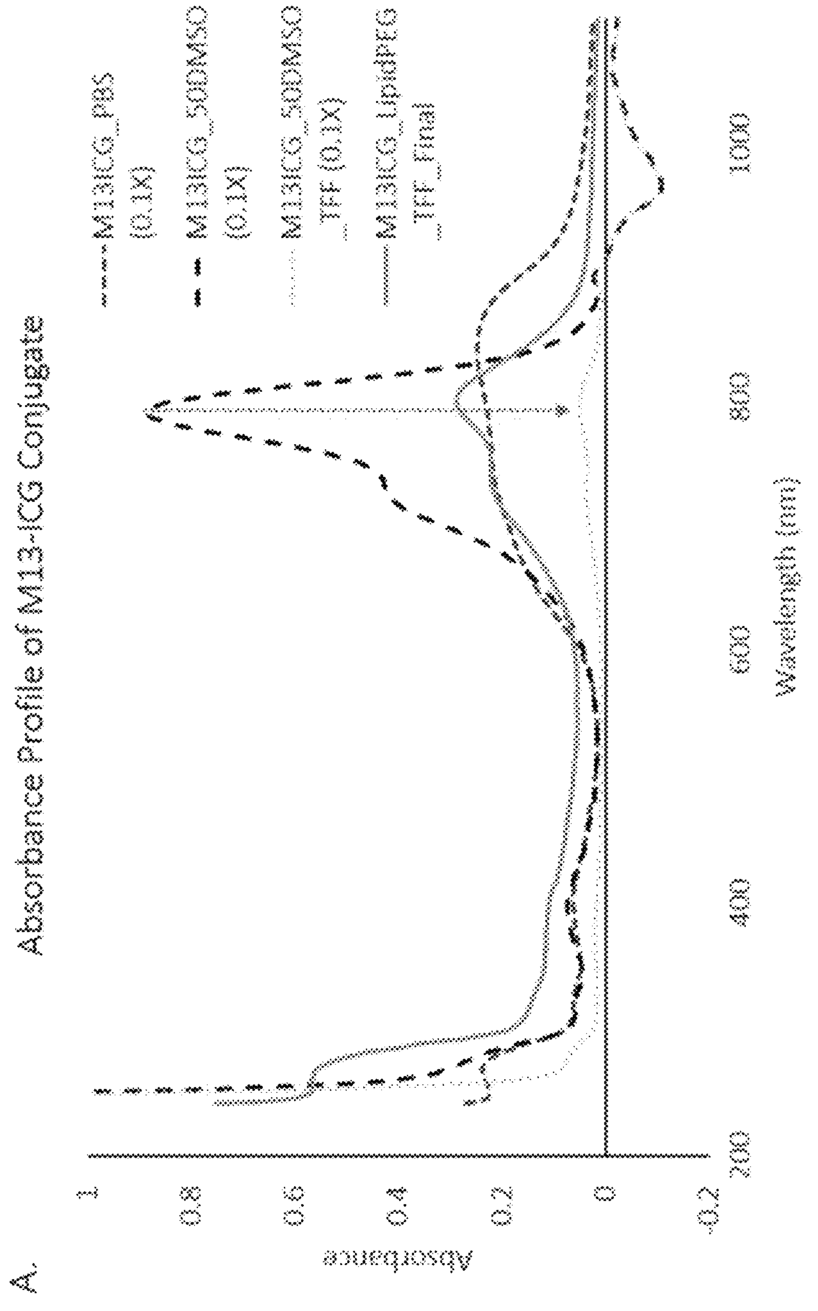
Figure 40B:
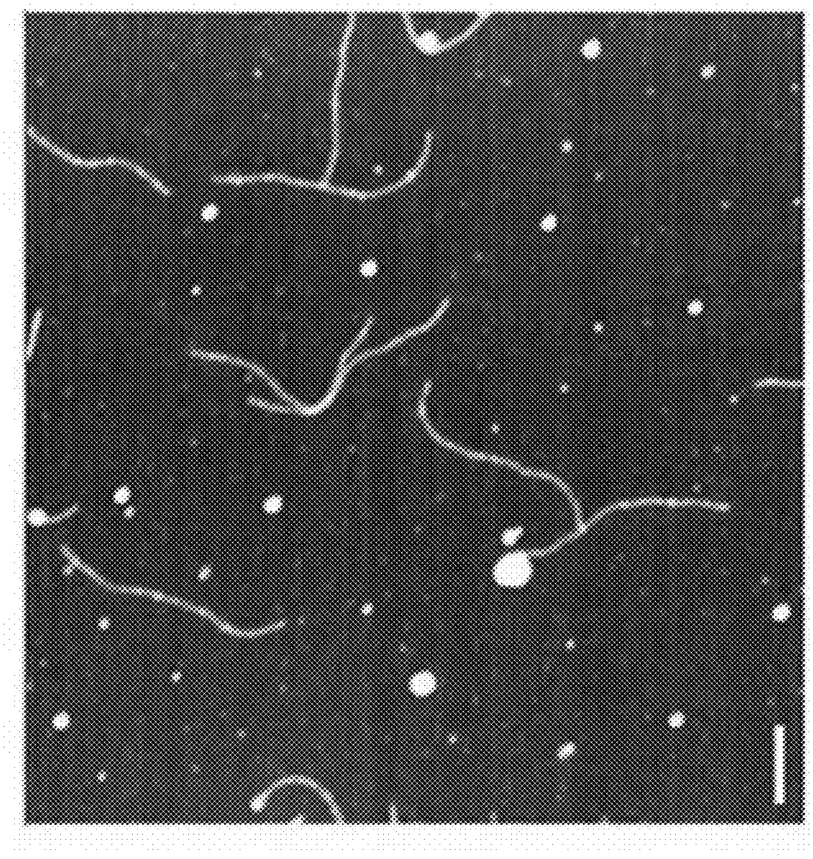

FIG. 40A-40B depict ICG phage conjugate cleaning from free dye aggregates. A) Reaction sample absorbance profile in PBS is flat and indicative of aggregation. Dilution to 50% DMSO results in dispersion of IGC aggregates and restoration of the ICG absorbance peak near 800 nm. TFF filtration of ICG-phage conjugates result in peak drop (green arrow) as excess dye is removed. 50% DMSO is diluted with 200 mMK DSPE-PEG-5K solution and filtered till excess DMSO is removed. Final sample peak absorbance is ~0.3. B) AFM profile of final ICG-phage conjugates suspended in bio-compatible 200 mM DSPE-PEG-5K solution.

Figure 41:
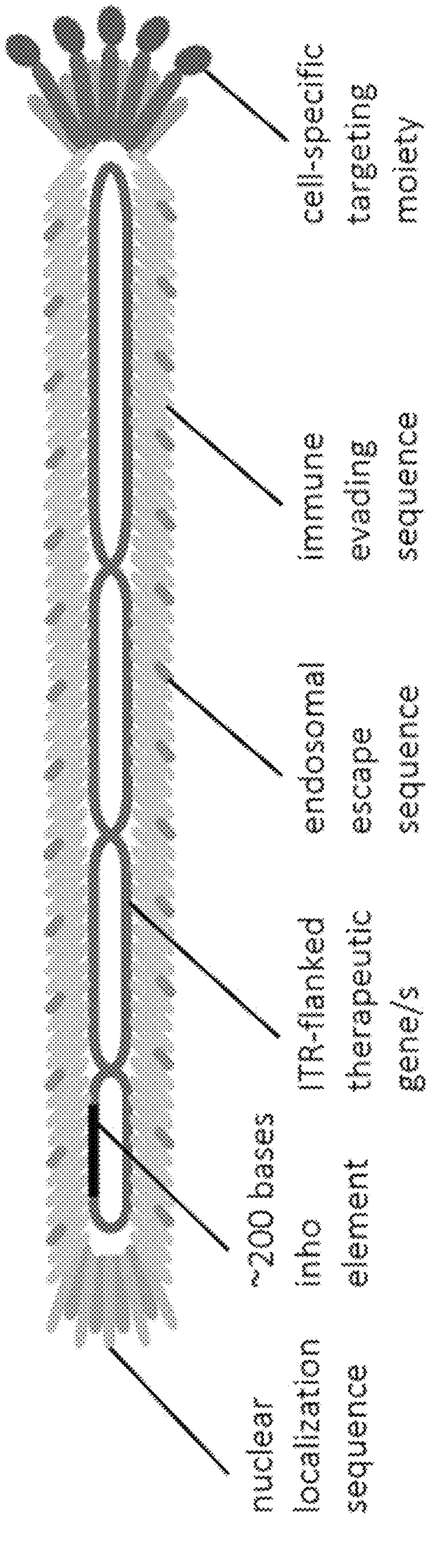

FIG. 41 shows an embodiment of an inho phage designed with a cell transduction type shell.

Figure 42:
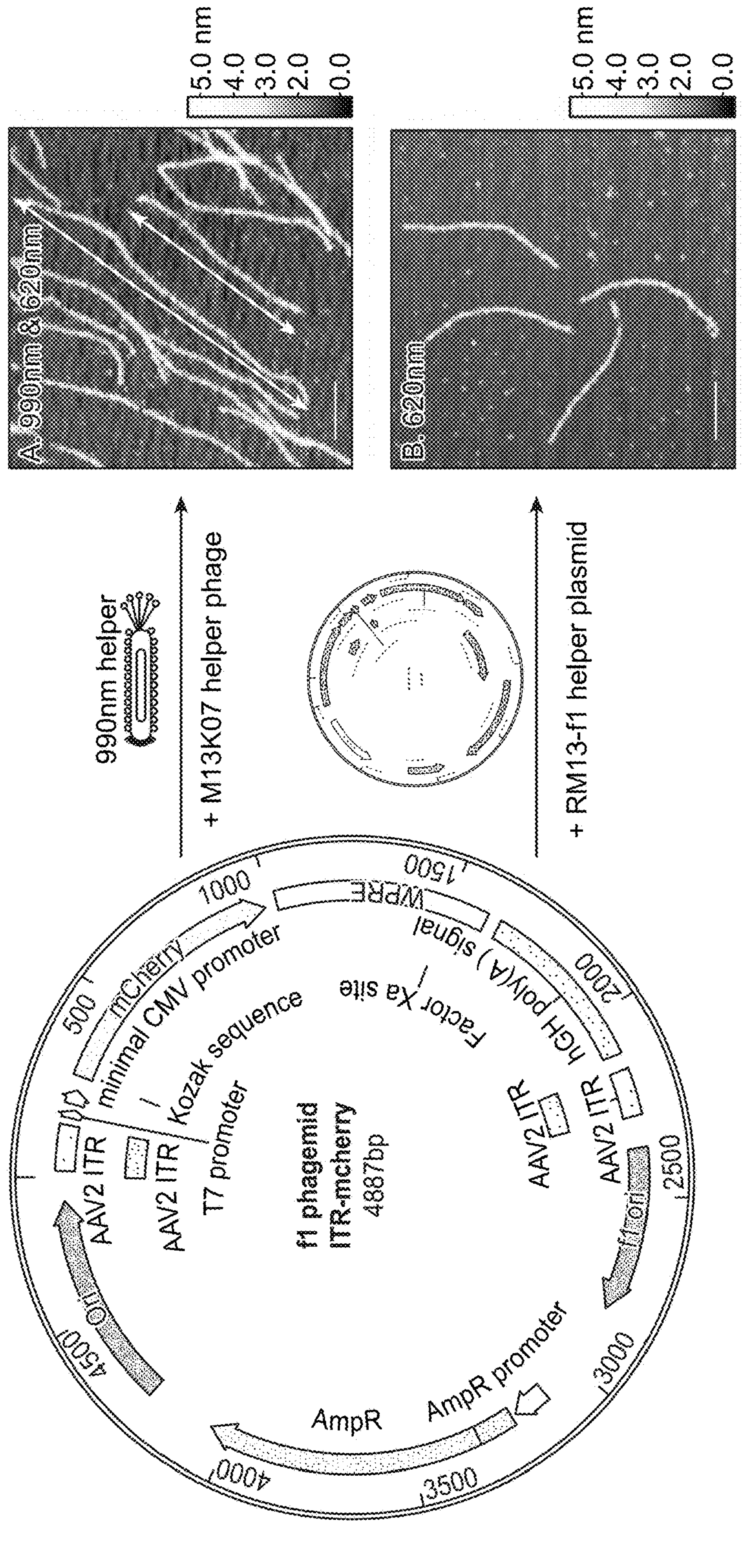

FIG. 42 shows helper packaging of target phagemid cassette. A) Helper (M13K07) phage phagemid packaging results in heterogenous distribution of phage products where 1 in every 9 particle is the original 990 nm helper phage. B) Helper plasmid RM13-f1 packaging of target phagemids result in clean homogenous batches of 620 nm phage particles with cssDNA ITRmCherry gene cassette of 4887 base length. (200 nm scale)

Figure 43:
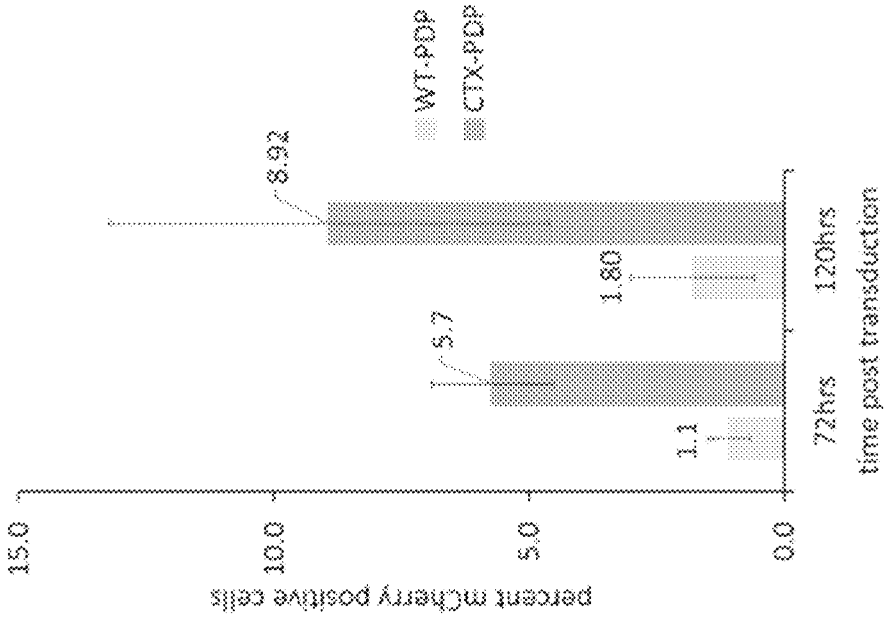

FIG. 43 describes the baseline transduction efficiency of a targeted PDP particle. ~620 nm phage particles with cssDNA carrying ITR flanked mCherry gene were incubated with GBM22 cells. CTX targeted phage show 5-fold improvement in transduction ability over wildtype phage at 72 hrs and 120 hrs post transduction protocol.

Figure 44A:
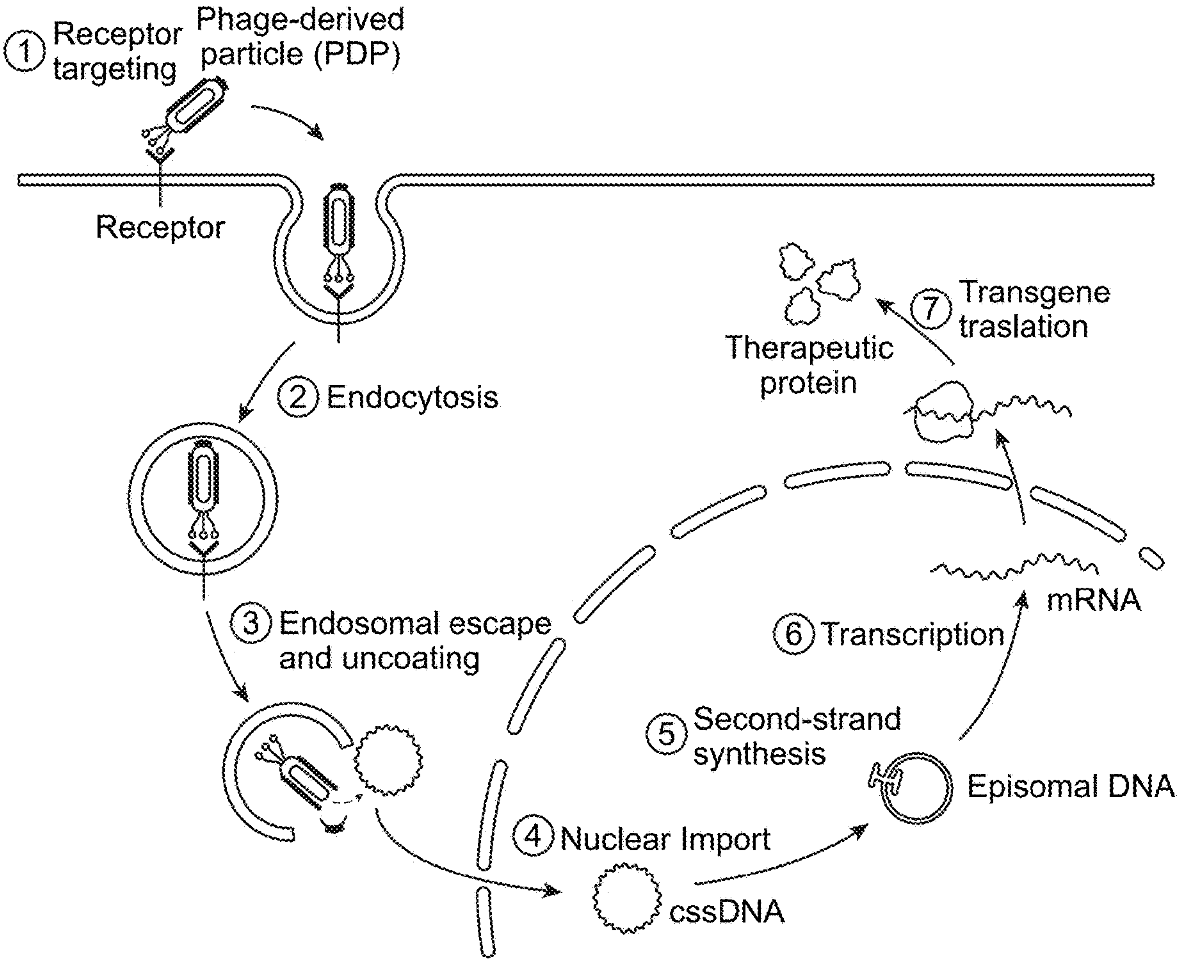
Figure 44B:
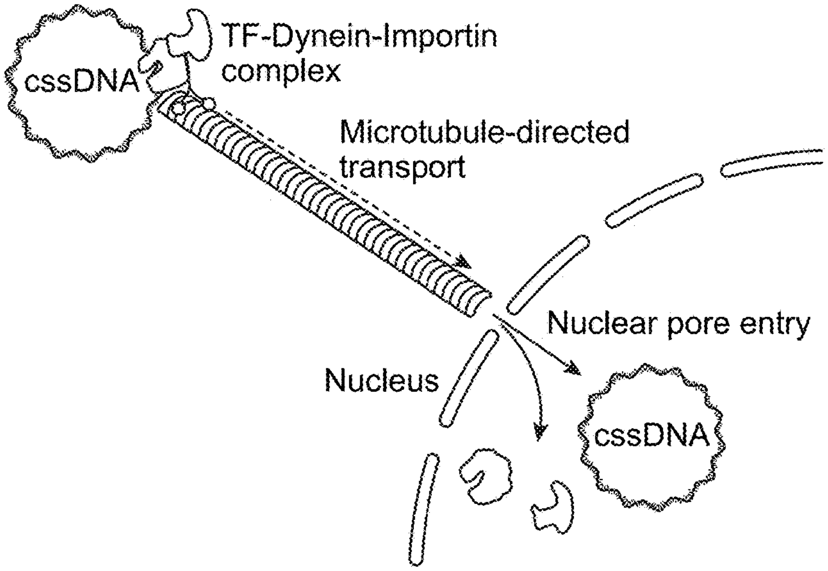

FIG. 44A-44B provide a schematic of the pathway to transgene expression with a phage particle. A) Steps from internalization to transgene translation. B) cssDNA nuclear import through transcription factor binding.

FIG. 45A-45D show transduction of cationic PDP complexes. AFM profile of A) CPTA conjugate ITRmCherry PDPs, B) DEAE.Dextran wrapped ITRmCherry PDPs, and C) PEI wrapped ITRmCherry PDPs. D) Transduction efficiencies of GBM22 cells with cationically modified PDPs (72 hrs post transduction protocol, 1e5 PDP/cell).

Figure 46:
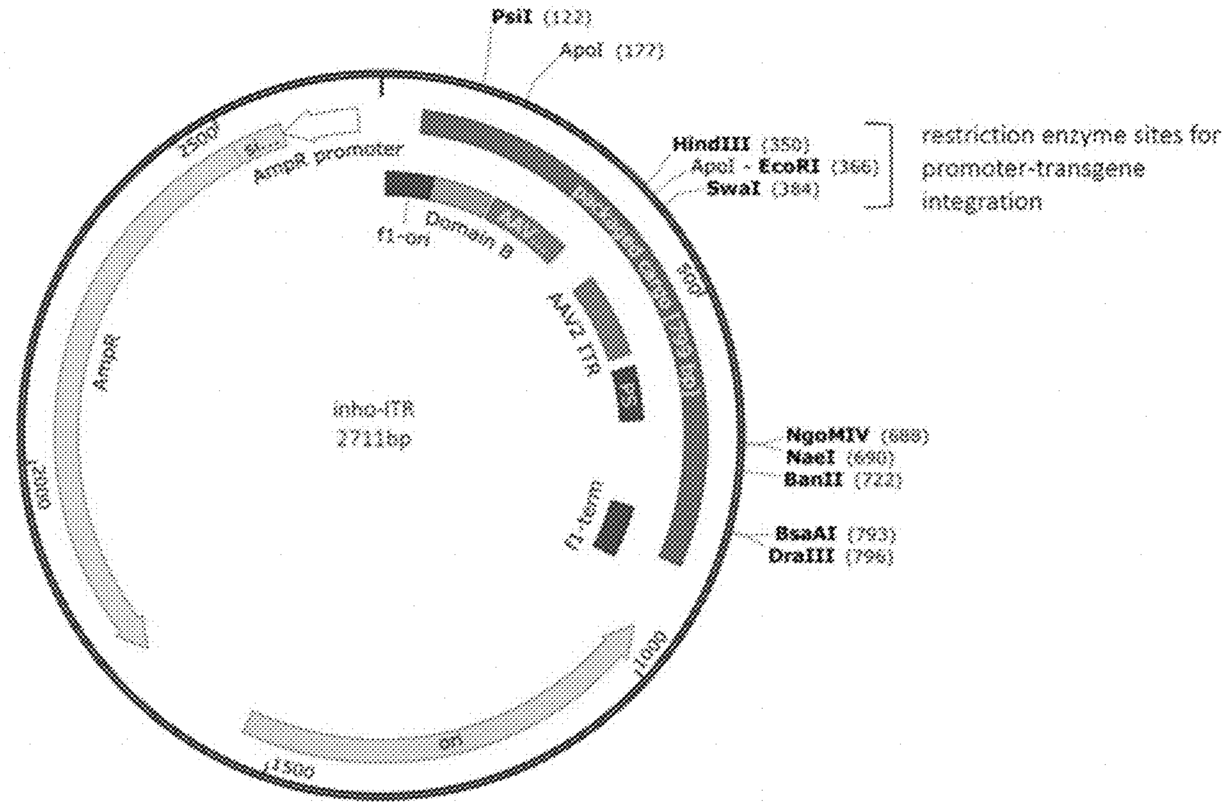

FIG. 46 shows one design of inho-ITR transgene construct. Inho type constructs with AAV flanked site for insertion of transgene of interest. Domain B and restriction length between PS and f1-term are included in design, but may be removed if desired. Expected sequence of final cssDNA product highlight in dark green.

Figure 47:
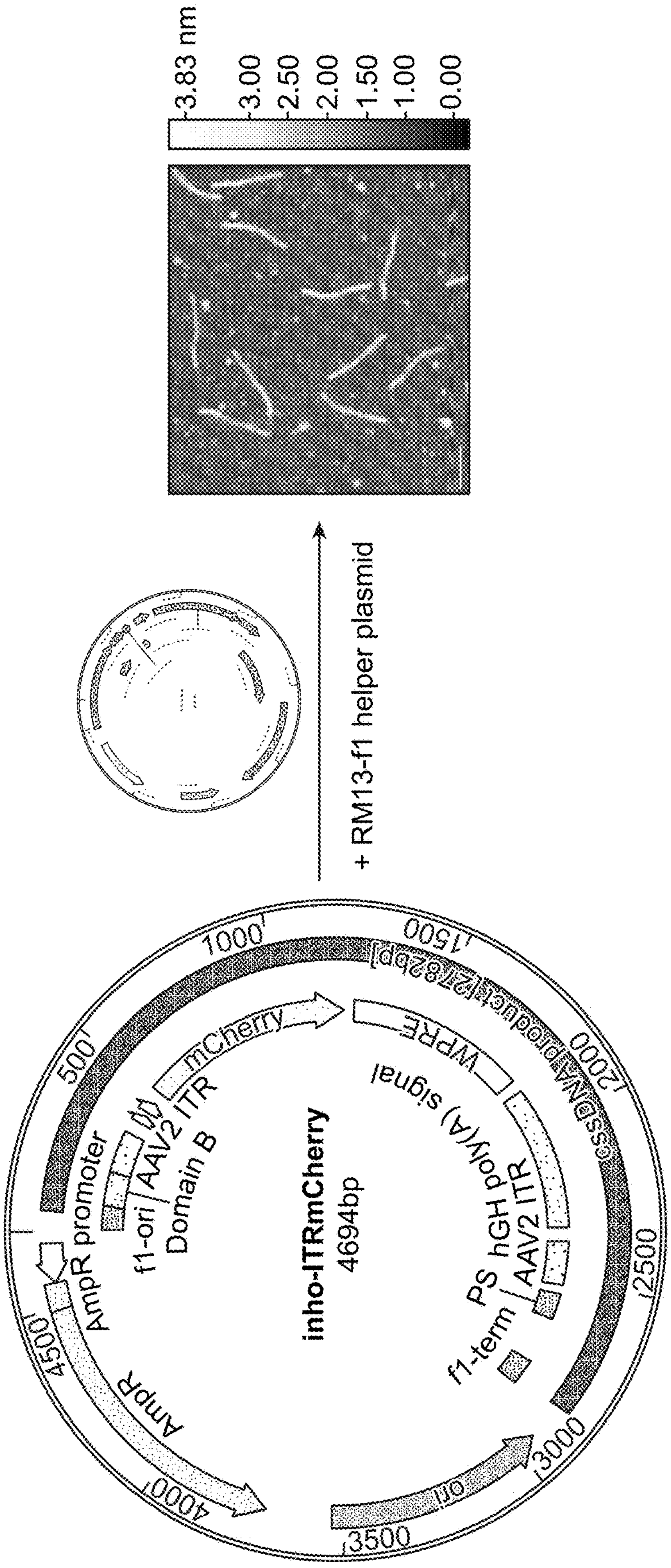

FIG. 47 shows one design of inho-ITRmCherry transgene construct. Inho type constructs with AAV flanked mCherry transgene. Final cssDNA product highlight in dark green of 2782 bases produced PDPs of 400 nm in length.

Figure 48A:
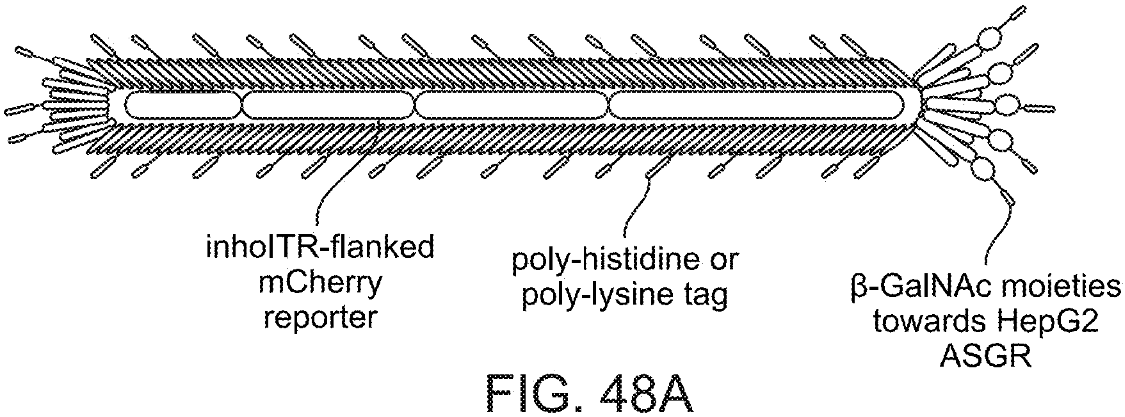
Figure 48B:
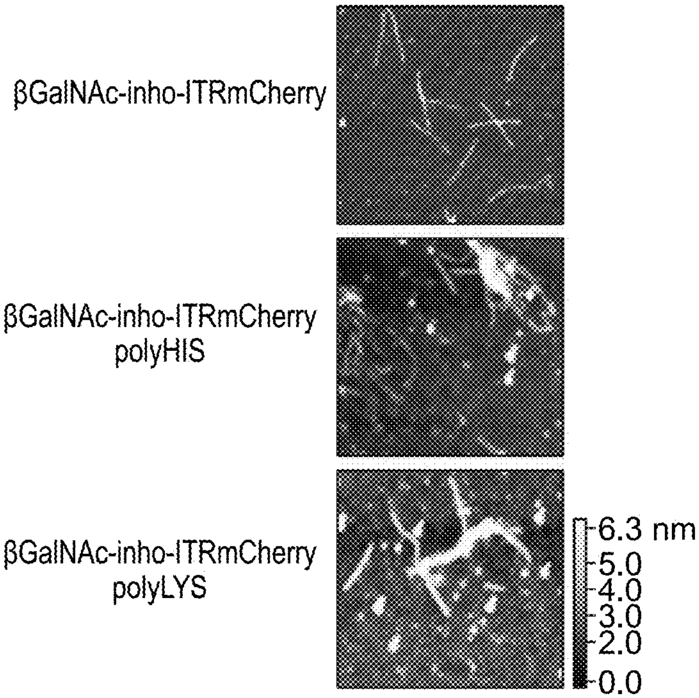
Figure 48C:
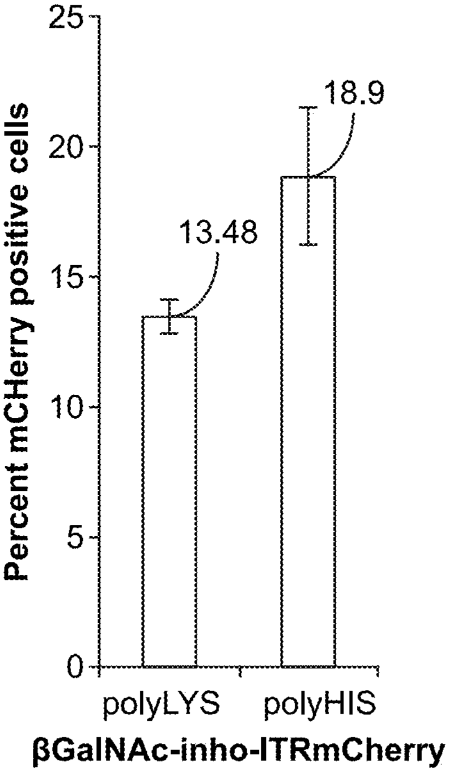

FIGS. 48A-C shows a design of an inho-ITRmCherry PDP with β-GalNAc and poly-histidine or poly-lysine moieties. A) Schematic of surface conjugate PDP model (inho-ITRmCherry of 2782 nts produced PDPs of 400 nm in length). B) Well dispersed inho phage sample profile post SMCC conjugation with β-GalNAc. The subsequent EDC chemistry with poly-histidine or poly-lysine results in minor clumping of phage samples (200 nm scale). C) HepG2 cell transduction efficiencies of targeted and cationic amino acid decorated phages (72 hrs).

Figure 49:
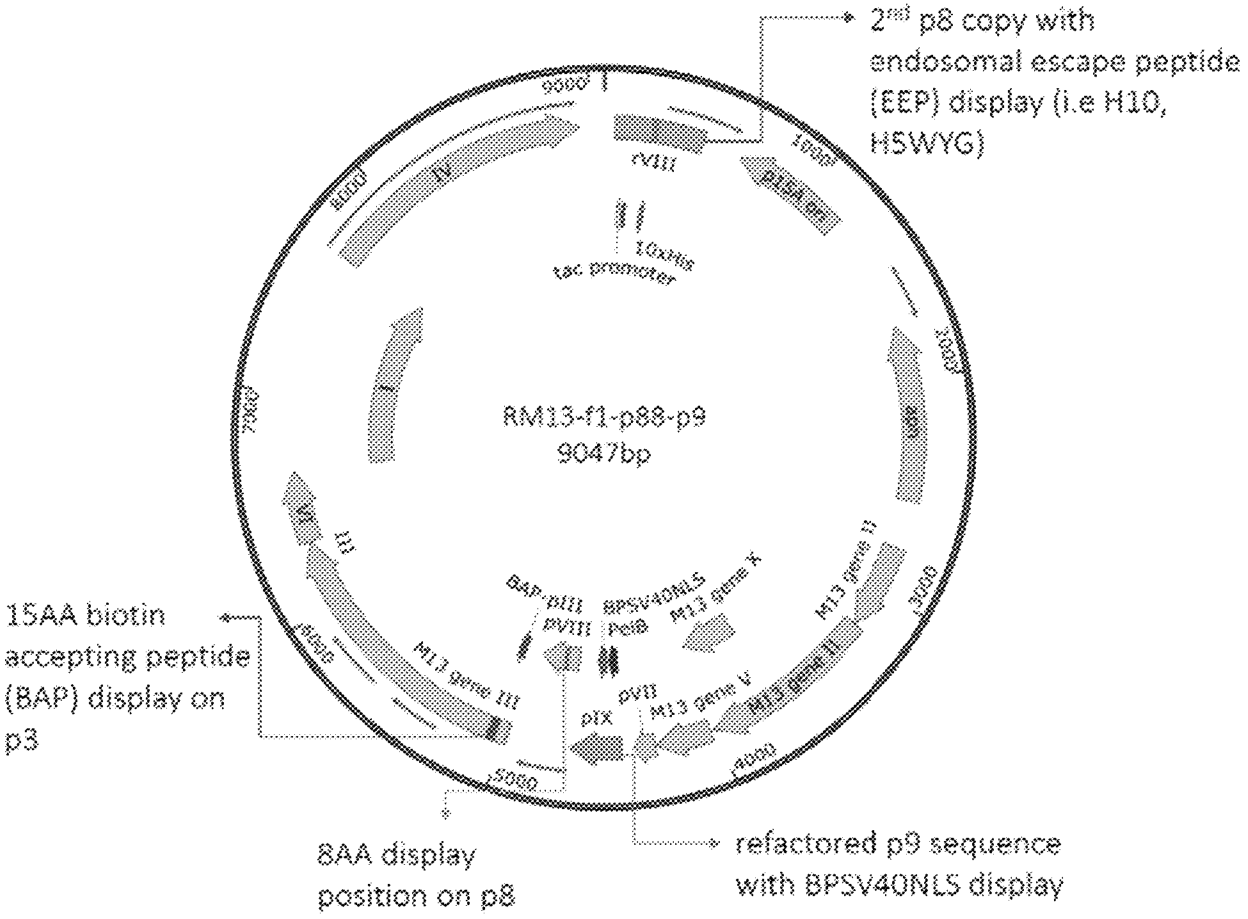

FIG. 49 shows a design of RM13-f1-p88-p9. Map of the main features of a p8, rp8, p9, p3 display capable RM13-f1 helper plasmid. Current version displays rp8-Hist10 tag, p9-SV40NLS, p3-BAP (biotin accepting peptide allows for quick biotinylation and streptavidin aided conjugation of moieties of interest such as mAb). Full sequence available in Appendix D. FIG. 49 discloses SEQ ID NO: 30.

Figure 50:
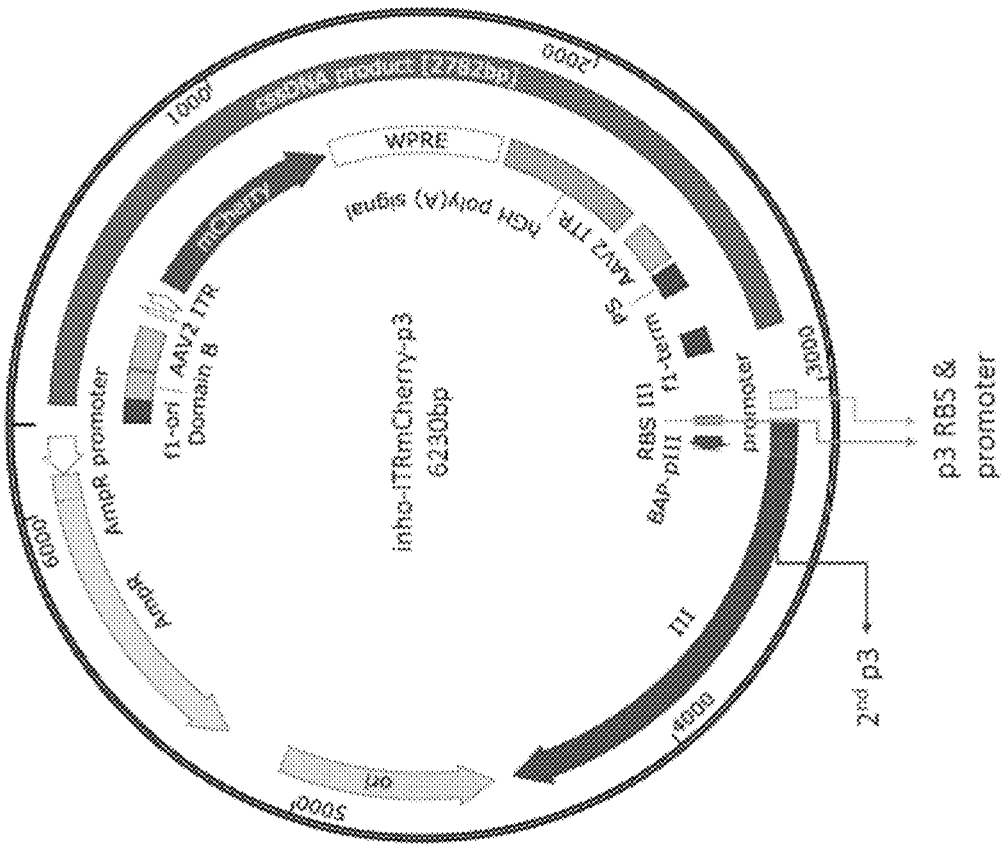

FIG. 50 depicts one embodiment of a map of inho-ITRmCherry-p3. The inho vector produce cssDNA of 2782 bases with mCherry reporter transgene for packaging as usual. Additionally, capsid genes, such as p3 is present, on the vector under appropriate promoter and accompanying RBS lengths. The inho based capsid production will complement the RM13-f1 type vector capsids and create a mosaic PDP structure depending on the choice of capsid variants.

Figure 51:
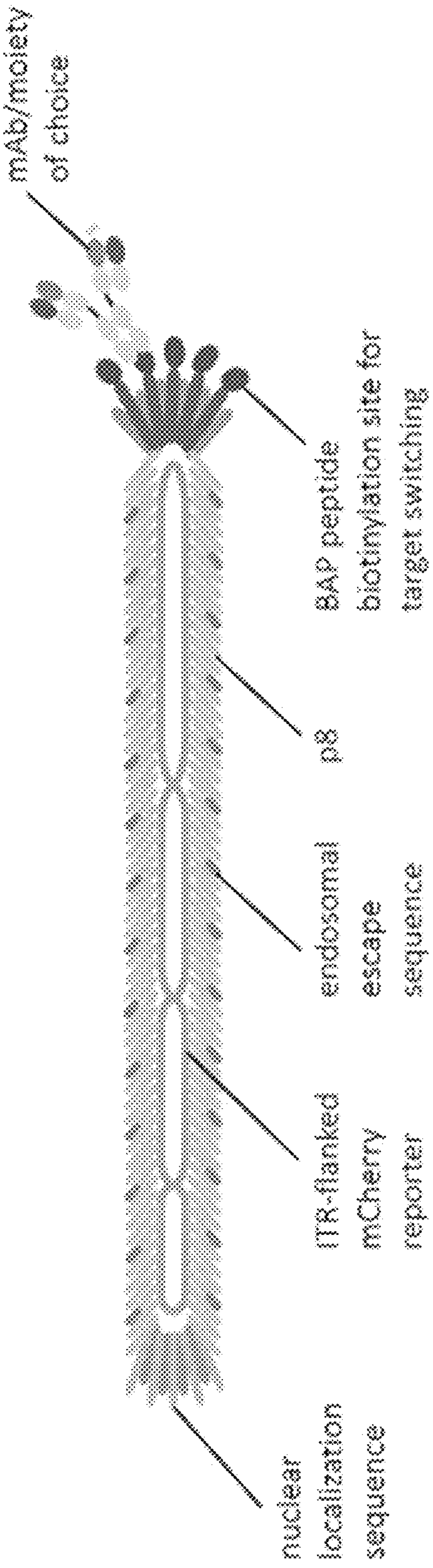

FIG. 51 depicts one embodiment of a rationally designed reporter gene expressing inho PDP. The RM13-f1-p88-p9 clone may be used with the inho-ITRmCherry vector to test sequences of interest on the p8 and p9 capsids. The p3-BAP design allows ease of target switching for transduction assays across cell lines.

Figure 52A:
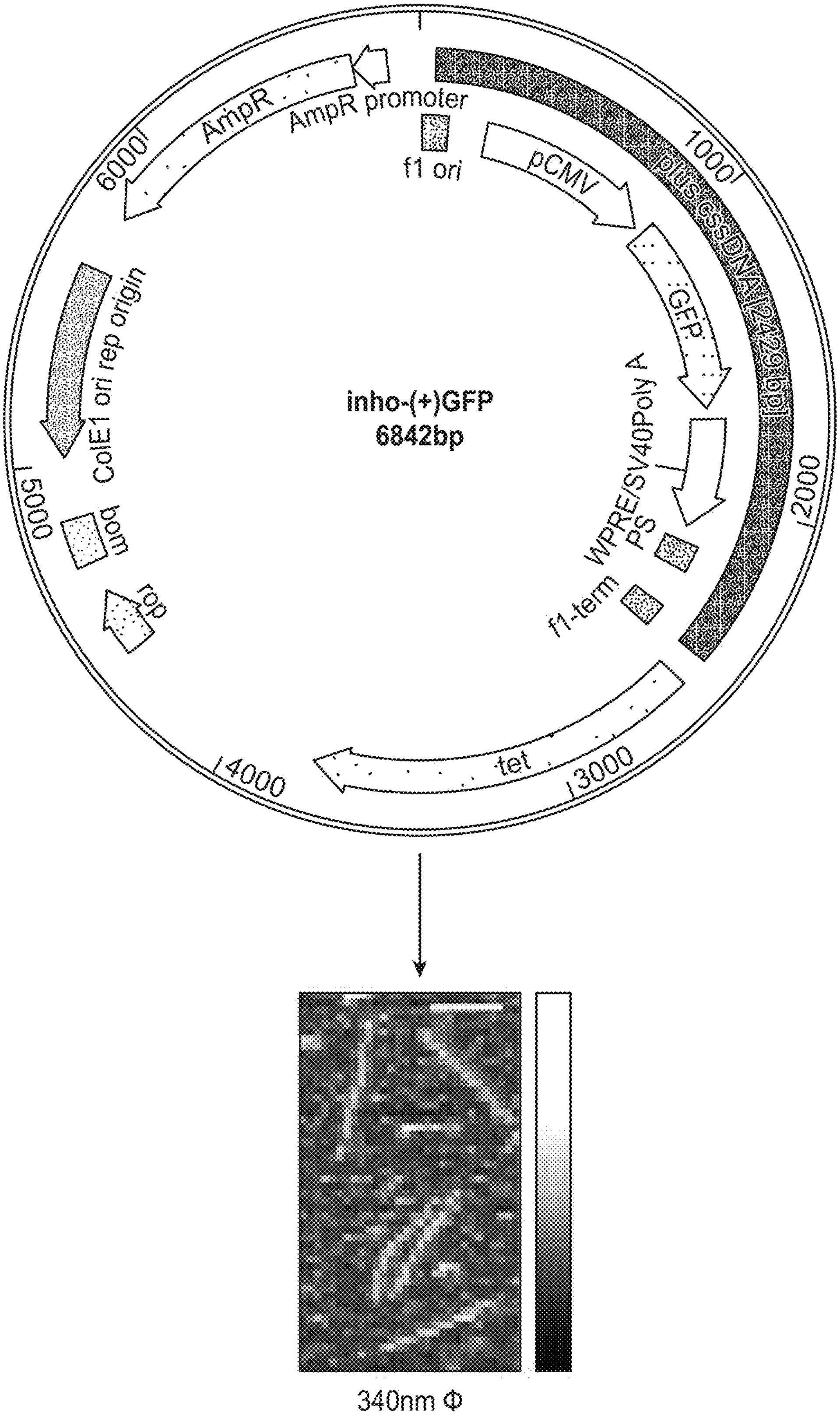
Figure 52B:
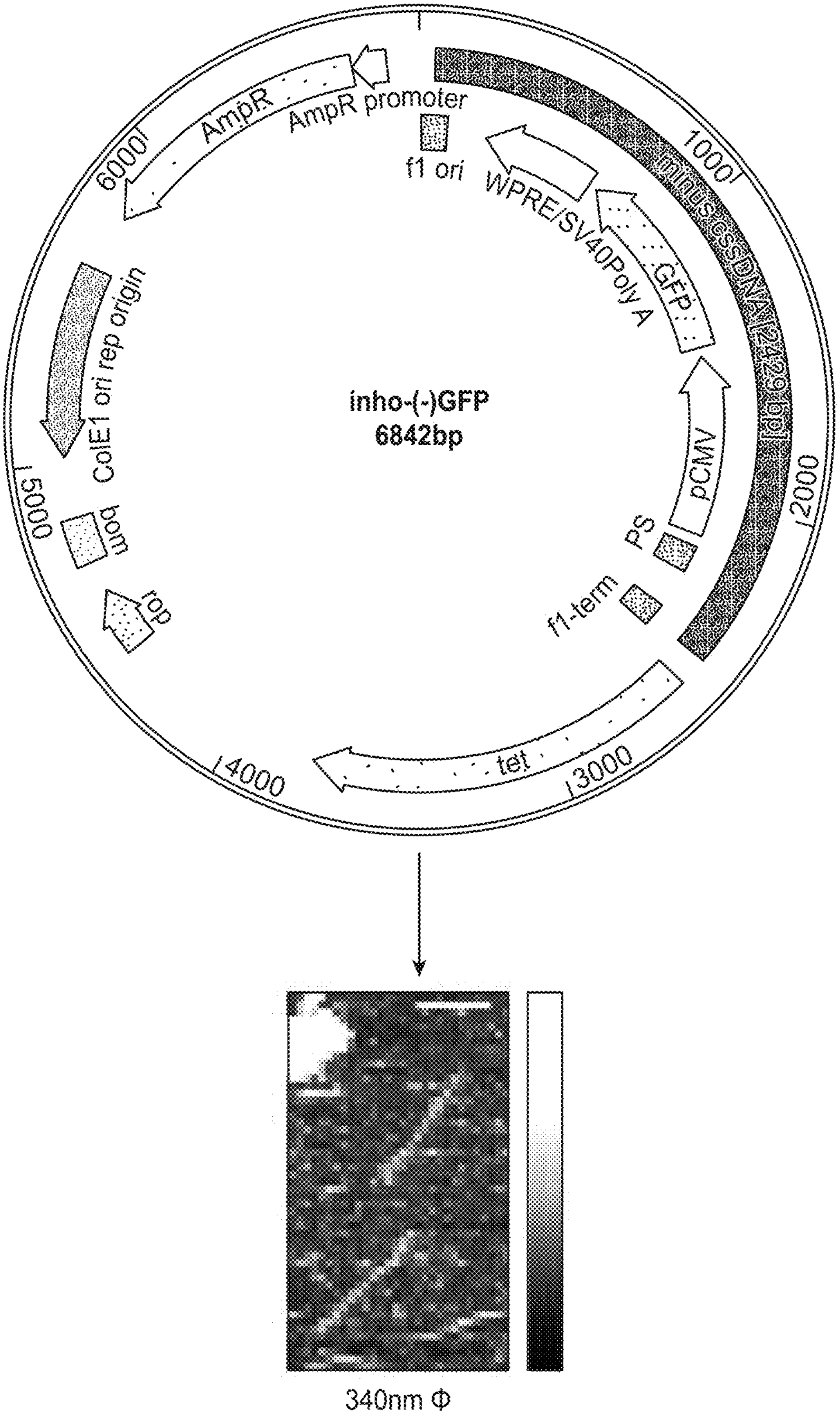
Figure 52C:
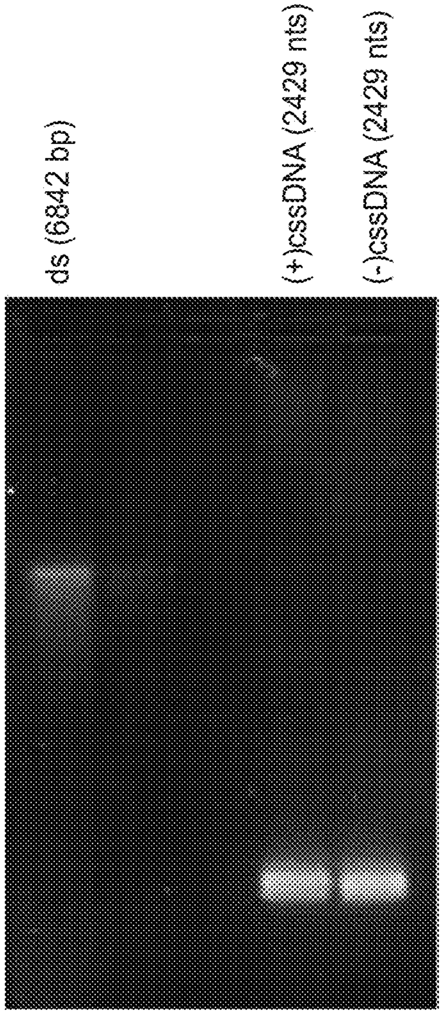

FIG. 52A-52C show production of inho-(+)GFP and inho-(−)GFP cssDNA. A) The plus sense GFP sequence is integrated to the inho phagemid design. B) The complementary minus sense GFP inho design. Both plus and minus inho designs were transformed with the RM13-f1 helper to produce identical 340 nm length phages (200 nm scale). C) Agarose gel run of (+) and (−) 2429 nucleotide cssDNAs extracted from 340 nm phages (SYBRgold DNA stain).

FIG. 53A-53B show transduction of GBM22 cells treated with phage extracted cssDNA. A) 72 hrs transduction efficiencies of inho(−)GFP-2429 nts cssDNA, inho(+)GFP-2429 nts cssDNA, ITRmCherry-4887 nts cssDNA, and their double stranded plasmid equivalents, inho(−)GFP-6842 bp, inho(+)GFP-6842 bp, ITRmCherry-4887 bp. B) 72 hrs transduction efficiencies of the single inho(+)GFP-2429 nts cssDNA, the plus and minus mix of the inhoGFP-2429 nts cssDNAs, pre-annealed plus and minus mix of the inhoGFP-2429 nts cssDNAs, and the double stranded plasmid inho (+)GFP-6842 bp. The number of complete cssDNA or ds strands are molar equivalents across comparable sample groups (n=3 per sample). Dual (+)/(−) samples are counted as ds samples.

Figure 54:
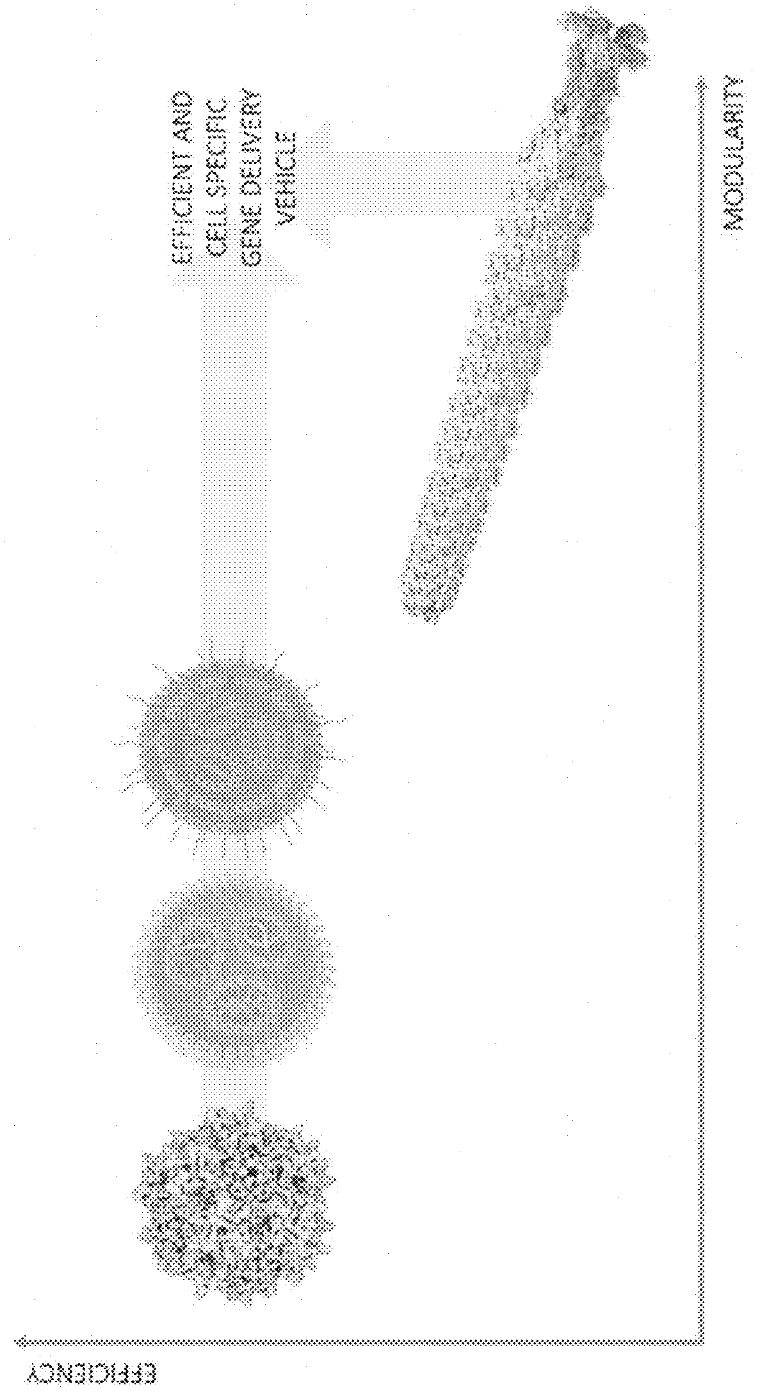

FIG. 54 depicts a hypothesis on the potential of modular in-vivo transduction platforms. Recombinant viral technologies are relying on discovery of less immunogenic and more selective variants. Lipid/synthetic delivery particles are adapting protein elements like fusogens and surface ligands to drive trafficking. The phage particles are at an optimal position of natural inactivity towards mammalian cells along with the natural evolutionary capability to embody complex biological mechanisms.

Figure 55:
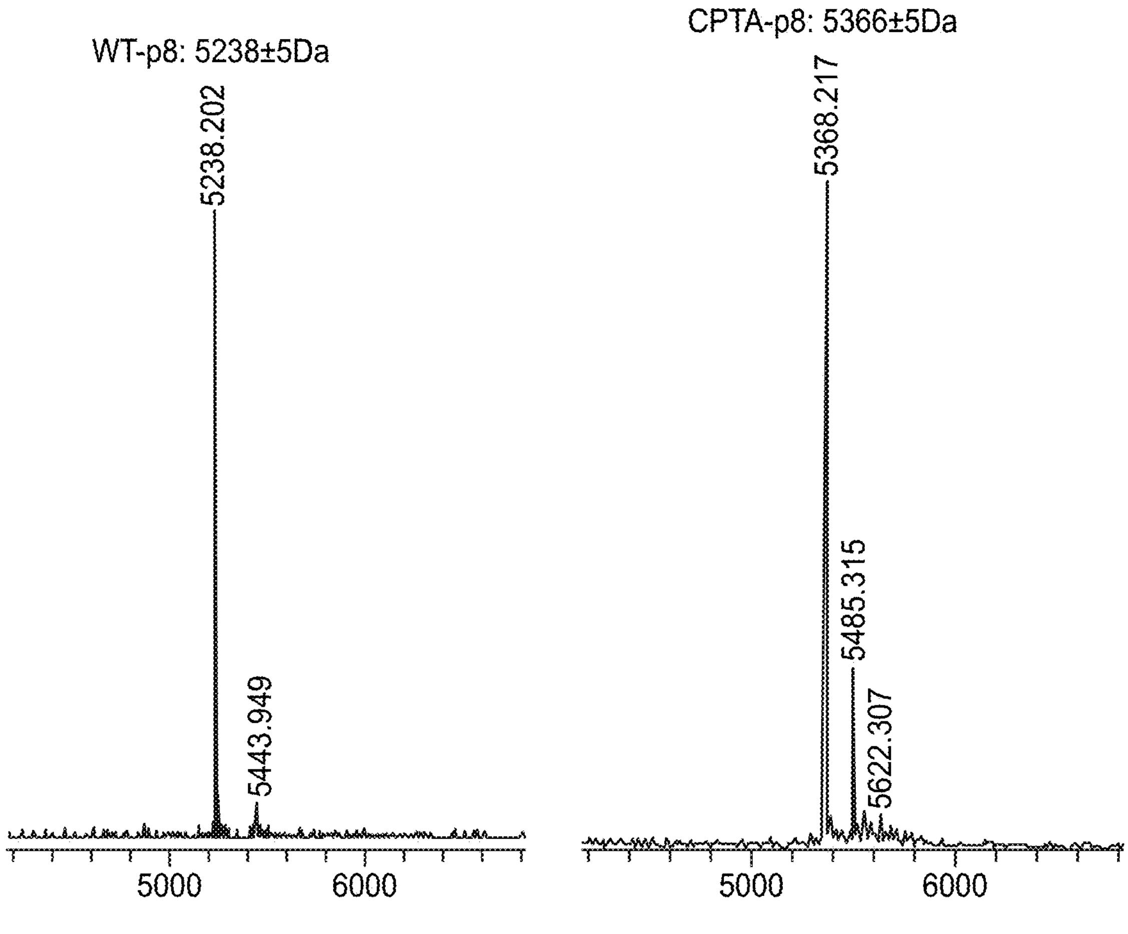

FIG. 55 provides a MALDI mass spectrometry of CPTA-p8. The p8 capsid mass differential between wildtype and CPTA conjugate p8 is congruent to the CPTA molecular weight addition with covalent conjugation (~128 Da).

FIG. 56 depict images showing the range of inho particle-derived particles.

Figure 57:
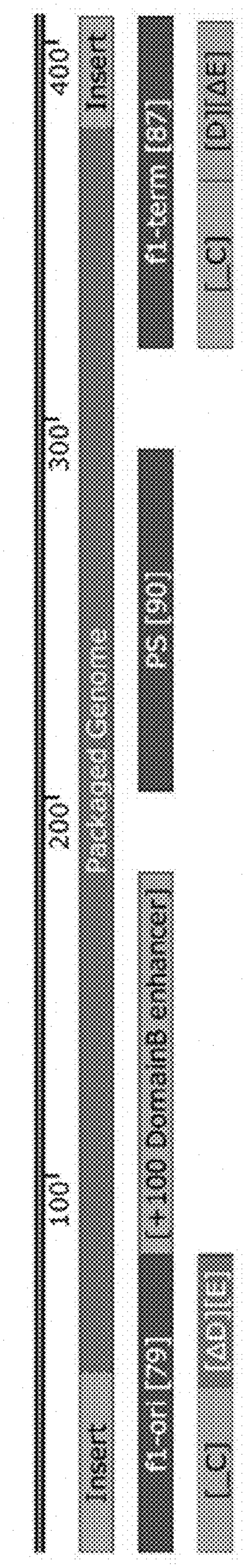

FIG. 57 describes embodiments of constructed f1-ori and f1-term flank chosen ssDNA for packaging.

Figure 58:
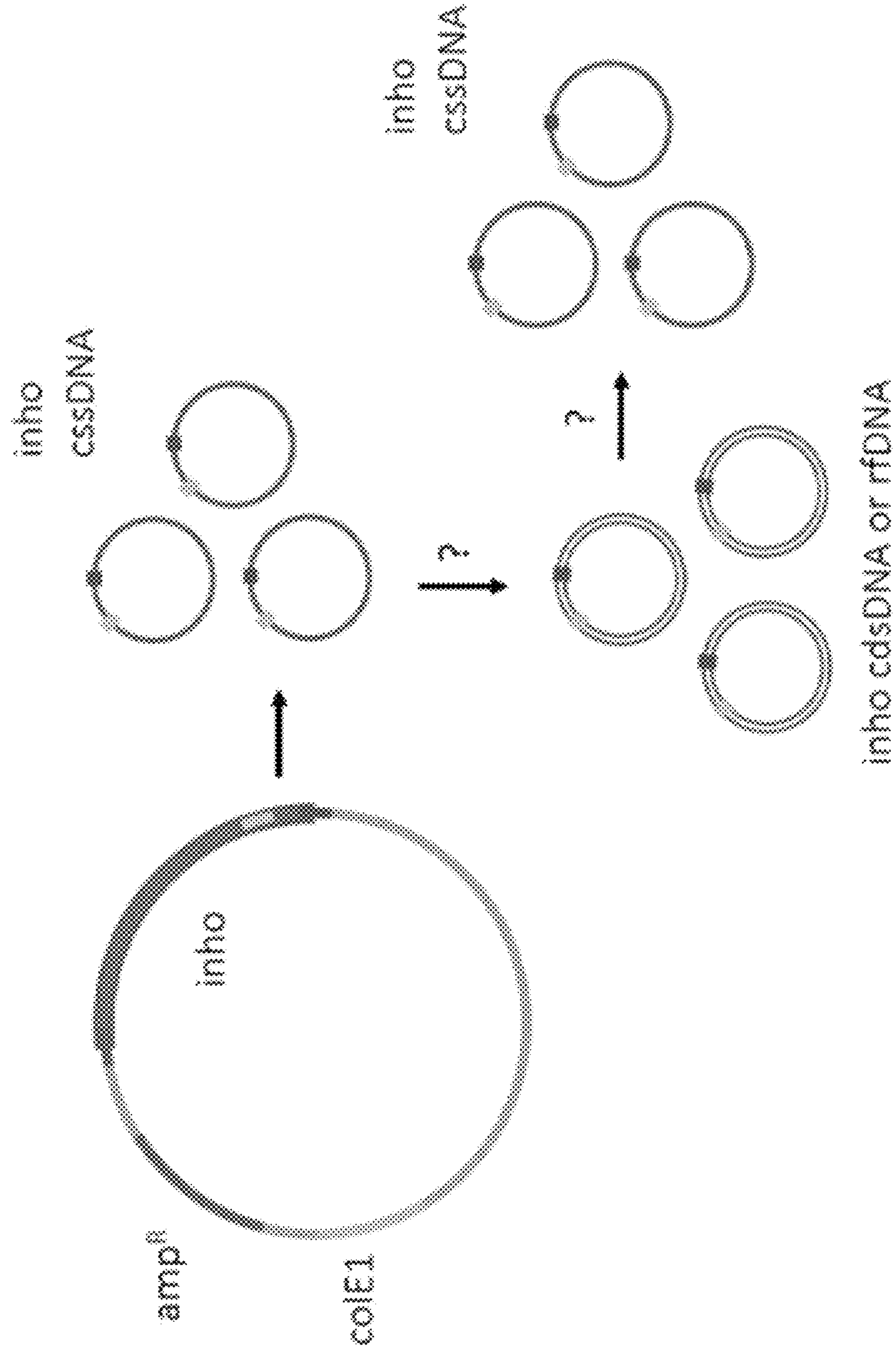

FIG. 58 is a schematic of possible inho cssDNA product. The schematic questinos whether the inho cssDHA product has an rfDNA intermediate.

Figure 59:
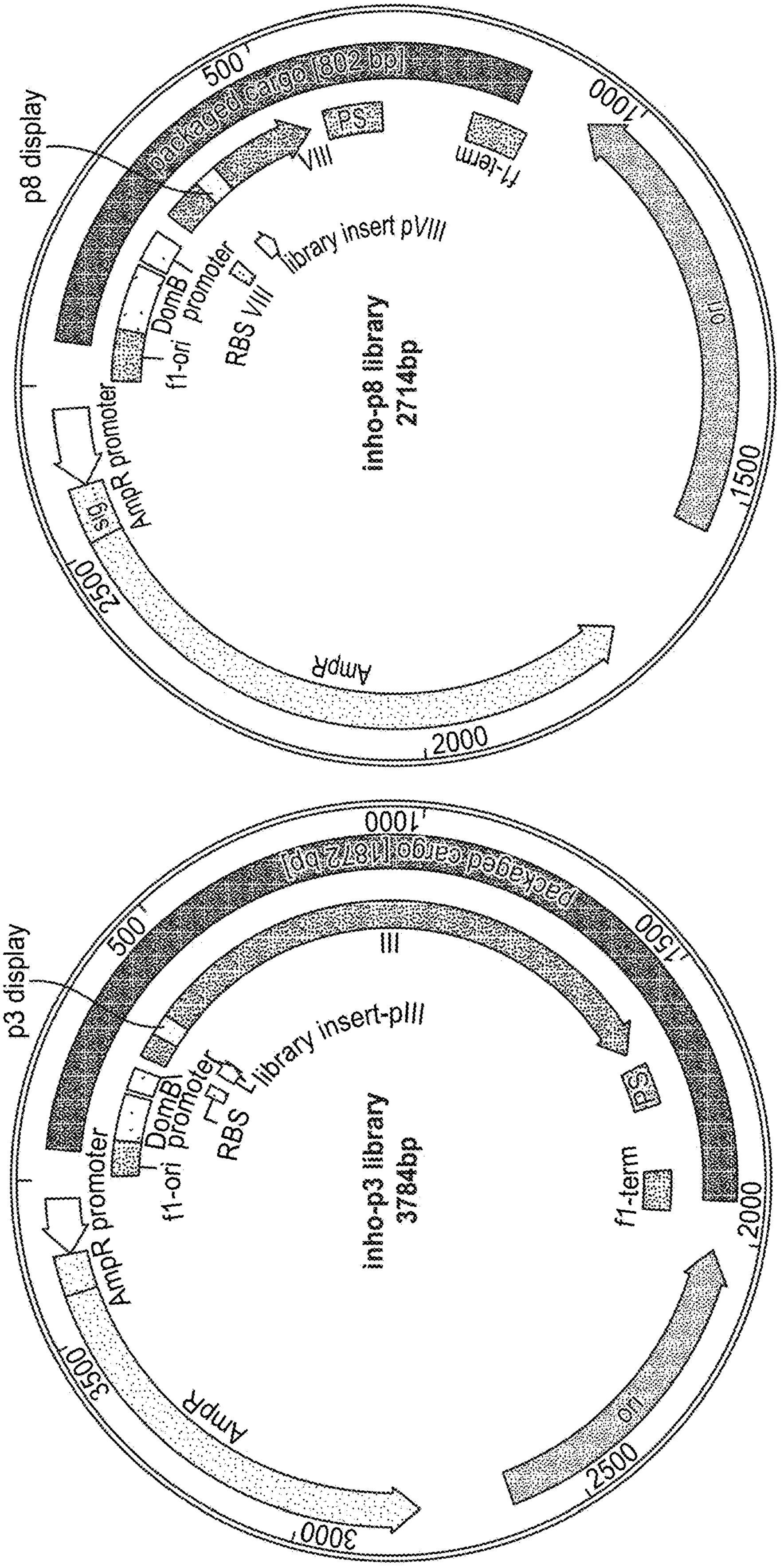

FIG. 59 depicts inho constructs encoding the display capsid within the packaged cargo region. The display capsids (i.e. p3 and p8) are incorporated within the cssDNA of the inho to link the PDP phenotype to the genetic barcode. Note that the length of the inho library can differ based on the capsid gene (unless controlled with stuffer bases).

Figure 60:
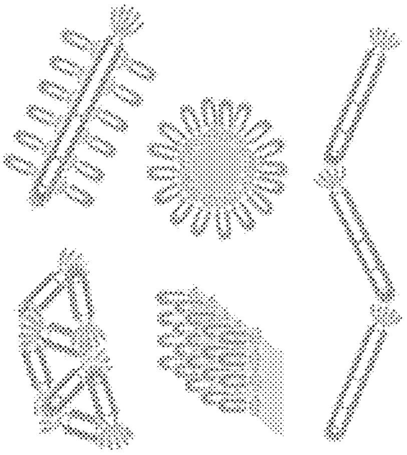

FIG. 60 shows phage nanostructures of directed assembly of inho length phage struts.

Figures 61A, 61B, 61C:
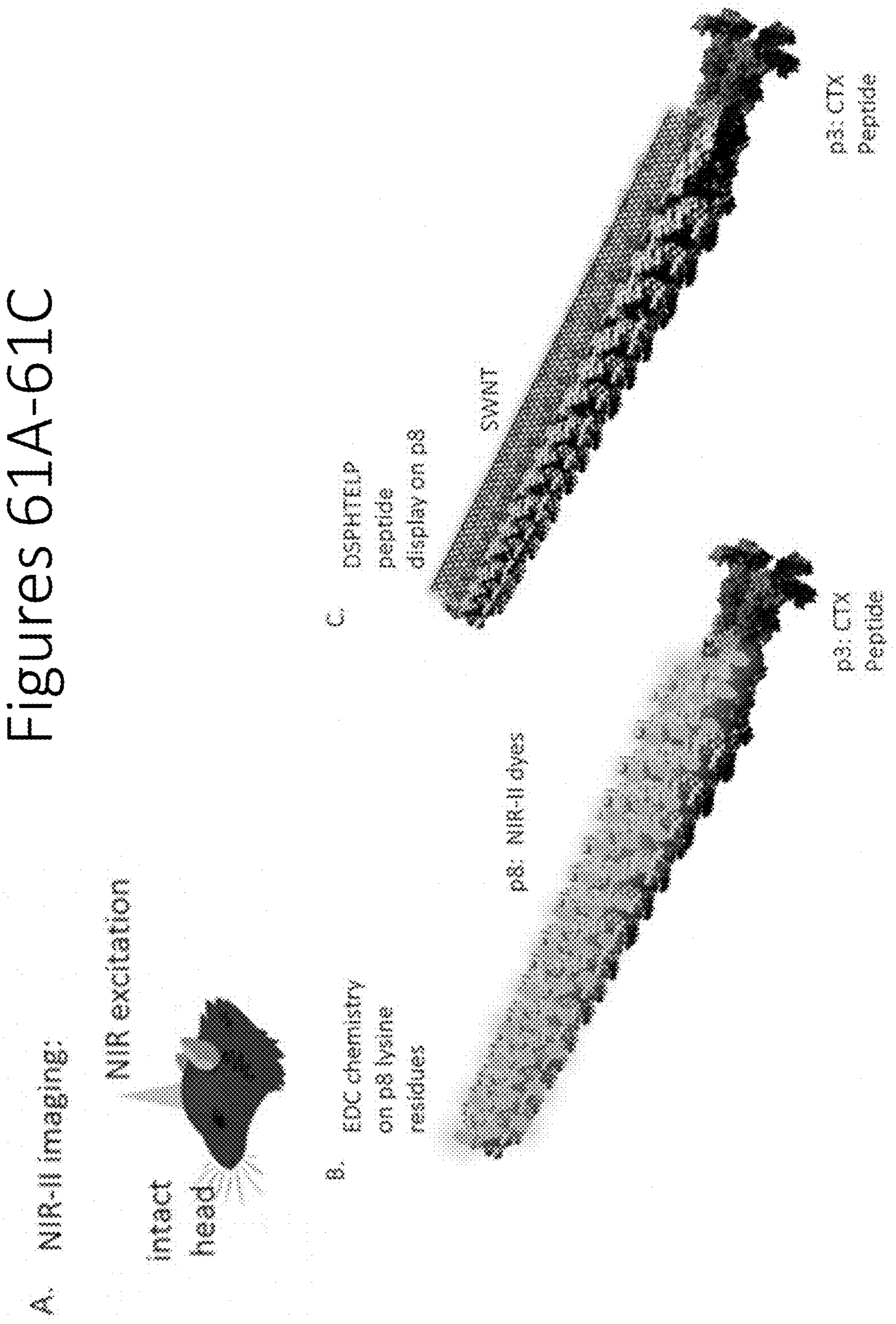

FIG. 61A-61C show loading phage with NIR-II imaging materials. A) Schematic of NIR-II penetrance through skull and scalp. B) Design of small molecule NIR-II dye loaded phage. C) Design of SWNT loaded phage. FIG. 61C discloses SEQ ID NO: 4.

Figures 62A, 62B:
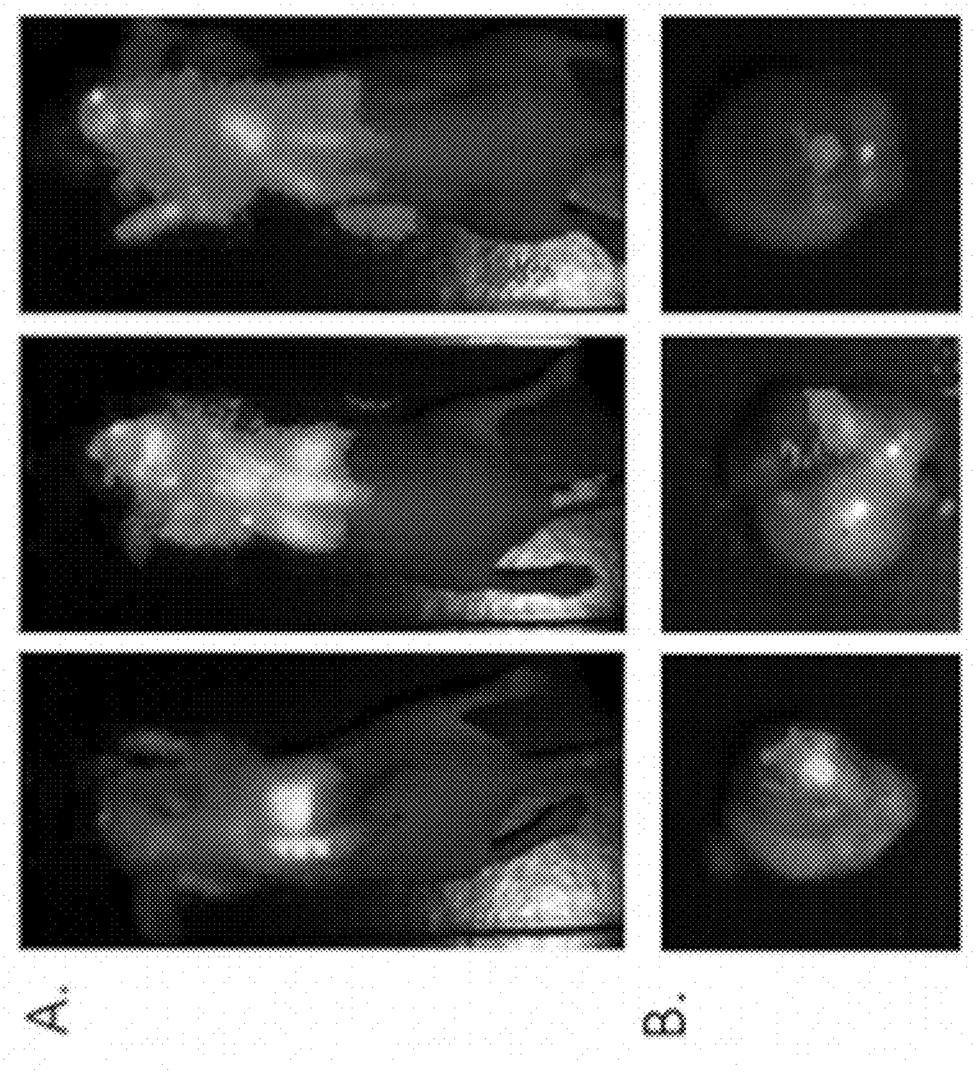

FIG. 62A-62B shows HiPCO loaded CTX-phage in U87MG orthotopic xenograft model. A) 808 nm ex., 1300 nm long-pass imaging of HiPCO signal in mouse (NCU-NU) body. B) Ex-vivo CTX-phage-HiPCO signal at tumor locale.

Figures 63A, 63B, 63C:
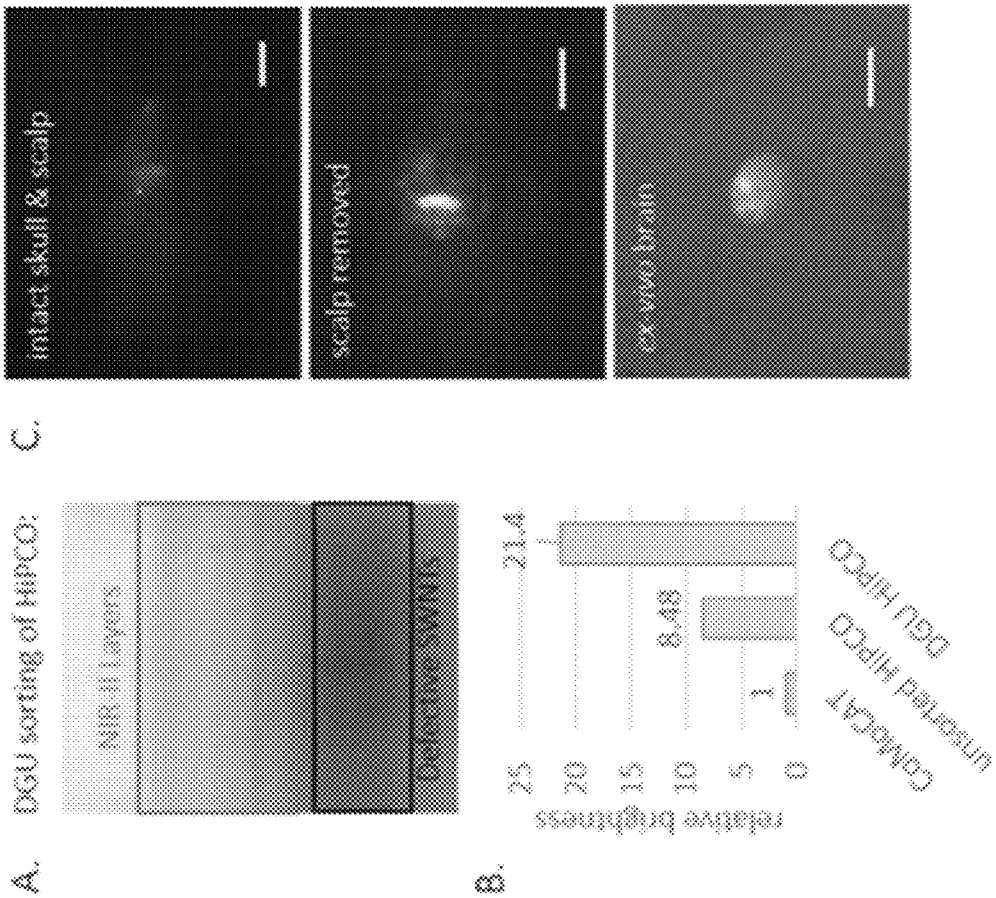

FIG. 63A-63C show DGU HiPCO loaded CTX-phage in U87MG model. A) DGU separation of fluorescent SWNT species from defective population. B) Relative intensity of SWNT samples. C) 808 nm ex., 1300 nm long-pass imaging of DGU HiPCO signal in NCU-NU mouse brain in-vivo to ex-vivo (1 cm scale).

Figures 64A, 64B, 64C:
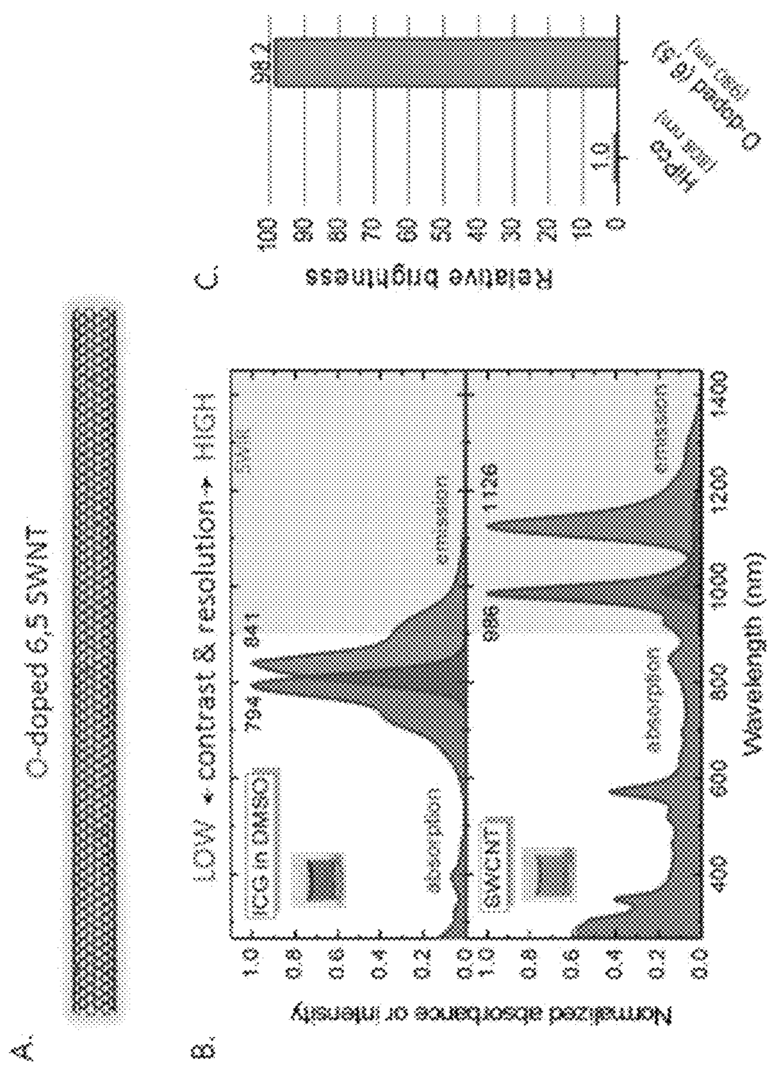

FIG. 64A-64C describes O-doped, 6,5 SWNT. A) Covalent quantum defects on body of SWNT. B) The absorption and emission shifted profile of O-doped SWNT relative to ICG dye. C) Relative intensity of O-doped SWNT to HiPCO.

Figures 65A, 65B:
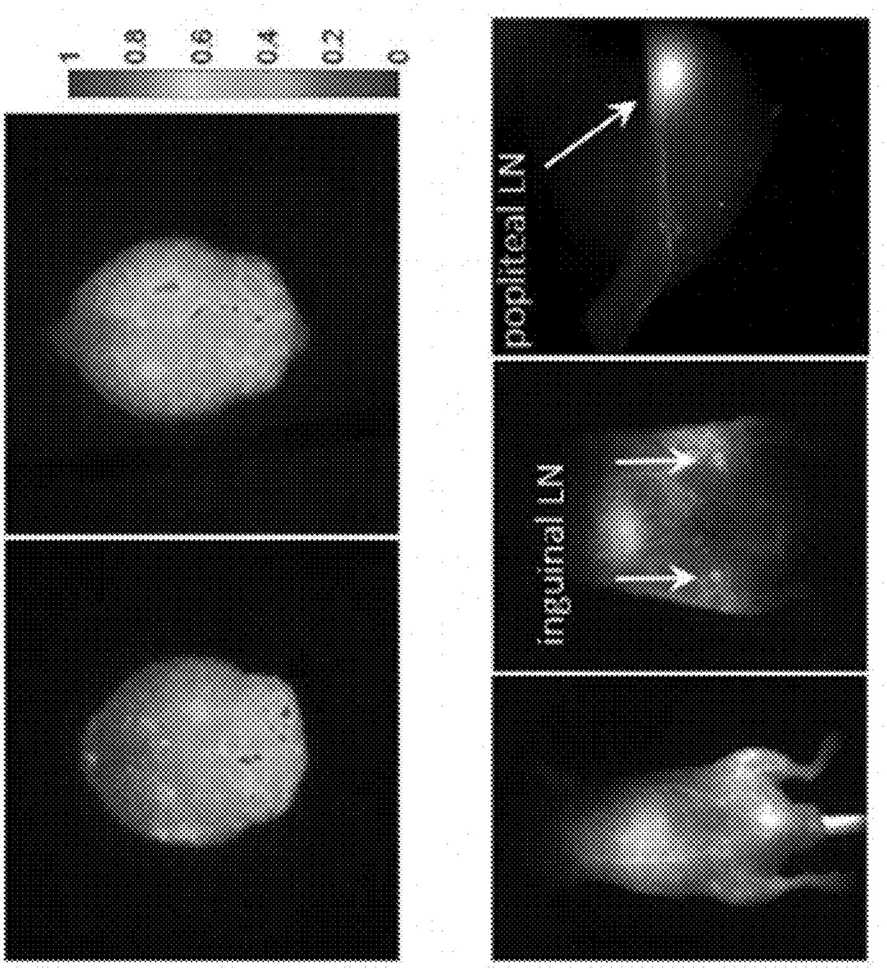

FIG. 65A-65B describes O-doped 6,5 SWNT resolution and contrast. A) O-doped SWNT loaded on CTX-phage light up vasculature and GBM22 tumor injection site with 980 nm ex., 1300 nm long-pass imaging. B) DSPE-PEG-5K wrapped O-doped SWNT particles have better circulation and dispersion, lighting up lymph nodes and fine vasculature details post tail-vein injection.

Figure 66:
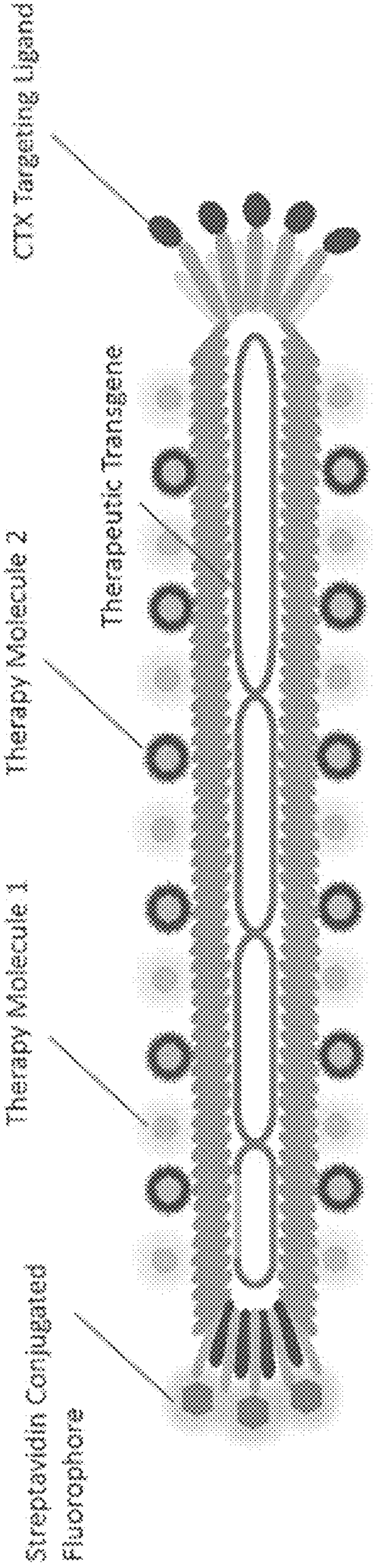

FIG. 66 depicts a schematic of a CTX-phage nanocarrier of combination drugs, imaging agent, and therapeutic genes.

Figure 67:
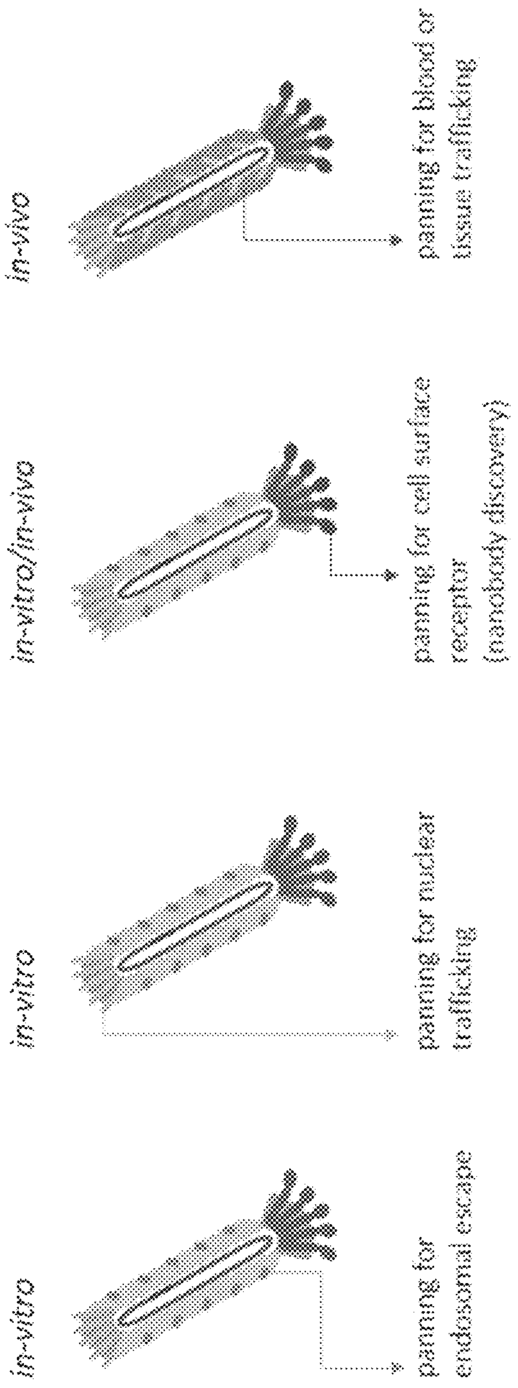

FIG. 67 provides a schematic of a serial evolution of various PDP capsids towards in vivo mammalian cell transduction.

Figure 68:
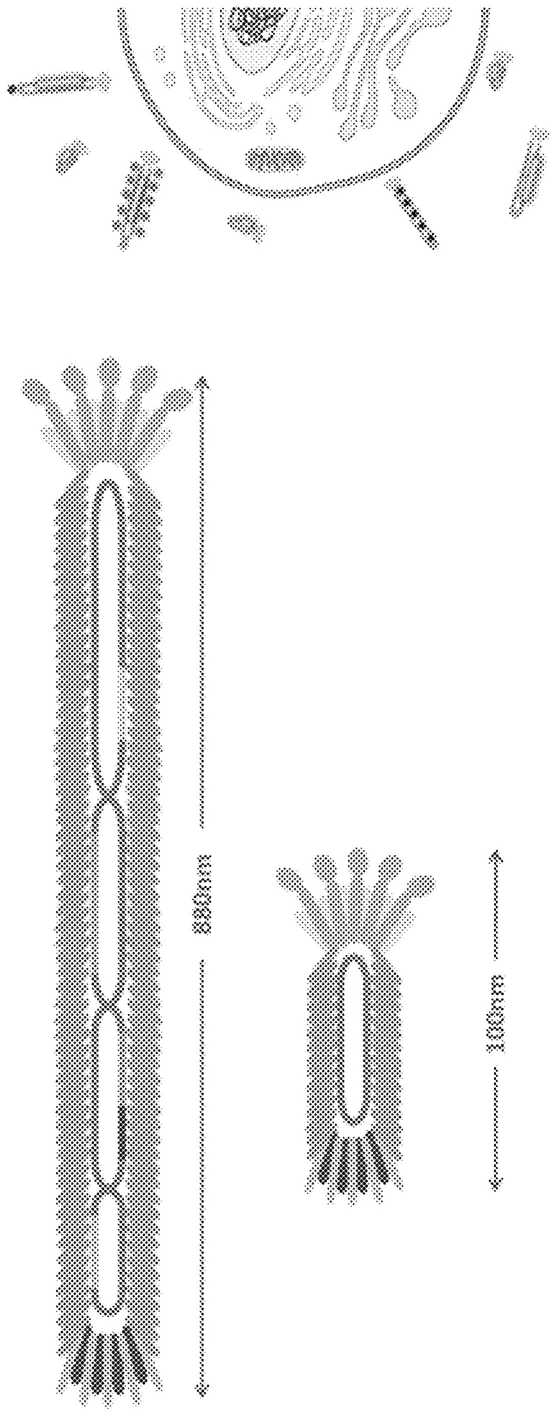

FIG. 68 shows a schematic of a multimodal phage derived nanoparticle with fine control over the capsid surface, the particle length, and the cssDNA content.

Figure 69:
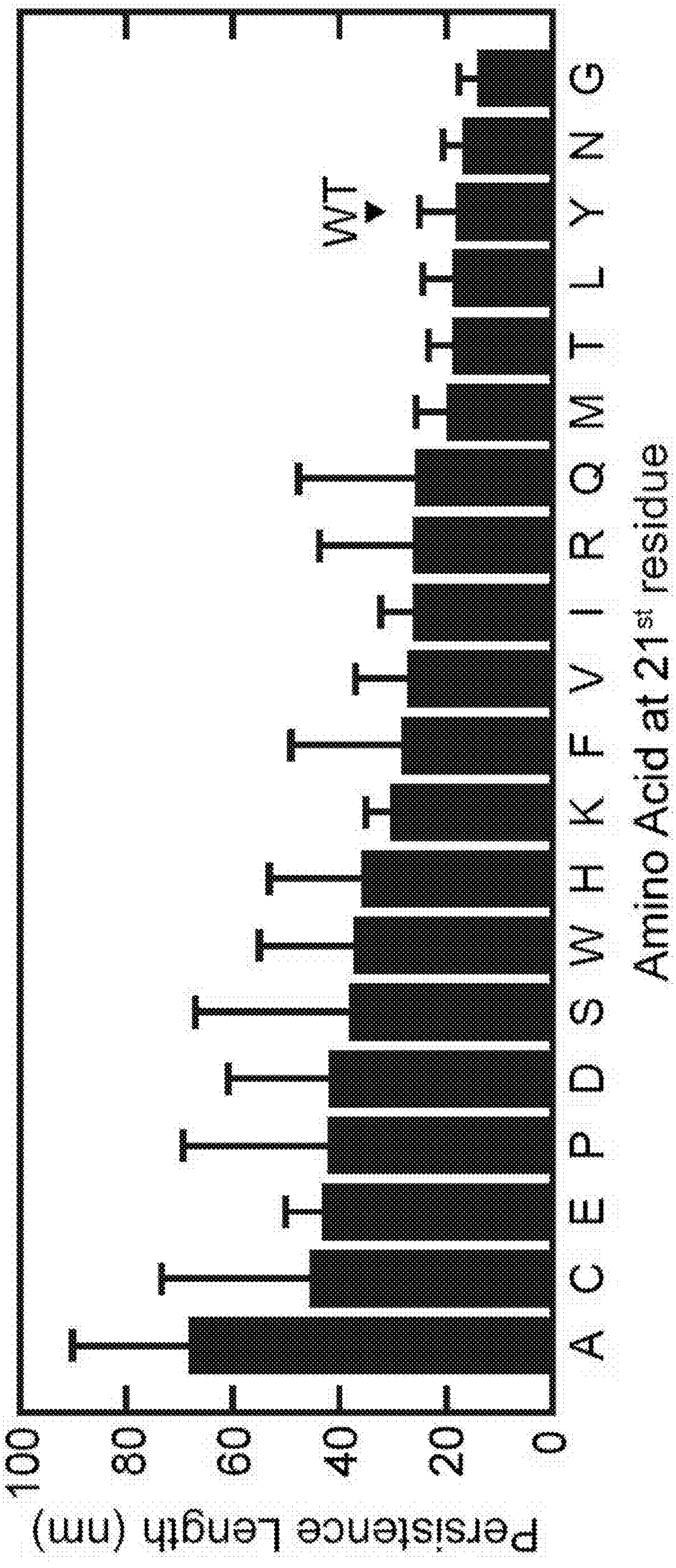

FIG. 69 provides a chart of the persistence length of p8 mutant 100 nm phages. The phage persistence lengths measured for 100 nm length p8 mutants at amino acid position 21. WT indicates the amino acid at position 21 of wild-type p8. (n=3 per group).

Figure 70A:
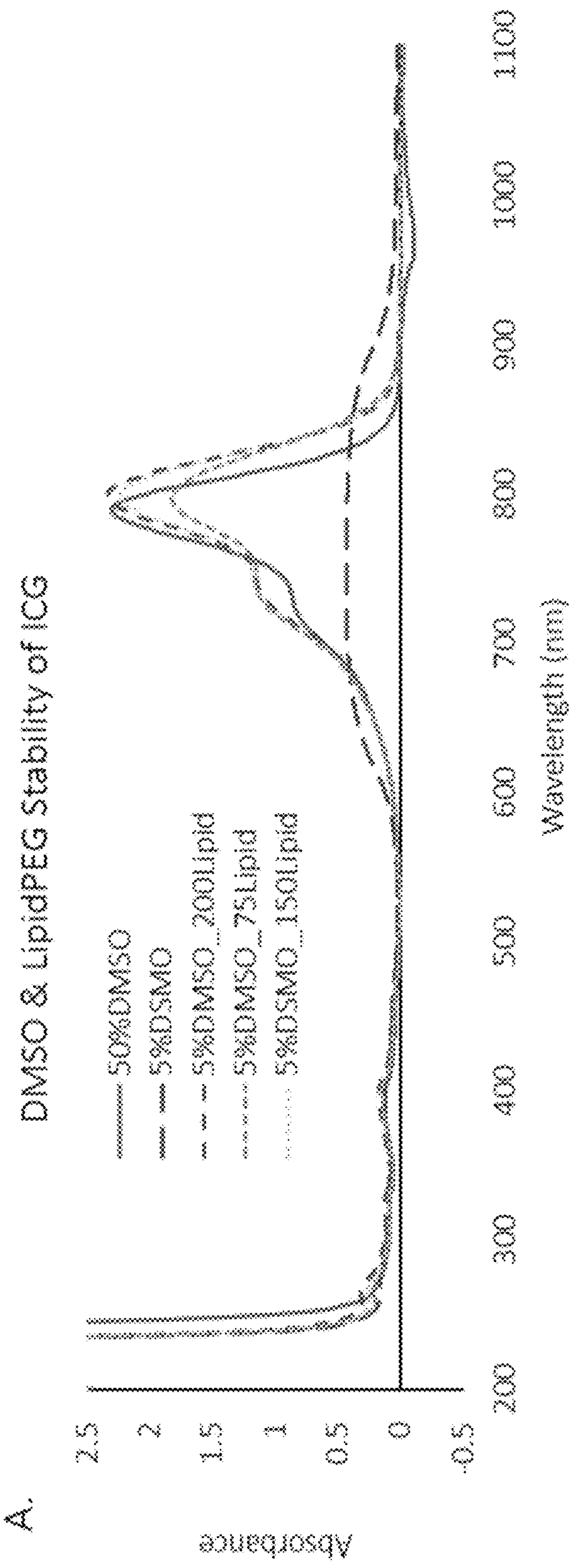
Figure 70B:
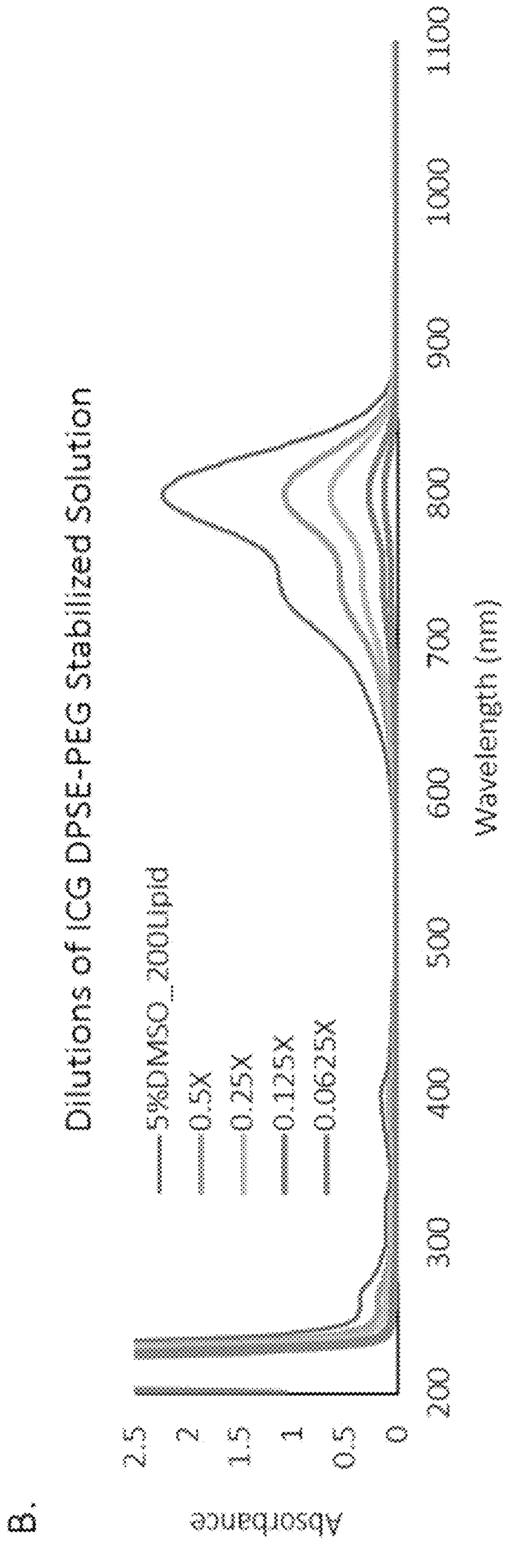

FIG. 70A-70B shows ICG solubility. A) The solubility of ICG dye molecules in various solutions formulated with κ-50/DMSO and 75-200 mM DSPE-mPEG-5K in PBS. Aggregated ICG can be rescued by lipid-PEG addition. The absorbance peak flatlines with PBS due to aggregation. B) Serial dilution of the lipid-PEG solubilized ICG shows that the absorbance peak profile is retained, suggesting that the stability of the ICG is not a result of a critical concentration of lipid-PEG.

Figure 71:
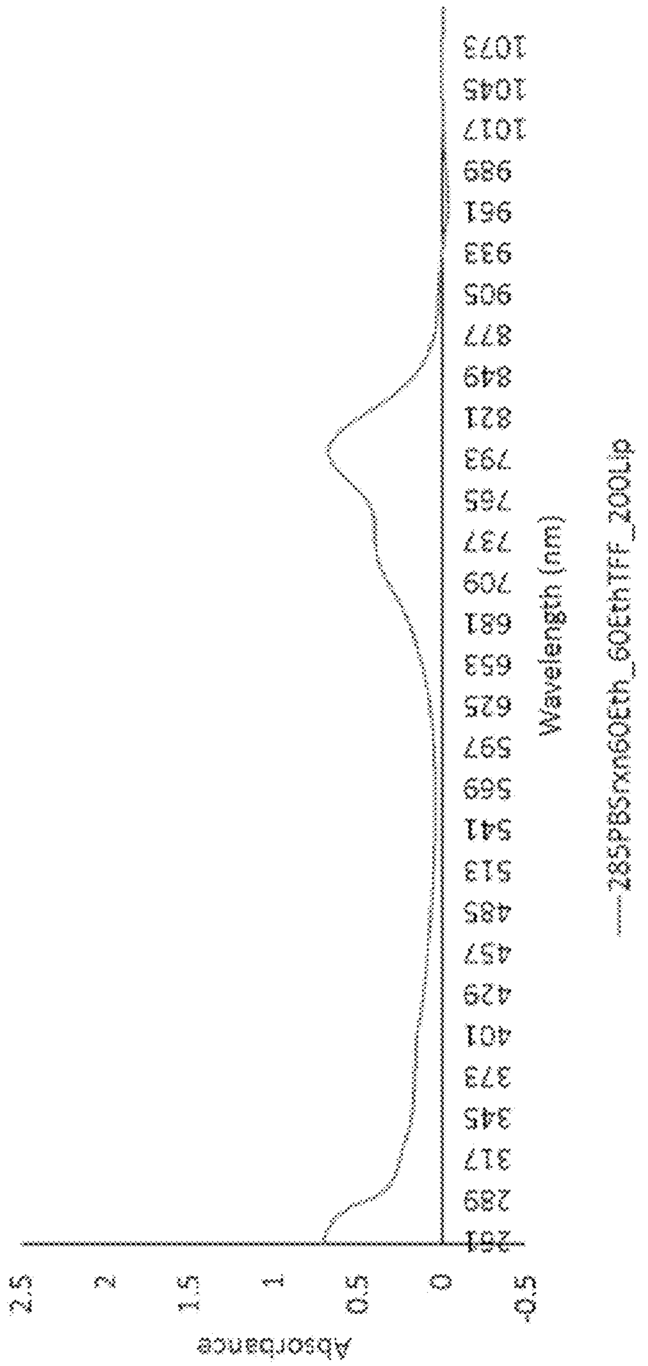

FIG. 71 describes a graph of excess ICG washed by 60% ethanol. Alternative to 50% DMSO TFF washing, the ICG-phage reaction may be dilute to 60% ethanol and TFF filtered with 60% ethanol to removed excess dye. The clean ICG-phage conjugates are similarly buffer exchanged to 200 mM DSPE-mPEG-5K solution for stability. Absorbance peak of final sample cleaned with 60% ethanol protocol shown.

Figure 72:
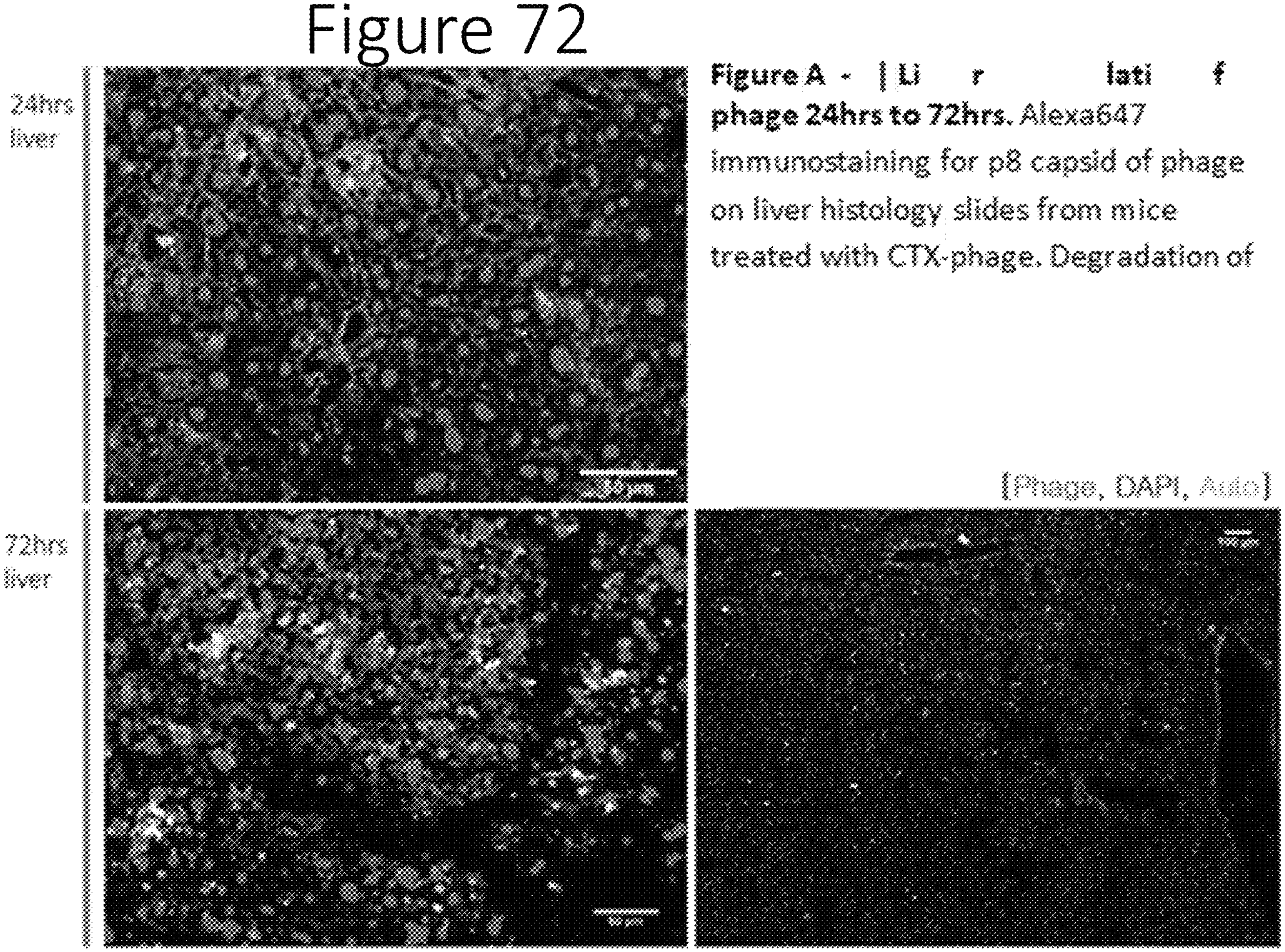

FIG. 72 provides images of liver accumulation of phage at 24 hrs to 72 hrs. Alexa647 immunostaining for p8 capside of phage on liver histology slides from mice treated with CTX-phage is shown. Degradation of phage observed by 72 hrs.

Figure 73C:
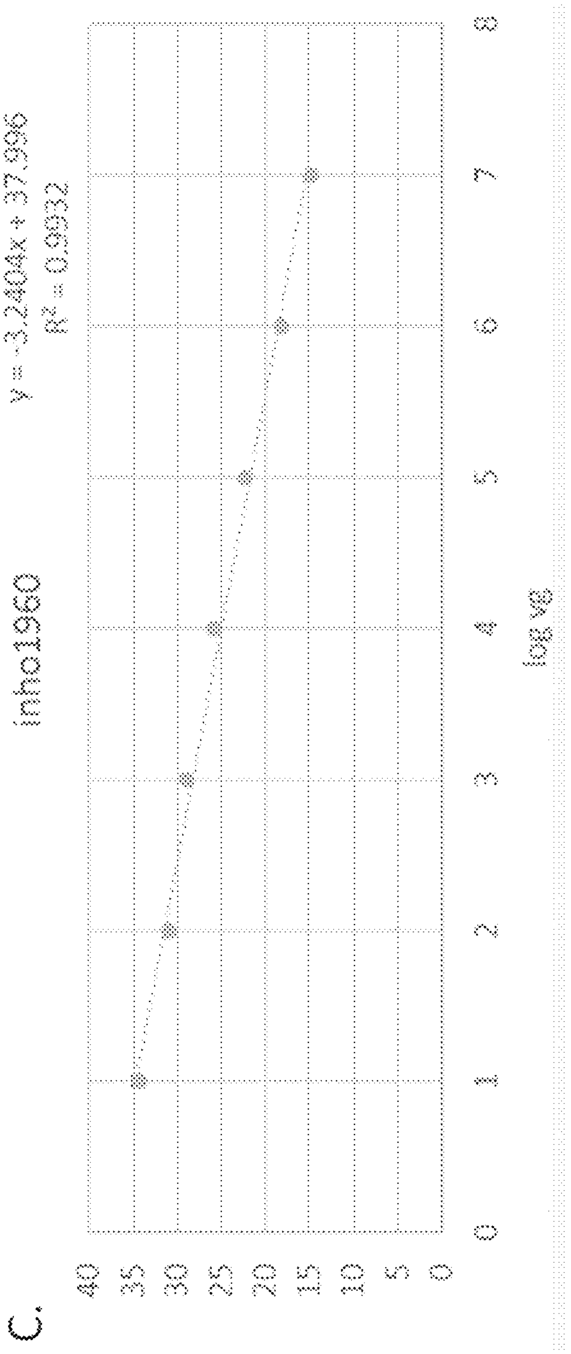

FIG. 73A-73C provides graphs of sample stand curves for a target phage gene. Examples of standard curves for absolute quantification of phage genomes for A) wildtype phage amplicon B) chlorotosin phage amplicon C) inho1960 phage amplicon. Each data point is averaged over 3 well signals. Every plate is run with a triplicate standard curve for the gene of interest.

DETAILED DESCRIPTION

Unless otherwise specified, “a” or “an” means “one or more.”

As used herein, the word “about” in front of a numeric value means ±10%, ±5%, ±2% or ±1% of the numeric value.

The present disclosure incorporates by reference in their entirety each of U.S. patent application publications Nos. 2019-0022155, 2021-0205381 and U.S. patent Ser. No. 10/987,388.

The present disclosure is directed to an engineered phage-derived particle (PDP) for expressing a transgene in a target cell transduced with a bacteriophage. PDPs can comprise: (i) less than about 500 bp of DNA from the bacteriophage genome, (ii) an ITR-flanked therapeutic gene up to 20 kb, (iii) an endosomal escape sequence, (iv) a nuclear localization sequence, and (v) a cell-specific targeting moiety, wherein the PDP escapes lysosomal degradation, traffics across the nuclear envelope and expresses a therapeutic gene in a mammalian cell.

M13 bacteriophage, a naturally monodisperse multifunctional nanostructure, consists of thousands of distinct protein subunits organized in a filamentous viral capsid; 900 nm in length and 6 nm in diameter. All M13 capsids are amenable to mutation and can be tuned for the binding and nucleation of inorganics and nanoparticles, and for the expression of ligands, functional moieties, and even enzymes. These capabilities for medical imaging and therapy have been harnessed by (i) tailoring the assembly of M13 into ultra-short, ‘inho’, phage derived particles, (ii) developing a chlorotoxin (CTX) motif on the M13 p3 capsid to enable phage particle crossing of the blood-brain-barrier and homing to glioblastoma cancer cells, and (iii) building ‘inho’ phage derived transgene cassettes for phage gene delivery in mammalian cells. Tight control over the genetic sequence provided by ‘inho’ phagemids allow production of phage particles ranging in length from 25 nm to over 2500 nm, as dictated by the length of the packaged DNA. This length control over the phage filament is used to demonstrate the impact of the particle length on the morphology of phage templated metal nanofoams and on the in-vitro and in-vivo tissue trafficking of targeted phage nanocarrriers. An optimal length for enhancing ion transport and active material access in MnOx cathodes is described. Chlorotoxin-phages, conjugate with indocyanine green dye (ICG), are visualized in-vivo in the second window near infrared (SWIR) and home effectively to mouse brain tumor. Ultra-short, 50 nm chlorotoxin-phage particles are shown to vastly improve this localization specificity. Additionally, the ‘inho’ phagemid system is engineered to produce ITR-flanked transgene cassettes. Such reporter genes packaged within targeted, cationically modified, ‘inho’ phages are able to transduce liver and brain cancer cells. The closed-ended, single-stranded ‘inho’ phage-derived cassettes have capacity up to 20 kilobases and can be delivered within phage particles as well as non-viral delivery vehicles. Ultimately, therapy or imaging agent carrying, miniaturized, chlorotoxin-targeted, M13 phage is considered here as a complete nanotheranostic platform that could augment the therapeutic efficacy of combination drugs shuttled to the site of glioma. The described multimodal, nanoplatform is re-designable for applications in nanomaterials, diagnostics, and across disease types.

The subject matter of the application is further illustrated by, though in no way limited to, the following examples.

EXAMPLE 1

Introduction

Biological materials and the wealth of chemistries adapted from natural inspirations has led to the development of some of today’s most promising new technologies from virus-like vehicles that enable new vaccine, drug, and genetic therapies to editors adapted from bacterial defense proteins like Cas. Bacterial systems and bacteriophages in particular are the most abundant bodies in the biosphere, and phages have recently been highlighted for their diversity even across the same bacterial host and their complex role in regulating the microbial environment. Since the discovery for phages in 1915 by William Tort, phages have played a fundamental role in the understanding of modern molecular biology. From 1930 to the 1970s, phage investigations resulted in central understandings such as the identification of DNA as genetic material and the deciphering of the 3-nucleotide codon and messenger RNA[1]. By the 1980s and 1990s, certain *E. coli* infecting model phages had been studied in great detail with the field beginning to use recombinant DNA techniques modified from phage vectors (i.e lambda vectors, cosmids, phagemids) for standard laboratory techniques[2]. Phage work additionally contributed a great deal to the library of restriction enzymes, first observed for their effect of restricting the growth of bacteriophage in bacterial cells[3], and to the host of DNA/RNA enzymes familiar to all biology labs today. However, since the burst of phage activity of the 1970s, bacteriophages have been generally relegated to the biological toolbox with a few new branches of phage work only recently gaining traction. The renewed interest in phage biology has come about due to the advent of sequencing technology which has revealed the impact of phage sequences in the genomic evolution of host bacteria as well as the dominance of phage numbers and varieties in all bacterial environments[1]. Recent estimates suggest that 10 to 100 times more phage particles than bacterial cells are contained in soil and water, with global phage numbers in the order of $10^{31}$ [2]. The complexity of phage-bacterial interactions and gene transfer is only just now being discussed for their implications in biogeochemical cycles as well as mammalian microbiome regulation and immune health. The threat of antimicrobial resistance in the public health sector along with contemporary interest in the function of the microbiome in human health has sparked a resurgence in the phage industry (forgotten cure). Phages are beginning to be considered as designer therapeutic or delivery agents due to their ability to transfer genetic information that can modulate the host cell.

The wealth of early work done with phage also means that today’s phage biologists have an abundance of phage engineering tools in their arsenal. Phage display especially is a highly efficient and established technique, which has played a crucial role in the field of antibody and peptide discovery[4-6]. While the early work of phage display libraries and enrichment panning have not been focused on inspecting the prospects of phage itself as a therapeutic or diagnostic platform, the years of research with filamentous and X phage variants has led to a deep knowledge of the engineering and mutagenesis potential of such phage vector capsids and their genomic DNA. Protein nanoparticles are increasingly being used to innovate at the interface of materials science and biology with recombinant viral particles, virus-like particles (VLP) and lipid nanoparticles (LNP) converging towards designs that can deliver therapeutic agents through a combination of synthetic (i.e., polymer/lipid layers) and biological (i.e. targeting ligands/fusogens) components that enhance trafficking, specificity, and interaction with the host cells. More than non-replicative recombinant viral particles, phage particles are easily manufacturable with highly specialized characteristics in mind due to their modular nature and the bacterial culture expertise of modern laboratories. Between the ability to vastly manipulate the assembly capsids and to control the DNA vector content of phage systems, the design of recombinant phage particles as a nano-theranostic platform is an exciting new arena of exploration.

1-1 M13 Phage Libraries and Display Technology

Figure 1:
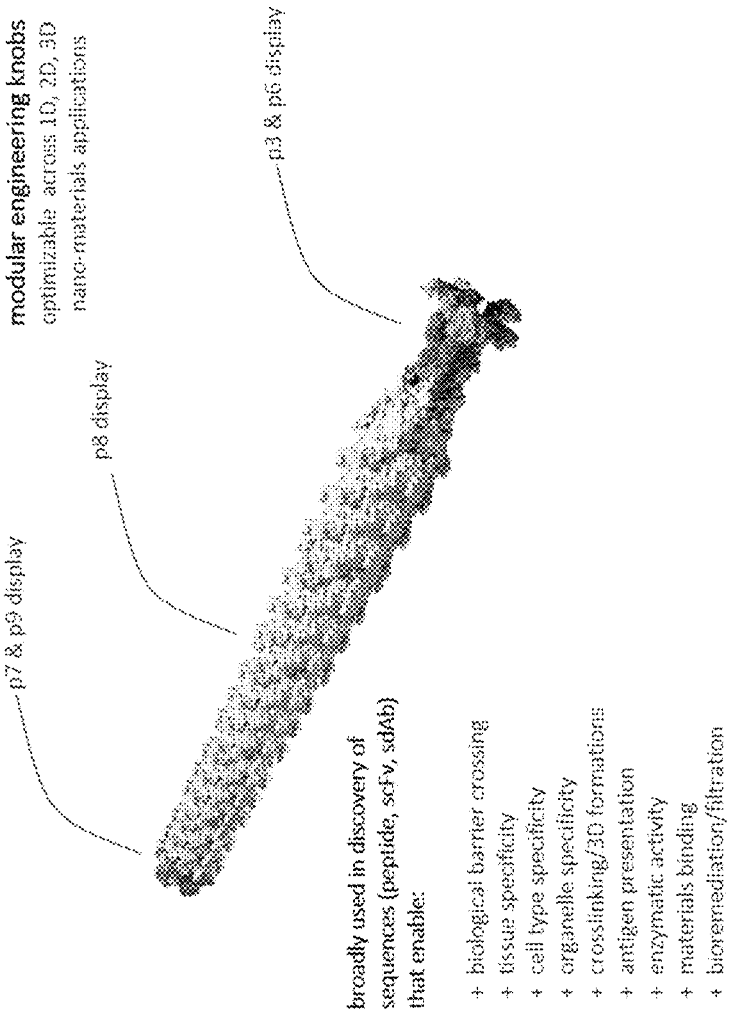
FIG. 1 depicts a schematic of the M13 phage, a highly modular, natural protein nanoparticle.

The phage of interest and the phage best studied for library production is the filamentous M13 bacteriophage. (FIG. 1) The M13 display techniques first published in the mid-1980s received the Chemistry Nobel in 2018 recognizing the contribution of M13 library technology towards advancing modern antibody medicines and tools. The body of M13 phage derived vectors consists of the five main capsid proteins of the M13 filamentous bacteriophage where the main alpha-helical p8 coat protein is repeated hundreds of times to wrap the circular single stranded genomic information (cssDNA) along the axis of the phage. This results in a filamentous phage with a long, flexible fiber-like structure with diameter of 6.5 nm and a length that is determined by the size of the engineered genome packaged along its axis. The design parameters of M13 phages have been utilized to construct randomized libraries on the major and minor coat proteins of the filamentous structure[7]. Specifically, the p3 capping protein, originally critical to the f-pilus interaction and infectivity of the phage particle, has been engineered for insertions of scFv, sdAb, and long peptide lengths retaining conformation and function[8,9]. Display on the p3 phage tail results with a maximum of five moieties per phage particle which has been powerfully employed for the panning and discovery of affinity proteins. Similarly, p9 is yet another end capsid that are amenable to large sequence insertions at five copies per phage[10]. Higher avidity display can be achieved on the p8 main body capsid. However, due to the alpha helical conformation and tight packing requirement of the p8 capsid arrays along the length of the phage, long sequence insertions to the p8 terminal render the assembly phage body untenable. 8-mer random libraries are generally well-tolerated with fusion peptide present at approximately 2700 copies. The f88 display vector type is another means by which long insertions are made possible on the filamentous p8 termini. The f88 vectors code for two p8 genes, one wildtype and another recombinant p8 (rp8) where DNA insertions can be made[11]. Here due to the mosaic nature of the p8 coat, large inserts are incorporated onto the filamentous body without disrupting assembly. We can expect few hundreds to several thousands of recombinant p8 insertions depending on the complexity and length of the foreign DNA. Note also that double gene type display may occur across two vectors as well (with each gene copy placed on separate vectors systems of a phagemid system and co-transformed for phage production as needed). The remaining capsid proteins p6 and p7 of the phage ends are lesser exposed to the surface and are not as popular for peptide mutations. P6 and p7 do have display potential with previous work demonstrating the incorporations of long sequences such as antibody $V_H$ in frame with p7[12] and cDNA libraries constructed on p6[13-15] Outside of N-mer peptide inserts, antibody fragments inserts or other rationally-designed/functional proteins, cDNA libraries or genomic libraries have also been transferred to the phage surface using covalent Fos-Jun leucine zipper linking strategies that overcome reading frame and orientation inefficiencies. Vectors such as the pJuFo encodes a p3 terminal Jun zipper and directs the cDNA-Fos translation to the periplasmic space where the Fos-Jun moieties may assemble together and the phage final product display the cDNA protein linked via the zipper to the p3 surface[16]. Additionally, post-translation modifications such as glycosylation may also be represented in phage display libraries[17,18].

Display of substrates for enzymatic functionalization such as substrate sequences for sortase specific modification[19] or biotin accepting peptides (BAP)[20] for enzymatic biotinylation of the display capsids are another example of the versatility of the phage as a building block. As filamentous phages are assembled through a secretion type mechanism, display proteins must be considered for their facility for crossing the bacterial cell inner membrane as part of the phage extrusion process. Generally secreted proteins such as Fabs do not have problems while proteins normally expressed and folded within the cytoplasm may require additional planning and optimization for the protein under study[7]. Double p3 vectors, f33 (like f88), p6 vectors, and permutations of p3/p8/p9/rp8 and p9/p7 vectors have all been validated for manufacturing of highly modular multi-functional M13 phage based particles. Taken all together, the wealth of vector discovery and validation around the capability of the M13 coat to handle multiple and complex peptide inserts highlight the engineer ability of the M13 base phage as a multi-functional protein nanoparticle.

TABLE 1

M13 phage display capsids and insert characteristics (adapted from Henry et al.[21])

| Capsid type copies | Capsid gene | Polypeptide insert copynumber | Polypeptide insert size limit |
|---|---|---|---|
| p3 | type 3 type 3/3 | ~5<br>~1 | >25 kDa |
| p6 | type 6 type 6/6 | ~5<br>~1 | >25 kDa |
| p7 | type 7 type 7/7 | ~5<br>~1 | >25 kDa |
| p8 | type 8<br>type 8/8 | ~2700<br>~1-300 | 8-mers<br>>50 kDa |
| p9 | type 9 type 9/9 | ~5<br>~1 | >25 kDa |

1-2 Phage Nanoparticles and Scaffolds

Beyond the utility of M13 libraries in affinity maturation techniques, the field has extensively explored the value of the M13 particle as an efficient nanoparticle system in 1D (NP), 2D (layers), and 3D (scaffold/foams/aerogels) constructs[22-25]. Nanowires, nanofoams, and multi-tiered nanostructures can be constructed. Specific control over the phage filament alignments and multi-phage architectures are also achievable through the display of attachment points at the ends or along the body of the phage, exertion of shear flows, or by driving electrostatic interactions with secondary materials[19,23]. Then, by surface functionalizing the filamentous phage particles, we can create materials of specialized electrochemical, optical and catalytic effects at exceptionally high surface area in either suspension or cross-linked formulations. The Belcher Lab has pioneered some of the first inorganic material nucleation and nanomaterial complexation onto engineered phage capsids. Due to the mutable nature of the coat, the phage surface is amenable to specialized peptide nodes for loading or nucleation of unique materials. High avidity p8 display sequences discovered for materials deposition such as the EEAE (E3) ("EEAE" disclosed as SEQ ID NO: 2) or EEEE (E4) ("EEEE" disclosed as SEQ ID NO: 3)[26-31] and for carbon materials complexation such as the EFE and DSPHTELP (SEQ ID NO: 4)[32-37] clones were instrumental in building phage-based templates that are applicable to energy materials. Phage based electronic materials, such as flexible batteries/electrode composites, energy-harvesting devices/solar cells, piezoelectric nanogenerators and fuel cells[22,24], have validated the applicability and easy functionality of M13 as a genetically encodable protein nanoparticle template. The high surface area of phage materials and the high valency of the phage body has also led to the exploration of M13 scaffolds for use in filtration, chemical sponge, bio-sensor, and bio-remediation devices. The monodisperse, self-assembling, engineer able and uniform, tessellated construction of M13 and the stability of the M13 capsid to solvents and pH ranges make the phage ideal as a unit component for many nanomaterial designs.

Figure 2:
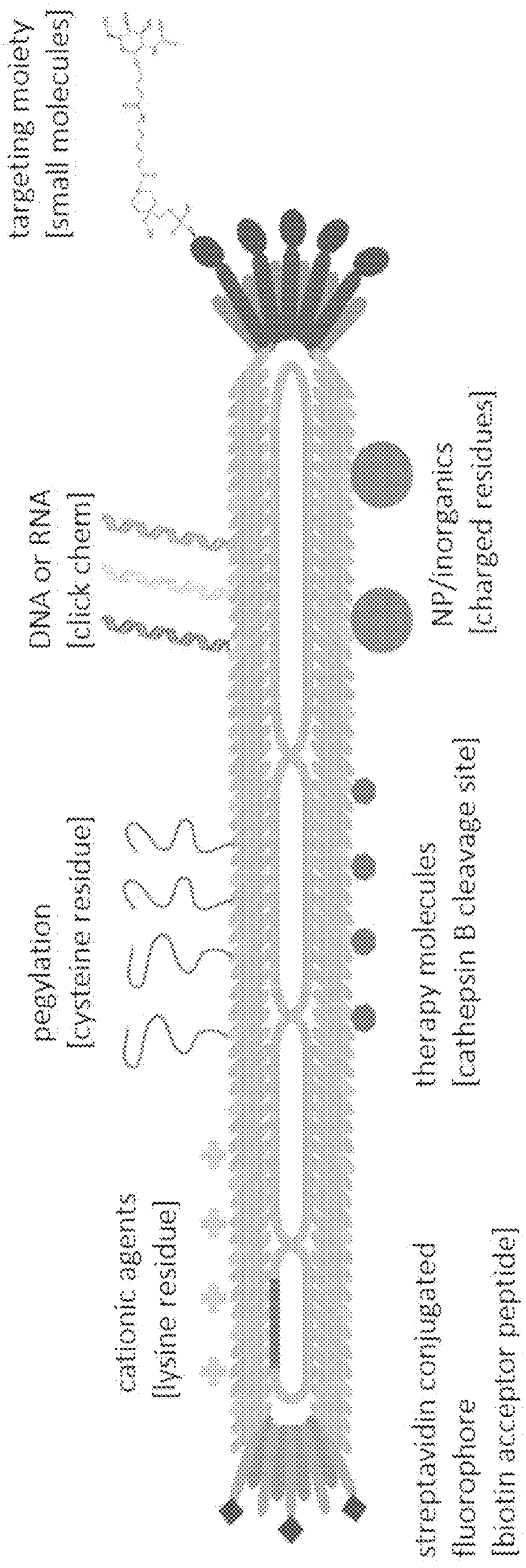
FIG. 2 depicts a schematic of the M13 phage chemical surface decoration concepts.

The functionality of the M13 phage surface can be extended beyond peptide display. Chemoselective approaches have been applied to phage particles to introduce conjugates onto specific amino acids present on the coat proteins. Residues such as lysine, aspartic acid, glutamic acid, cysteine, and tyrosine are covalently modifiable mild reactions including EDC/NHS activation, maleimide-thiol coupling, diazonium reagents, and similar click chemistries[23]. Such semi-specific conjugation spots can be used to decorate the phage particle surface with RNA/DNA[26], PEG/lipids[38,39], active imaging or dye agents[20,33,34], nanoparticles[31,40,41], small molecules, sugars and recombinant protein[42] materials to name a few. (FIG. 2.) Additional to the covalent chemical conjugations, M13 phages are also modifiable through electrostatic interactions to its mostly negative surface. The assembly of the phage capsid around the axial cssDNA, negatively charged, is mostly driven by electrostatic interactions with the c-terminal end of the major capsids. For instance, the p8 helices covering most of the phage body is positively charged at the DNA interaction end, negatively charged at the exposed end, with the two termini bridged at the middle by highly hydrophobic region that drive the tight stacking of the individual p8s[43-46]. The negative body of the phage can then be wrapped with positively charged materials to form complexes as has been tried for polymer-phage hybrids[47-49] or matrices[21,22,24,50]. Such cationic polymer incorporations can serve to overcome the limitations of the M13 capsid in displaying highly positive charges, which can be disruptive to the assembly process.

1-3 Engineered Phage Particles as Diagnostic and Therapeutic Agents

Besides phage-templated materials synthesis, the best example of the nanoparticle use of phage is the theranostic power demonstrated with disease specific phage variants that are covalently or electrostatically tagged with imaging and therapy agents. In most early phage display works, sequences discovered though phage library panning were often reserved for downstream combination with small molecules, NPs, LNPs and VLPs and other such trending therapeutic modalities. More recently, the field has shown that the capacity of the phage capsids to carry active materials can be combined with its capacity for complex functional protein fusion in contrast enhancing or delivery applications. In example, tumor or infection specific phage were loaded with dyes or nanoparticles that allow for in-vitro or in-vivo visualization of the diseased cells or mass[22,51]. The Belcher Lab has illustrated the effective targeting of imaging materials and subsequent image-guided tumor de-bulking in ovarian and prostate mouse models using tumor-specific M13 phages such as SPARC binding peptide displaying phage or antibody targeted phage[20,31,33,34]. The loaded materials may also have additional therapeutic functions or capability to respond to external stimuli. Photothermal therapy of bacterial infection population sand local tumor was achieved through gold/silver nanorod phage complexes[40,52,53]. Small molecule therapies such as chemo-therapies or anti-microbials may also be carried on the phagebody[20,54,55] in order to limit the systemic exposure and dosing required to achieve curative effect with toxic chemicals. The filamentous structure of the phage provides minimally ~2700 p8 capsids for therapy loading, with likely multiple molecule docking possible in certain cases.

Targeted phage particles have demonstrated proof of concept for use as biosensors as well. Engineered phage variants may be used ex-vivo in food safety and disease detection. Given the simplicity of labeling phage particles, conferring pathogen type specificity to the coat proteins, and inherent signal-amplifying production cycle of phage, biosensors envisioned around electrochemical, optical, genetic reporter, and mass-based systems are all highly viable[56]. Detection work using filamentous phage displaying scFv against *E. coli, Staphylococcus epidermidis, Listeria monocytogenes, Salmonella typhimurium*, and *Bacillus anthracis* have been exhibited through labeling, colorimetric, amplification, surface plasmon resonance, piezoelectric transducer, linear dichroism, and magnetoelastic sensor technology[21,56,59,60]. Bacterial contamination detection of live produce and eggs as well as cancer cell proliferation marker and cell type detection using M13 phage immobilized devices are commonly described in the field[21,56,59,60]. The sensitivity of M13 systems also lends these sensing devices to specific chemical and toxin exposure control applications as well[24].

Design of the phage as an immuno-oncology therapy agent has also been validated through the display of targeting peptides along with immune stimulating antigenic moieties[6]. Early anti-phage antibody examination revealed that immunogenic response is elicited by wildtype phage, though only the p8 and p3 are targeted for neutralization[61]. Phage p8 in particular proved to be an attractive for phage vaccine development with high valency, stable display of foreign antigens. Epitopes associated with bacterial, fungal, parasitic, and viral pathogens such as malaria, HIV-1, hepatitis B have been tested with p3 and p8 display[21,62-64]. Such antigen display has been shown to drive immune activation and immunogen specific response (with greater success experienced with p8). Generally, antibodies that cross-react with the full immunogenic protein and achieve some neutralization of the virus/pathogen of origin were obtained. Phage cancer vaccines aimed at priming cytotoxic T-cells (CTLs) against tumor growth proved successful in several studies where tumor epitope (i.e. P1A, MAGE-A1, DEC-205/ovalbumin marker, Δ16HER2, α-GalCer) presentation on phage and mouse immunization with such phages resulted in prolonged survival[21,61,65-68]. It has also been speculated that the accumulation of phage materials itself to the tumor mass could contribute to the triggering of the immune activity at the cancerous site. Administration of targeted M13 phages have shown an increase in the tumor infiltration of innate immune cells and maturing of dendritic cells at lymph nodes in mouse models of colorectal cancer[59,69]. Phage carried epitopes in general are conjectured to induce stronger CTL effects due to enhanced cross-presentation of phage particles to the MHC class I pathway[21]. Additionally, the phage particle is self-adjuvanting, where bacterial lipopolysaccharide (LPS) may associate with the coat proteins during production, and the phage's inherent genomic CpG motifs are known to play an immune role[63]. Currently, phage vaccine technology is considered most useful for cases of peptides with low inherent immunogenicity where the high valency display and phage triggered adjuvant city can be of impact. Unlike natural pathogens capable of inducing strong response, the immune-suppressive environment of tumorous masses is especially relevant for activation through targeted phage vaccines.

The filamentous nature of the M13 is particularly useful in the context of hydrogel and aerogel formation. Outside of the metal nanofoam structures possible due to the polymer-like geometry of the phage, engineered phage hydrogels are highly applicable as in-situ therapeutic or regenerative scaffolding or as tissue culture material. The decorated surface of the phage is amenable to highly controlled presentation, release, and coordination of hydrogel formulations that are biocompatible for in-vivo and in-vitro applications in cellular modulation. Phage nanofiber matrices, often composed of engineered phage capsids expressing signaling and cytokine motifs (i.e. RGD, IKVAV (SEQ ID NO: 5), DGEA (SEQ ID NO: 6), hIL-3, hCNTF), achieve differentiation and directional growth of progenitor cells[6,24,70,71]. This is particularly exciting for the potential use of directed phage gels for regeneration in neuronal, bone, and skin/wound tissues. Furthermore, phage hydrogel forming technologies vary widely from non-specific protein gelling, electrostatic layering, enzymatically driven bonding, light-induced chemistries, and residue specific chemistries to metal-ion chelation. The multitude of design parameters in forming M13 hydrogels may be optimized for application specific preferences. Phage hydrogel in combination with surface displayed moieties, conjugate or mixed active agents/biologics or cells, and programmable cross-linking strategies could be designed as highly modular matrices for prolonged localized therapeutic effect. Recent work with alginate gels loaded with immune stimulating factors demonstrated the potential of peritumoral injected gels to repolarize tumor-associated macrophages towards an inflammatory M1-like phenotype and improve antitumor efficacy[72]. Such gel harbors can serve as local immune cell trafficking hubs to activate or modulate the suppressive tumor micro-environment. These can additionally be deployed in-vitro for antigen specific T cell expansion for subsequent patient administration[73]. The highly engineer able nature of M13 phage-based hydrogels lends the technology to be considered for similarly complex in-situ medical platforms.

1-4 Phage Clinical Use Expectations

The bacteriophages have previously had a robust history of usage in medicine during the pre-antibiotic and Soviet eras as antimicrobial cocktails that were either orally ingested, systemically infused, or locally administered to infected sites with a 90% reported cure rate. Phage based therapy of this nature is still ongoing in institutes in Russia, Georgia, and Poland and is now the last front for many modern day antibiotic resistant cases in the West[74]. As the antibiotic resistant pathogens continue to emerge, there has been a resurgence of interest in phage-based clinical technologies and the use of medicinal phages. Since phage was first used as therapy for acute and chronic infections by Felix d'Herelle in the 1920s, the essential features of phage biology and varieties have been extremely well characterized, but few Western countries have since adopted the clinical strategy. While phage therapy and clinical use was never abandoned in the former USSR and satellites, Western research has only just recently returned to consider the advantages of phage use with some human experiments conducted in the 2000s and the first phase I randomized U.S. trial of phage therapy published in 2009 (studying safety of a cocktail of phages directed against *E. coli, S. aureus*, and *Pseudomonas aeruginosa* in 42 patients with chronic venous leg ulcers)[75]. While the tolerance of phage in clinical use is empirically reported, large randomized trails are yet to be evaluated and much of the observations from the European use cases are obscured by language and standardization differences. Recently, the Center for Innovative Phage Applications and Therapeutics (IPATH), the first U.S. center for phage therapy, opened in June 2018 at the University of California, San Diego. Compassionate use case studies[76,77] and small-scale clinical studies of multi-dose intravenous infusions of phage variants are now beginning to emerge from the IPATH efforts. Initial reports validate the experiences described from Poland and the former USSR where high dose and repeat infusions during the therapy window (weeks to months) seem to be without significant adverse effects in healthy adults[78].

Phages are natural antibacterials that are capable of very specific modulation of target bacterial populations and have mechanisms of action very different from antibiotics, retaining activity against multiple resistant strains[75]. Due to the specific nature of phage-bacteria pairings, phage therapy is shown to have single species impact and spare damage to bystander microbial populations in both animal[79] and human studies[80,81]. As extensively discussed, phage particles can be engineered beyond their natural tropisms and functions, which equally applies to the case of phage designed for antimicrobial action. Lytic phages in general are preferred for anti-infection and anti-biofilm deployment. These virulent phages immediately begin replication and quickly lead to the destruction of the host cell within minutes to hours[82]. Temperate (lysogenic) phages like M13, have been documented mostly for transfer virulence factors and other genetic material between bacterial cells. However, temperate phages can be engineered towards bactericidal activity and these synthetic phages are much less likely to cause potential immunogenic side effects from rapid cell death and LPS release of bacterial hosts as observed with lytic cycles. For instance, M13 and Pf3 filamentous phages engineered to express BglII restriction enzyme, lambda phage S holin protein, or a catabolite gene activator protein were all successfully deployed against *E. coli* and *Pseudomonas aeruginosa* with no associated release of LPS[21]. We know that with synthetic phages, host specificity is not a limiting factor where native infectivity can be disrupted and re-targeted for the host of choice, reducing the burden of discovering the pharmacokinetics of specific phage variant for every disease target. Furthermore, phage resistance by bacterial hosts is usually driven by evolution of the surface viral receptor, and pressure for these mutations appear to be avoided by phage cocktails, where targeting of independent infection and cell killing pathways is achieved[82]. Such reductions of bacterial evolution pressure though multivalent therapeutic strategy is easily realized with synthetic, modular phages. To increase potency of natural phages, companies such as Locus Biosciences are currently engineering natural phage variants to code for CRISPR-Cas3 capable of shredding the bacterial DNA. Other such additional therapeutic actors delivered encoded within the phage genome is likely to play a big role in the future of microbial disease treatments with phages.

For our phage of interest, the human administration experience stems from early phage library panning work. Cancer patients were given intravenous phage peptide or scFv library infusions of 1e11 pfu/kg up to 3 times during the study window of 10 days[83,84]. Tumor biopsies were analyzed for tumor homing peptide/scFv variants and isolated for further studies. The experience in patients here established the safety of M13 administration and the weak anti-phageIgG response profile tracked over 75 days of the study. Other temperate phages of the Inoviridae family such as Pf phages have also been evaluated in patients with chronic *Pseudomonas aeruginosa* wound infections and chronic lung infections associated with cystic fibrosis[85].

Paradoxically, wound healing delay observed in these cases were associated with the immunosuppressive effect of temperate phage internalization, with reduced TNF-alpha and other chemokine and cytokine production by immune cells[85-88]. Similarly, study of the MyD88 and TLR9 immune mounting pathways for wildtype M13 inoculation of mice 97 days apart revealed a paradoxical down-regulating effect of the TLR9 on the IgG reponses[63]. Research around the human phage-ome and evolution of the human micro-biome has also recently highlighted the far reaching distribution of phages across the various organs and bloodstream[89-93]. It is estimated that 31e9 phage particles are naturally transcytosed across the epithelial cell layers of the gut each day[94]. The ubiquitous nature of phage particles is confirmed by new sequencing of human clinical samples as well as observed in library panning experiments where tissue specific phage variants are detected in difficult to reach ecosystems such as the CNS parenchyma[21,82,95]. While individual phage type and characteristics determine the likely immunologic outcome of phage clinical administration and potential therapeutic loss from repeat exposures (antibody development and rapid clearance), the field has more recently hypothesized the likely immune modulating role of phage particles that result in strong human tolerance[91,96]. Ultimately, the implication of systemic and sustained phage exposure in human patients requires extensive exploration. Pre-existing immunity, if any, need also be understood as well. Though infusion safety is better understood, the clearance, neutralizing antibody persistence, and tolerogenic profile of repeat vaccination with phage remains unknown for most phage administration route and phage variant combinations including that of M13.

Overall, the clearance of phage is driven by anti-phage capsid antibodies in human patients. Wildtype phages are generally cleared within hours to the liver, spleen, and kidneys (reticuloendothelial system, RES). Case in point, phage blood circulation in X-linked agammaglobulinemia patients can be tracked up to 7 weeks post exposure, while healthy subjects are able to mount anti-phage IgGs to eliminate phage from circulation[97]. Hence, evasion of the anti-phage sera is a parameter for synthetic phage design that may be essential for improved therapeutic effect during the infusion window. Increased circulation time or ability to minimize opsonization by anti-phage IgG would drive greater accumulation to the disease site or bacterial host population. M13 phages have been engineered for less immunogenic variants, for cloaking from the anti-capsid neutralizing antibodies, as well as for increased blood circulation. Antibodies are mounted against 3 factors on the phage coat. These include the n-terminal 12 residues of the p8, the n-terminal N1 and N2 domains of the p3[21]. These immunodominant residues can be altered or eliminated from the phage surface such as in the case of p3 to create a truncated p3 variant that lack the N1 and N2 domain. This results in a non-infective phage that has a much-reduced antibody mounting ability in mice[98]. On the other hand, charge modifying AKAS display (SEQ ID NO: 140) on the p8 surface appears to confer antibody evading abilities to M13 particles[99]. Finally, blood circulation may also be raised through library searches for long circulating species, these are often described to have interaction with platelets that helped prolong the residence time in the circulation[100]. These strategies for working with the immune response expected from phage administration in the clinical translation underline the advantage of M13 as a foundational platform for synthetic phage particles, easily designed for the specifications required.

The renewed interest in phage antimicrobials have led to the establishment of a variety of companies focused on the large-scale manufacture of phage for agricultural and food usage. Through their efforts, phage cocktails use in food production has been approved by the FDA in 2006[101]. Companies such as PhageGuard, Intralytix, FINK Tec are all operating in this arena and have in recent years expanded their pipelines for phage products intended for human therapeutic use as well. Clinical application of phages hence benefits from already existing industry experience with large batch phage production not limited to 10,000 L[74]. Due the intrinsic bacterial cell production of phages, the cost of phage production is exceptionally economical and efficient. The M13 lysogenic, extrusion assembly into the media supernatant is an extremely expedient for the separation and purification of the particles through centrifugation, precipitation, and filtration methods. Unlike many lytic or non-secreted biologics, cell lysis is unnecessary in M13 processing. The large-scale manufacturing potential of M13 has also been a driving factor the popularity of the phage technology in materials applications where many grams of phage templates are necessary for bulk synthesis. Still, the primary concern for human application of M13 remains the purification requirements to reduce bacterial cell contaminants. Any LPS embedded on the phage coat is a major concern for adverse effects. Simple preparations of filamentous phage are reported to contain endotoxin units (EU) in the range of 10e2 to 10e4 per ml[102,103]. Additional, purification through detergent washing, polymyxin chromatography, and size exclusion chromatography have been shown to achieve levels below 1 EU/ml, which is well below the FDA limit of 5 EU/kg body weight/dose[21]. Lastly, highly engineered phage variants may suffer from yield, but given the already high titers observed (1e14 to 1e15 particles per L), even 90% reductions due to difficulty of clone assembly are able to be tolerated for most applications. IOL batches of M13 phage particle production would yield enough phage for single patient dosing in almost every case.

1-5 Phage DNA Technologies and Gene Therapy

Phage therapeutics industry leaders, such as BiomX, Enbiotix, EligoBio to name a few, are harnessing not only the mutable phage coat but are also heavily engineering the packaged genetic information to build the new wave of clinical phage products. While the phage particle has been explored with much interest for its surface modifications, the genetic load of the phage has not often been considered outside its usefulness in sourcing ssDNA material and in barcoding libraries. The incorporation of novel antimicrobial protein sequences in antimicrobial phage therapy particles has highlighted the opportunity for engineering the phage genome for gene therapy purposes. M13 phages are especially translatable to delivery of transgene cassettes as the topology and functions of the M13 genome and its replication sites are well characterized and have already been successfully employed in phagemid systems that ensure packaging of a target DNA sequence completely independent from the assembly protein sequences. Designer sequences comprised with a M13 f1 origin region are routinely packaged within filamentous phage bodies by employing helper plasmids, helper phagemids, helper phages, and helper cells[104].

Moving beyond the natural target microbial targets of phage, the highly engineered and synthetic phages of the future are also contenders for gene therapy in mammalian cells. The field has explored already the broad penetrance, re-targetability, and tolerance of M13 phage-based technologies in animal and human tissues. The main hurdle to the transgene cassette delivery with M13 phage-based particles is the natural lack of a cellular trafficking mechanism of the phage virion. Unlike popular mammalian viral vehicle for gene delivery, such as AAV, adenovirus or lentivirus, the capsid of the M13 phage is not evolved for mammalian cell infection. In spite of this, the extensive techniques available from the learning of phage display and directed evolution of phage libraries may be easily applied to optimize or rationally design for M13 phage coats that maximize for the mammalian cell penetrance and subsequent nuclear delivery of the cssDNA cargo.

The idea of phage packaged transgene cassette delivery and expression in mammalian systems has been tentatively explored in the academic setting over the last 20 years with major breakthroughs recently demonstrated by the Hajitou Lab at Imperial College. Some of the first attempts at characterizing the expression of M13 phage cssDNA in mammalian cell lines yielded 4-10% transduction rates. Andrew Baird and David Larocca led efforts in FGF2, transferrin, and EGF fusion targeted M13 phage delivery of reporter genes in the early 2000s. Various other p3 fusion targeting were similarly shown with anti-CD30 scFv-phage transduction of CD30 positive Hodgkin-lymphoma cells, anti-ErbB2 scFV-phage transduction of SKBR3 cells, adenovirus penton protein fused phage transduction and RGD4C fused phage transduction across a range of integrin type (integrin $\alpha v\beta 3$) specific cell lines[105-110]. These earlier studies validated the favorable internalization as well as the specificity of uptake of targeted M13 phages by mammalian cells. Though targeted phage particles could be internalized efficiently, the transduction rates remained low. Treatment with genotoxic and proteasome inhibiting reagents could raise the percent transduction expected from phage particles to 30-45%, which confirmed the suspected major loss of the internalized phages to the endo-lysosomal degradation pathway[106,111-113]. Cationic wrapping of the phage particles to induce endosomal escape were shown to boost phage transduction rates to over 60%[47,48,114]. Additional design features such as incorporation of AAV inspired inverted terminal repeats (ITRs) flanks and promoter specificity to the transgene design were also shown to improve on the gene expression and durability[110,115]. Such targeted phage gene therapy particles have been determined to have complete curative ability in mouse and canine tumor models, where suicide genes such as TNF-alpha were robustly expressed at the tumor site and lead to tumor reduction and prolonged survival of the animal group[116-121]. Rational design of phage p8 and p3 capsid inserts to enhance phage particle endosomal escape and nuclear localization have been the latest in the development of such M13 based gene delivery particles[99]. The design of a M13 phage-based platform for gene delivery is likely to continue to evolve as the parameter space across all capsids is yet to be optimized for the challenge of mammalian cell trafficking.

The cssDNA of phage has been valuable source of ssDNA material in sequencing and DNA topology research. More currently, the growth of DNA technologies has fueled the demand for easy and inexpensive DNA manufacturing tools. The almost all non-phage methods used in ssDNA synthesis use purified enzymes or deoxynucleotides and tend to be limited to the μg to mg scale[122]. On the other hand, the use of M13 ssDNA in the production of bulk DNA origami materials has led to the optimization of M13 DNA extraction protocols as well as DNA packaging protocols[122,123]. Bioreactors able to produce gram scale of ssDNA phage extracts form single liter fermentation are under development[122]. M13 phagemid based DNA production inherently maximizes for the accuracy of the desired DNA sequence with lengths over 20 kbs and ensures high purity and yields. The cost of M13 cssDNA production is directly translatable from phage production with the minor extra burden of phage lysis and DNA precipitation processing. Furthermore, as has been proven by M13 phage gene delivery development, the cssDNA of phages are transcriptionally active and highly engineerable for add-on features impactful towards gene expression such as ITRs and promoters[115]. Given the manufacturing, size, and precision advantages of M13 cssDNA, phage DNA extracts could serve as a novel DNA source for non-phage derived gene delivery solutions such as LNPs and VLPs.

1-6 Overview and Objectives

Figures 3A, 3B, 3C:
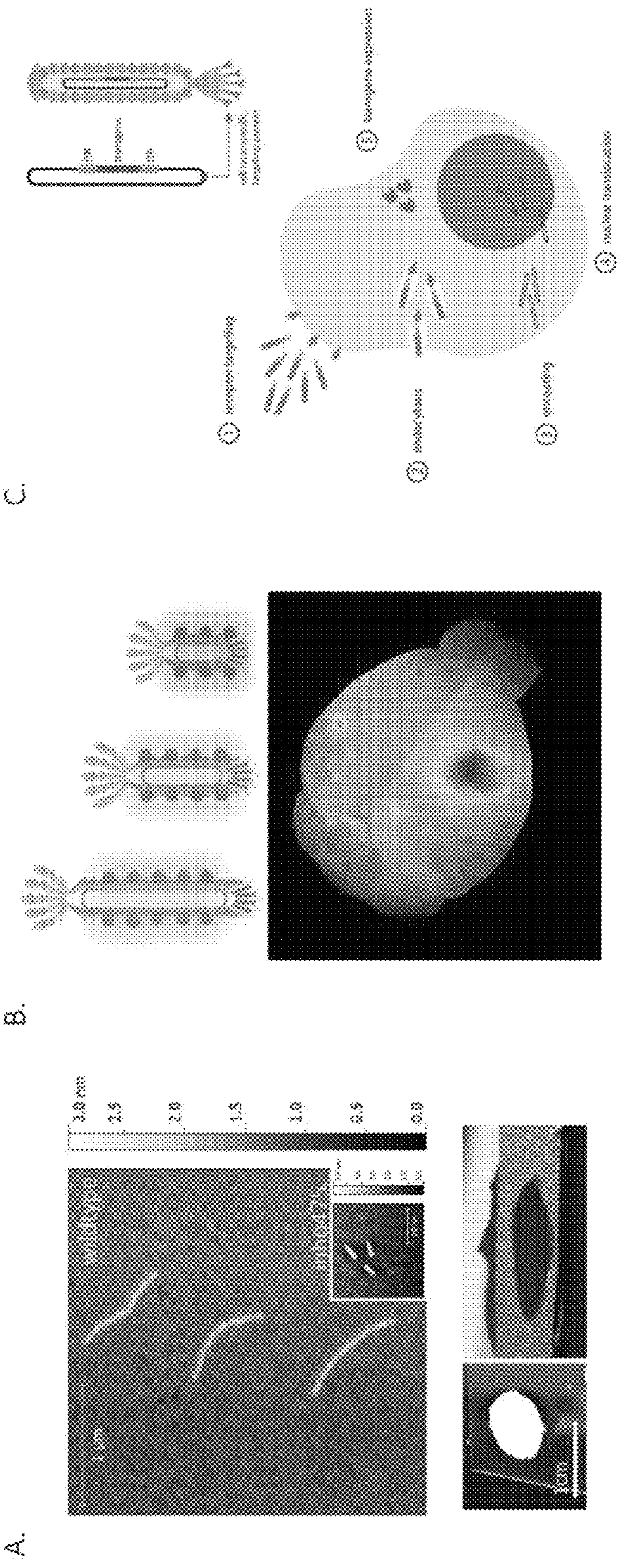
FIG. 3A-3C show various embodiments.

The applications of M13 phage described in the field share a common reliance on the uniquely engineerable physicochemical and biological properties of the phage. (FIG. 3A-3C.) M13's ability to display a wide range of biomolecules across all its capsid proteins and its robustness to manipulations of the phage genome and assembly process has made the filamentous phage a popular industry workhorse. Yet, the development of M13 phage-based therapeutics is only just gaining traction. To further validate the applicability of phage derived particles (PDPs) to nanomedicine and medical diagnostics, a novel chlorotoxin-p3 fusion phage nanocarrier is explored for targeted brain tumor imaging. This work is then expanded by optimizing for phage brain tissue trafficking based on the phage shuttle size. An innovative phage production system, termed 'inho', designed for tight control over phage length and phage cssDNA sequence is described. Additionally, electrode materials produced from varying inho-phage lengths is analyzed for enhanced battery performance. Finally, the unique inho system is used to access the feasibility of robust gene expression in mammalian hosts using surface engineered inho phage derived particles.

In Section 2, the functional elements of the filamentous phage replication origin, f1, is engineered to produce phages with less than ~200 bases of M13 genomic sequence. This inho system is able to tune the length of phage nanoparticles from 25 nm to over 2500 nm at high yield, homogeneous batches. The Section contains as well an exploration of the impact of various inholengths on the morphology of foams formed from the phage particles. We produce battery cathodes composed with manganese-oxide active material deposited on phage-nickel-nanofoamsto test the phage template strut length influence on battery capacity.

In Section 3, chlorotoxin fusion phage is produced for targeted imaging of GBM22 xenograft glioblastoma in mice. Indocyanine green (ICG) dye surface functionalization of phage particles is used enable imaging in the second window near infrared (SWIR) with clear signal through the skull and scalp. The targeted phage nanocarrier extends the half-life of the small molecule dye by 30-fold and demonstrates the vastly reduced material dosing required when using a target specific phage carrier. Targeted inho phages of 50 nm, 100 nm, and 300 nm are introduced and establish the enhanced specificity and accumulation profile possible with a targeting moiety on shorter phages.

In Section 4, the inho system is engineered to produce gene delivery phages. An inho vector with an ITR-flanked, AAV-like transgene cassette is produced. An accompanying capsid helper vector is engineering to allow for display of at least four functional moieties. Surface modifications that would drive gene expression from phage delivery is discussed, and cationic polymer wrapping and cationic polyamino acids conjugation on targeted phage is shown to transduce 20-30% of cells within 72 hrs of in-vitro incubation.

The primary conclusions of all Sections are presented in Section 5, along with recommendations for future work based on this thesis. Briefly, the inho phagemid is discussed for the creation of short phage library for panning and peptide discovery. Inho struts are considered for highly controlled protein assemblies. To improve on the chlorotoxin phage diagnostic potential, a number of imaging agents in the second window near infrared (NR-II) optical window may be loaded on the phage particle for optimized in-vivo results. Carbon nanotubes of varying formulations are explored in this aspect. A treatment course harnessing the tumor suppressive properties of chlorotoxin and various small molecule chemotherapies is suggested for combinational therapy with a multi-functionalized phage carrier. A gene therapy component is also suggested with combination with surface loading. Finally, the potential for directed evolution of the phage capsids for enhanced mammalian cell transduction is described with focus on internalization rate dynamics, endosomal escape, and proteasome bypassing. The production of inho cssDNA transgene cassettes with functional elements to drive high gene expression is discussed and the potential creation of cdsDNA is explained. With over 20 kb capacity, the inho transgene cassettes are considered highly useful as a genetic cargo source in PDP, VLP, LNP, and exosome applications.

2-1 Phage Assembly

Filamentous bacteriophages such as M13 are a family of single-stranded DNA (ssDNA) containing viruses that infect only gram-negative bacteria. M13 falls under the Ff class of viruses which infect host cells via the F conjugative pilus on the surface of male *E. Coli*. Ff viruses are parasitic rather than lytic in nature with the infected cells continuing to divide and grow, though at a reduced rate. Phage proteins make up 1-5% of total protein synthesis in the cells and this metabolic load can reduce growth by up to 50%. However, the phage reproduction cycle is very rapid where the first secretion of phage progeny appears within 15-20 minutes of infection, and M13 produces up to 2000 viral progeny per cell over its cell doubling time. Upon infection, the phage cssDNA strand (+) is translocated to the cytoplasm where host enzymes synthesize the complementary strand (−), forming the double stranded parental or replicative DNA (rfDNA). The rfDNA is replicated to about 100 copies per bacterial cell and acts as the template for synthesis of cssDNA genomes for encapsulation. The circular supercoiled ssDNA occupies the axis of the M13 phage for almost its entire length. The size and base-pair distribution of this enclosed genome dictates the length of the phage. The wildtype M13 bacteriophages have a long, flexible rod-like structure with a diameter of about 5 to 6 nm and a length of 880 nm.

Figure 4:
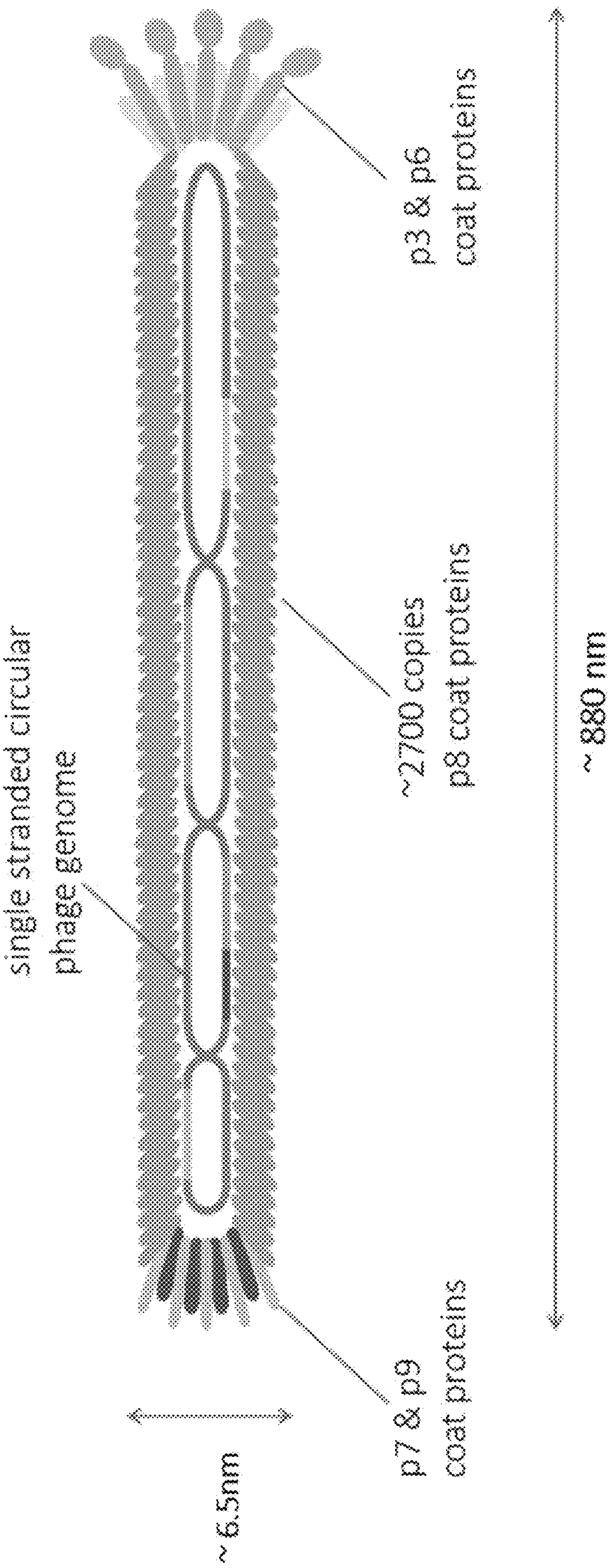
FIG. 4 depicts a structure of a wildtype M13 bacteriophage (5 capsid proteins and anaxial cssDNA encoding the assembly and capsid proteins).

The wildtype M13 phage genome (6407 nucleotides) encodes a total of 11 proteins-five of which are the main phage structural proteins. The five structural proteins-p3, p6, p7, p8, p9-make up the body of the M13 phage and are inserted into the inner host cell membrane prior to assembly of the phage. p1, p11, and p4 are the morphological proteins that locate on the inner and outer membrane of the bacteria and coordinate to form a 7 nm exit pore structure through which the assembling viral particle is extruded from the cell. Replication proteins-p2 and p10-facilitate phage DNA synthesis while DNA binding protein, p5, localizes the intracellularcss DNA. (See FIG. 4.)

The distal end of the M13 phage is the part of the phage that is assembled first and has approximately 5 copies of the two coat proteins p7 and p9. The p9 protein interacts with the negatively charged hairpin loop known as packaging signal sequence (PS) of the phage cssDNA and plays a major role in the initiation of assembly. The PS tags viral cssDNA for encapsulation. Along the length of the phage, approximately 2700 copies of the p8 protein are required to fully coat the M13 virion cssDNA during extrusion/elongation. As a result, the concentration of p8 proteins in the inner cell membrane is extremely high. The p8 is α-helical in structure and wraps around the virion axis in a right-handed helical sense. The proximal end of the phage consists of approximately five copies of p3 and p6 each. The p3 protein is the largest and most complex component of the M13 structure and is extruded last during the assembly process. The amino terminus of the p3 was the first location used for the display of proteins and peptides on M13.

The p3 protein is required for both termination of phage secretion and is also necessary for host binding during infection. Non-infectious, multi-length polyphage is produced in the absence of p3 capping protein resulting from the encapsulation of multiple phage cssDNA units.

Overall, the M13 bacteriophage exhibits nonlytic infection, simultaneous single and double stranded viral DNA with little size constraints on DNA length (up to 20 kb), and very high titer capacity (1e14 to 1e15 pfu/L of culture). All of these characteristics have made the M13 a very popular tool for biomolecular applications. Moreover, the assembly of the M13 is now well enough understood to allow for manipulations that have had significant impact on the ease of cssDNA isolation and *E. coli* infection/transformation of foreign sequences carried by phage.

Phagemid systems and helper phage systems have borrowed or altered M13 f1 origins of replication that allow for the packaging of foreign sequences within a phage body. Generally, a template phagemid with an f1 origin insert is co-infected with a helper phage/plasmid that will express all the necessary phage assembly proteins to yield phages carrying the sequence from the template phagemid. These phage particles can be produced in bacterial culture at high yields and purified for acquisition of desired cssDNA sequences and structures as is done in the field of DNA origami. Outside of phage based production, single strand DNA synthesis at scale remains challenging as ssDNA are derived from double-stranded DNA (dsDNA) sources via degradation of one of the two strands, and there are major limitations to the in-vitro enzymatic processing here that hinder sequence length and the final yield of ssDNA[1,2]. Conversely, the research interest in ssDNA purification and engineering methods have been instrumental in expanding the assembly possibilities of M13.

Though successful in producing ssDNA scaffolds, we should note that while phages produced in a phagemid system no longer contain genomic sequence outside of the M13 f1 origin (~381 bases), the system may also package elements commonly necessary to plasmid production and transformation such as a host origin (i.e ColE1) and antibiotic resistance. These fragments take up 2-3 kb of nucleotides of real estate in the phage cssDNA which restrain the ultimate DNA packaging capacity as well as the minimal size achievable by phage particles.

2-1 Inho Phage Assembly

Due to their proven utility in both biomedical and biomaterials application, filamentous phages of varying particle lengths are of particular curiosity in research. Length control is a parameter of M13 production which can provide optimization value to any filamentous phage-based technology. As we know, the length of the circular ssDNA packaged by M13 correlates with the size of the virion. Hence, we can control the length (or the number of p8 coat) of the M13 phage in a linear fashion by manipulating the length of the circular ssDNA packaged during the M13 assembly process.

To manipulate cssDNA size, deleting unnecessary regions of the M13 phage genome does not significantly reduce the length as most of the M13 genomic DNA is essential for assembly. However, as discussed, helper phagemid systems allow packaging of a secondary target vector and can be used to create phages containing less than the genomic 6407 nucleotides. Yet, the required presence of the M13 f1 origin, taking at least 381 bases, as well as the need for antibiotic resistance and bacterial replication origins constrain the minimal size of phage produced in such a way to 400-500 nm in length. To overcome this limitation, preceding work by Specthrie et al. created a phagemid that generated a minimal packaging construct by flanking the replication start/stop components of the f1 origin on either end of the desired sequence. They were able to use an f1 replication origin, packaging signal, and a modified f1-ori, termed f1-oriΔ29, that acts to terminate replication to package ultra short fragments of 292 bases. In this manner, Specthrie et al. produced a mixed population of full length phage and microphage that are 50 nm in length (though only 1-3% by mass of total population)[3-5]. In this way, groups have shown that the phage can be shortened to as little as 50 nm (~95 p8 copies)[4,5]. However, the f1-ori/f1-oriΔ29 construct achieve very low yields of the intended cssDNA products and unintended longer"genomes" can be produced from the phagemid content starting at f1-oriΔ29 and ending at f1-ori in the reverse of the intended sectioning. Phages produced from the f1-ori/f1-oriΔ29 system require an additional purification step to ensure uniform length phage batches, thus compromising the inherent scalability of the phage amplification process for downstream materials applications. Learning from the experience of isolating the essential functions of the f1 origin sequence, we have expanded on the previous work by creating our own short f1 fragments that guarantee high yield, homogenous distribution of phage products and phage cssDNA lengths as low as 135 bases.

Figure 10:
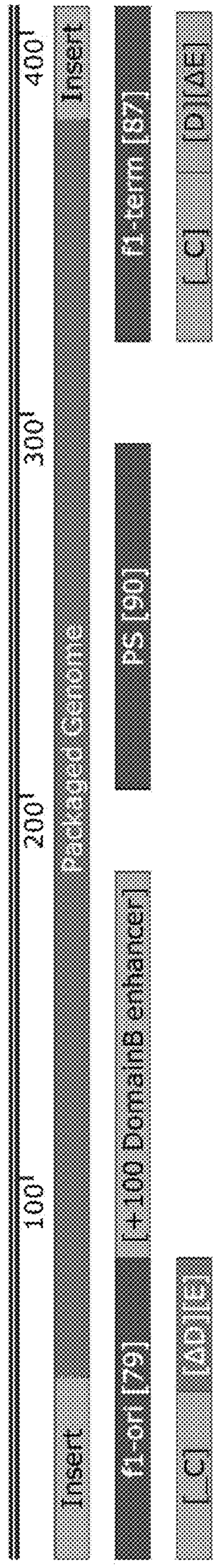
FIG. 10 shows an embodiment of a constructed f1-ori and f1-term flank chosen DNA for packaging.

We have created a new phagemid, termed "inho," that generate package-able viral circular ssDNA with chosen sizes (i.e. 100s to 1000s base-pairs), which are much shorter than the 6407 nucleotides observed in wildtype M13 (~880 nm in length). These package-able genomes can be of varying lengths and contain the phage packaging signal and newly modified f1 origin and modified f1 termination of replication but none of the phage protein genes or any plasmid elements. In effect, sequences flanked by the novel f1-on and f1-term set produces cssDNA, of a deliberate length and sequence, and can also contain the signal sequence (PS) for optimized trafficking of the cssDNA for membrane extrusion and assembly into phage particles (FIG. 10). In the absence of M13 protein coding in our packaged inho constructs, we constructed a second plasmid, RM13-f1, which expresses all essential phage assembly components but itself lacks a functional f1 replication origin. Transformation of *E. coli* with the protein genome will lead to kanamycin resistance and to the production of the M13 assembly and coating proteins but no extrusion of phage will take place without properly labeled cssDNA available to package. Only in the presence of both engineered plasmids, inho and RM13-f1, is phage production observed (FIG. 10), where inho cssDNA products are packaged by the proteins translated from the unpackaged RM13-f1 helper plasmid.

2-1-1 F1 Origin Functional Components

Figure 5:
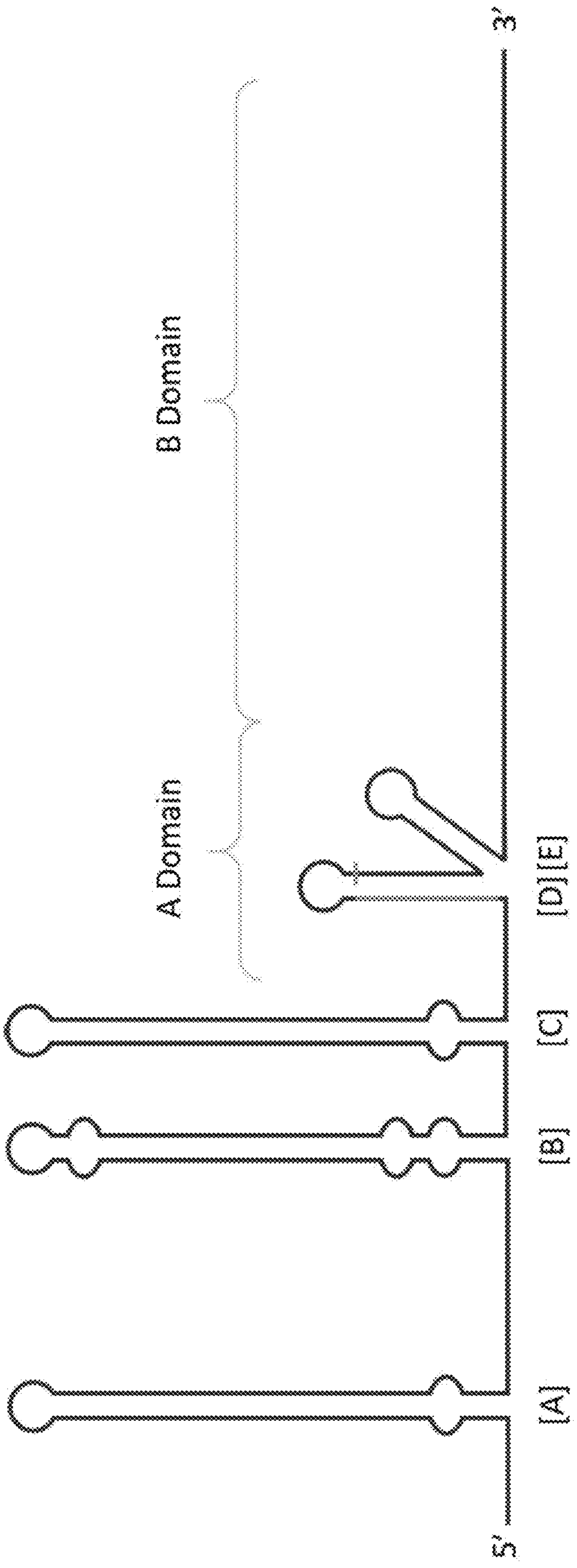
FIG. 5 depicts M13 f1 origin hairpin structures [A] through [E] and domains A and B.

The f1 origin of replication is densely populated with hairpin structures which have been mapped for specific functions in previous work[6-12]. The M13 f1 origin is represented below (FIG. 5) and the key elements are described in Table 1.

TABLE 1

M13 f1 origin hairpins and domains and their functions and features.

| Structure | Function | Features |
|---|---|---|
| Hairpin [A] | Packaging signal | |
| Hairpins [B] & [C] | Conversion of (+) strand to rfDNA and (−) strand origin | |
| Hairpin [D] & [E] | Palindrome needed to close single strand ring. Interaction with P2 in the formation or initiation movement of the replication fork that follow nicking | First 10 nucleotides (AGTCCACGTT (SEQ ID NO: 7) shown in pink) only required for termination<br>Next 35 nucleotides, necessary for termination and initiation, contains the nicking site (marked by orange tick) and the 3 repeat sequences β, γ, δ |
| Domain A | (+) strand origin together with Domain B | 40 nucleotides including pins [D] and [E] |
| Domain B | Replication enhancer | Distal 100 nucleotides rich in AT |

Figure 6:
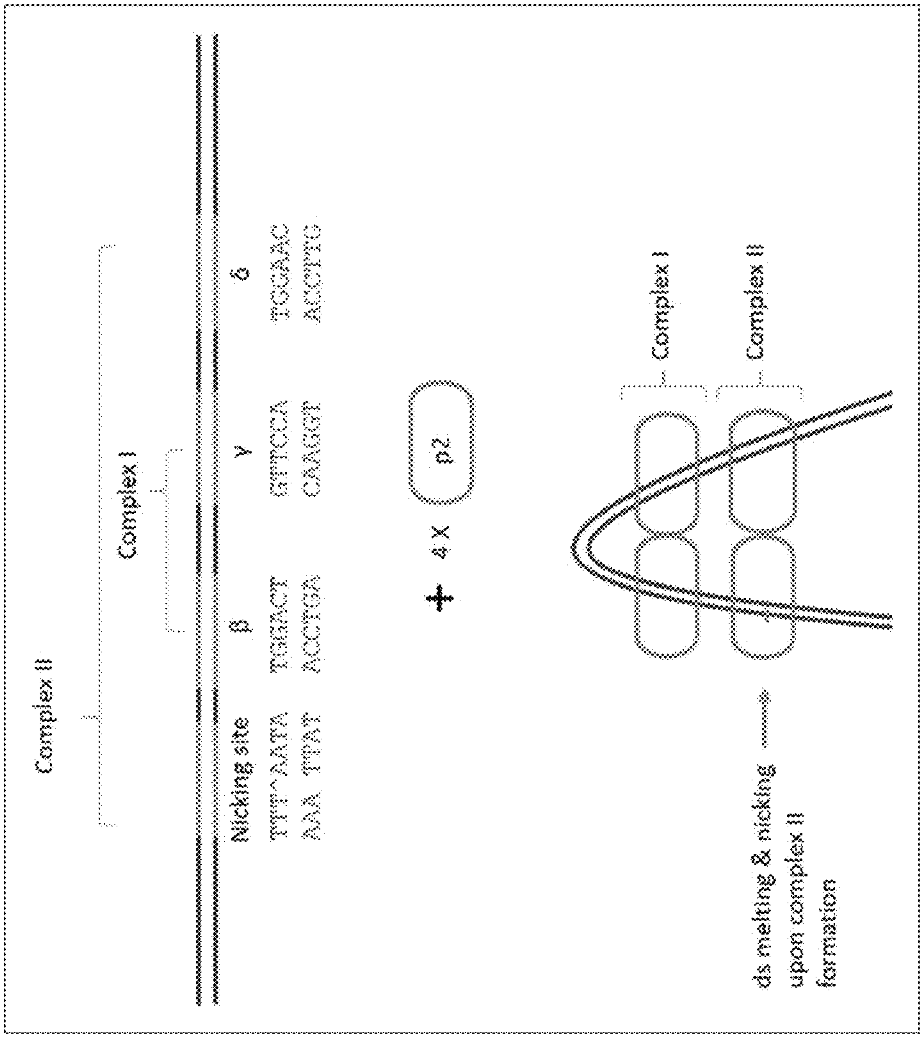
FIG. 6 depicts p2 complexes formed with β, γ, δ, and nicking locations of hairpin [D] sequence.

Of particular note is the p2 nicking site located on hairpin [D]. Here p2 forms two complexes at the nick, β, γ, and δ sites to melt the double strand to single strand, allowing for incision (FIG. 6)[7,9,12-16]. Replication can then begin on the (−) strand while the displaced (+) strand form additional rfDNA. rfDNA formation is slowed when enough p5 have been translated to fill the p5-cssDNA complexation needs and more (to set the ratio of dsDNA to cssDNA, p5 negatively regulates p2 synthesis by binding the gene 2 mRNA)[17-22]. Following complexation and nicking at hairpin [D], hairpin [E] provides the scaffolding for p2 initiated replication fork progression. On the other hand, the first section of the [D] hairpin (also the last section on the replication path) includes the short ten nucleotide sequence necessary to close the ssDNA ring and ensure termination[6]. As pictured in FIG. 2, Domain A encompassing hairpins [D] and [E] and domain B together make up the complete (+) strand origin of replication. Domain B is a replication enhancer whose removal can drop DNA replication to 3% of regular levels[7,8,23-25]. However, research has shown that replication levels sans Domain B can be rescued with addition of mutations that either enhance p2 or hyper produce p2. In one instance, the p2mp1 mutant can be used (generally found with the M13KE NEB phagemid). The [Met40→Ile] of the p2mp1 increases the cooperativity of the protein such that only repeats β and γ are necessary to form the complete nicking complexes[23,26,27]. On the other hand, to hyper produce p2, we can reduce the ability of p5 to repress p2 mRNA. This can be done by either a mutation within the p5 protein or mutation within the p2 mRNA leader sequence. Examples include the [Arg214→Cys] mutation inp5 or a [G→T] mutation within the p2 sequence leader TTTTTGGGGCTTTT (SEQ ID NO: 8)[25,28]. Both methods lead to tenfold increase in p2 concentration[23,25,27,28].

2-1-2 Inho and RM13-F1 Plasmid Constructs

Figure 7:
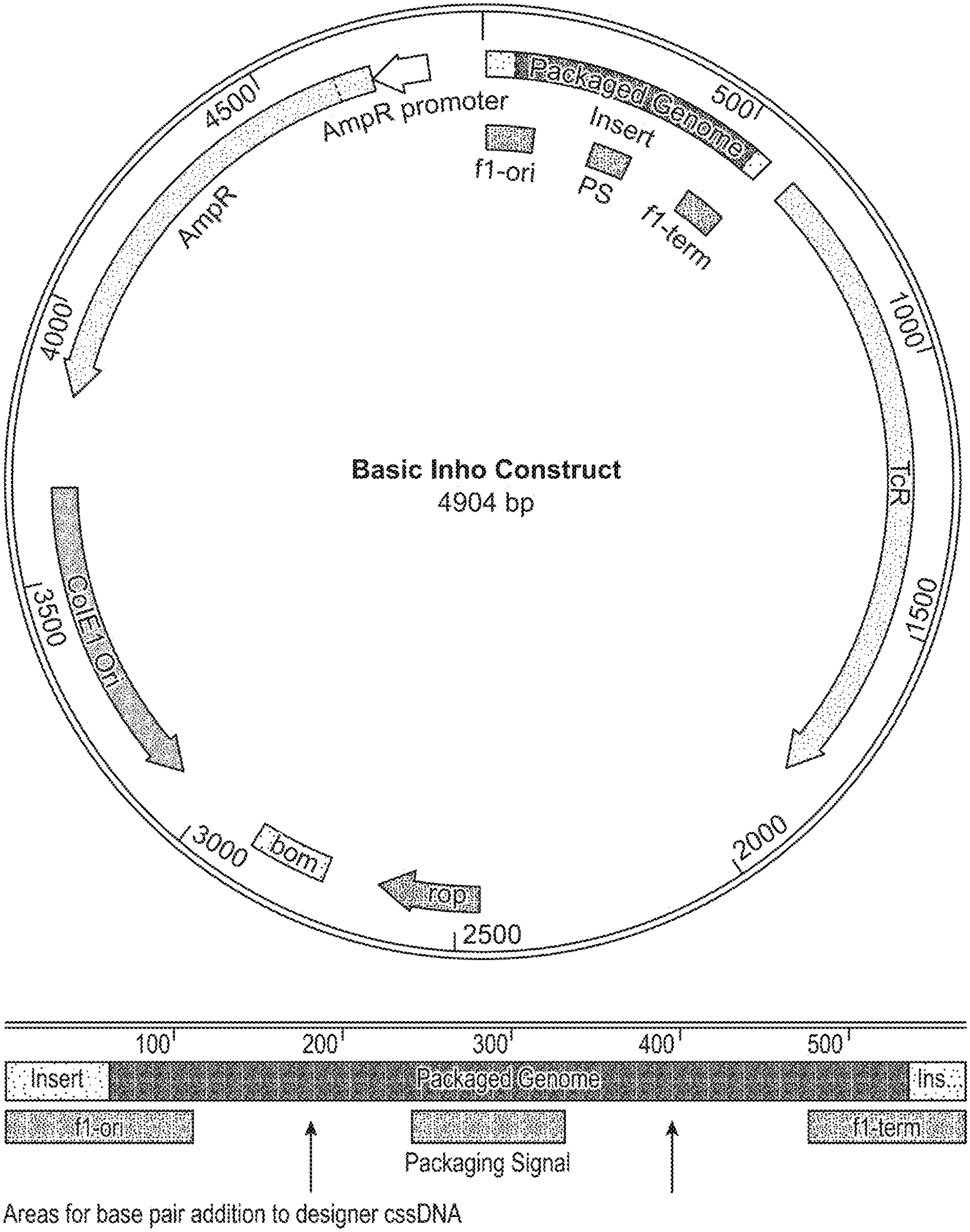
FIG. 7 shows a general map of an Inho construct.
Figure 8:
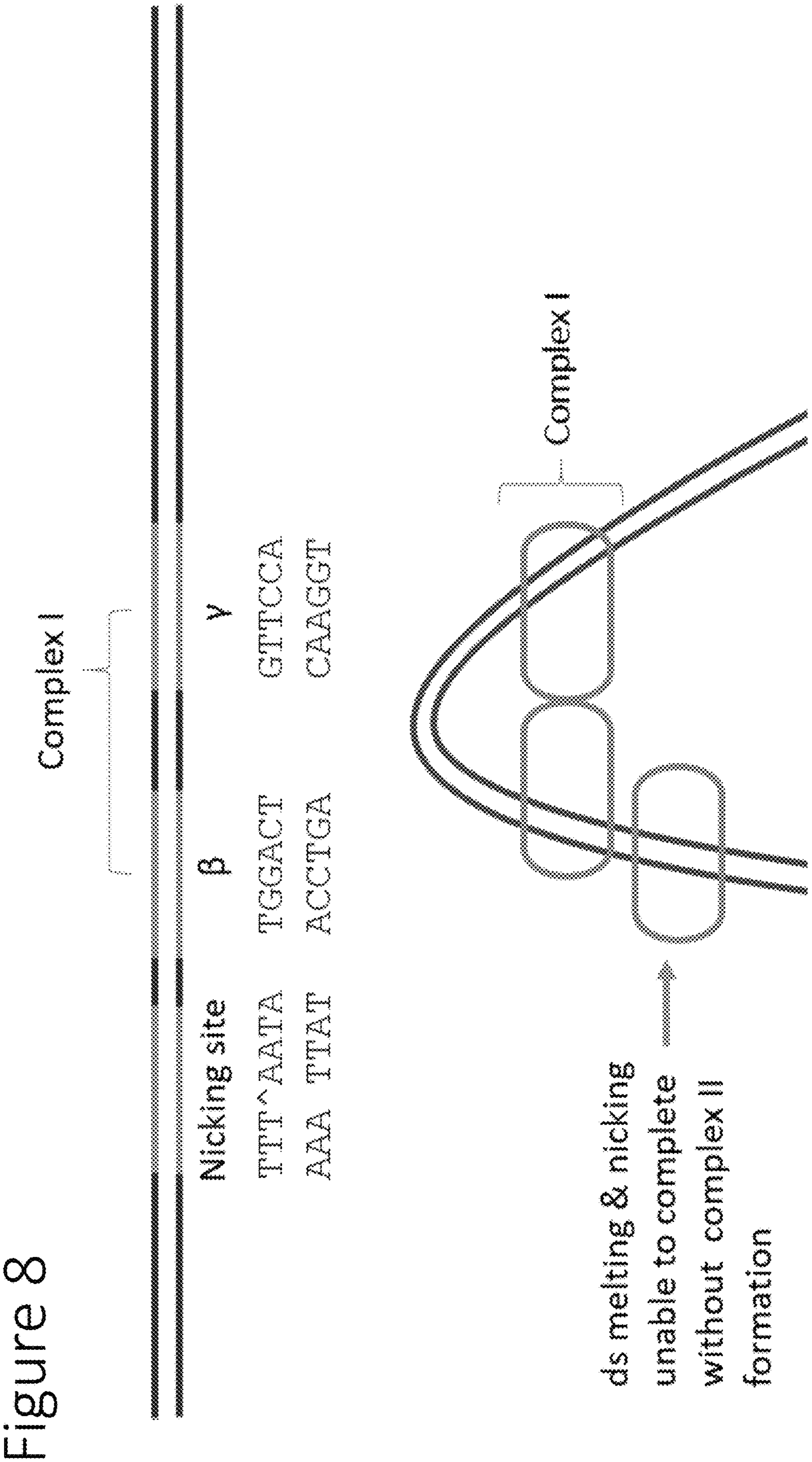
FIG. 8 depicts an example of the Complex II formation by p2 proteins disrupted by deletion of 6 landing site.

Knowing the essential sites of the (+) strand origin, we are able to engineer the [D] hairpin for the constructions of a f1-ori and a f1-term that will flank a chosen sequence for replication and circularization. This chosen sequence will have a packaging signal and contain short fragments of the f1-ori and f1-term in the final ssDNA phage product. These inho constructs reduces the number of requisite f1 origin elements to less than 200 bases, leaving almost all 20 kb of space available for designer sequences. The phagemid map in FIG. 7 gives a general outline of the inho constructs that produce our packaged ssDNA. Beyond the ampicillin and tetracycline resistance and a ColE1 plasmid origin of replication, the construct encodes an insert comprising of a modified f1-ori and f1-term and a packaging signal. The length of the final ssDNA product of an inho construct does not suffer from any extra plasmid elements, such as TcR, as only the insert portion (highlighted in green, encompassing one packaging signal) flanked by our new f1-ori an f1-term is replicated for (+) synthesis and circularized.

The f1-ori was constructed between a minor fragment of hairpin [C] and modified hairpins [D] and [E] where the 10-nucleotide region (AGTCCACGTT (SEQ ID NO: 7)) necessary for termination of replication has been removed from hairpin [D]. The f1-term was constructed from a minor fragment of hairpin [C] and hairpins [D] and [E] where the complex forming site 6 (TGGAAC) has been removed from hairpin [E]. The removal of 10 bases from [D] ensures the new f1-ori functions only as an initiator of replication. Likewise, the removal of the 6 site ensures that p2 is unable to complex at the new f1-term and that the term sequence only functions as a point of replication closure. A small section of [C] was included in the cloning of the [D] and [E] regions. Domain B may be included at the tail of the new f1-ori as per the requirements of the plasmid system. As previously described, if p2 hyper producing mutations are also utilized in the helper phage protein plasmid, the domain B bases are no longer necessary to guarantee high yield of cssDNA. It is important to note that p2 enhancing mutations that improve protein cooperativity is not compatible with the inho system as the f1-term function relies on the inability of the p2 to form the second complex needed for nicking.

The linear view (FIG. 10) further illustrates the key regions of code that facilitate the production of small package-able cssDNA from our inserts. Note that the final strand replicated for packaging includes the full DNA packaging signal but not the full f1 origin or full f1 termination regions. The size of the cssDNA is manipulated by the addition of base pairs via standard cloning techniques (i.e. Gibson) between either the f1 origin and the packaging signal or packaging signal and the f1 termination region. Exact sequences of our f1-ori and f1-term and PS used the inho construct outlined in FIG. 9A. And the expected packaged cssDNA sequence is outlined in FIG. 9B.

Figure 11:
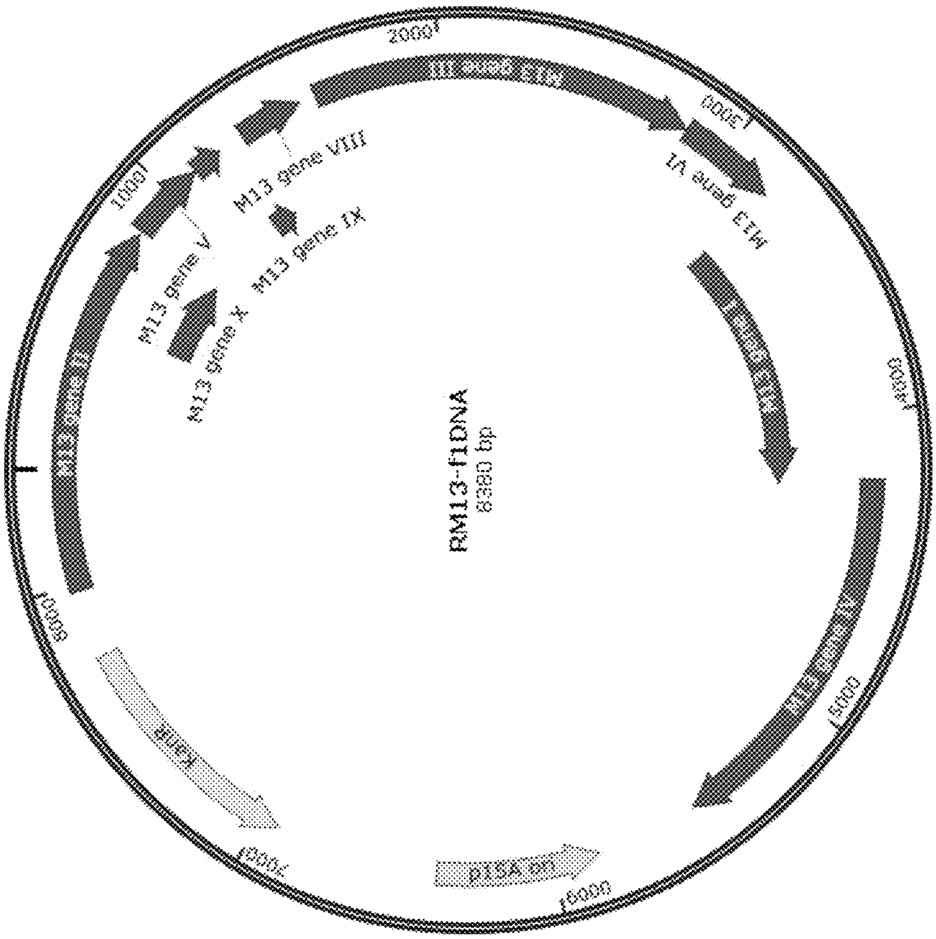
FIG. 11 depicts an embodiment of RM13-f1 lacking a functional M13 origin and requiring bacterial origin for replication. P5[Cvs21] mutant may be recommended for systems without enhancer Domain B.

The complement to the inho construct is the RM13-f1 helper plasmid which provides the coding for all the assembly and coat proteins of the bacteriophage. The key to the helper plasmid is the disruption of the f1 origin on any M13 plasmid such as M13mp18, M13K07, R408. As we will have removed the hairpins important to (−) strand synthesis and (+) strand synthesis from the M13 plasmid, the new RM1-f1 will require a bacterial replication origin such as ColE1 or p15A-ori such that it is compatible with the bacterial propagation origin of the accompanying inho construct. In our case as ColE1 is used on our inho constructs, we include a p15A origin on the RM13-f1. Contrasting to the inho ampicillin antibiotic resistance, kanamycin is also added to the RM13-f1 to ensure controlled co-transformation, plating, and amplification of the double plasmid system. Without the sequences necessary for nicking and cssDNA and rfDNA production, the RM13-f1 is solely dependent on the bacterial propagation origin and establishes a pool of dsDNA that serve as templates for translation of bacteriophage proteins. These proteins are then hijacked by the inho cssDNA in the final extrusion of phage particles. To ensure high yields of the flanked cssDNA segment, the RM13-f1 helper code for the low efficiency mutant of the rfDNA nicking protein p2[Met40] and high efficiency mutant of the cssDNA binding protein p5[Cys21]. The p5 requirements ensure that the loss of the f1 distal replication enhancing Domain B is compensated by the hyper production of p2 resulting from the p5[Cys21] mutant. If the Domain B is chosen to be included in the inho construct, then the p5 mutant is not necessary for the RM13-f1 design. (See FIG. 11.)

Figure 12:
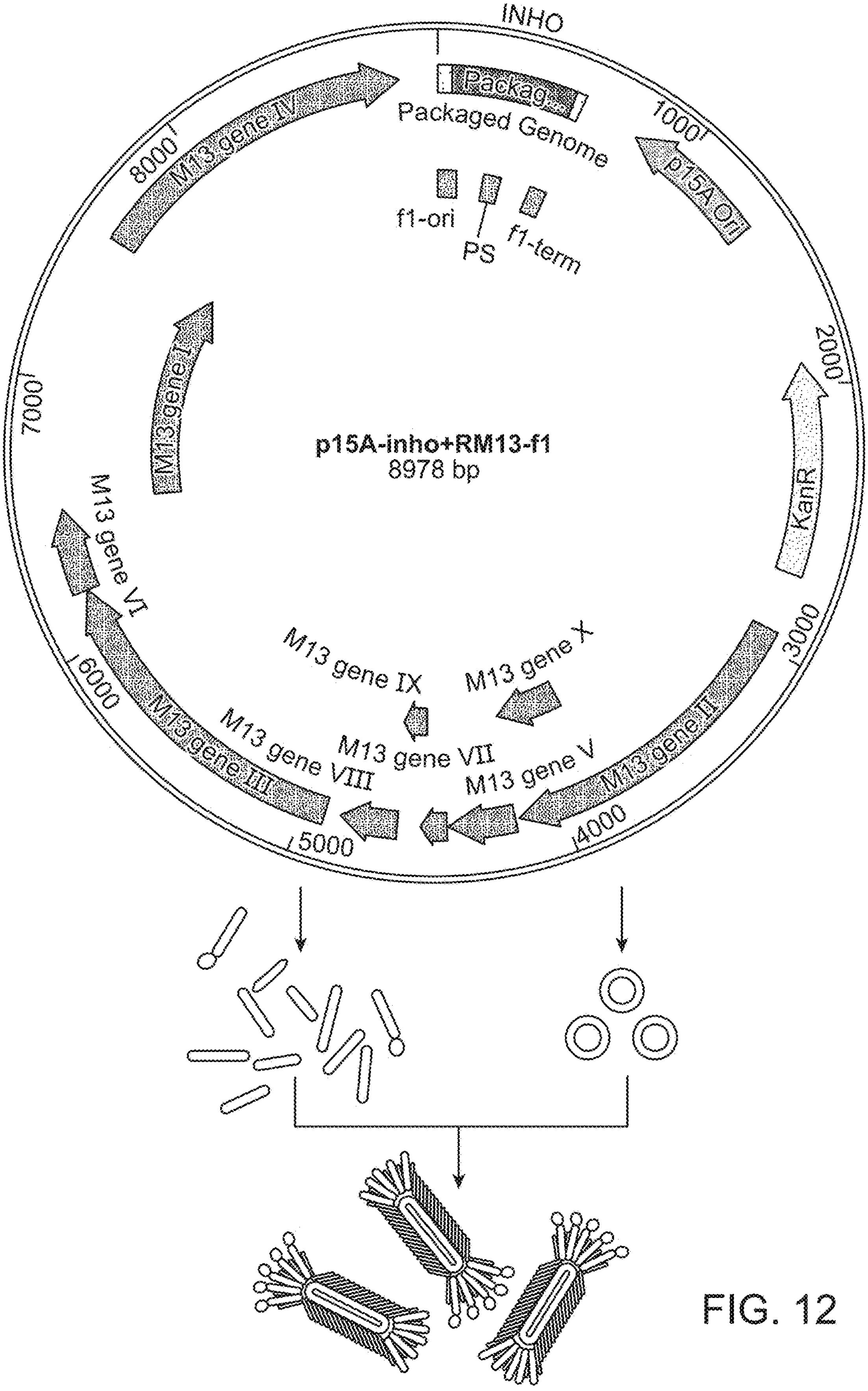
FIG. 12 depicts an example of a single vector design for inho phage production constructs.
Figure 13:
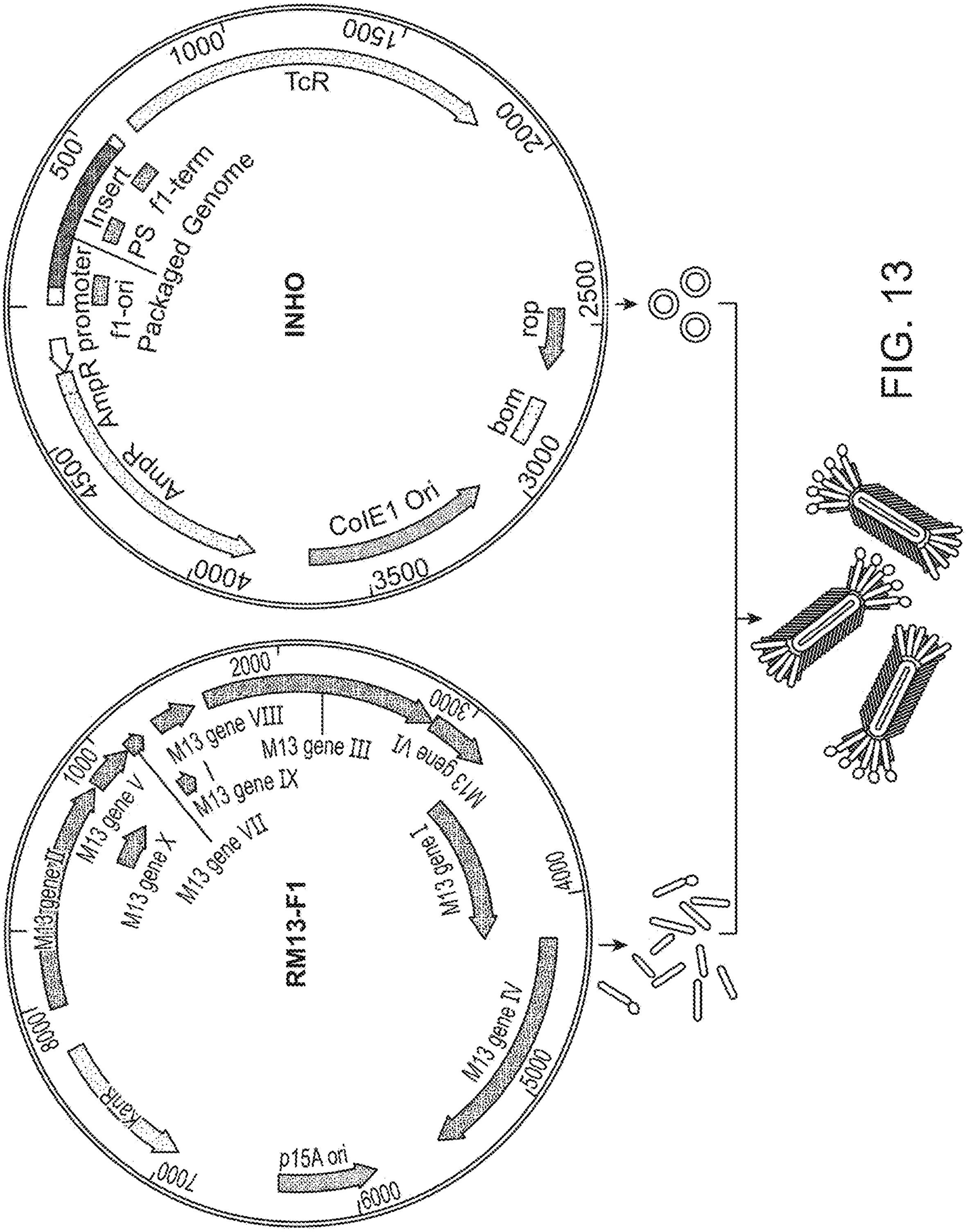
FIG. 13 shows Inho-phage production with RM13-f1 and inho cssDNA.

Additionally, the RM13-f1 and inho constructs do not necessarily require separation onto two constructs. The cssDNA producing elements of the inho can be introduced to the RM13-f1 plasmid to attain the same results as co-transformation of the two plasmids to complete assembly. This is easily achieved due to the flanking scheme of the inho that leads to cssDNA products that are completely unadulterated by any coding on the plasmid outside of the f1-ori and f1-term boundaries (FIG. 12). The combination of the protein and inho plasmids very much simplify the inho-phage assembly system and can be utilized efficiently when the preferred phage product (of known size, capsid variants parameters) is well defined and unlikely to require iterative cloning. For testing of parameters across multiple variants such as when comparing different sizes or coats, the two-plasmid system can be particularly suited to producing numerous phage lengths without requiring superfluous cloning of new vectors. For this reason, the inho phages discussed henceforth have all been produced through the co-transformation of a RM13-f1 clone and an inho clone. In this way, size and coat protein permutations are better manageable.

Inho plasmids when co-transformed with RM13-f1 plasmids coding for phage proteins produce short phage that packages the inho genomes, which control the length of the phage. The current inho cssDNA structure includes 179 original phage derived bases. This number may be even further reduced with by excising more of the [C] hairpin fragment from the f1-term design. The packaging signal region may also be wholly removed and the cssDNA production can be enough to begin p5 interaction and assembly can still take place at lower efficiencies, with only 89 prokaryotic f1 origin bases represented in the final products[28-31]. The RM13-f1 helper is equally amenable to capsid variants as any other phage vectors. The inho-RM-f1 system is capable of producing cssDNA and phages that can span the full range of phage applications already described to date (Section 1), with the slight modification of libraries requiring the randomized insert capsid gene to be present within the inho vector to ensure the genetic barcoding of the phage surface capsid of a given inho phage particle. Conclusively, with the inho construct, we have fuller control over the cssDNA content and final length of the phage particles. (See FIGS. 11 and 12.)

2-1-3 Inho-Phage Batches of Varying cssDNA Lengths

Co-transformation of an inho and the protein construct into a competent bacterial strain (XL-1, DH5a, SS320, ER2738, TG1) and overnight amplification of the co-transformed colony in ampicillin and kanamycin LB or 2×YT media provide abundant number of phages for analysis(1e13 to 1e15 phages per liter of bacterial culture). Tetracycline addition to the broth is generally not required as the bacterial culture does need to maintain f-pilus surface expression for infection. The inho system does not rely on infectivity for high yields. Using these two plasmids in concert, we can then proceed to purification of the extruded phage-inho for biomedical and biotech applications and characterization of the phage derived particles. Inho phages are pelleted from growth media solutions via standard bacterial centrifugation followed by PEG-8000/NaCl precipitation at 4° C. For shorter phages, 10% PEG-8000/NaCl is recommended over the standard 2.5% in wildtype phage preparations in order to better separate the smaller particles. Once pelleted, phage can be resuspended in subsequent cleaning buffers such as $MgCl_2$/TBS/DNaseI for digestion of all external DNA debris in the pellet. Dialysis of such samples against PBS or milli-q water for 72 hrs with frequent buffer changes also recommended prior to visualization or further processing. Tangential flow filtration at 10 kDa-300 kDa can be used to speed up the sample cleansing process and can be crucial to sample concentration when necessary. Gradient ultracentrifugation in 1.6 g/mL to 1.2 g/mL range CsCl densities is recommended for ultra-pure phage band extraction near the 1.25 g/mL to 1.3 g/mL layers. For applications in biomedical research, endotoxin content should be carefully controlled for adverse effects on animal or cell health.

Figure 14:
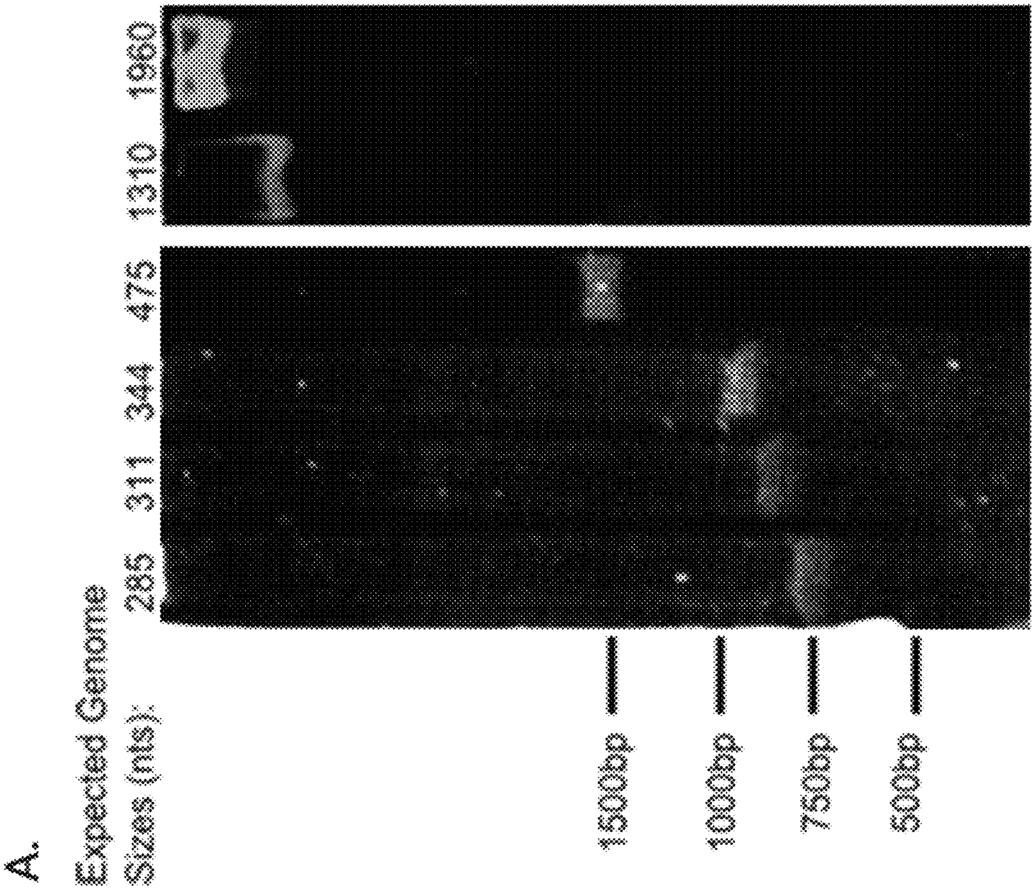
FIG. 14 shows an analysis of expected packaged genome sizes.

Testing the range of phage sizes, we began work with inho cssDNA designs of 285, 311, 344, 475, 1310, and 1960 bases in length. These DNase and dialysis purified inho samples were lysed by SDS and heat and run on a TBE-PAGE gel which was stained with SYBR-Gold. The gel shows different genome sizes for each of the inho constructs and we see the correct relative changes in cssDNA lengths (FIG. 14A). Note that the gel ladder for these runs do not necessarily reflect true lengths as the electrophoresis process is affected by the circular and single stranded nature of the phage DNA. M13 spin kits were also used to extract the inho ssDNA loops for sequencing. Verification of the packaged cssDNA code further confirms that our inho phage batches all contain the designed inho genomes.

Figure 15:
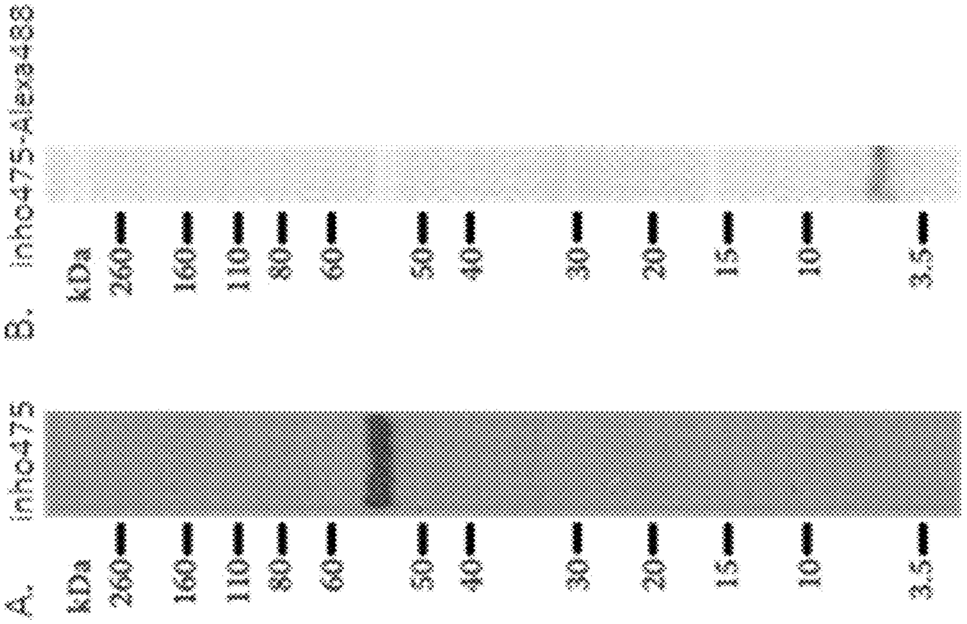
FIG. 15A-15B show staining for capsid protein p3 and coat protein p8. SDS and heat lysed inho475 phage were analyzed on a NuPAGE Noves 4-12% Bis-Tris Gel with 1%

The inho-phage samples (post SDS and heat lysing) were also run on Nu-PAGE gels for anti-p3 western blotting, (FIG. 15.) Coomassie and Ponceau staining to check for the presence of phage capsid proteins. Inho-phage samples EDC-conjugated with AlexaFluor488 was analyzed for labeled p8 proteins. As western blotting against p8 can give tentative results depending on manufacturer antibody development variances as well as due to peptide display variants which may not be bound by anti-wildtype peptide antibodies. On the other hand, anti-p3 antibodies, usually developed against the conserved C-terminal region of the p3, is reliable across phage display variants that present on the N-termini of the p3 proteins. P3 at 406 amino acids and 42,522 MW runs at between 60 to 50 kDa on Nu-PAGE 4-12% gel, while P8 coat protein 50 amino acids and 5,235 MW appear between 10 and 3.5 kDa (Table SI). Phage coat protein p8 and capping protein p3 are both present as expected in our samples signifying proper body and tail cap assembly and complete extrusion of the inho phages.

Figure 16:
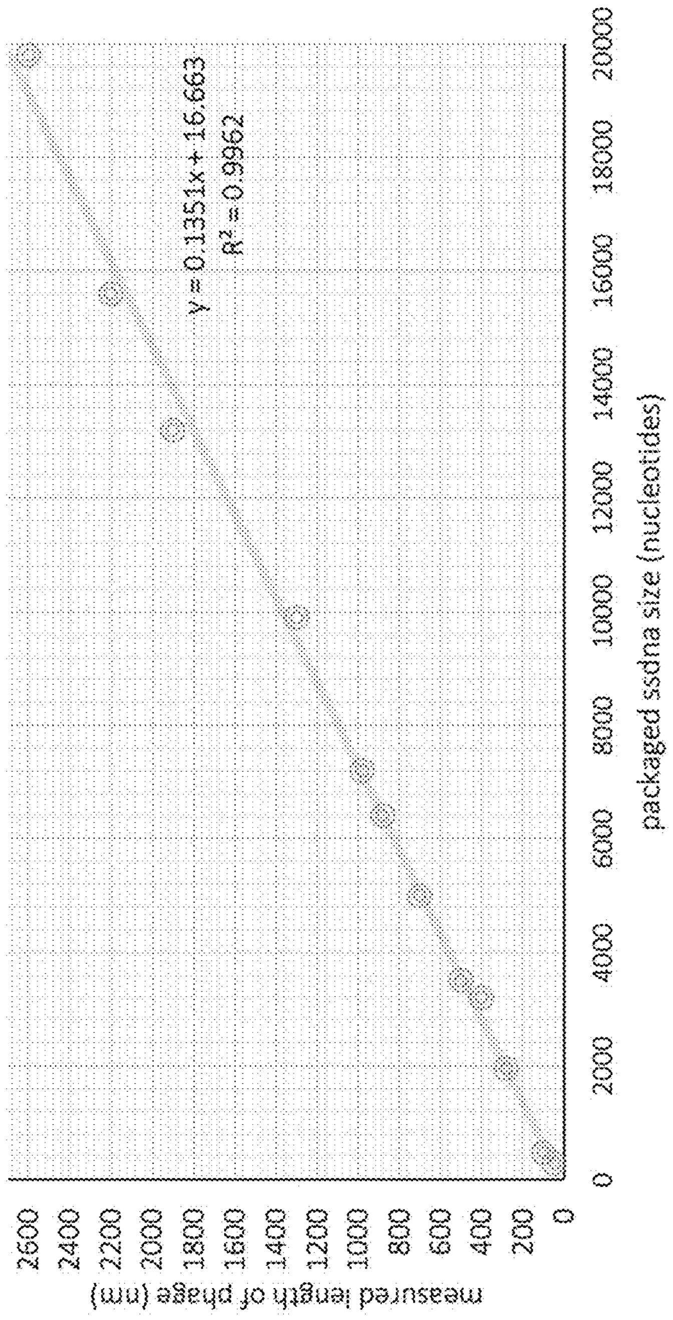
FIG. 16 provides a graph depicting the linear trend between cssDNA size and nm length of inho phages of 135 to 19800 nucleotide bases.
Figure 17A:
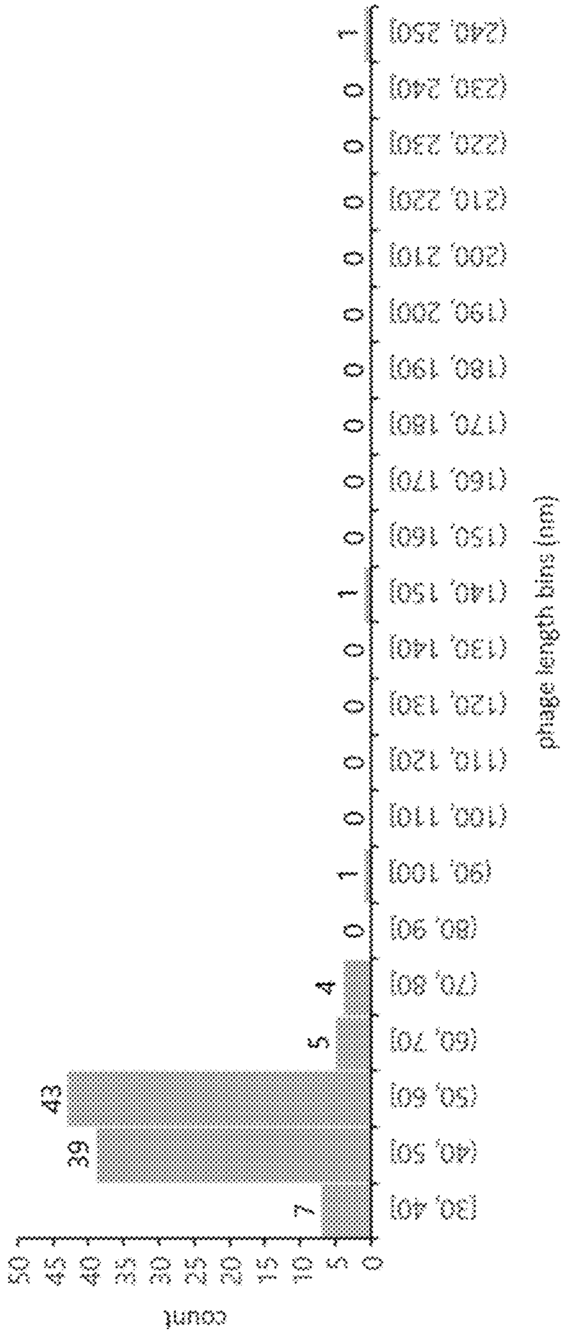

Highly pure phages samples dialyzed against milli-q water were used to visualize the inho phage batches and capture the physical length of our short, filamentous phages under AFM and TEM. Alternatively, Ni-NTA affinity column purification provide ideal batches. For Ni-NTA columns, inho-phage was produced by using a RM13-f1 plasmid clone coding for two histidine residues per p8 wrapping protein (DDAHVHWE clone (SEQ ID NO: 9)). Expression of his6 tag (SEQ ID NO: 1) on the tail p3 protein proved to be insufficient for column binding. DDAHVHWE (SEQ ID NO: 9) should be displayed on all p8 copies which allows for improved avidity binding to the nickel column. For visualization, samples clean from salts and the probable bacterial debris are required to ensure easy tracking of the phage particles, proper quantification of the phage profile, and a neat field for imaging. For AFM samples, a total of 1e11 phage are diluted to 100 ul with milli-q deionized water and deposited on a 10 mm diameter mica disc for 1 hr before drying with argon gas. The mice discs are then installed on the AFM stage for profiling. Initial examination shows that example inho1960, inho475, and inho285 constructs with RM13-f1 gives us phages of approximately 280 nm, 100 nm, and 50 nm in length respectively. Moreover, the inho batches are highly homogenous in size distribution with over 90% of phages falling within 10 nm of the measured size (FIG. 17) allowing for measurement errors. As expected, we can confirm that the phages assembled by the inho system produce phages of lengths that are linearly related to the designed cssDNA as shown in FIG. 16. Interestingly, the y intercept at 16 nm correlates with the predicted span of the $p^3$ (42,522 Da) and p6 (12,342 Da) capping complex of the phage. The p7 (3,599 Da) and p9 (3,650 Da) together measure close to the p8 (5,235 Da) in size and contribute similarly as p8 to the length of the phage.

Figure 19:
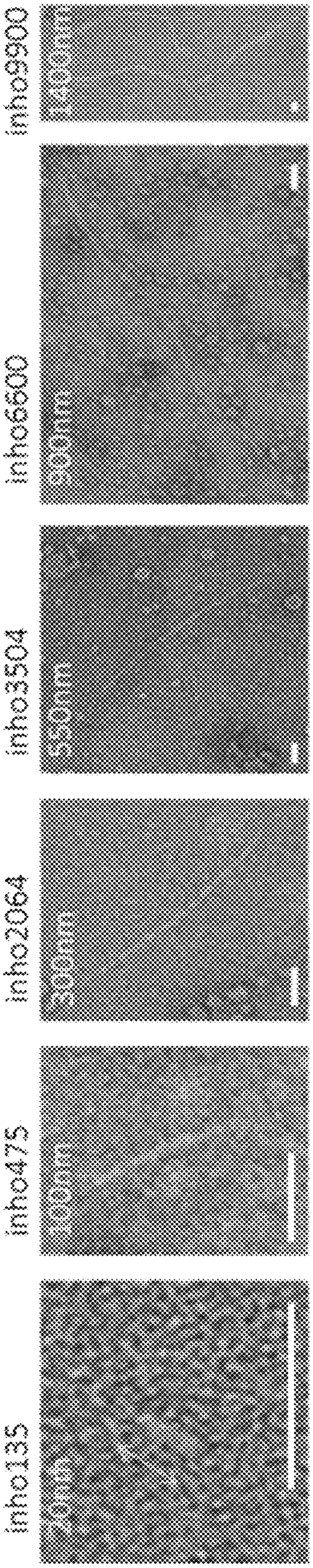
FIG. 19 provides TEM images of inho constructs. Phage sizes of approximately 20 nm, 100 nm, 300 nm, 550 nm, 900 nm, and 1400 nm lengths recorded for various length inho cssDNA constructs (100 nm, 50 nm scales).

TEM (Zeiss 10) examination of the phage particles was performed post typical uranyl acetate (UA) staining. 10 μL highly purified phage solution was applied onto a form var-coated TEM grid for 5 min. Post phage absorption, the rest of the solution was wicked from the edge of the grid by filter paper. Immediately, 10 μL 0.5% UA solution (pH=4.5) was applied to the specimen for 10 seconds. The stain solution was also wicked from the edge of the grid by filter paper and the TEM grid was dried by rapidly with gas prior characterization under TEM. The resulting TEM images of additionally constructed inho135 through inho9900 reveal lengths of approximately 25 nm, 100 nm, 300 nm, 500 nm, 900 nm, and 1400 nm. (FIG. 19.)

Figure 20:
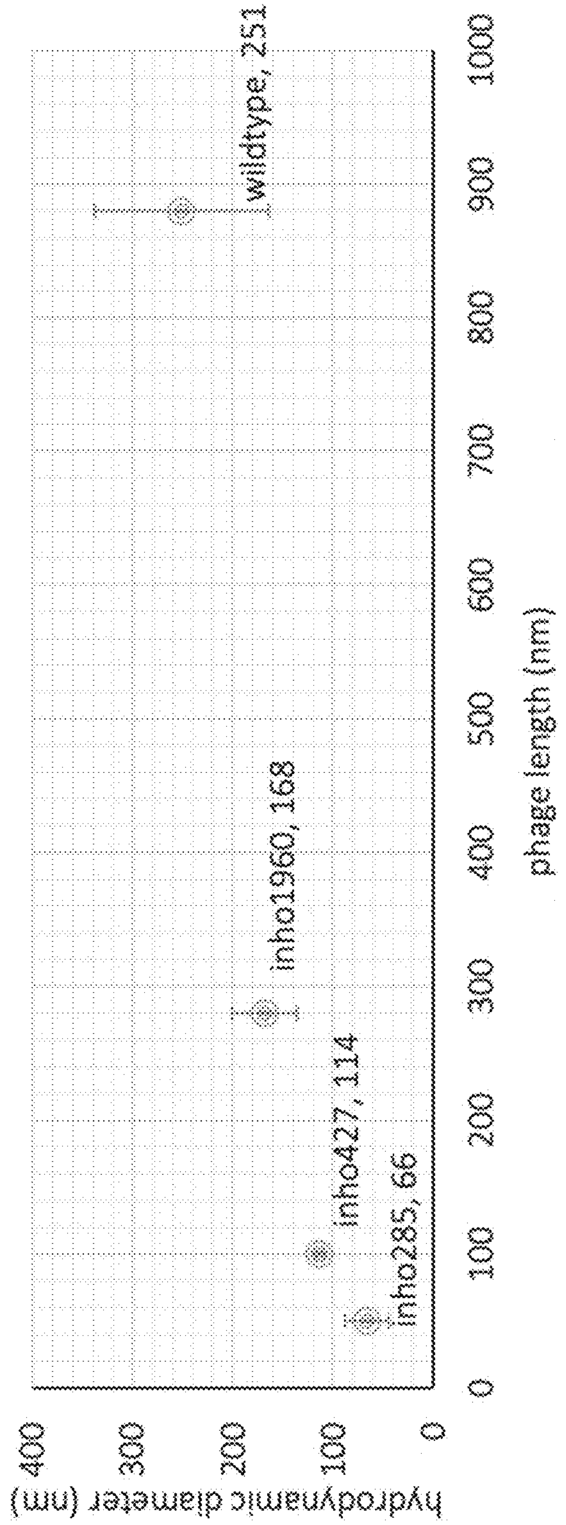
FIG. 20 provides a graphical representation of the hydrodynamic diameter of shorter phages. Globular diameter of inho-phages as measured by dynamic light scattering (n=6 per group).
Figures 23A, 23B, 23C, 23D:
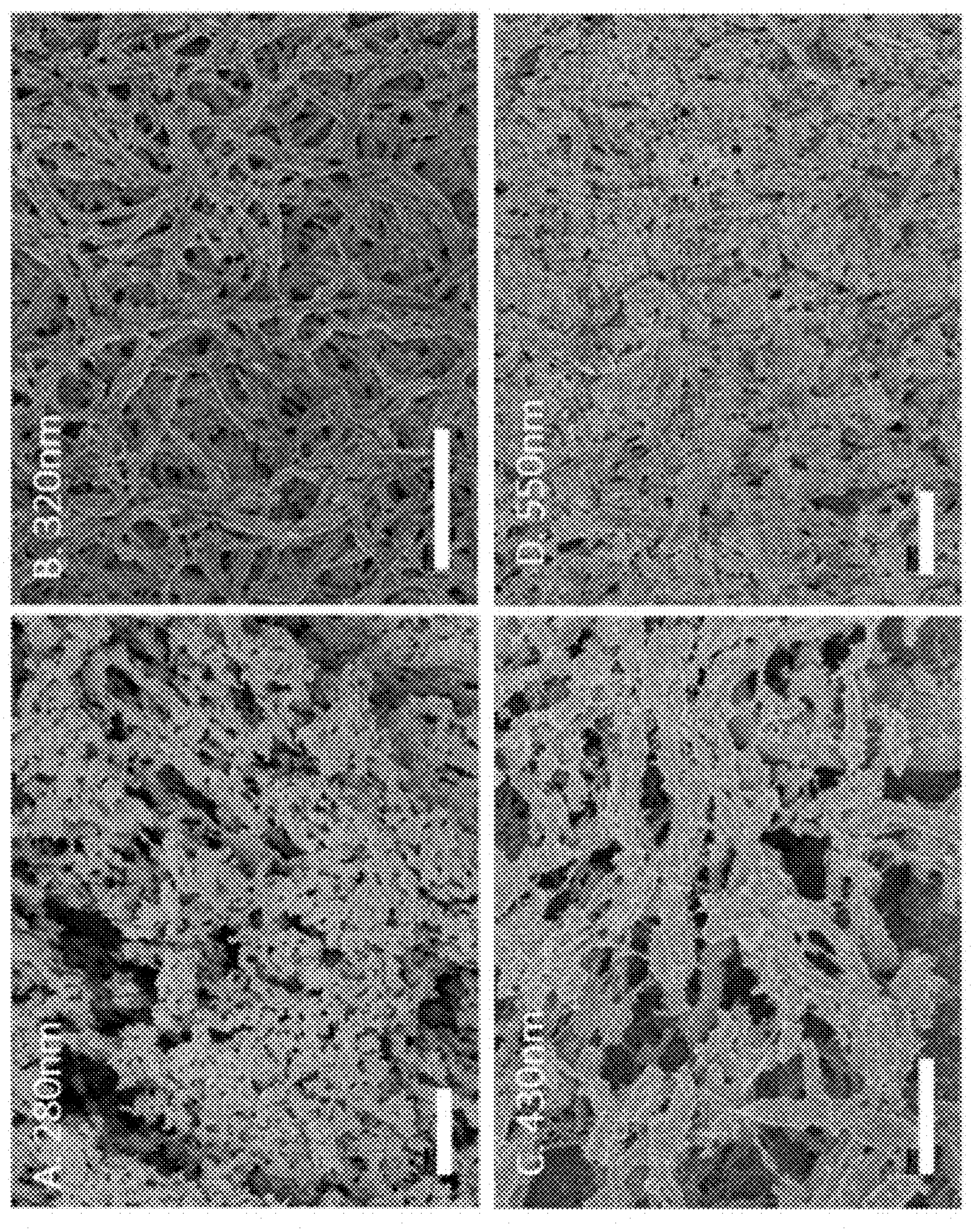
FIG. 23A-23H provide SEM imaging of Ni nanofoams. Foams formed from phages lengths of 23A) 280 nm; 23B) 320 nm; 23C) 430 nm; 23D) 550 nm; 23E) 750 nm; 23F) 960 nm (WT); and 23 G) 1400 nm (K48A mutant) (10 μscale). 23H) Percent of the foam images un-occupied by nickel nanowires as analyzed by ImageJ thresholding functions (n=5 per group).
Figures 23E, 23F, 23G, 23H:
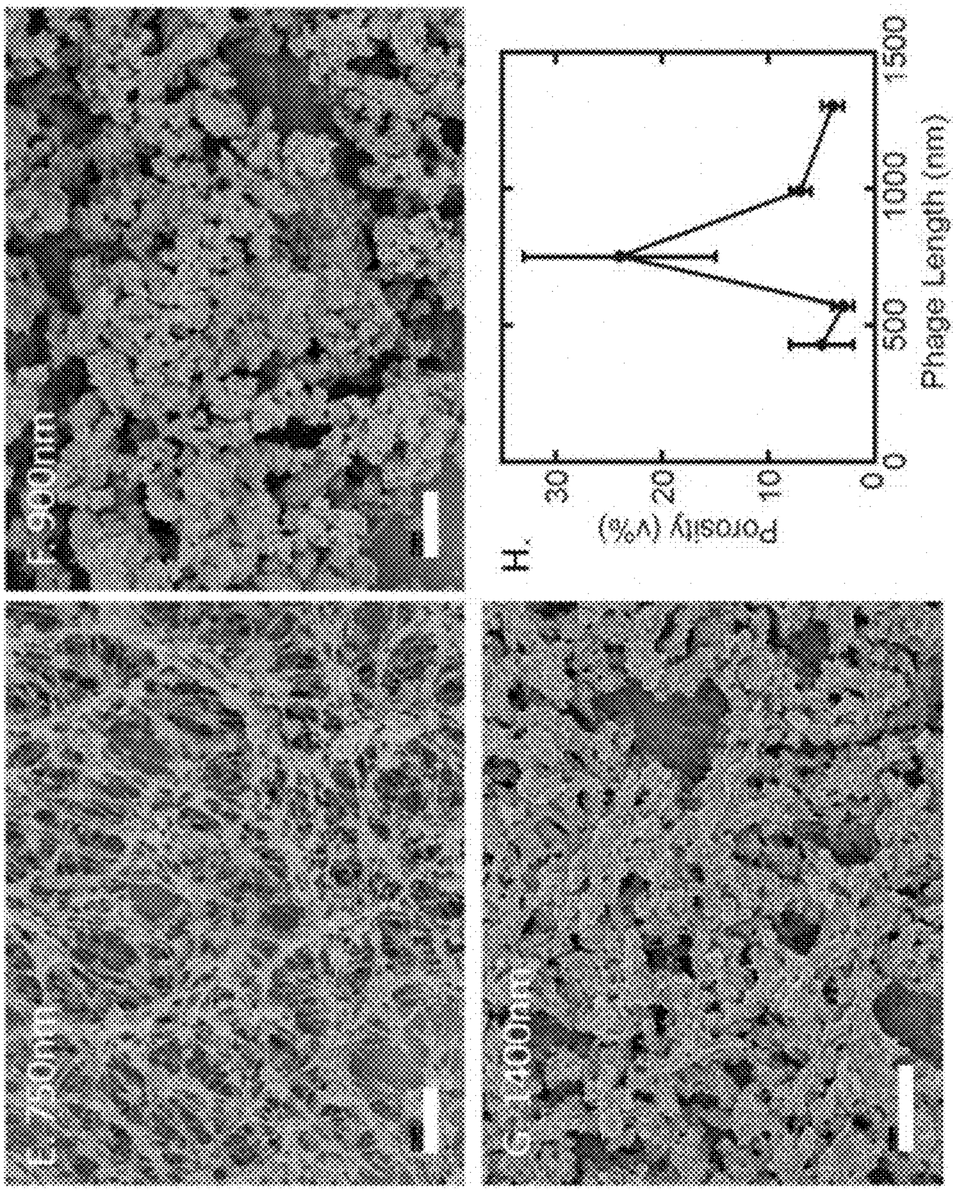

Dynamic light scattering of the inho phages hint at the more rod-like behavior of the shorter phage constructs. (FIG. 18.) In general, the long filamentous wildtype phage measures a hydrodynamic diameter near 300 nm due to its floppy, high aspect ratio geometry. In comparison, shorter phages are much more rigid in structure and measure hydrodynamic diameter closer to their physical length. In example, 50 nm phage, inho285, gives a hydrodynamic diameter near 66 nm. The hydrodynamic readings suggest that the geometric presentation of the small phages will be much more inflexible and bar-like in an aqueous environment than longer phages. (FIG. 20.) This difference could have significant implications for the cell and tissue interactions and trafficking of inho phages in biomedical applications. At the same time, as a scaffolding for nanomaterials, the rod-like shape could be of interest to nano-construction of shapes and particles or the porous morphology of bulk phage templated materials.

2-3 Inho Phage Cell and Tumor Interactions

The Biomolecular Materials Lab (Belcher Group) has previously demonstrated that targeted M13 bacteriophage conjugated with fluorescent materials can perform in vivo molecular imaging of tumors. M13 filamentous bacteriophage major coat protein p8 and minor cap proteins p3, p9 can be engineered to display or attach various targeting ligands and nanoparticles or drug molecules-effectively creating a phage shuttle that carry imaging or therapy agents to specifically targeted cancer cells[32-37]. However, this method can be limited by inefficient extravasation of the probe from the circulation due to the length of phage (880 nm). With our inho system which can control and shorten the length of phage while maintaining its multi-functional capsid, we can test the effect of length on the tumor penetration of phage. However, it is clear that in optimizing for biological tissue trafficking by size, we will be required to trade-off for the loading capacity of phage particles as shorter phages inherently have lesser capsid surface for material complexation. The high avidity enjoyed by phages of full length in previous studies must be compensated by greater inho particle counts per treatment in our case, to satisfy the dosing requirements for therapeutic effects or diagnostic signal. Ultimately, nanoparticle materials research patently highlight that geometry and size can play a significant role in the transport, biodistribution, and internalization of nanoparticles[38-44]. By understanding how our aspect ratio affects tumor distribution properties, we can determine the ideal length of phage for the different in-vivo cancer applications we have demonstrated such as diagnostic imaging or drug and therapy delivery. The application of inho phage of sizes ~50 nm, ~100 nm, and ~300 nm lengths to this end are presented in Section 3, where glioblastoma targeting and in-vivo imaging in the second window near infrared (SWIR) optical window is explored at length with convincing data on the impact of size on the tumor accumulation and specificity of phage particles.

The interaction of the phage particle with cells in-vitro already highlight the difference length can make in the tissue interaction of our filamentous phage. Using chlorotoxin targeted phage design (CTX-phages described in Section 3) and the GBM22 glioblastoma cell line, we tested the uptake of phages varying in length (~100 nm, ~300 nm, and 900 nm). GBM22 cells were incubated in a serum free media containing Alexa647-fluorophore conjugated phage particles and trypsinized prior to flow cytometry readings. Presence of Alexa647 signal post rigorous PBS washing and trypsinization of the cells was interpreted as very strong interaction or uptake by the cells. The cells were first incubated with p8 equivalent numbers of phage. In other words, three times more inho1960 phage particles were dosed than the 900 nm phages (M14KE-CTX) to simulate the same number of p8 fused delivery of materials. In this case, the speed of binding and uptake is much greater with increasingly shorter phages (FIG. 21A). Clearly the increased ratio of p3 CTX targeting proteins to p8 coat proteins represented by the shorter phages enhanced interactions with the cell surface and allowed for uptake in a much quicker period of time. It is also possible that shorter phages are internalized more rapidly due to the lower energetic requirements for endocytosis of smaller materials at the cell membrane. This possibility can be better ascertained through incubation of cells with equivalent particle units of the phage variants and closer visualization of the internalization behaviors in future work.

However, initial comparison of GBM22 cell uptake of studies where cells were treated with equivalent particle numbers suggests that there is indeed surface interaction and endocytosis speed gains observed with shorter phage particles. When ~1e6 count/cell 900 nm phage are compared with the ~1e6 count/cell of 100 nm phage uptake profile, the longer filamentous phages are slower to exhibit engagement with the cell population over the 6 hour time series (FIG. 21B).

To meet the growing demands for highly capable electrochemical energy storage technologies, much attention has been given to the development of nanofoam materials that could provide promising new alternatives to traditional electrodes. Metal nanofoams are of particular interest as they provide the malleability and catalytic and conductive properties of metals with the low density and high gravimetric surface area of porous materials[45,46].

Engineering ion transport is key in the production of high-performance batteries, catalysts, super-capacitors, and fuel cells[47-49]. Increasing reaction area between electrolyte and active materials is also crucial to improved performance. Nanofoam architectures fulfills both of these functions, forming light-weight interconnected networks of high specific surface area.

There has been great interest in using synthesis methods based on biology to engineer the properties of metal nanofoams[50-60]. Precise molecular control of metal catalyst and electrode structures is often achieved using sophisticated techniques such as atomic layer deposition (ALD) or more generally, chemical vapor deposition (CVD). While these techniques are very powerful, they suffer from disadvantages such as high cost, a need for extremely pure substrates, and slow reaction rates. Nature, on the other hand, has evolved countless organic macromolecules capable of specific and efficient self-assembly into amazing nanostructures under very mild conditions. Protein motors, telomeric quadruplexes, and lipid bilayers are all examples of these elaborate and highly functional self-assembled nanostructures. The design rules and building blocks of biology are attractive resources in the creation of synthetic inorganic or hybrid nanomaterials, especially those built in a bottom-up, hierarchical manner.

M13 bacteriophage, a naturally monodisperse, multifunctional nanostructure, is especially well-suited for active material templating and assembly under mild conditions. The phage consists of thousands of distinct protein subunits organized in a high aspect ratio, filamentous viral capsid. As explored, copies of the major coat protein (p8) form the bulk of the phage filament, while minor coat proteins cap each end (approximately five copies each of p3 and p6 at one end, p7 and p9 at the other). Both the major and minor coat proteins are amenable to mutation, and thus can be chemically tuned for such abilities as programmable assembly, the binding, nucleation, and capping of inorganic nanoparticles, chelation of metal ions, and even expression of small enzyme catalysts in the case of p3[61-64]. Unlike other protein nanoparticles, phage is tolerant of a wide range of temperatures and solvent[65,66], making it a good candidate for use in a variety of material synthesis applications. Further, purification of bacteriophage for materials applications occurs via simple precipitation and centrifugation, compared with the more complex and expensive ultracentrifugation and ion-exchange chromatography that are necessary for many other protein nanoparticles[67]. The use of large-scale bioreactors allows for production of gram-scale quantities of phage in just two days. All of these characteristics have made the M13 a very popular tool for biomaterials applications.

As such, the Belcher Group have successfully demonstrated the synthesis of aerogels and metal nanofoams using full length, M13 bacteriophage-based templates for a number of exciting energy storage and catalysis solutions[50-58]. Aerogels, ultralight materials with high surface areas and low densities, are ideal for battery component design. Aerogel-based battery chemistries and battery performance is highly dependent on the pore size and volumes which have previously been controlled by varying synthesis conditions including acid concentration, solvents, freezing conditions, and gas pressure[49,68-83]. Conversely, the Belcher Lab has illustrated that aerogels can be templated by crosslinked M13 phages. Such aerogels have densities between 2-5 $mg/cm^2$ and porosities as high as 99%[52]. Here, with the inho assembly system, we demonstrate that the electrochemical and materials properties of gel-based nickel metal foams can be further tuned by altering the length of M13 struts. Ni—$MnO_x$ cathodes produced from phage nickel foams were incorporated in battery cells. Batteries made using these nanofoams vary in ion transport properties and performance. The inho strut design is shown to give us biological control over the underlying morphology of the metal cathodes and consequently play a critical role in their electrochemical properties. This can be extended to catalysis and other fields where nano-structured materials could provide significant impact including filtration and desalination, tissue or antimicrobial scaffolds, electromagnetic composites, hydrogen storage, and more.

Additionally, the material properties of nanofoams such as aerogels have been shown to be appealing for applications in flexible, wearable energy devices.

2-4-1 Inho Phage Metal Nanofoams

Inho-phages cloned for the display of EEAE peptide sequence (SEQ ID NO: 2) on p8, as utilized by Nam et al., were used for the production of inho-phage based metal nanofoams[54]. The decrease in zeta potential conferred by the p8 display of E3 enhances the material nucleation and metal deposition onto the surface of the phage scaffolds. To form nanofoams, the phage particles are first crosslinked through exposure to glutaraldehyde that reacts between the L14 residues of the major p8 coat proteins creating a network of phage. These hydrogels can be formed on diverse substrates, such as metal foams and foils, or produced as freestanding gels. The hydrogel is then sensitized by exposure to a palladium-based catalyst that electrostatically binds to the negative surface charge on the virus capsid. Electroless deposition is subsequently used to deposit nickel onto the hydrogel, resulting in a bio-templated nickel foam (FIG. 22). During electroless deposition, the bio-templated gels are immersed in electroless bath, were the time of immersion affords quantitative control over the thickness of the struts in the 80-300 nm regime.

Bio-templated metal foams produced in this way with the varying phage sizes (ranging from 280 nm to 1400 nm) demonstrated distinct morphological traits. SEM visualization of the inho-templated nickel nanofoams reveal pronounced maximal porosity for the nanofoam formed from phages of 750 nm in length. With shorter and longer phages, nanofoams exhibit more aggregated structures with lower percent porosity scores as analyzed by ImageJ black and white image thresholding that defined nanofoam struts as white and the visible pores as black (the ratio of black space taken as percent empty volume). (FIG. 23A-D.)

As shown in the SEM results, phage length has a significant effect on foam morphology. This morphology is expected to determine rate capability by influencing charge transport, and to affect the mechanical properties of the electrode. To better assist the phage foam making process, a model was developed relating bacteriophage length to the crosslinking process and to the properties of the ultimate composite material. The model is based on the observation that in some regimes, SEM of Ni foams reveals large aggregates while in other regimes the foam is homogeneous. While precipitation at high concentrations is expected, phage are frequently observed to exhibit this aggregation at low concentrations and low phage lengths. We hypothesize that phage may aggregate during crosslinking at low concentrations because the effective volume occupied by the phage present is insufficient to form a uniform hydrogel (illustrated in FIG. 24A).

Figures 24A, 24B, 24C:
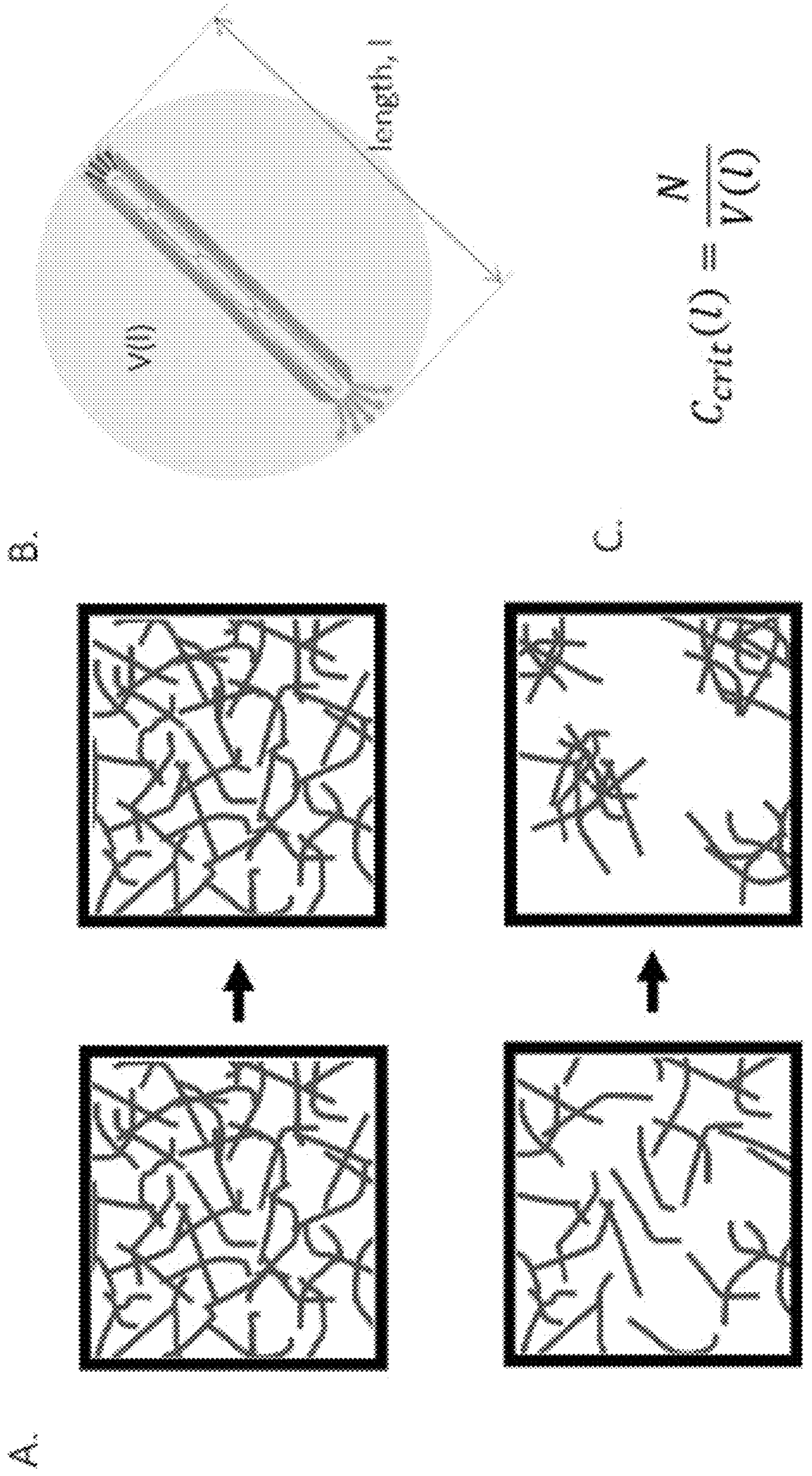
FIG. 24A-24C show that hydrogel gel formation is dynamic of phage particles.

In our model, phage are assumed to occupy a volume equivalent to a sphere with radius determined by the phage length (FIG. 24B). In order to generate a uniform hydrogel, there must be sufficient overlap of these spheres. This degree of overlap was empirically determined by dividing the thickness of phage hydrogel struts by the diameter of the phage (FIG. 22B). Using this, we determined a length-dependent critical concentration $C_{crit}(l)$ such that at concentrations lower than $C_{crit}$, the given phage is likely to produce aggregated foams.

Figure 25:
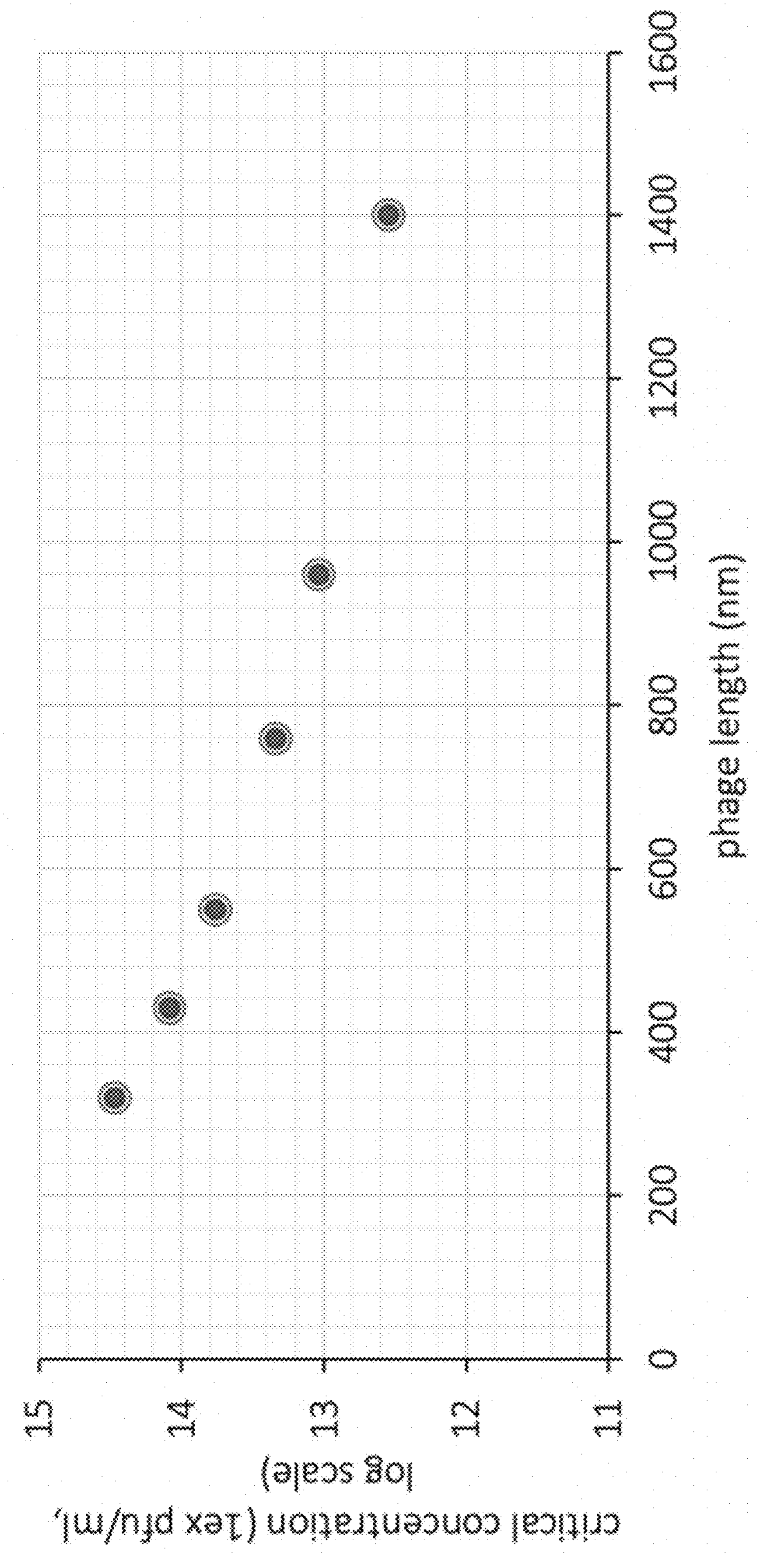
FIG. 25 shows a graph of critical gelling concentrations calculated across phage lengths. The target strut width is assumed to be ~25 nm where N=5.

In the proposed formula (FIG. 24C), l is the length of a phage clone, V(l) is the volume occupied by a virus particle of length 1, and N is the average width of a hydrogel strut in phage diameters (equivalently the degree of overlap required between the occupied volume of phage). The resulting $C_{crit}$ is shown in FIG. 25. The critical concentration corresponding to wild-type phage, 1.1e13 pfu/ml, agrees well with empirical experience. Further validation of this model, by evaluating phage of different lengths at different gelling concentration may be of interest for future work. Optimization of hydrogel forming condition could be essential for building highly porous nanofoam templates using very short or very long phages (<750 nm, >750 nm).

2-4-3 Inho Templated Battery Capacity

Following nickel deposition, transition metal oxides can be electrodeposited onto the phage nanofoams as active material precursors. These electrodes consisting of bio-templated current collectors and electrodeposited active material precursors are then processed at low temperatures in order to produce battery electrodes. This results in an internally 'wired' electrode in which the bio-templated metal foam forms a percolating network. Here, strut connectivity and morphology, active material chemistry, and lithium diffusion length through the active material are each independently tunable.

Figures 26A, 26B:
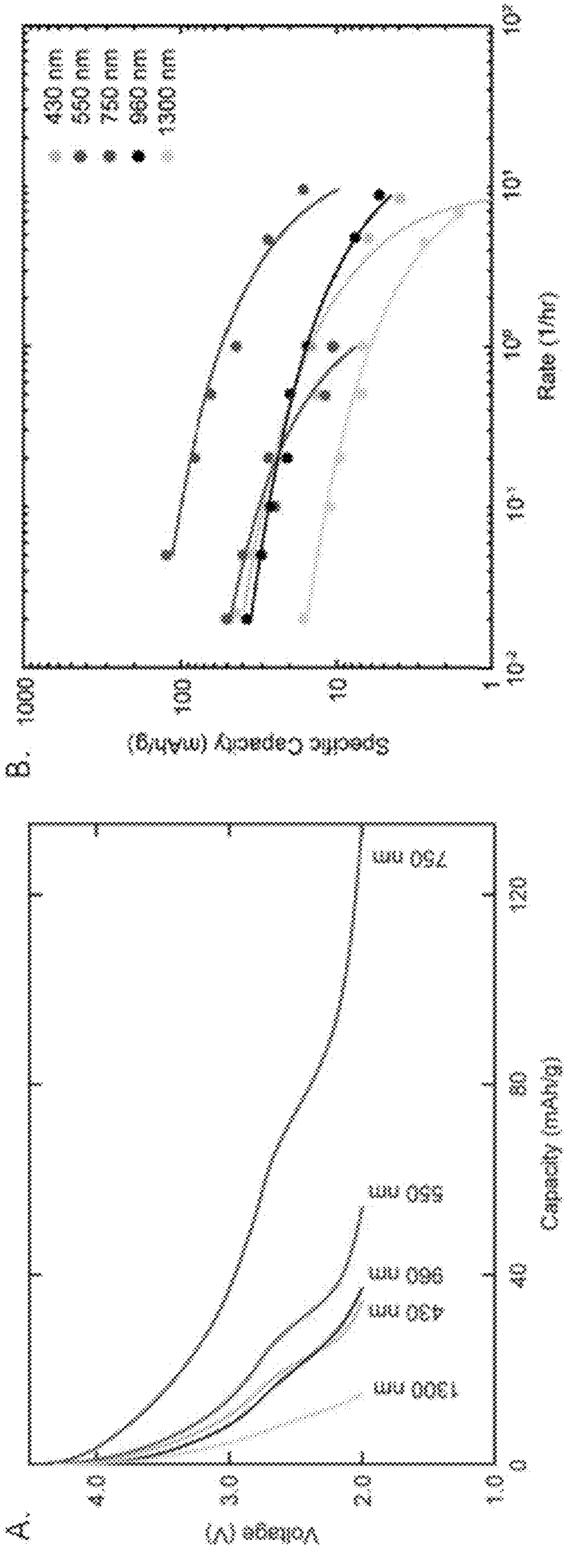
FIG. 26A-26B depicts graphs of electrochemical cycling of Ni—$MnO_x$ cathode materials.

Phage foams produced from lengths ranging from 320 nm to 1400 nm EEAE phages (SEQ ID NO: 2) were treated for manganese oxide active deposition. Batteries were constructed using these biotemplated Ni-MnOx nanofoams as cathodes[57,58,84,85]. The batteries cells were assembled using lithium foil as the negative electrode, a celgard separator and an electrolyte consisting of 1M LiPF6 in EC:DMC (Methods). The rate capability, a metric expressing the ability of a battery to rapidly charge or discharge, was determined by electrochemically cycling these batteries using different currents. Typical discharge curves are shown in FIG. 26A. Electrodes made using higher porosity nanofoams such as with the 750 nm length phage show a pronounced shoulder near 2.8V corresponding to manganese oxide intercalation. Electrodes based on lower porosity samples, by contrast, show a sloped capacitive behavior with no shoulder. This indicates that intercalation plays less of a role in electrochemical cycling when the porosity is low such that lithium diffusion through the liquid electrolyte is hindered. This effect of biologically controlled porosity on electrode rate capability was assessed by comparing Ragone plots of batteries made using phage of different lengths (FIG. 26B). The notable difference observed for the rate capability in these batteries based on the porosity differential indicates that the lower porosity electrodes comprise electrochemically inaccessible active material.

Figures 27A, 27B:
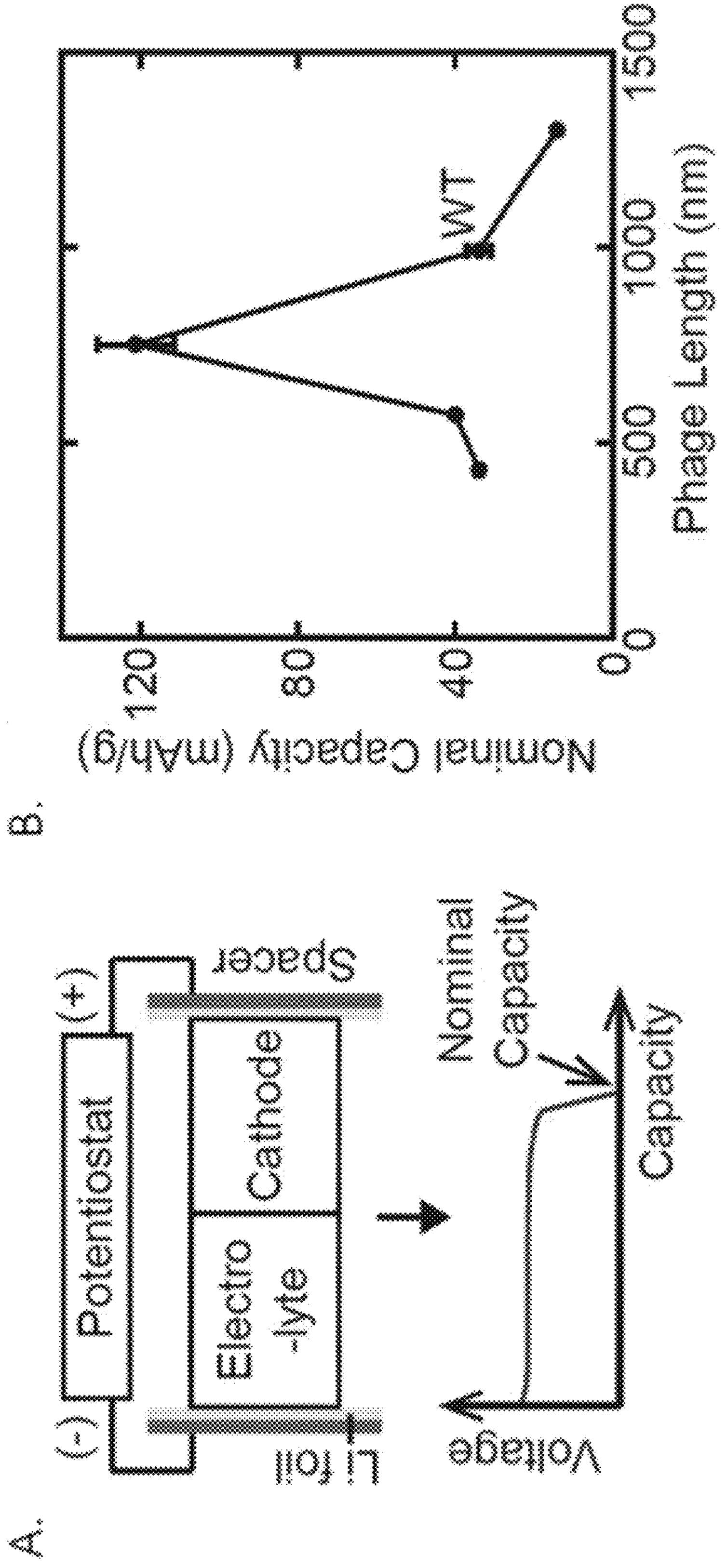
FIG. 27A-27B show nominal capacity of phage templated Ni—$MnO_x$ cathode batteries.

Corresponding to the porosity characterization, the measured nominal battery capacity of the bio-templated electrodes exhibit an optimal performance with the 750 nm phage templated foam. The active material mass was calculated by weighing dry electrodes both before and after active material deposition, and nominal capacity upon discharge was calculated by dividing the electrochemical discharge capacity measured during cycling by this active material mass. The peak value of 121 mAh/g here is similar to the theoretical maximum capacity of the manganese oxide active material of 147 mAh/g, indicating an 82% active material utilization (FIG. 27B). As the active chemistry is the same for these materials, the optimal value found at 750 nm phage strongly suggest that morphology changes the lithium ion transport through the liquid electrolyte of such battery structures. Materials with lower porosity contain a lower volume fraction of liquid electrolyte, resulting in a corresponding rate limitation due to lithium diffusion constraints.

2-5 Conclusions

A phagemid system was created that eliminate most of the prokaryotic sequence of a phage cssDNA. This inho system utilizes 179 bases of the M13-ori and only 89 of these bases are considered absolutely necessary for production with this design (as demonstrated with inho135 phage of ~25 nm size). The inho construct has the largest cssDNA/phage length range of any natural or helper assembly processes described to date for M13 phages production in bacterial cells. The extremely low base count possible with inho allows us to produce filamentous phage particles that are over an order of magnitude shorter than natural M13.

As discussed, inho type manufacturing can be very attractive to cssDNA production pipelines as well as applications focused on phage nanoparticles where the length scales likely impact the biological trafficking and cellular interaction dynamics. This is further explored in Section 3 and 4. In addition, the genetic control over phage length is particularly interesting for encoding the structural features of aerogel and hydrogel 3D nanomaterials. The uniformity of the phage units, the scalability of production, and non-toxic processing gives M13 an advantage over other scaffolding materials in the field of nanomaterials. The filamentous geometry of the M13 has proven valuable to templating of a large range of materials, including batteries, catalysts, photovoltaic cells, sensors, optical tools, flexible electronics, filtration devices, and biomedical gels[61,86-94]. In our study, the porosity of the phage scaffold, as dictated by the length of the phage strut, proved to be a powerful contributor to the battery performance of phage foam based Ni—$MnO_x$ cathodes. In electronic applications, the morphology of the phage foams is crucial to ion transport efficiencies. This is demonstrated by the correlation in nominal capacity and porosity measured for the 750 nm phage-based battery. As this is the first foray into battery materials synthesis using phage struts of varying lengths, further optimization may yield new aerogel/nanofoam formation processes that better harness the morphological profiles possible with shorter phage struts. As described, we know that controlling for the clumping of phage materials during the crosslinking process is crucial to the homogeneity of gelling and may be controlled by a critical working concentration. This is a clear route for continued testing of novel foams produced with ultra short phages.

Phage derived particles with their multi-functional coats and modular lengths are extremely appealing to consider for nanotheranostic formulation and bio-templated materials synthesis. Equal to any phagemid, the RM13-f1 assembly plasmid of the inho system is amenable to manipulations such as the addition of p8, p3, or p9 protein display. Such surface modifications allow improved specificity or trafficking of the phages in the in-vitro and in-vivo settings and allow nanomaterial designs with enhanced binding and nucleation of active materials. For augmented nanomaterials, carbon nanotube incorporation by display of the uniqueCNT binding sequences[34,51,53] or phage filament stiffness modulation through the Y21× substitution in the p8 capsid sequence are additional avenues for exploration[95]. (Phage filament persistence length and stiffness can be modulated through the cloning of the Y21 position of the helical p8 capsid. The Y21M substitution, for instance, has been reported to increase the persistence length and invert the helix chirality[95]. Persistence length changes for 100 nm phages across all 20 amino acid substitutions are described in Appendix A). As our ultra short phages retain all capsid functions, we can harness the field learnings from varying 8 coat charge, peptide library panning, and conjugate material explorations to further test optimal inho phage particles designs for the target application.

a. Materials and Methods Construct Cloning

The f1-ori, f1-term, and PS sequences were cloned into standard ampicillin selection/colE1 origin plasmid vectors such as pUC19 or pUC57. Commercially available helper phage templates M13KE, M13K07, and R408 were used to create RM13-f1 constructs where the intergenic region is reassembled to disrupt the origin for packageable cssDNA replication (the f1 nicking/p2 complexation sites, in particular, was removed). Kanamycin resistance site was added to the constructs for selection purposes and p15a-ori plasmid replication site is included to achieve optimal copy numbers during *E. coli* growth. Additional functionalization (peptide display on p3-CTX, p8-DDAH, p8-E3, and the required p5[Cys21] and p2[Met40] mutations) of the phage is easily also achieved through standard cloning methods. Briefly, plasmid cloning with restriction enzymes or gibson master assembly techniques were used to create constructs from fragments of interest, to add display insertions, and to change the length of the inho-phage constructs. All oligos and small DNA inserts were purchased through IDT. PCR reactions were performed (KAPA HiFi Kit) to amplify inserts and vectors with enzyme cut sites or gibson overlapping overhangs. PCR products were purified through a 1.2% agarose gel run and extraction (QIAquick Gel Extraction) or DNA spin columns. Fragments products were processed for enzyme digestion (NEB) followed by ligation using T4 DNA (NEB) ligase if ends were restriction designed or fragments were processed for standard Gibson (NEB) if end were designed with overhangs. Cloning products were transformed and plated for single colony picks. Full length sequencing of the mini-prep (Qiagen) purified plasmids were verified for desired final RM13-f1 and inho construct clones. Complete sequences of RM13-f1 and its p2/p5 assembly or p8/p3/p9 display variants and inho285, inho475, and inho1960 are presented in Appendix D.

Large Scale (10-Liter) Inho Phage Amplification

RM13-f1 and inho plasmids were co-transformed into XL10 or XL1 Blue chemically competent *E. coli* cells. A single colony was selected and grown in 5 mL LB for approximately 6 hours. This culture was then used to inoculate 100 mL LB, which was grown for three hours before being used as inoculant for the 10 liter culture. All cultures were grown in the presence of kanamycin and ampicillin. Ten liters of LB+Kan/Amp was pumped into a 20 liter single-use WAVE cellbagbioreactor (GE Life Sciences). After addition of the 100 mL inoculant, the culture was grown for approximately 15 hours (37° C., 30 rpm, maximum oxygen flow rate, no pH control). A 5 mL sample was removed for DNA isolation and sequencing (Quintara Biosciences). Cells were then isolated from solution by centrifugation (7,600 RPM, Beckman JLA 8.1 rotor, 30 minutes, 10° C.), and the supernatant (containing phage) was concentrated and buffer exchanged into DI water using tangential flow filtration (GE Hollow Fiber Cartridge, 500,000 nominal molecular weight cutoff, 2000 cm2). The resulting ~one liter sample was then centrifuged (7,600 RPM, Beckman JLA 8.1 rotor, 30 minutes, 10° C.) to remove any remaining cell debris, and PEG/NaCl (final 10% PEG, 0.5 M NaCl) were added. The slurry was incubated at 4° C. overnight and centrifuged (8,000 RPM, Beckman JLA 8.1 rotor, 1 hour, 4° C.) to obtain a phage pellet. This pellet was dissolved in 100 mL DI water, centrifuged (15,000 RPM, Beckman JA25.50 rotor, one hour, 4° C.) to remove debris, and DNAse treated (final 5 µg/mL DNAse, 10 mM Tris-HCl, 2.5 mM MgCl2, 0.5 mM $CaCl_2$), pH 7.6; 37° C., one hour). The sample was then centrifuged again as before, placed in 100 kDa molecular weight cutoff dialysis tubing, and dialyzed against DI water or 1×PBS for at least 48 hours (50:1 ratio sample:buffer or water, minimum four changes).

Small Scale (0.8-Liter) Wildtype Phage Amplification

DNA for phage clones of wild-type length and longer was transformed into XL1Blue chemically competent *E. coli* cells, and the transformation outgrowth was titered for viral plaque formation. Specifically, various amounts of outgrowth were mixed with 200 µL of healthy XL1 Blue cells for 5 five minutes, 4.5 mL top agarose was added, and the mixture was placed on an agar plate containing tetracycline, IPTG, and X-gal. Single plaques were selected after overnight incubation at 37° C., and were used to infect a 100-fold dilute healthy XL1Blue culture. This culture was grown at 37° C. overnight, DNA was isolated and sequenced, and the supernatant was used as the amplification-quality phage stock. For amplification, 5 mL healthy XL1 Blue cells were used to inoculate 0.8 L LB. The culture was grown to OD ~0.3, then infected with a 5 mL culture containing XL1Blue cells and phage (200 uL plaque supernatant and XL1 Blue cells were added to 5 mL LB and grown to confluency). The infected 0.8 L culture was grown overnight. Cells were isolated from solution by centrifugation (7,600 RPM, Beckman JLA 8.1 rotor, 30 minutes, 10° C.), and PEG/NaCl (final 4% PEG, 0.5 M NaCl) was added to the supernatant. The mixture was incubated at 4° C. overnight and then centrifuged (8,000 RPM, Beckman JLA 8.1 rotor, 1 hour, 4° C.) to obtain a phage pellet. This pellet was dissolved in 10 mL DI water, centrifuged (15,000 RPM, Beckman JA25.50 rotor, one hour, 4° C.) to remove debris, and DNAse treated (final 5 µg/mL DNAse, 10 mM Tris-HCl, 2.5 mM MgCl2, 0.5 mM CaCl2, pH 7.6; 37° C., one hour). The sample was then centrifuged again as before, placed in 100 kDa molecular weight cutoff dialysis tubing, and dialyzed against DI water or 1×PBS for at least 48 hours (500:1 ratio sample: buffer or water, minimum four changes).

MALDI-TOF Mass Spectrometry

MALDI-TOF analysis of phage was performed to confirm that the observed p8 mass was as expected for each sample (this was added confirmation on top of sequencing data). Analysis was performed by the MIT Koch Institute Swanson Biotechnology Center using a Bruker MicroFlex instrument. For samples with a p8 concentration greater than 140 uM, 1 uL of each sample was mixed with 2 uL matrix solution (sinapinic acid), and 1 uL was then spotted and analyzed. For samples with a p8 concentration less than 140 uM, 1 uL of each sample was mixed with 1 uL matrix solution (sinapinic acid), and 1 uL was then spotted and analyzed.

Dynamic Light Scattering

Dynamic light scattering was performed using a cuvette-based DLS instrument (Wyatt Technology Corporation, DynaPro NanoStar). A 450 µL aliquot of phage solution was pipetted into a plastic cuvette (Eppendorf, 952010069) and the hydrodynamic radius <R2> of phage was measured.

Alexa Labeling of Phage

NHS-ester Alexa Fluor dyes (ThermoFisher) were incubated with phage samples in phosphate buffered saline (PBS) for 1 hr at room temperature at a 1:1 ratio to every p8 major coat protein present in sample. Labeled samples were dialyzed against PBS using 12-14 kDa cutoff Repligendialysis tubing to remove unconjugated dyes. Dialyzed samples were further cleaned and concentrated to desired phage per ml with tangential flow filtration at 10 kD cutoff using MicroKros 10 kDa MPES column (Repligen).

Chlorotoxin-Expressing Phage In-Vitro Cellular Uptake Flow Cytometry

Human GBM22 cells were grown in 6 well plates to 60% confluence (HyClone DMEM, 10% FBS). Chlorotoxin phage samples were conjugated with Alexa647 dye was incubated 2.7 µg per cell or at 1e6 phage per cell for 2-6 hours in serum free media. Wells were washed three times with PBS followed by enzyme free (Gibco Cell Dissociation Buffer) re-suspension of the treated GBM22 cells and control untreated GBM22 cells. The collected cells were spun and re-suspended in PBS and pipetted through the cell strainer cap of 5 ml (Falcon 353325) flow tubes. Tubes were maintained on ice for flow cytometry (640 laser excitation, 660/20 filter) readings on FACS Canto II HTS-1 machine with BD FacsDiva software. Acquired data was analyzed using FlowJo package.

Fabrication of Phage-Templated Cathode

Metal nanofoam current collectors were synthesized following a procedure previously described, with the following modifications 94. The 1013 phage particles/mL solution in PBS buffer was prepared as described above. Substrates for electrode samples were cleaned by immersing electrode spacers (Pred Materials International, SUS316L) in 18 M sulfuric acid (VWR, 470302-872) for 30 min followed by thorough rinsing with DI water. Substrates for additional samples were prepared by cutting glass slides into 0.5 cm2 chips and treating with ozone (UV-03 exposure) for 10 min. To crosslink the phage, 10 µL of phage-PBS solution was pipetted onto the substrate and enclosed in a polypropylene chamber (1 L volume) with 20 mL excess DI in order to maintain humidity for 4 hr. Samples were then removed and allowed to sit in 0.2 mL 50% glutaraldehyde (Sigma Aldrich, 340855) under ambient conditions for 8 hr in order to evaporate excess liquid. These samples were rinsed 3 times with DI water in order to remove glutaraldehyde. Samples were sensitized for 30 min using 10 mM tetraamminepalladium chloride solution (Sigma Aldrich, 323438), and rinsed three times with DI water. The nickel electroless deposition solution was made in a 2,000 mL glass bottle (VWR, 10754-822) by first mixing 1,000 mL of DI water with 7.17 g sodium DL-lactate (Sigma Aldrich, L4263) and 20.93 g 3-(N-morpholino) propanesulfonic Acid (MOPS, Sigma Aldrich, 69947) and adjusting the pH to 7.0 using sodium hydroxide (Sigma Aldrich, S8045). Nickel sulfate hexahydrate (Sigma Aldrich, 227676) (8.411 g) was added and dissolved by stirring, followed by the addition of 3.948 g borane dimethylamine (Sigma Aldrich, 180238). Samples were exposed to the electroless deposition solution for 45 min, followed by rinsing three times with DI water. The sample is then dried under ambient conditions.

Deposition of Manganese Oxide Active Material

An electrodeposition solution of 0.1 M manganese acetate (Sigma Aldrich, 221007) and 0.1 M sodium sulfate (Sigma Aldrich, 239313) was prepared and kept in a glass bottle. Nickel current collectors were fabricated as described in the previous section and then heated in air in a small box furnace (MTI Corporation, KSL1200XJF, 6° C./min ramp followed by holding at 350° C. for 30 min). The nickel current collectors were weighed following heating. The back of the sample was covered with Kapton tape (Uline, 5-11730) in order to block deposition. The sample, Pt counter electrode (Millipore Sigma 298093) and reference electrode (Ag/AgCl, BASi MF-2052) were placed in a 3-electrode setup using 50 mL of deposition solution. Electrodeposition was performed using a potentiostat (BioLogic VMP3) by maintaining −1.8 V versus the counter electrode for 15 min (−1.0 V versus reference electrode). Samples were then washed three times using DI water, allowed to dry and heated in air in a box furnace (6° C. min-1 ramp followed by holding at 350° C. for 30 min). As-deposited manganese hydroxide films were golden brown and turned black upon conversion to manganese oxide during heating, forming the Ni-MnOx electrode. The nickel current collector weight was subtracted from the final weight of the Ni-MnOx electrode samples in order to determine the active material mass.

Scanning Electron Microscope

Sample slides were first coated with thin Au films using an Au sputter coater in a vacuum (Quorum Technologies, SC7640). SEM images were obtained at randomly chosen locations using SEM (JEOL 6010 LA, JEOL) with a tungsten lament. The beam voltage was set to 20 kV and samples were investigated in secondary electron imaging (SEI) mode.

Transmission Electron Microscopy

A 10 μL aliquot of phage solution was deposited on a 200-mesh formvar/carbon-coated copper TEM grid (Electron Microscopy Sciences, FCF200-Cu). The spot was allowed to rest for 3 min and then the excess liquid was removed using a Kimwipe. The phages were stained using 10 μL of 1% uranyl acetate alternative (Gadolinium Triacetate, Ted Pella, 19485) that is deposited on the TEM grid and allowed to rest for 20 min. The excess stain solution was removed using a Kimwipe. High-resolution TEM (JEOL 2010) was performed at 200 kV accelerating voltage(Electron Microscopy lab at the Center for Materials Science and Engineering CMSE, MIT.

AFM Sample Preparation of Phage Particles

Purified phage particles were dispersed in 100 μL milliQ water to a total count of 1e11 phages. AFM sample discs were prepared with mica sheets and sticky tape was used to peel a fresh mica surface for sample deposition. 100 μL phage preparation was deposited on the mica for 30 min to an hour. Prior to AFM visualization, the phage sample was wicked from the mica surface and the mice surface was then quick dried with nitrogen or argon has stream. To quantify phage length, the AFM images were analyzed using Gwyddion software. For each phage the line was manually drawn along the phage, and then the ruler command was used to measure the line length. The histograms were drawn by randomly sampling ~100 phage particles. The experiments were performed as three replicates where bacterial growth was initiated on different days and even numbers of phage particles were selected from each replicate (e.g., the 100 particles come from 3 replicates and 33 particles from each replicate).

Porosity Calculation

The porosities of nanofoams were calculated from SEM images. Grayscale images were loaded into FIJI/ImageJ and processed using the thresholding function (Image>Adjust>Threshold). The B&W setting was selected such that nanofoam struts would appear white and the background would appear black. The ‘Auto’ setting was used to automatically choose a thresholding value that typically divided a bimodal brightness distribution between a bright foreground and a dark background. Following thresholding, the resulting average pixel value was measured (with Analyze>Set Measurements, select Limit to threshold setting enabled, the average pixel brightness was measured with Analyze>Measure). This pixel value was divided by the maximum brightness of 255 to achieve the fraction of the image occupied by nickel nanowires on a scale of 0 to 1 (in which 1 is 100% strut and zero porosity). The porosity was calculated by subtracting this value from 1. This analysis was performed on images from each condition, and the average porosity was calculated from these values.

Battery Testing

Electrochemical cycling tests were performed in CR2016 coin cells (Pred Materials International) assembled in an Argon glovebox (Mbraun; Airgas AR UHP300). Biotemplated Ni-MnOx electrode samples were dried overnight under vacuum at 80° C. for use as cathodes. These samples were placed on the coin cell casing spring and 30 μL electrolyte (1M LiPF6 in 1:1EC:DMC, Sigma Aldrich 746711) was added. Two pieces of 11⁄16" diameter separator (Celgard3501) and a 9⁄16" diameter piece of Li foil (Alfa 15424745) were added and the coin cell was sealed using a digital pressure-controlled crimper (MTI, MSK-160E). Samples were removed from the glovebox and electrochemically cycled using a potentiostat (Biologic VMP3). For cycling tests, the rates were calculated using the active material mass measure and using a theoretical capacity of 147 mAh/g. Samples were charged to 4.4V, and then discharged at varying rates to a lower voltage cutoff of 2V. The measured specific capacity at a given rate was the total discharge capacity over this voltage range divided by the active material mass. Three cycles were performed at each rate and averaged to calculate the discharge capacity.

Designing M13 Phage Particles for Targeted Glioblastoma Delivery and Imaging 3-1 Phage in the CNS In the early development of in-vivo panning with M13 phage-based libraries, the broad distribution of phage particles across most tissue sections of interest was observed. This distribution could then be driven towards tissue types of interest through preferred variant enrichment and serial panning[1,2]. The ability to access anatomical compartments generally not considered reachable by protein particles was also observed. Injection of phages, regardless of the route of administration, introduce them to the circulatory system[3,4]. Wildtype M13 phages are cleared from the circulation with a half-life of 4.5 hours, and within the first hour of administration, the phages can be found in all organ tissues including the brain[2,3,5,6]. Re-targeting and modification of the phage surface can drastically alter the half-life (as low as <20 min) of the phage particle either as a result of the enhanced tissue homing or due to surface modifications that more actively engage phagocytic systems. For brain tissue, tracking of the brain/blood ratio of wildtype M13 phages identified the peak tissue accumulation (60,000 fold ratio) point at 24 hours post systemic administration, followed by almost complete clearance by 48 hours 7. The baseline brain penetrance observed with natural filamentous phage has fueled efforts to better harness phage particles for brain delivery.

The route of administration, circulation time, and dosage of targeted phage variants all play roles in the phage brain penetrance reported by researchers. The loading of phage to the brain is also dictated by disrupted vasculatures that may result from localized disease modes. The earliest characterization of phage in brain was conducted in 1943 showing local multiplication of bacteriophage and positive phage therapy outcomes for mice infected with Shiga bacteria[8].

However, brain infection models, similar to tumor and plaque models, likely suffer from blood brain barrier (BBB) disruptions, and replication-intact phages do benefit from local amplification in bacterial disease models. More recently, intranasal injection proved to be effective in directing M13 phage vectors to the central nervous system (CNS) via the olfactory neuron system. Anti-beta amyloid scFv-phage effectively labeled amyloid plaques in mouse brain from intranasal administration[9]. Unusually, while filamentous phage was detected in the brain from intranasal injection, a chemically treated spheroid form of M13 failed to show up in the brain, suggesting that the unique high-aspect ratio geometry of the phage could be important in this instance. Full length M13 phages were also successfully distributed in primate brain gray matter and white matter through convection enhanced delivery, establishing wide spread and axonal transport despite the unusually large molecular weight of the phage filaments[10]. Intrathecal injection of M13 phages were also attempted, reporting general safety and ~50% initial dose (ID) retention in the cerebral leptomeningeal space in rat and macaque[11]. Yet, highly efficient brain homing by phage from systemic circulation remains a challenge with functionalization of phage through active BBB crossing mechanisms still being explored.

Studies focused on BBB crossing peptide discovery highlight the potential to engineer for active phage transport to the well protected brain parenchymal spaces. A number of small peptide sequences were discovered from serial panning of libraries against the BBB and employed in complexation with imaging and therapeutic materials[12-16]. These in-vivo and in-vitro panning experiments employed phage libraries for serial enrichment of transcytosing phage variants. The intranasal pathway was further explored, where phage recovered from rat brain post intranasal delivery provided a peptide sequence to enhance nasal to brain passage, with 50-fold higher efficiency observed over random phage[17]. Nanobody (VHH) phage variants panned

TABLE 1

Brain homing phage variants: reported tissue uptake quantification.

| Model (dose) quantification (24hrs) | Control phage | Selected phage quantification (24hrs) | Phage motif (p3) | Ref |
|---|---|---|---|---|
| ICR mice (1e11 pfu) | ~1.2e4 pfu/g | ~50e4 pfu/g | CTSTSAPYC (SEQ ID NO: 10) | 7 |
| ICR mice (1e11 pfu) | ~2.5e4/g | ~4e4 pfu/g | TGNYKALHPH NG (SEQ ID NO: 11) | 18 |
| SD rats (1e11 pfu) | ~1.7e6 pfu/g min | ~7e6 pfu/g min | AC-SYTSS TM-CGGGS (SEQ ID NO: 12) | 19 |
| Balb/c (1e10 pfu) | ~2e2 pfu/60 ng DNA | ~8e3 pfu/60 ng DNA | CRTIGPSVC (SEQ ID NO: 33) | 20 |

against in-vitro BBB transmigration model attained accumulation up to 5% ID/g of brain tissue in mice[21]. Transcytosis model across MDCK cells was used to enrich a phage variant with 1000 to 10,000 fold basal to apical crossing profile[22]. Mouse brain perfusion model demonstrated additional peptides capable of improving phage ability to bind to the brain tissue by 5 to 6 fold[23]0.7-mer peptide library phages recovered form mouse parenchyma led to the discovery for a phage clone with 41-fold higher translocation efficiency over random phages[7]. The sequence here was noted for its disulfide bond and cyclic conformation which was critical to its brain affinity. A cyclic 7-mer library yielded 349 unique phage variants that mediate tropism to the brain microvasculature. C-SXTSSTX-C (SEQ ID NO: 14) sequences were found in high abundance and an idealized version C-SYTSSTM-C (SEQ ID NO: 15) was tested against control phage with 5 fold brain accumulation observed[19]. Staquicini et al. also worked with cysteine $CX_7C$ phage libraries to isolate a CRTIGPSVC (SEQ ID NO: 13) clone which was chosen from the final enrichment group for its similarity to transferrin (Tf). The chosen Tf-mimic phage maximizes for the likely targeting of the Tf-receptors that are abundant to the CNS and that are also overexpressed in human glioblastoma.

Ultimately, a 40-fold intact BBB crossing was demonstrated by the discovered clone over control phages[20]. Overall, such selection of phage display variants relies on receptor accessibility to the circulating phage particle and can in many cases be blind to the exact mechanism behind the uptake patterns observed. A major question since the introduction of in-vivo panning has been the lack of clarity between phage targeting to the endothelial markers[24-26] of the specific organ system or if the enriched peptide is actually driving deeper parenchymal tissue access.

To address the concerns over active transcytosis from vasculature to the extracellular matrix space, the phage panning process can be tailored towards specific tissue and fluid compartments of the organ of interest. In the case of the CNS, the blood-cerebrospinal fluid barrier (BCSFB) or choroid plexus (CP) has been proposed as an interface of relevance for phage transport. The CP capillaries are considered to be more permeable than the BBB and ventricular CSF borne agents are generally thought to achieve widespread and substantial penetration to brain areas[27]. Baird et al. describes the advantage of screening phage libraries for CP targeting species in CP cell culture, intact CP explant, in-vivo ICV injection, and through CSF collection to isolate variants[28]. $CX_7C$ phage library was panned against CP explant in this way to discover phage that homed to the CP post ICV injection[29] and EGF targeted phage were also used to engage CP epithelia EGFR, and upon ICV injection, could deliver a GFP report gene to transduce the CNS epithelia in the ependyma and CP in-vivo[30]. CSF targeting of phage variants from the systemic circulation however is yet to be attempted and remains an area for discovery. Another exciting pathway proposal for brain homing phage discovery is through retrograde axonal transport mechanisms ascribed to mammalian viruses such as HSV, rabies, and polio.

Intramuscular injection of phage libraries to the CNS peripheral gastrocnemius muscle can lead to discovery of motor neuron soma homing M13 phage variants[31]. Such phage derived targeted axonal import (TAxI) peptide could mediate transport to the spinal cord motor neurons and showed delivery to 50% of neurons in a motor unit from a single IM injection[31]. Phage mutant application to cell-specific enrichment across not only the BBB but the various CNS interfaces such as the CSF, CP, and spinal cord is the next step towards phage derived CNS delivery.

3-2 Glioblastoma

Glioblastoma multiforme (GBM) is a particularly aggressive form of tumor that occur in the brain or spinal cord, originating from astrocytes and oligodendrocytes. GBM accounts for 52% of all primary brain tumors and typically develop in the frontal and temporal lobes of the brain. Glioblastoma is a very fast-growing tumor type that do not benefit from regular screening practices and is often diagnosed at much later stages of the disease, usually post onset of disruptive behavioral and physical symptoms. Upon diagnosis, surgical resectioning remains the primary mode of brain cancer therapy today. However, general surgical debulking is highly dependent on the surgeon's ability to successfully separate cancer tissue from its surrounding healthy tissue. The surgeon's precision, especially in highly sensitive organs such as the brain, can directly affect patient survival rates[32]. The rapid progression associated with brain tumors as well as the difficulty of properly separating the cancerous tissue and reducing the potential of relapse make tumors of the neural systems particularly deadly, with survival rate of patients rarely exceeding sixteen months[33]. Consequently, recent research has closely focused on improvements in monitoring and guidance systems (PET, CT, MRI) as well as contrast agents used before and during surgeries. In-situ placement of chemotherapies such as local implantable drug reservoirs (i.e. Gliadel used to line surgical cavity[34]) and microchips and catheter infusions during surgery have been utilized to some success but have not been able to overcome the high prevalence of tumor recurrence and metastasis. Temozolomide remains the standard of care post-surgical chemotherapy, yet the its poor circulation time and low vascularization leads to low penetrance of the drug and frequent dosing requirements that quickly cause systemic toxicity in patients[35-37]. As well, the highly heterogeneous nature of the tumor cells and the overexpression of drug efflux units characteristic of glioma cells make the GBM particularly chemo-resistant[38]. Ultimately, the tenacious resistance of GBM to conventional treatment regimens is underscored by the oft fatal relapse and metastasis seen in most cases and the limited capacity of the brain to repair itself, a fact which precludes more invasive strategies.

Alternate non-invasive, non-surgical treatment tactics involving systemic delivery and small molecule formulations very specifically targeting glioma cells have also been considered. The blood brain barrier (BBB) here plays a critical role in impeding therapeutic and diagnostic efficacy during such intervention of tumor masses of the central nervous system (CNS). The BBB, lining the interface between the blood vasculature and the brain parenchyma, regulates the traffic of nutrients and metabolites to the brain and curtails most therapeutic access to the brain tissue. The endothelium is characterized by tight and adherens junctions, efflux transport systems, and low number of pinocytic vesicles. Consequently, the BBB excludes brain access of about 98% of small molecule drugs and all macromolecules[39]. Of course, bypassing of the BBB altogether through intrathecal injection to the cerebrospinal fluid and intranasal delivery for passage across the nasal mucosa is practiced as well, but suffer from rapid clearance from the CSF and low efficiencies despite the intrusiveness of the procedure. Additionally, each time accessing the intrathecal space raises risks for infection, bleeding, and CSF leak.

As the efficacy of treatments for diseases of the CNS are highly limited by the heterogeneous distribution and low passage of materials across the BBB[36,37,40,41], nanoparticle and receptor mediated delivery and chemical and focused ultrasound barrier disruption methods have been offered as potential solutions. Chemical disruption of the BBB can be achieved through osmotic agents that widen junctions over 15 minutes to 4 hours or chemical inflammatory agents (i.e. IL-2, bradykinin, alkylglycerols) that signal for vasodilation, enhancing permeability over 3 to 15 minutes at a time[42]. Physical disruptions to the BBB are possible through ultrasound and magnetic waves, and short pulses of focused ultrasound in concert with microbubbles introduced to the bloodstream have been of particular interest here. The microbubbles respond to the pulse to enforce wide junction gaps and clinical trials are underway for use of the focused ultrasound technology with TMZ, DOX, immunotherapies and stem cell therapies. Yet, BBB disruptions are regarded with some caution due to the non-specific effect throughout the brain, the potential for the spread of the tumorous cells, and the exposure of the cerebral tissue to the contents of the blood.

The engineering problem of designing targeted particles for honed cancer cell killing has been an exciting topic of exploration for the past twenty years. Such nanotheranostics span new and strategic preparations of a whole range of materials including traditional chemotherapy agents, metallic particles, carbon nanotubes, lipid particles, immunogenic agents, fluorophores, metabolites, small peptides, antibody fragments, DNA, RNA, viral vectors, stem cells, CAR-T, and so on. In the case of brain tumor, the cancer therapy modalities must also take the BBB into consideration. Biologics with natural tropism for brain entry despite their large size has been of certain interest. Synthetic mutants, reprogrammed for enhanced penetrance has been an exciting avenue for viral vector and cell mediated brain entry development. AAV9 brain homing serotypes have undergone capsid mutations that increase brain transport and transduction efficacy by 40-fold[43-45]. Additionally, the field is also beginning to better understand the immunological profile of the brain space. Recent discovery of lymph nodes and potential transmigration of microglia and others immune cells though the BBB has fueled interest in the path to reach brain parenchyma through immune actors[46-48]. Recently, EGFRvIII directed CAR-T cells were also able to control tumor growth in xenogeneic subcutaneous and orthotopic models of human EGFRvIII+ glioblastoma[49]. This has been followed by a phase 1 clinical study of CAR-T cells transduced with humanized scFv directed to EGFRvIII in patients with either residual or recurrent glioblastoma[50].

The dominant barrier crossing mechanism of the targeted therapy is very much individual to the specific formulation. The permeability of the BBB to nanoparticles and biologics is affected by a number of factors including size, charge, geometry and surface chemistry of the particles[41,51-56]. Upon entry past the BBB, the diffusivity of the particles is another crucial element dictated by the chemical and biologic structure of the drug complex. The BBB has been documented to be most accessible with small, lipid soluble molecules that may diffuse through the transmembrane. Materials such as temozolomide exhibit CSF to plasma ratio of about 20%[57]. On the other hand, ligands directed towards transporters may be harnessed with a general BBB crossing improvements of 10 fold[58]. To allow for selective passage across the BBB, larger nanoparticles are complexed with such ligands to facilitate active receptor-mediated transport.

This active transport is ultimately dependent on the availability of receptors, the circulation and clearance dynamics of the particle, and disease states. In the case of brain tumor, the disruption of vasculature of the tumor environment is advantageous to the accumulation of materials[59,60]. Malignant gliomas are shown to infiltrate the surrounding normal brain parenchyma, resulting the vascular permeabilization and the breakdown of the nearby BBB[59]. Hence, while the BBB poses a severely limiting barrier to localized therapy, the case is often helped by the physiological abnormalities often associated with diseases of the CNS.

3-3 BBB-Penetrating Nano-Phages for In-Vivo Glioblastoma Imaging

The blood brain barrier (BBB) specifically plays a critical role in impeding therapeutic and diagnostic efficacy during clinical intervention of tumor masses of the central nervous system (CNS). We test this trafficking barrier via active transport of materials with a M13 phage particle shuttle. The M13 capsids can be quickly cloned for combinatorial display of tissue specific moieties and of residues suited for loading of relevant molecular agents, making a compete theragnostic platform for nano-medicine. As described, previous research has shown that M13 bacteriophage display of such peptide libraries is useful as a technique for the panning of ligands against biological barriers such as the BBB, the gastro-intestinal track, and the human mucosal barriers and against target tissue populations such as cells of the central nervous system[12,14,16,61-65]. Blood brain barrier crossing sequences have been discovered from M13 phage libraries on a number of occasions for use with CNS transport of nanomaterials, therapies, and engineered viral technologies such as AAV[7,13-21,23,28,31]. We also know that M13 phage display technology (with control over all five capsids and the packaged genome) enables us to engineer the M13 phage itself as a multi-functional transporter of imaging and therapeutic agents and of genetic cassettes encoding cancer cell killing genes like TNF-alpha[61,66-76]. Here, we develop a phage clone that encodes for chlorotoxin (CTX) on the p3 capping protein of the M13 phage and demonstrate that these targeted phage particles can be loaded efficiently to the site of glioma.

CTX-phages carrying indocyanine green (IGC) imaging agent allow for non-invasive detection of orthotopic glioblastoma in-vivo in the second window near infrared (SWIR) regime.

Chlorotoxin is a 36 amino-acid (3995.8 Da) peptide derived from the venom of the *Leiurus quinqueestriatus* scorpion. Recent studies show that the CTX peptide selectively binds to and invades malignant gliomas and tumors of neuroectrodermal origin such as medulloblastomas, neuroblastomas, melanomas, PNETS, and small cell lung carcinoma[32,33]. Molecular targets for chlorotoxin include voltage gated chloride channels (GCC), calcium-dependent phospholipid-binding protein annexin-2, the inducible extracellular enzyme matrix metalloproteinase–2 (MMP-2), and membrane type 1 MMP. Chlorotoxin's specificity to these targets important to glioma invasion, cell shape and proliferation underlines its anti-neoplastic potential[77-81]. Recognized for its highly specific properties in halting glioma progression, chlorotoxin has been evaluated in phase III human clinical trials as a targeted radiotherapy and imaging agent[77,82-84]. These trials show chlorotoxin to be safe for patient administration and define chlorotoxin as an important new treatment and tumor tracking tool. Fluorophore conjugated chlorotoxin, termed 'tumor paint', has been effectively used to image various tumor types[77,85], and other combinations of CTX with nanoparticles (comprising fluorophores, siRNA, & other drugs), CAR-T, chemo-therapeutics, and MRI contrast agents have also been studied[32,33,52,77,79,83,84,86-90]. Native CTX as well as conjugated tumor paint display the ability to pass through the blood-brain tumor barrier (BBTB) and binds >80% of brain tumor cells, despite the heterogeneity of GBM cell populations[86], which makes it an ideal trafficking peptide for nanoprobes designed for brain tumor diagnosis and theragnosis.

Additionally, in order to observe the impact of the phage size on the tumor homing ability and bioavailability of targeted phages across the BBB, we hack the M13 assembly system to package pre-determined ssDNA genomes of different sizes to make short phages (achieving sizes below ~50 nm, a twenty-fold decrease from regular M13 length). These mini-phages retain the five capsid types of the multi-functional M13 phage platform and allow us to explore the benefits of shorter, more rod-like geometries in trafficking to in-vivo targets. The miniaturized phage platform carrying imaging or therapy agents can reach deeply embedded tissue sites and will allow for early diagnosis and treatment simultaneously. CTX displaying mini-phages (approx. 50 nm, 100 nm, 300 nm variants) show enhanced specificity up to 80-fold to the location of brain tumor while, surprisingly, circulation half-life drops for the smaller particles below 300 nm in length. Ultimately, current clinical procedures could highly benefit from the introduction of targeted carriers such as phage derived particles that can clearly define the boundaries of tumor masses and that provide a multi-modal structure for simultaneous distribution of theranostic cytokines, enzymes, genes, or chemical agents.

1-3-1 Chlorotoxin-Phage Homing to GBM22 In-Vitro and In-Vivo

M13KE (NEB) phagemid was cloned with CTX sequence insertions at the p3 display site. Anti-p3 protein and anti-his western blots of a CTX-6HIS expression variant demonstrated the complete insertion of the CTX protein sequence (FIG. 38). The engagement of phage with cancer cell surface and subsequent clathrin-mediated internalization[81,91-93] are enhanced by the display of CTX. Phages conjugated with AlexaFlour647 dye through EDC chemistry were incubated with GBM22 cells (FIG. 28). Flow cytometry of GBM22 cells incubated with wildtype or CTX displaying phage at 10,000 phage/cell reveal increased uptake rates for CTX-phage. The CTX peptide disperses in the cytoplasm in normal human fibroblasts and localizes near the Golgi in human glioma, lung carcinoma, and vascular endothelial cells[78,81]. In GBM22 cells, chlorotoxin presenting phage similarly localize to the golgi while wildtype equivalents are not visible in most cells (FIG. 28C). Wildtype M13 phage are generally not actively internalized and are non-specifically internalized at very low rates to endo-lysosomal pockets and rapidly degraded by the proteasome in mammalian cells[91,93-96].

Figures 29A, 29B, 29C:
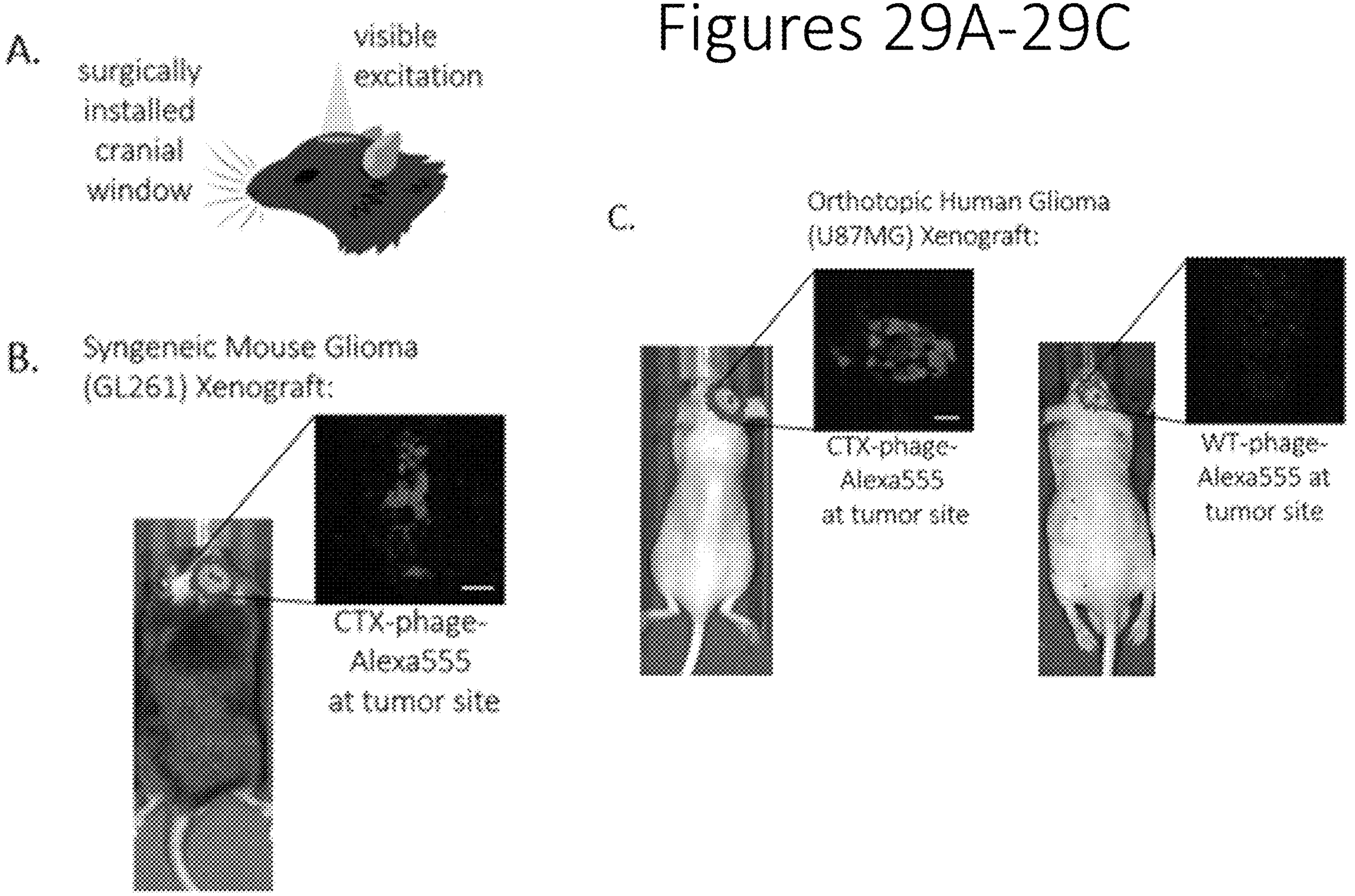
FIG. 29A-29C relate to P3 expression of chlorotoxin peptide.
Figure 30A:
FIG. 30A-30D shows the assembly of 50 nm, 100 nm, and 300 nm chlorotxin-phages. 30A) Key initiator, terminator, and packaging signal sequences of the inho mini-phage assembly system, with the nicking sites designated by ^ and packaged sections illustrated in light and dark green. 30B) Schematic of inho production of cssDNA an helper CTX-RM13-f1 production of phage assembly proteins and CTX displaying p3 capping proteins. 30C) Atomic force microscopy (AFM) imaging of 50 nm, 100 nm, 300 nm phages assembled from cssDNA f 285, 475, and 1960 nucleotide lengths (200 nm) scale). 30D) The designer cssDNA length directly dictates the phage length.
Figure 30B:
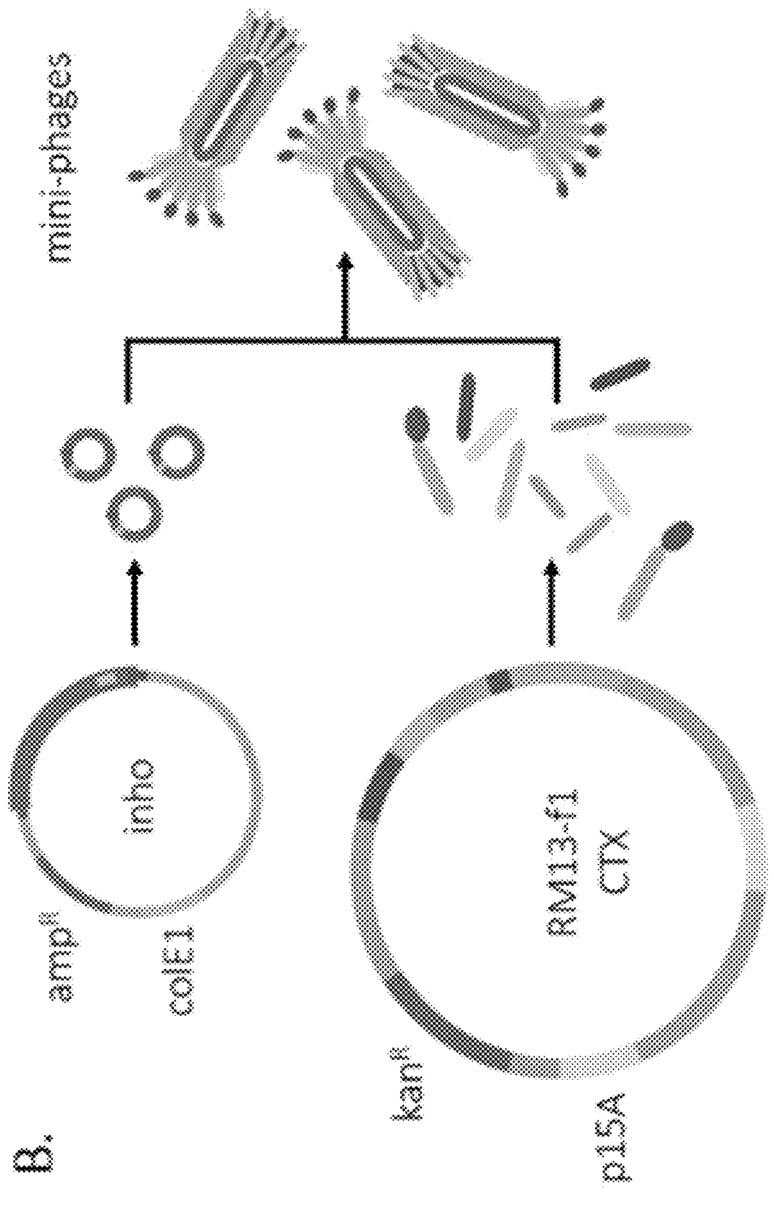
Figure 30C:
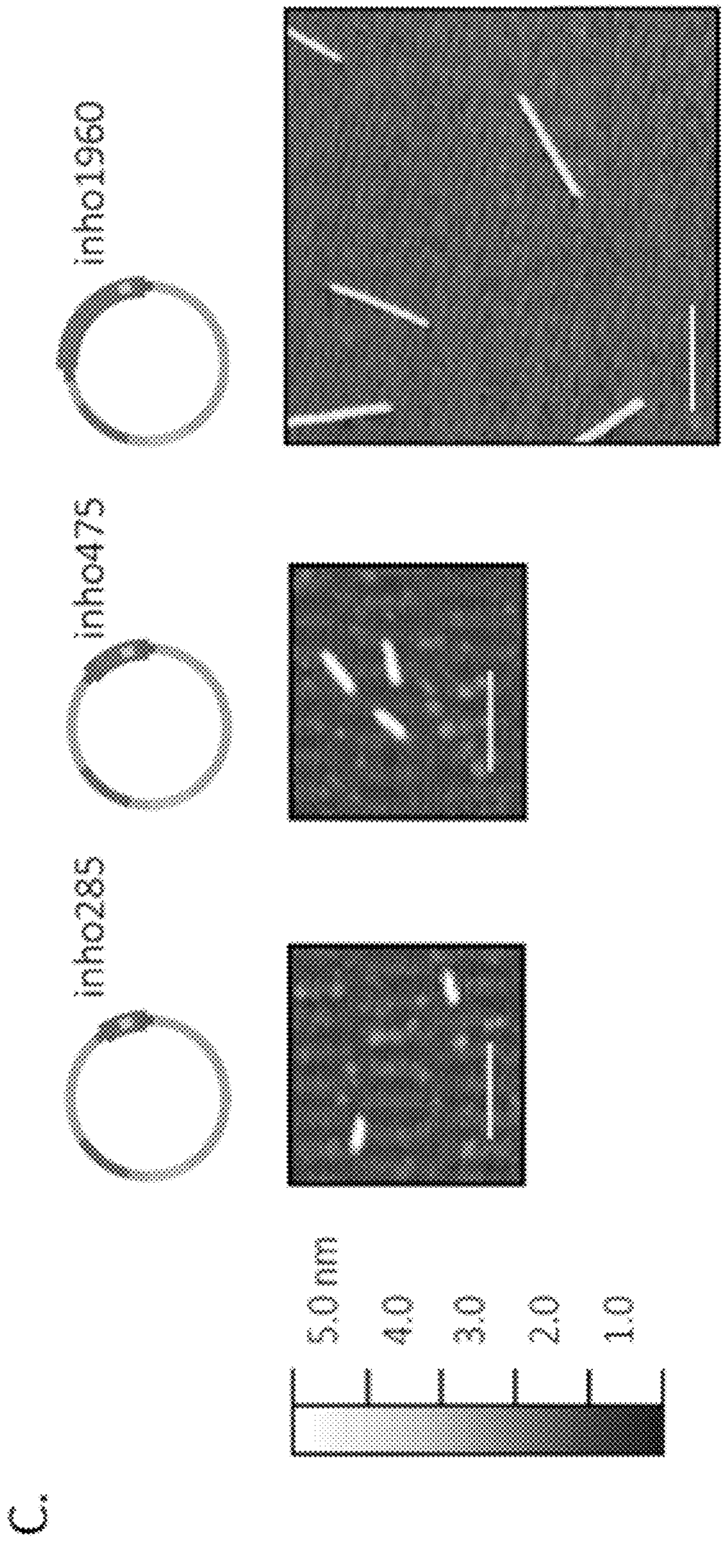
Figure 30D:
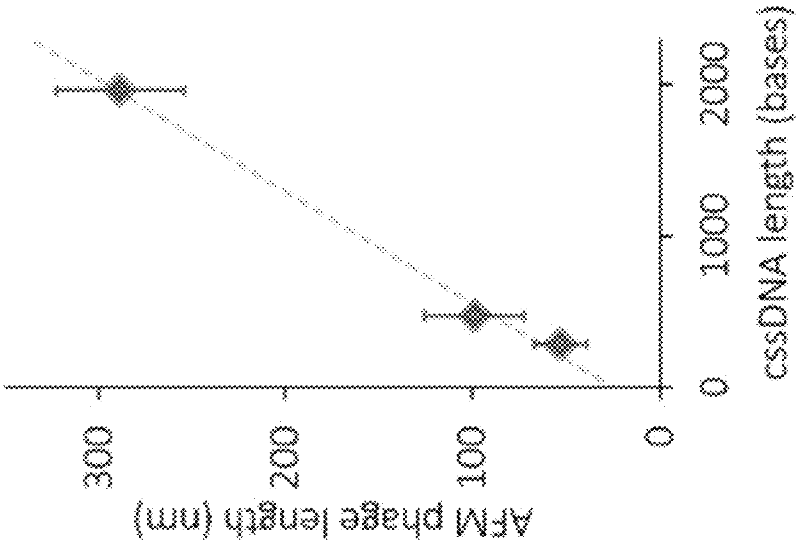

To validate the in-vivo tumor homing potential of CTX-phages, CTX-phages and wildtype phages conjugate with Alexa555 dye was dosed to tumor bearing BL6 immunocompetent and NCR-NU immunocompromised. In both GL261 and U87 xenograft models, cranial window imaging through mouse skull reveal the fluorescent staining of the tumor tissue with dye bearing chlorotoxin phage (FIG. 29B,C). Limited tumor fluorescent staining is observed with non-specific wildtype phages accumulation at the disrupted tumor vasculature.

1-3-2 Chlorotoxin Inho-Phage Assembly

As described in Section 2, a novel phagemid system, termed inho, can be employed to generate package-able viral genomes with desired sizes, 100s to 1000s bases, which are much smaller than the 6407 nucleotides observed in wild-type M13 cssDNA (~880 nm in length). These package-able genomes are highly controlled for length and contain the phage packaging signal (PS) and newly modified f1-origin and f1-termination of replication. The bacterial plasmid production or selection elements such as bacterial origins and antibiotic markers are excluded from the novel mini genomes. In effect, construct with our f1-on/f1-term/PS inserts produce cssDNA from the sequence length flanked by the f1-ori and f1-term and is tagged to be packaged. To produce minimally sized cssDNA, the packaging signal region may also be removed and the cssDNA titer can be enough to begin assembly. In the absence of M13 protein coding in our packaged genomes, we constructed a helper plasmid (RM13-f1) which expresses all essential phage assembly components but itself lacks the packaging signal and f1 replication structures. To ensure that the modified f1-ori and f1-term produce pure, high yields of the flanked cssDNA segment, the RM13-f1 helper code for the low efficiency mutant of the rfDNA nicking protein p2[Met40] and high efficiency mutant of the cssDNA binding protein p5[Cys21]. Only the low efficiency DNA nicking p2 mutant is compatible with the sequence modifications of the novel f1-term as explained in Section 2. The loss of the f1 distal replication enhancing Domain B is also compensated by the hyper production of p2 resulting from the p5[Cys21] mutant[97-101]. Transformation of *E. coli* with the helper RM13-f1 will lead to kanamycin resistance and to the production of the M13 assembly and coating proteins but no extrusion of phage will take place without inho cssDNA available to package. Only in the presence of both of the RM13-f1 and inho constructs is phage production of the given size observed, where inho cssDNA are packaged by the proteins translated from the RM13-f1 plasmid. Like any M13 helper phagemid, the RM13-f1 can be modified for display of peptides. RM13-f1-CTX helper plasmid was constructed for display of CTX on the p3 capsid of mini-phages. Inho constructs for 50 nm, 100 nm, and 300 nm length phages were cloned for production of CTX mini-phages in XL1-blue cells (FIG. 30).

Figure 31B:
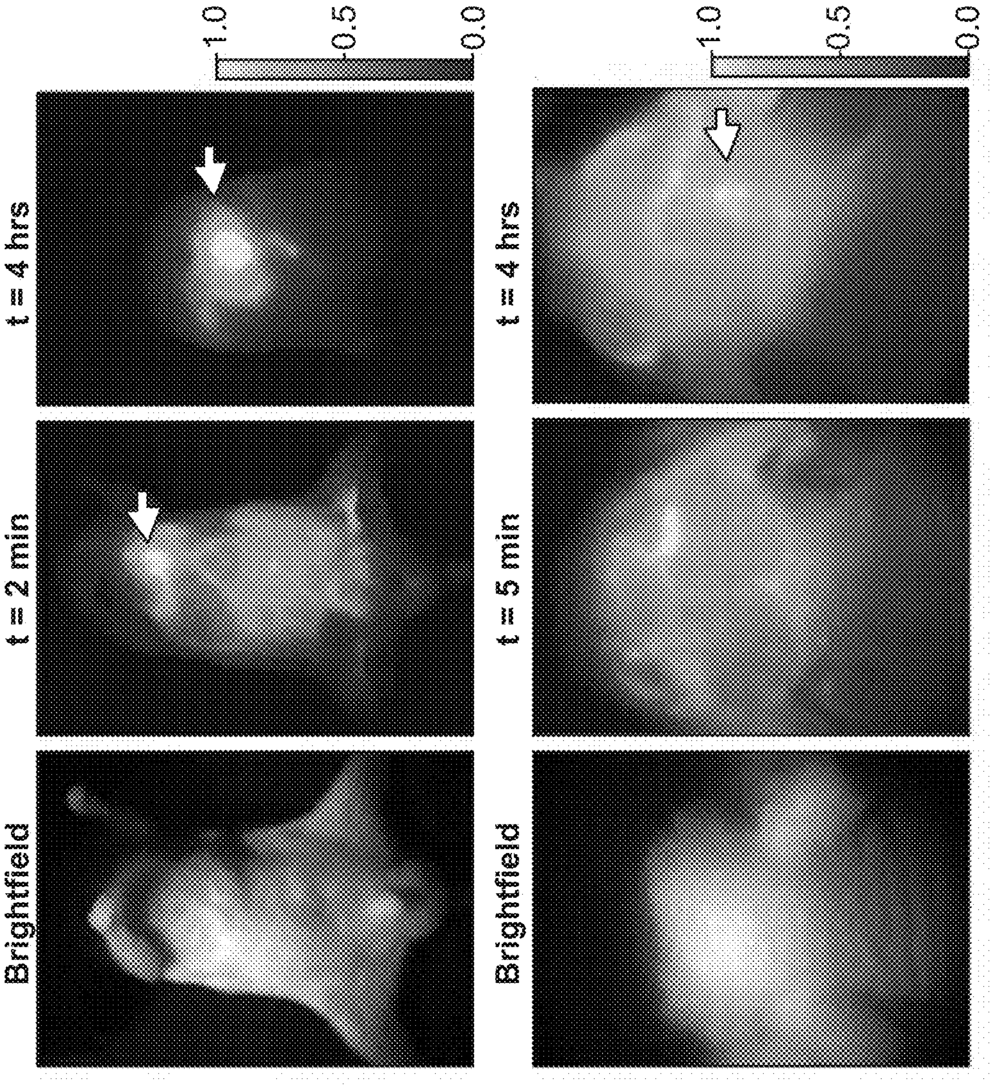
FIG. 31A-31E show tumor accumulation of chlorotoxin-phages. 31A) ICG loaded phages were injected to the tail vein of mice with established GBM22 orthotopic xenografts, measured by luciferin bioluminescence. 31B) Whole body and brain imaging of ICG phage in mice. Soon after injection, mostly vasculature structures are visible in brain and body with the heart (arrow) clearly highlighted. 4 hours post injection, signal from the body is from the liver and spleen (arrow) and the brain tumor (arrow) accumulation is clearer. 31C) Serial imaging of mouse dosed with 900 nm CTX-phage-ICG. 31D) Signal decline over 3 days normalized to highest accumulation at 24 hrs. 31E) Tumor accumulation of 300 nm, 100 nm, 50 nm CTX-phage-ICG.
Figure 31A:
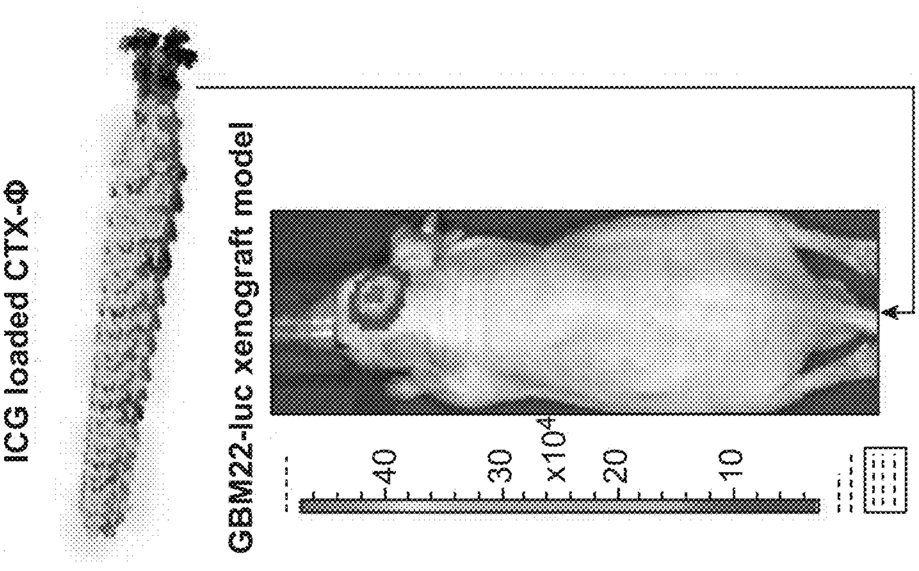
Figures 31C, 31D, 31E:
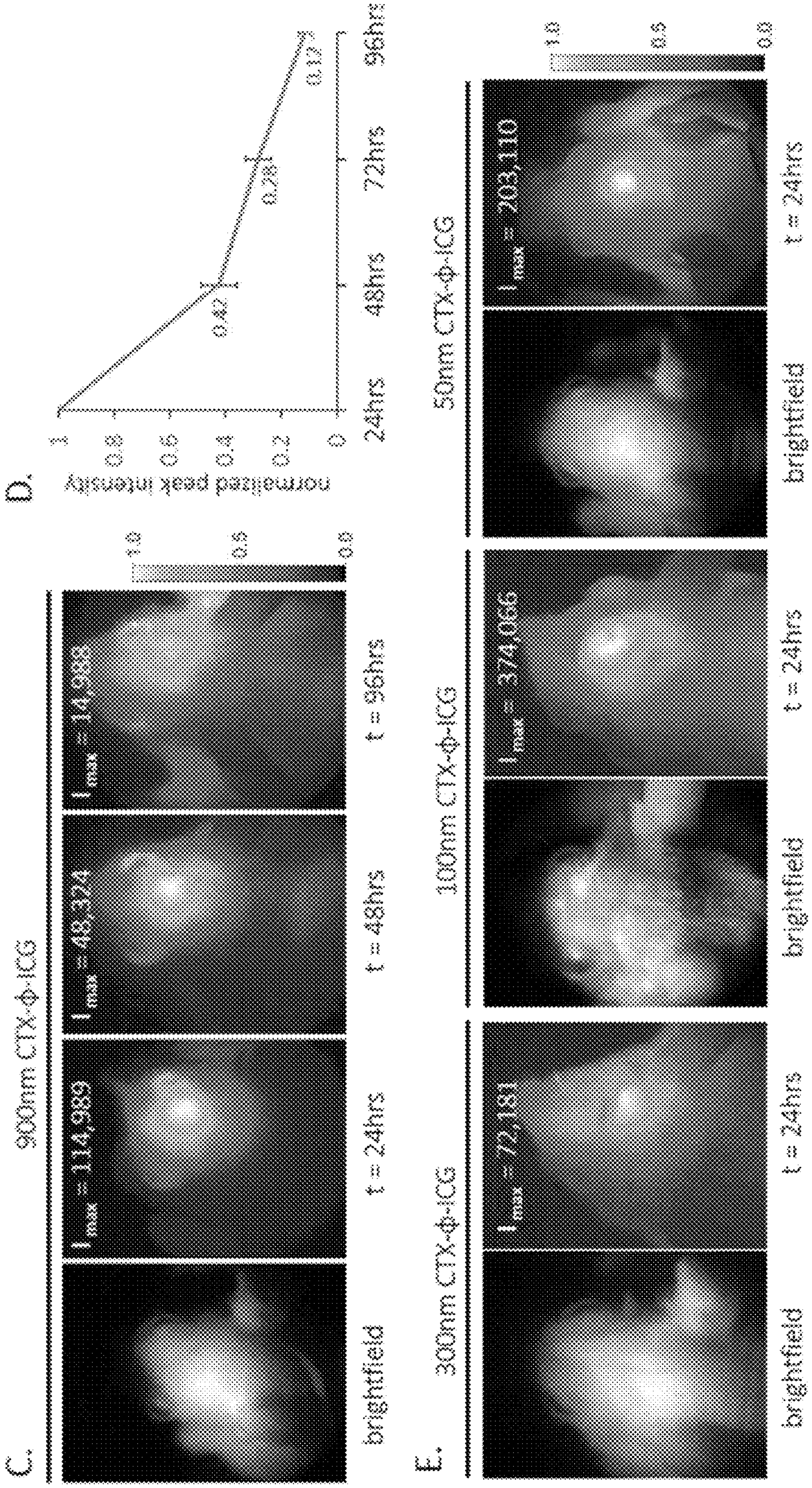
Figure 32A:
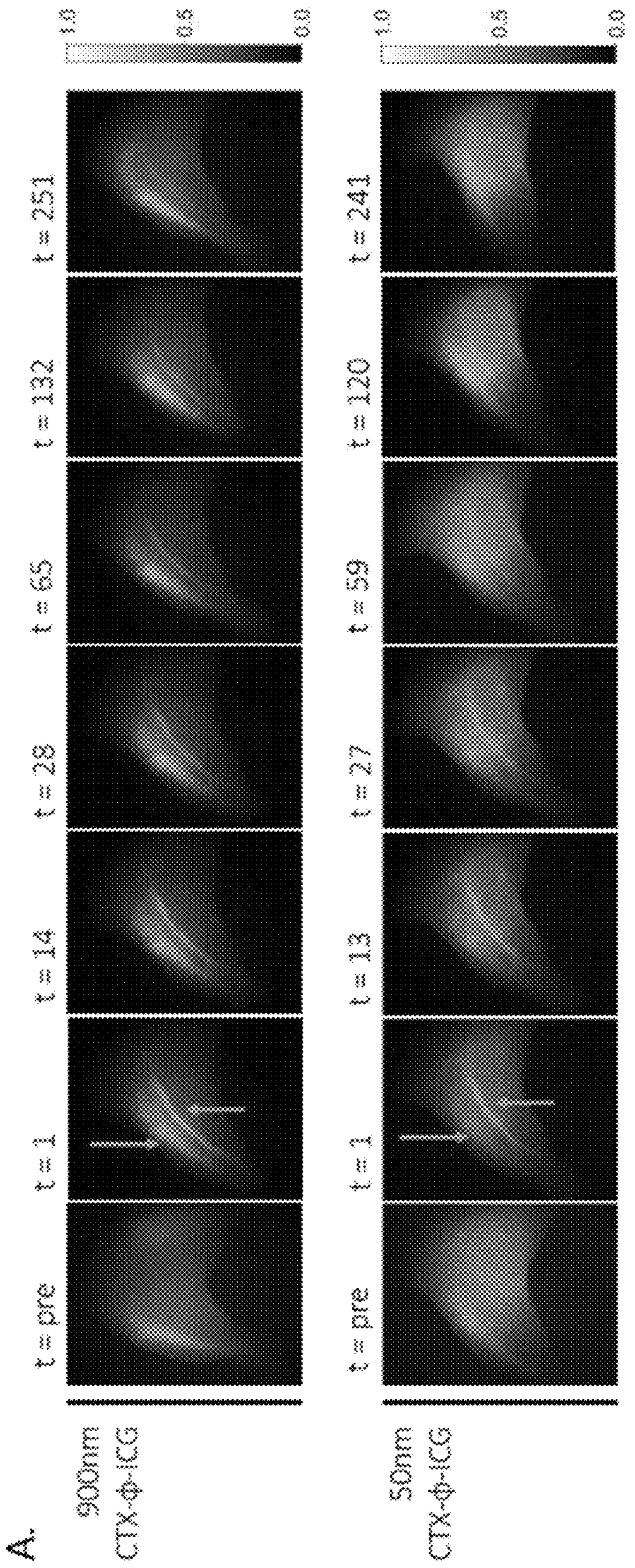
FIG. 32A-32E shows the circulation profile of chlorotoxin-phages. 32A) Example hind leg time series imaging of mice dosed with 900 nm and 50 nm CTX-phage-ICG. Femoral artery (orange arrow) and bone (blue arrow). Signal intensity from femoral artery, normalized over peak signal, tracked over time for 32B) free ICG dye, 900 nm phage-ICG, 900 nm CTX-phage-ICG and 32C) 900 nm, 300 nm, 100 nm, and 50 nm CTX-phage-ICG. 32D) Half-life's calculated from decay fits of 50 nm, 100 nm, 300n, 900 nm, and 1400 nm CTX-phage-ICG femoral artery signal tracked over 8 hrs (n=3 per group, f(5)=12, p<2.63e−5, ANOVA) 32E) Exponential decay fit and half-life model for normalized signal tracking.
Figures 32B, 32C, 32D, 32E:
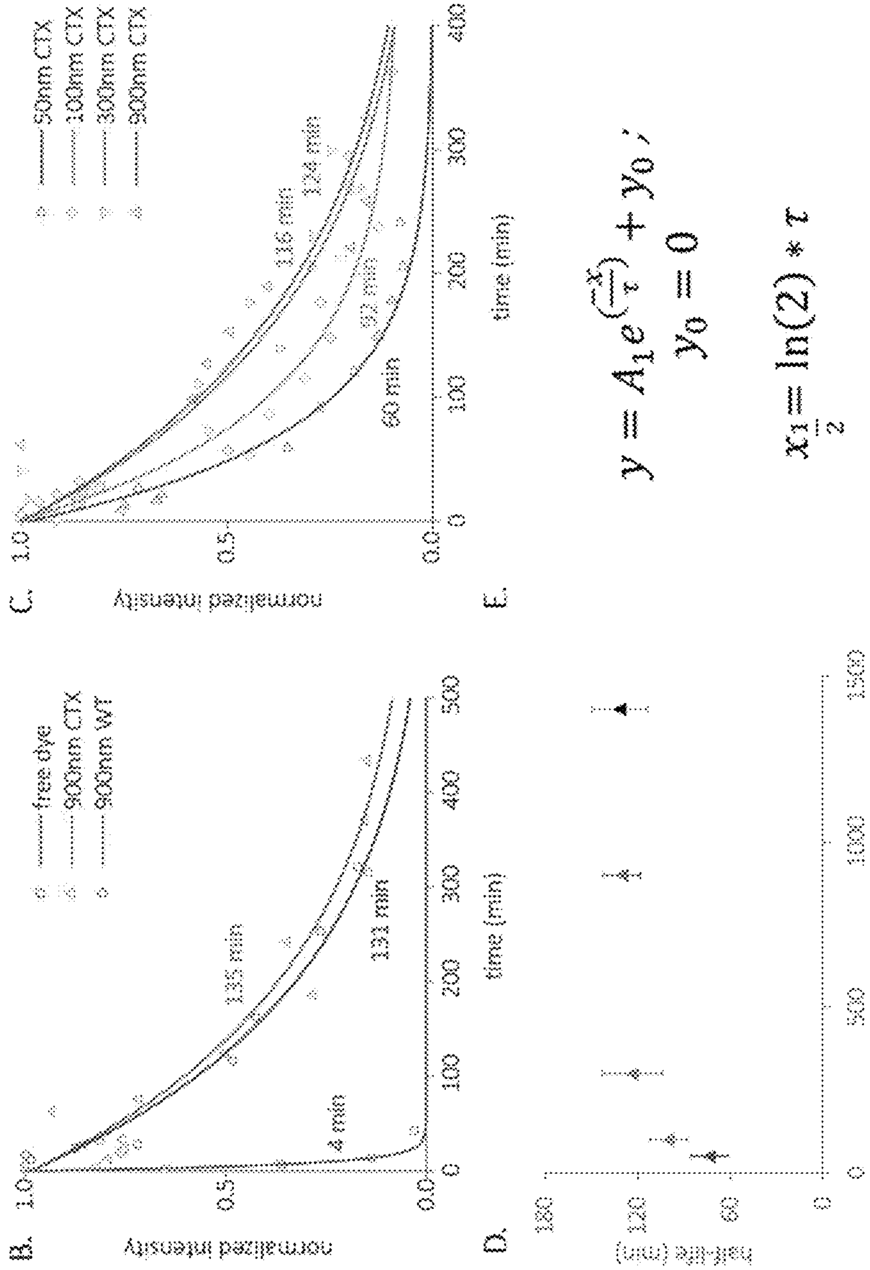

1-3-3 Chlorotoxin-Phage SWIR In-Vivo Visualization of Orthotopic GBM22 Xenograft Chlorotoxin displaying M13 is evaluated for their ability to accumulate to the site of orthotopic GBM22 in NCR-NU mouse model. The phages are visualized in-vivo by EDC chemistry conjugate indocyanine-green (ICG) molecules that have long tail fluorescence in the second window near infrared (SWIR) window between 900 nm-1700 nm[83,102-104]. Using our previously described SWIR imaging modality[67,69,105], we tracked the circulation and localization of CTX-phages. 2e12 plaque forming units of CTX-phage were dosed per glioma bearing mouse with ~100ICG molecules loaded per 900 nm length CTX-phage (ICG extinction coefficient 2.621e5 M−1cm−1 at 780 nm)[104,106]. We observed strong signal contrast (808 nm ex. and 1150 nm longpass filter) in mouse vasculature minutes post tail vein injection in the major femoral and mammary veins and arteries leading to the heart (FIG. 31B). The half-life of the 900 nm ICG loaded phage was observed to be close to 2 hrs (FIG. 32). Signal accumulation to the site of tumor is observable 4 hrs post injection (FIG. 31B). Tumor localization signal increases over the next 20 hrs as background noise from mouse circulation clears and tissue accumulated phage signal becomes more visible. ICG fluorescence clearance from the site of tumor begin −24 hrs post injection time and accumulation site contrast is lost at the 96 hrs timepoint (FIG. 31C,D). ICG loaded phage without CTX targeting have non-specific accumulation to the tumor site which is too weak to allow for strong in-vivo signal contrast (FIG. 36A). Any tumor localization of WT-phage at signal intensities below 15,000 is difficult to distinguish from the background observed from the highly vascularized retro-orbital sinus. 50 nm, 100 nm, and 300 nm CTX-phages loaded with ICG dye also demonstrate clear in-vivo tumor signal with equivalent ~2e13 ICG dosage per mouse. Peak signal intensities at 24 hrs accumulation with phage correlate with the size and progression of the individual tumor growths.

1-3-4 Chlorotoxin-Phage Circulation Dynamic Based on Size

The circulation time of ICG loaded CTX-phages of 50 nm, 100 nm, 880 nm, and 1400 nm length (M13 Y21M clone tested) show surprising trend towards lower circulation at smaller sizes. ICG loaded phages of varying sizes were dosed to mice at equivalent weight (~2e14 ICG per mouse) and the ICG signal decay in the mouse femoral artery was tracked over 8 hrs. The signal decay fit time constant, T, was used to determine half-life of variants. 300 nm, 900 nm and 1400 nm phages all exhibit half-life near 2 hrs. Drop in the expected half-life from wildtype M13 phages of ~4.5 hrs[2,5,6] to approximately 2 hrs result from the conjugation of the highly hydrophobic ICG dye molecules to the surface of the phage with no observable difference noted between CTX targeted and WT phages. At 100 nm, we see ICG loaded phage circulation half-life begin to drop from ~2 hrs to ~100 minutes. 50 nm ICG loaded CTX-phage circulation half-life is even lower at around 70 minutes. On the other hand, phages longer than 900 nm, such as 1400 nm ICG dye loaded CTX-phage, does not prolong circulation time. The 100 nm threshold for drop in circulation underline the effect of the −5 nm diameter of the filamentous phage structure on the clearance dynamic of the particle. 50 nm length, 5 nm diameter phages likely experience extravasation and potential shift towards renal clearance that reduce the vasculature residence time of the particles. As reported the half-life of free ICG dye is observed to be near 3-4 minutes[102,103,107], which is much improved by phage derived particle loading to over an hour depending on size. Only about ~10 (50 nm phages) to ~100 (900 nm phages) ICG molecules per phage particle was necessary to achieve high vasculature contrast and vastly reduces the high ICG dosages generally required for contrast enhancement in the clinical setting due to its extremely rapid clearance and lack of specificity[107].

1-3-5 Chlorotoxin-Phage SWIR Ex-Vivo Characterization of Tumor Localization

Figures 33A, 33B:
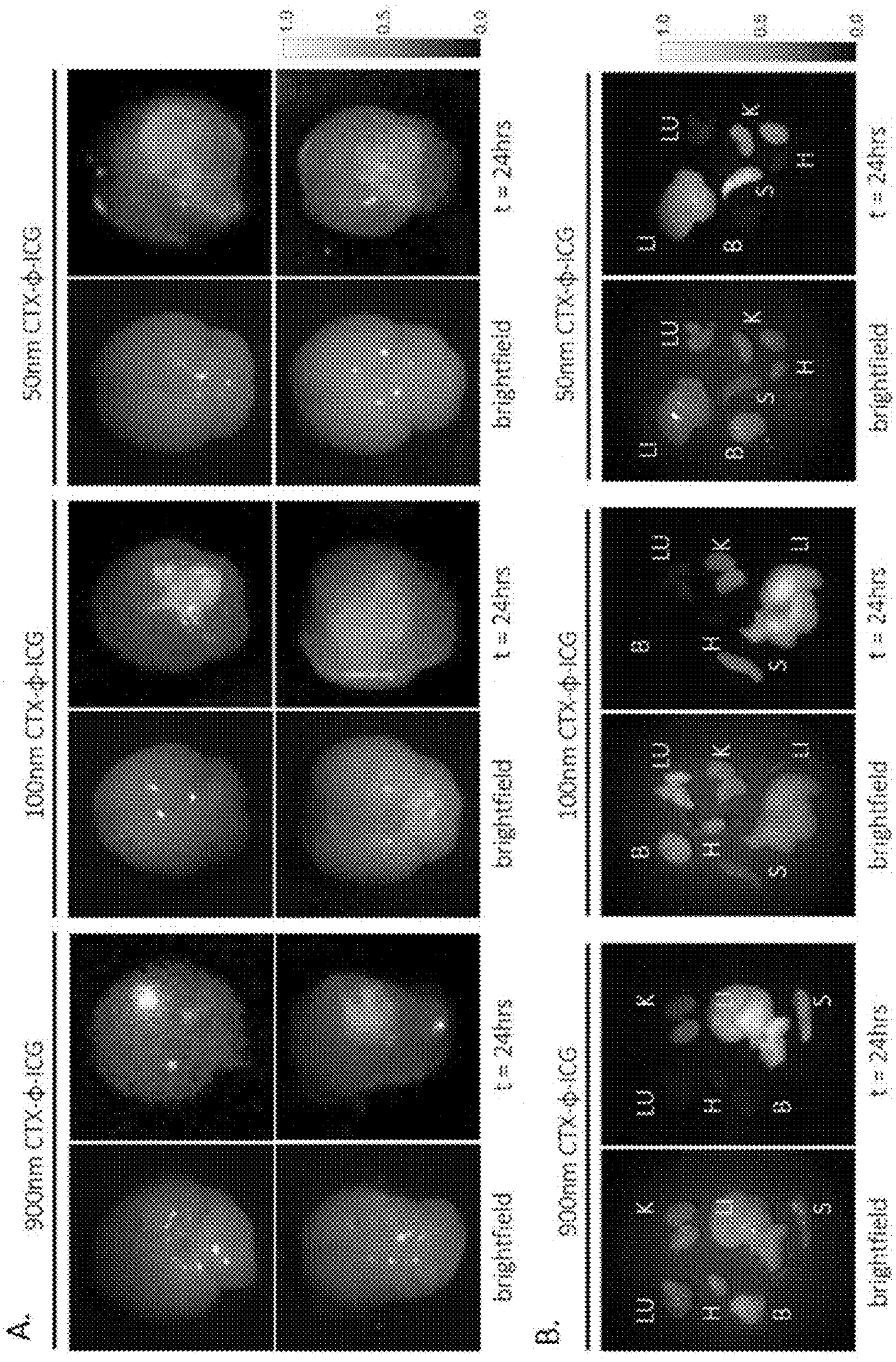
FIG. 33A-33D shows the ex-vivo characterization of tumor accumulation of chlorotoxin-phages. 33A) ICG loaded phage accumulation to brain tumor masses imaged from whole brain tissue extracted 24 hrs post injection of 900 nm, 100 nm, and 50 nm CTX variants. 33B) ICG signal from major organs dissected from mice dosed with 900 nm, 100 nm, 50 nm CTX-phage-ICG. Histology H&E (1 mm, 50
Figures 33C, 33D:
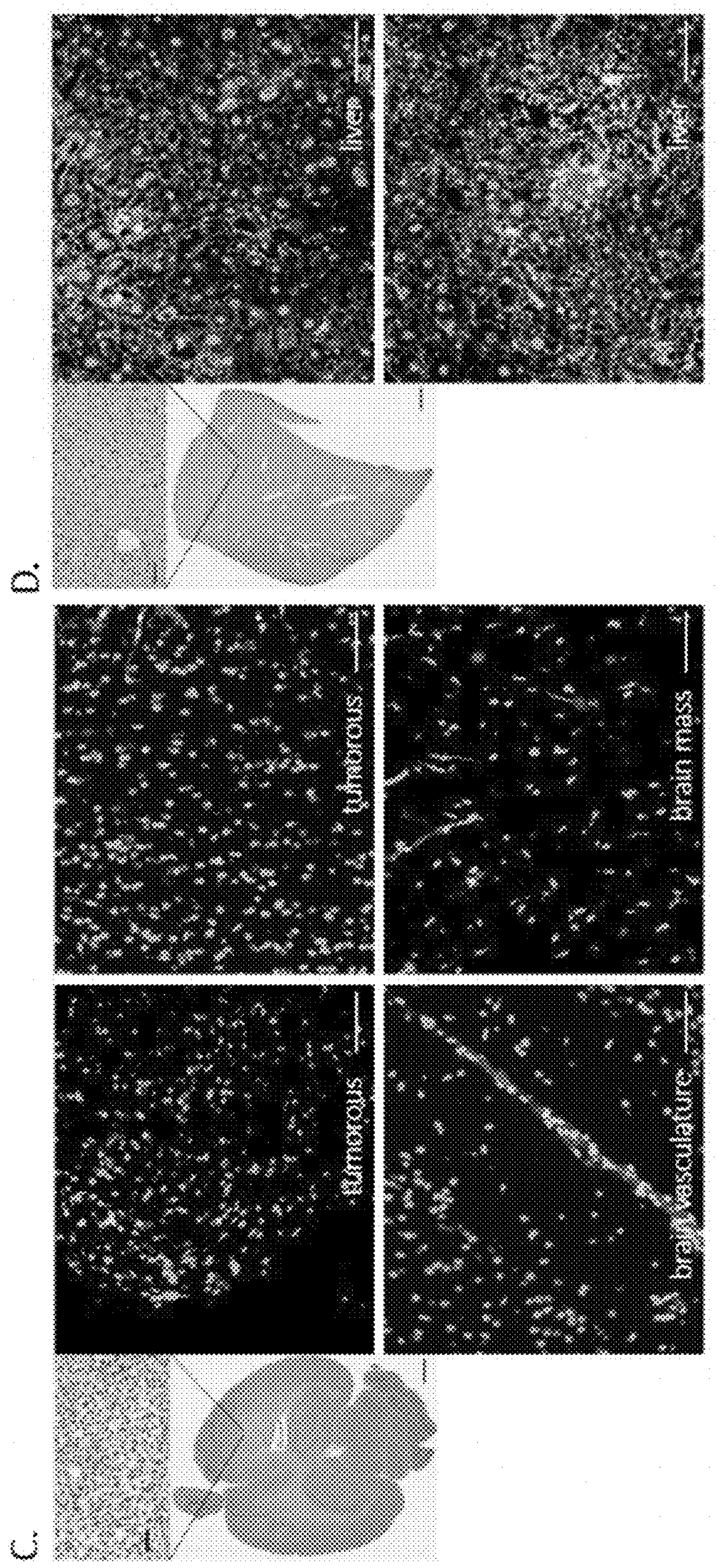

Ex-vivo SWIR (808 nm ex. and 1150 longpass filter) capture of mouse brain clearly demonstrate localization of ICG-loaded phage to GBM22 xenograft at 24 hrs. Tumor size 3 mm to 5 mm in diameter are clearly visible (FIG. 33A) with CTX expression, while weak, spotty coverage of tumor location is observed with wildtype phage (FIG. 36B). Immunohistochemistry staining for p8 phage coat protein show phage lining the brain vasculature, areas of dense tumorous cells, and sparsely throughout the brain mass in non-specific regions 24 hrs post tail vein delivery (FIG. 33C). Irrespective of length, ICG loaded CTX-phage organ biodistribution is parallel to that of wildtype filamentous phages, mostly visible in the RES clearance organs, the liver, spleen, and kidneys (FIG. 33B).

1-3-6 Chlorotoxin-Phages BBB Transmigration and Specificity to Tumor Mass by Size CTX expressing phage and non-targeted phage of wildtype 900 nm length (2e12 pfu per mouse) were introduced to non-tumor bearing NCR-NU mice (n=3 per group) to determine the brain tissue specificity of the modified phage. The left and right frontal cerebral cortex tissue was harvested 24 hrs post injection and processed for qPCR analysis to quantify phage genome content. Approximately 6.3e6 wildtype phage particles were detected per 100 ng of DNA. This phage loading was increased ~4 fold to 2.5e7 phage particles per 100 ng with CTX expression (FIG. 34A). Given an average mouse brain DNA content of 15 μg, 0.8% of wildtype phage initial dosing (ID) is retained in the brain tissue, while CTX fusion provides 3% ID retention 24 hrs after exposure.

In GBM22 bearing mice dosed with phage variants (2e12 particles per mouse), the tumor tissue (right frontal cortex) and the unperturbed left frontal lobe tissue were collected for qPCR relative quantification of the phage specificity to tumor site (n=4 per group). We find 2-fold phage accumulation to tumor sites with wildtype phage due to the leaky and disruptive nature of the tumor mass. This specificity to tumor is increased to ~5 fold with CTX-phage and allows for the signal contrast driving SWIR visualization of the GBM growths. CTX-phages of 300 nm, 100 nm, and 50 nm lengths hugely enhanced the ability of the CTX fusion protein to drive tumor specificity. 300 nm, 100 nm, and 50 nm phages were respectively ~10, ~25, and ~80 fold more present in tumorous tissue over corresponding cortex brain tissue of the left, non-tumorous brain hemisphere (FIG. 34B).

Phage cocktails of mixed sized long and short phages were introduced to glioma bearing mice for visualization of phage extravasation to glioma and brain based on size. Mixtures of 50 nm/900 nm, 100 nm/900 nm, and 300 nm/900 nm CTX-phages were administrated where each sample contained equivalent particles amounts of AlexaFlour555 conjugate small CTX-phage of a given size (50 nm, 100m, or 300 nm) and AlexaFlour647 conjugate 900 nm CTX-phage. 48 hrs post injection, mice were sacrificed for brain histology sectioning and fluorescent imaging of short and long phage localization in the brain. Shorter phages were evident at much higher quantities than the wildtype length counterpart in all cases and demonstrate the size effect on brain and tumor tissue penetrance (FIG. 35).

a. Conclusions

M13 phages modified for tumor specificity can be used to visualize orthotopic GBM tumors in-vivo in the second window near infrared using ICG dye. The signal at the tumor site is clearly visible through the scalp and skull tissue and demonstrate the ability of CTX targeted phage particles to diagnose diseased tissue using known active agents. FDA approved ICG dye issued for intraoperative delineation of brain tumors in patients at 2.5 to 5 mg/kg doses with effectivity over a short window of time and rely on the non-specific enhanced retention and permeability at tumor sites to drive contrasts[83,102,107]. Phage nanoparticles are able to reduce the ICG dosing necessary to below 10 μg/kg with signal contrast visible over 3 days for tumors 5 mm and below in size. M13 phage shuttles can also be modified in size to take advantage of the enhanced trafficking profile of smaller particles in circulation and in tissue. Inho-phages of 50 nm, 100 nm, and 300 nm were seen to penetrate the tumor site at greater numbers and augment the impact of the CTX fusion peptides to introduce specificity to over 80-fold at 50 nm. It is likely p3 presented CTX ligands are better accessible on the phage bodies of shorter length and also the less filamentous, more rod-like geometry of the shorter phage must enhance the vascular marginalization and extravasation potential of the particle[108-116]. Prior studies indicate the geometry and size can play a significant role in the transport, bio-distribution, clearance, and internalization of nanoparticles[109,111,112,114-116]. Upon injection, nanoparticles must demonstrate the ability to evade immune macrophage during blood circulation, high marginalization or ability to escape the blood flow and reach the blood vessel walls, ability to extra vase to the tumor interstitium, and finally capability to either bind or internalize to cancer cells[113]. Though spherical particles have been the norm in nanomedicine research, recent works indicate that non-spherical nanoparticles (i.e. rods, chains, ellipsoids) are perhaps effective in these areas[111,117]. Not only are chain or rod-like structures more likely to avoid internalization by macrophages, their shape subjects them to certain torque and tumbling motion that increases contact with the vessel walls. Furthermore, oblong shaped particles are more likely to form multivalent occurrences essential for targeting[110], and in the case of the filamentous bacteriophage, avidity of binding can be highly enhanced by the display of materials on all copies of the body p8 protein. Size considerations must also be made to accommodate for the high interstitial flow pressure typical of tumor masses. Due to high leakiness and reduced lymphatic drainage in the area, extravasation to tumor tissues is highly enhanced with smaller particles in the ranges 50-150 nm[109,113]. Below 50 nm, toxicity to normal tissue (sub 50 nm) and rapid clearance by the kidneys (sub 10 nm) can negate the efficacy of nanoparticle carriers, while above 200 nm, removal from the blood by the complement system hinder delivery[109,114]. Once at the site of the tumor, the targeted nanoparticle internalization to the cancerous cells is dictated not only by the ligand affinity but more so by the size[92,118,119]. Hence, the aspect ratio considerations as well as size control of particles is vital to the design of biomedical nanoparticles.

In considering targeted phage particles for materials delivery, shorter phages provide the greatest tissue specificity but do suffer from circulation time trade-off. In this use case, we find that the 50% drop in half-life for 50 nm lengths did not hinder the nano-phage ability to localize effectively to the tumor mass. In fact, the application of M13 in-vivo library panning and serial enrichment could benefit greatly from introducing display on shorter phages, potentially leading to detection of library variants that would otherwise have been eliminated due to the difficulty of trafficking 900 nm phage particles to the preferred tissue surfaces. In addition to the trafficking potential of mini-phages, the newly constructed short phages described here are also uniquely engineerable for cssDNA content with less than 200 bases of original M13 genomic sequence. In addition to surface expressed or loaded materials, genetic cassettes packaged within the phage may serve as another kind of therapeutic cargo to drive genetic effect in targeted cells.

Overall, M13 phages displaying CTX on p3 capping protein enhanced retention in brain tissue of healthy mice and enhanced specificity to disease in GBM22 tumor bearing mice such that in-vivo visualization was made possible in the second window near infrared regime with inexpensive, human safe dye. The CTX molecule is well characterized for its ability to recognize cells across the tumor spectrum and overcome the heterogeneity of tumor populations such as found in glioma. CTX expressing phages hence exhibit 5-fold particle accumulation to GBM22 tumor over normal brain tissue. Additionally, mini-phages 3 to 18 fold shorter than wildtypeM13 increased the tumor targeting capacity of CTX peptides such that 50 nm CTX-phage are 80 times more likely to be found at the tumor site over normal brain tissue. We illustrate the potential of mini-phages in driving tissue trafficking in especially difficult to reach areas such as the CNS where active receptor mediated blood brain barrier crossing is highly affected by particle size and targeting ligand accessibility. As filamentous phage technologies in the bio-templating, material synthesis, infectious disease, and nano-theranostic fields continue to advance, the ability to alter the particle size and optimize across applications will be of particular impact.

b. Materials and Methods Chlorotoxin Gene Insertion

The 108 base pair chlorotoxin gene sequence (FIG. 37) flanked by 20 bases on each side with the p3 insertion site sequences was fulfilled on a pUC57 plasmid vector by Genscript. CTX vector, M13KE (NEB) phage vector, and RM13-f1 phage vector (Section 2) oligos were designed for Gibson assembly insertion of the CTX vector PCR product. Gibson assembly protocols according to the NEB 2× Gibson master assembly mix resulted in N-terminal CTX presentation on p3 protein. N-terminal His6 tagged CTX gene ("His6" disclosed as SEQ ID NO: 1) was also cloned to ensure that p3 terminal CTX insertions were not enzymatically cleaved during assembly (FIG. 38).

Phage Growth Conditions

XL1-Blue *E. coli* strains (Agilent) and Difco LB Broth cultures were used in all amplification and cloning of inho/RM13-f1 and M13KE-CTX phagemids at 37° C. with continuous 215 rpm shaking. For chlorotoxin-phage, overnight 5 ml *E. coli* cultures was used to begin 1 L batch growths. Phage plaque picks were used to inoculate the 1 L bacterial culture (40 μg/mL tetracycline) growths which were allowed to amplify overnight. For inho-phage, bacterial dual vector co-transformations or colony swabs were cultured overnight in 5 ml volumes under appropriate antibiotic restrictions (100 μg/mL ampicillin, 50 μg/mL kanamycin). The overnight growths were then used to culture 1 L LB medium batches with appropriate antibiotic restrictions and allowed to amplify overnight prior to phage purification.

Phage Purification

1 L bacterial growths were spun at 8000 rpm (Beckman Coulter JLA 8.1000) for 1 hr to pellet out bacterial cell bodies. The phage supernatant was collected and phage precipitation was facilitated through the addition of PEG-8000/NaCl (final 2.5% PEG/0.5M NaCl for CTX-phage; 10% PEG/0.5M NaCl for inho-phage) and incubation at 4° C. overnight. Post precipitation, phage supernatants were spun at 8000 rpm (Beckman Coulter, JLA 8.1000) for 1 hr to pellet out the phage particles. The phage pellets were resuspended in 1×TBS/$MgCl_2$/DNaseI solution (final 5 μg/mL DNAse, 10 mM Tris-HCl, 2.5 mM MgCl2; 25° C.) and incubated minimum of 1 hr on a benchtop shaker to facilitate digestion of DNA contaminants. Post digestion, the phage suspension was separated under CsCl gradient ultracentrifugation (1.2 g/mL to 1.6 g/mL gradient, SW32, 30,000 rmp, 4° C. for 4 hours) where the extracted phage band was further purified of salts via dialysis or TFF: 12-14 kDa or 100 kDa cutoff dialysis against 1×PBS over 72 hrs with frequent buffer changes or 10 kDa to 100 kDa tangential flow filtration against PBS for 5× volumes (MicroKros MPES columns, Repligen). Finally, purified and concentrated phage samples were filtered through 0.45 μm syringe filters (Pall, 4614) prior to use with cell or animal work.

Purified phage particles were dispersed in 100 μL milliQ water to a total count of 1e11 phages. AFM sample discs were prepared with mica sheets and sticky tape was used to peel a fresh mica surface for sample deposition. 100 μL phage preparation was deposited on the mica for 30 min to an hour. Prior to AFM visualization, the phage sample was wicked from the mica surface and the mice surface was then quick dried with nitrogen or argon has stream.

Alexa Labeling of Phage

NHS-ester Alexa Fluor dyes (ThermoFisher) were incubated with phage samples in phosphate buffered saline (PBS) for 1 hr at room temperature at a 1:1 ratio to every p8 major coat protein present in sample. Labeled samples were dialyzed against PBS using 12-14 kDa cutoff Repligendialysis tubing to remove unconjugated dyes. Dialyzed samples were further cleaned and concentrated to desired phage per ml with tangential flow filtration at 10 kD cutoff using MicroKros 10 kDa MPES column (Repligen).

Indocyanine Green Labeling of Phage

NHS-ester ICG dyes (Iris Biotech) were incubated with phage samples in PBS for 1 hr at room temperature at a 1:1 ratio to every p8 major coat protein present in sample. The conjugated sample is spiked with DMSO to final solution of 50% DMSO/PBS so that ICG aggregates (>150 kDa)[120] formed due to the hydrophobicity of the ICG molecules are dispersed from the phage surface conjugated ICG. The sample was then filtered against 50% DMSO/PBS solution via 10 kDa cutoff TFF (Repligen MPES columns) to remove the dispersed free dye molecules (the 50% DMSO exposure of phages was limited to maximum of 1 hr to conservatively safeguard the infectivity/viability of the phage particles). The ICG-phage in 50% DMSO suspension was diluted 10× by addition of DSPE-mPEG-5K (Laysan Bio) solution in PBS. Lipid-PEG must be at a 10:1 ratio with ICG in the sample to ensure that the ICG-phage conjugates remains stable once clean of free dye aggregates. This final 5% DMSO and DSPE-mPEG-5K mixture with ICG-phage was then buffered exchanged with DSPE-mPEG-5K/PBS using 10 kDa TFF to remove excess DMSO content of the sample. Alternatively, 60% ethanol/PBS may be used to wash free dye from the reaction instead of 50% DMSO/PBS if longer phage exposure time to wash buffer will be required (up to 3 hrs) (FIG. 71).

Chlorotoxin-Expressing Phage In-Vitro Cellular Uptake Imaging

Human GBM22 glioblastoma cells were grown on glass coverslips coated with Poly-L-lysine(Gibco) in HyClone High Glucose DMEM cell media (SH30022.01) supplemented with 10% fetal bovine serum (Sigma). Cells were incubated at 37° C. with Alexa555-conjugated CTX-expressing M13 phage for 4 hrs. Coverslips with GBM22 cells were washed three times with PBS before fixing with 4% paraformaldehyde and processed for immunofluorescence.

Immunofluorescence was performed on cells using anti-golgin-97-Alexa488 (Bioss BS-13486R-A488) as a Golgi marker and DAPI (ThermoFisher) as a DNA stain for colocalization. Images were captured on an EVOS fluorescent microscope (Life Technologies) or a Nikon Eclipse 80i fluorescence microscope.

Chlorotoxin-Expressing Phage In-Vitro Cellular Uptake Flow Cytometry

Human GBM22 cells were grown in 6 well plates to 60% confluence (HyClone SH30022.01 DMEM, 10% FBS). Chlorotoxin phage and wildtype phage conjugated with Alexa647 dye was incubated at 10,000 phage per cell for 2 hours in serum free media. Wells were washed three times with PBS followed by enzyme free (Gibco Cell Dissociation Buffer) re-suspension of the treated GBM22 cells and control untreated GBM22 cells. The collected cells were spun and re-suspended in PBS and pipetted through the cell strainer cap of 5 ml (Falcon 353325) flow tubes. Tubes were maintained on ice for flow cytometry (640 laser excitation, 660/20 filter) readings on FACS Canto II HTS-1 machine with BD FacsDiva software. Acquired data was analyzed using FlowJo package.

Multiphoton Intravital Imaging of In-Vivo Tumor Uptake by Chlorotoxin-Expressing M13phage Through a Cranial Window All animal experimentation was in adherence with the National Institutes of Health (NIH) *Guide for the Care and Use of Laboratory Animals* and received institutional approval. To fashion a cranial window, the skull was thinned away using a sterile stainless steel 2 mm diameter cylindrical drill bit attached to a high-speed hand drill until the underlying dura mater is exposed. Multiphoton imaging was performed on an Olympus FV-1000MPE multiphoton microscope (Olympus Americas, Waltham, MA) using a 25×, N.A 1.05 water objective. Excitation was achieved using a DeepSee Tai-sapphire femtosecond pulse laser (Spectro-Physics, Santa Clara, CA) at 840 nm. The emitted fluorescence was collected by PMTs with emission filters of 425/30 nm for Collagen 1, 525/45 nm for GFP-labeled tumor cells and 668/20 nm for Alexa-647 phage particles. Collagen 1 was excited by second harmonic generation and emits as polarized light at half the excitation wavelength. Images were taken 24 hrs post-IV injection of chlorotoxin-expressing M13 phage. All images were processed using ImageJ.

U87 mg, GBM22, and GL261 Orthotopic Intracranial Tumor Implantation and In-Vivo Tumor Monitoring All animal experimentation was in adherence with the National Institutes of Health (NIH) *Guide for the Care and Use of Laboratory Animals* and received institutional approval. U87MG human glioma cells were purchased through ATCC and maintained in DMEM media (Gibco) with 10% FBS (Hyclone). GL261 mouse glioma cells were a gift from Dr. M. Hemann and were maintained in DMEM (Gibco) with 10% FBS (Hyclone), 1× Glutamine (Gibco), and 1× Pen/Strep (Sigma). GBM22 human glioma cells were procured courtesy of Mayo Clinic and maintained in HyClone (SH30022.01) DMEM with 10% FBS. Cell lines were transduced with alentiviral pLMP-GFP-Luc vector to allow for stable expression of GFP and firefly luciferase prior to implantation. Six week old NCR-NU (Taconic) or C57/BL6 male mice (Taconic) were used to generate intracranial orthotopic U87MG and GBM22 or GL261 gliomas, respectively. In brief, mice were anesthetized using 2% isoflurane and their heads immobilized in a stereotactic headframe using atraumatic ear bars. A burr hole was made using a steel drill bit (Plastics One, Roanoke, VA, USA) 1.4 mm right of the sagittal and 1 mm anterior to the lambdoid suture. 105 glioma cells were stereotactically injected 3 mm deep from the dura mater into the brain using a 33-gauge Hamilton syringe. Tumors were allowed to grow for 14 days prior to commencement of study. Intracranial tumor growth was monitored in-vitro using bioluminescence IVIS® imaging(Xenogen, Almeda, CA) equipped with LivingImage™ software (Xenogen). Mice were treated 15 minutes prior to imaging with 15 mg/g D-Luciferin.

In-Vivo and Ex-Vivo SWIR Imaging

All animal experimentation was in adherence with the National Institutes of Health (NIH) Guide for the Care and Use of Laboratory Animals and received institutional approval. Study mice were anesthetized using 2% isoflurane. ICG conjugate phage samples were injected in 200 μL final volume to the tail vein of tumor bearing NCR-NU (Taconic) mouse and the mouse was immediately transferred to the imaging stage fitted with isoflurane nose cone for SWIR fluorescent image acquisition using an 808 nm diode laser (CNI laser) for excitation and an InGaAs camera (Princeton Instruments OMA V-2D:320) for emission detection. An 1150 nm long-filter pass (Thorlabs FELH1150) was placed in the collection path and the camera lens (Navitar MVL25M1) and an achromatic doublet (Thorlabs AC508-075-C-ML) were used to focus the imaging plane. The treated mouse was positioned for whole body, brain, or hind leg signal detection for tracking organ distribution, brain tumor signal localization, or circulating particle intensity as observed in the femoral vein at the study time points (15 min intervals, 30 min intervals, 2-4 hours intervals, or 24 hours intervals). At study end point, mouse major organs were imaged for ICG signal.

Circulation Half-Life Calculation

The signal intensity measured (over 8 hrs in 5 min, 15 min, and 1 hour intervals) from a single location of the femoral vein was normalized to the peak signal value and plotted over time using OriginPro software. The signal decay was fitted for exponential decay as described. See decay fit $R^2$ and half-life statistical ANOVA test across phage groups in Appendix Table A2-2.

Histology Section Preparation

Brain and liver tissues harvested from mice groups treated with phage samples were immediately flash-frozen over liquid nitrogen in plastic cryomolds with OCT compound (FisherScientific).

Slide preparation was performed by the MIT Koch Institute Swanson Biotechnology Center. Briefly, frozen tissue was sectioned for 5 μm thickness and prepared on slides for antibody/DAPI and H&E staining. Prior to immunostaining, the slides were treated with TrueBlack lipofuscin autofluorescence quencher (Biotium: 23007) per manufacturers recommendations. Anti-p8 phage capsid primary antibody (Abcam 9225, 1:1000 dilution) and Alexa647 secondary antibody(Abcam 150115, 1:500 dilution) were used to stain for phage in brain and liver tissue sections. If mouse was treated with Alexa-conjugate phage particles, only DAPI staining was conducted on slides. Slides were imaged using a Nikon A1R Ultra-Fast Spectral Scanning ConfocalMicroscope and processed using ImageJ.

qPCR Quantification of Phage Particles in Brain Tissue

Brain tissue harvested 24 hrs post injection of phage material was sectioned for 25 mg left frontal healthy brain tissue and 25 mg tumor tissue from the right cerebral cortex. Left and right healthy frontal lobe tissues were also both harvested for intact BBB crossing study in normal mice.

Samples were processed using Qiagen DNeasy Blood & Tissue Kit with overnight incubation at 56° C. during the suggested digestion step. 100 ng of gDNA extracted from brain sample was then prepared with iTaq Universal SYBR Green Supermix (Biorad) and 500 nM forward and 500 nM reverse primers (primers designed for approx. 200 bp amplicons) as required by the phage gene target in total of 20 μL volumes. Pure phage cssDNA were extracted from 900 nm WT and CTX, 300 nm CTX, 100 nm CTX, and 50 nm CTX phages using the E.Z.N.A. M13 DNA Mini Kit.

Known cssDNA dilutions from 10 v g to 1e7 vg was used to create standard curve sets for all phage types. 96-well plates (Axygen PCR96LC480W) were run with Roche Light Cycler 480 using standard SYBR Green/HRM Dye template. All samples were presented in triplicates, negative controls of milliQ water, untreated brain and tumor, and housekeeping control for GAPDH gene were included. Melt curves were verified for clean, single peaks for samples and standard curve fits with slopes ($C_t$/log DNA) ranges −3.1 to −3.4 and r-squared values above 0.95 were observed (Appendix A3).

TABLE M1

Phage, mouse and tumor xenograft tissue qPCR amplicon primers.

| target | forward primer | SEQ ID NO: | reverse primer | SEQ ID NO: |
|---|---|---|---|---|
| CIX-phage | ATGTGCATGCCGTGCTTTACC | 16 | AAGTTTTGTCGTCTTTCCAGACGT | 23 |
| WT-phage | CTCACTCGGCCGAAACTGTTGA | 17 | CAGGGATAGCAAGCCCAATAGG | 24 |
| inho1960 (300 nm) | GATCGTCGACATTCCTGAGATTCC | 18 | TGTCCACCTGGCCCTGGATCTTG | 25 |
| inho475 (100 nm) | TAAGGGATTTTGCCGATTTCGGC | 19 | GTGCCGTAAAGCACTAAATCGGA | 26 |
| inho285 (50 nm) | CCTATCTCGGGCTATTCTTTTGAT | 20 | CCCACTACGTGAACCATCACCC | 27 |
| human GAPDH | GTCTCCTCTGACTTCAACAGCG | 21 | ACCACCCTGTTGCTGTAGCCAA | 28 |
| mouse | CATCACTGCCACCCAGAAGACTG | 22 | ATGCCAGTGAGCTTCCCGTTCAG | 29 |

Section 4

Building A M13 Phage-Based Gene Therapy Platform c. M13 Bacteriophage Development for Mammalian Gene Transduction Bacteriophages can transfer DNA from one bacterium to another and can also be adapted to transduce DNA to mammalian cells. Studies have demonstrated that M13 filamentous phages as well as T4 phages can be used as a capsule to deliver recombinant adeno-associated virus (AAV) similar transgene cassettes into tissue-targeted human cells[1-7]. Such chimeric systems have previously been described as prokaryotic-eukaryotic hybrid viral vectors or hybrid AAV/phage (AAVP). The encapsulation of AAV-like transgene cassettes in a bacteriophage shell allows us to take advantage of well-established phage display and bio-panning methods, large-scale bacterial vector production infrastructure, lack of pre-existing capsid immunity and immune tolerance, and most importantly, gene cargo sizes that can exceed 4.7 kilobases, the current limitation of AAV (Table 1). The packaged AAV transgene designs, a target gene flanked with ITRs (inverted terminal repeats), then confers the phage platform with a DNA cargo topology that has innate adaptions for nuclear localization, double strand synthesis, and long-term stability of expression

TABLE 1

Phage derived particle (PDP), AAV, and non-viral gene therapy technologies

| Technology | PDP | AAV | Non-viral gene therapy |
|---|---|---|---|
| payload type & size | closed-ended cssDNA, 20 kb | Linear ssDNA, 4.7 kb | closed-ended dsDNA, 12 kb |
| cell specificity | scFv, sdAb, peptide specificity | serotype-based tropism | ligand incorporation |

TABLE 1-continued

| Phage derived particle (PDP), AAV, and non-viral gene therapy technologies | | | |
|---|---|---|---|
| Technology | PDP | AAV | Non-viral gene therapy |
| manufacturing | bacterial culture 1e15 vg/L in 48 hrs | cell culture 1e13 vg/L in 144 hrs, high (~50%) empty shell contamination | process-intensive across particle/cargo manufacturing and assembly |
| redosability | repeat dose tolerance expected | pre-existing, single dose | re-doseable |
| engineerability | highly modular multi-functional capsid | short peptide randomizations | difficult formulation control, polydispersity issues |

As discussed in Section 1, the engineering of M13 phage for mammalian gene therapy has had over 20 years of research history in the laboratories of Andrew Baird, Renata Pasqualini, and Amin Hajitou. Today's leading phage derived vectors were first proposed by Hajitou et al. (2006) and the group has since demonstrated the efficacy of directed AAVP gene delivery by integrin targeting to tumor vasculature in canine and mouse models[4,5,11,12,12-16]. Tumor inhibiting genes such as TNF-alpha and or the Herpes Simplex Virus thymidine kinase (HSVtk) in combination with its substrate, ganciclovir (GCV), were delivered via RGD4C phage display on p3 and resulted in complete regression of tumor over serial treatment up to 8 weeks.[17] (HSVtk converts GCV into a toxic metabolite that kills cells, a mechanism widely used in cancer therapy). Reporter gene transduction efficiencies of 10-20% is observed with this first technology proof-of-concept[17]. The maturation of such phage derived gene delivery technology to achieve clinical grade transduction efficiencies is an on-going process. Additional developments such as the incorporation of endosomal escape capabilities on the phage coat, the wrapping of phage delivery particles with cationically charged polymers, and hydrogel formulations of phage gene delivery vehicles have boosted the mammalian cell transduction values to 60-80%[18-22]

The current dominant viral gene delivery technology, AAV particles, can range in transduction efficiency from 5%-99% based on cell/tissue type and viral serotype[9,23,24]. Systemicuse of AAV serotypes can result in a ranging distribution across organ systems along with the dominant tissue target. This broad tropism raises concerns for off-target effects. The directed evolution of AAV variants for highly specific tissue or cell targets is a newly developing field with limitations set by the compact icosahedral capsid structure of the virus[25,26]. In contrast, the field of phage coat engineering is well-established and has led to the use of phage as the work-horse behind nanobody (sdAb), antibody (scFv), and peptide discovery work in research and industry. The M13 bacteriophage particularly is well known for its robust genotype to phenotype linkage in phage display techniques across all of its five capsids[27-34]. With M13 phage derived particles (PDPs), we can easily choose to express known targeting ligands or sequences that demonstrate high specificity and affinity for cellular targets[35,36]. Identifying the ideal targeting ligand has a significant effect on the transduction efficiency of a PDP which would not naturally engage with a mammalian cell surface marker. Specifically, the p3 capsid protein at the tail end of the phage has been particularly well characterized for display of targeting moieties of over hundred amino acids and gives us the ability to introduce targeting via high affinity tools such ascamelid nanobodies (sdAb) and antibody fragments (scFv) up to five copies per phage. Antibody fragment and peptide targeting of PDPs through the p3 capsid has proven successful in cell targeting, cell internalization, and cell transduction specificity[2,37-49]. Additionally, as outlined in Section 1, higher avidity p8 display is also possible with hundreds of copy insertions of sequences as large as 50 kDa[50], which has been exploited to introduce transduction enhancing endosomal escape peptides on the phage body[22]. Currently, additional functionalization across the p6, p7, p9 capsids have yet to explored for the particular purpose of mammalian cell transduction with PDPs. The natural inability of phages to infect human cells and the malleability of the phage capsids to highly specific cell targeting will allow for systemic trafficking of the phage vectors with little off-target effects. Clearance organs such as the liver, kidney, and spleen are unlikely to be affected by the accumulation of phage particles. And we note that bacterial infectivity of M13 phages can be easily disrupted by p3 manipulation[51] if the GI tract or microbiome population is deemed to be a likely sink for the administered phage like vectors. The broad trafficking of phages through the tissue parenchymal spaces is another learning from the field's library panning experience that will aid in the therapeutic optimization of phage gene vectors. The isolation of phages that home to deeper tissue regions such as the muscle, heart, brain parenchyma, spinal neurons, pancreatic inlets, and so forth[45,52,52-61] attest to the tissue penetrance of M13 phage derived particles.

As noted, phage derived particles are designer friendly due to their highly malleable capsid proteins and well understood genomic cssDNA, both of which can be engineered to mimic to the efficiencies of the mammalian viral transduction pathway (i.e. endosomal escape, viral uncoating, nuclear localization, single to double strand DNA conversion). Phage library discovery can be quickly employed to uncover PDP variants with enhanced tissue specificity, neutralizing antibody evasion[22], endosomal escape[22,62], nuclear localization[63,64], and biological barrier crossing (i.e. BBB or mucosal layers[55,56,60,65-70]) in a combinatorial fashion as all M13 capsids are amenable to mutagenesis. Given a transducing PDP lead product, unutilized surface capsids of the PDP may be tailored to the specific trafficking demands of the tissue target and disease type. Not only are fused libraries possible, the coat of PDP's can be designed as conjugation sites for the decoration of the particle with moieties that are not able to be produced in a bacterial cell or that are too large for coat incorporation. Some decoration examples that could be used to enhance the pharmacokinetic or transduction efficiencies of PDPs include PEGylation, cationic polymer wrapping, small molecule conjugates (i.e. GalNac), nanoparticles and inorganic elements, and DNA or RNA lengths[18,44,71-77].

Additionally, the body of research on the manipulation of the phage coat proteins provide us with avenues of in-vivo optimization. Coat proteins of filamentous phages have previously been engineered for long-circulation (evading immune clearance) as well as increased residence time upon cellular internalization (evading the lysosome)[78-80]. Systemic intravenous filamentous phage delivery to animals are commonly conducted in research and report no toxicities or reduction in therapeutic effect from multiple administrations. For instance, cancer cell killing gene expression and tumor regression profile is observed to be unaffected by pre-vaccination of mice with phage gene delivery vehicles[18]. M13 filamentous phage particles have also been reported previously for multiple dose usage in clinical trials of cancer bio-panning with no reported adverse effects and up to seven days delay before maximal immune response[79,81-83].

Likewise, temperate filamentous phage type, Pf, against *Pseudomonas* cells have also been tested clinically for cystic fibrosis patients expected tolerance and immune suppressive effects[84-86]. Mimotopes designed on filamentous phages have previously been considered for vaccination applications but often require strong adjuvants to ensure enduring immune outcomes[87-92]. While non-infective to mammalian cells and having a long history of human administration as antimicrobials, bacteriophages delivered systemically can induce specific immune response and trigger innate or adaptive immune reaction which will need to be better characterized for safe phage dosing and potential re-dosing as discussed extensively in Section 1[93-103]. The high residence of phage populations in the human biome and the broad penetrance of these phages throughout the healthy human body is not well researched. Newer work shows the potential immune modulating role of the phageome[95,96,104-106]. Still, the engineerable nature of the M13 major coat proteins will be particularly advantageous in designing for immune evasion if necessary. Charge modification of the p8 coat protein has previously been reported to reduce the effect of phage neutralizing antibodies (nAbs) against AAVPs. Bringing the zeta potential of the phage particle closer to neutrality with AKAS peptide fusion (SEQ ID NO: 140) on every p8 significantly lower the ability of nAbs to deactivate the phage[22].

Finally, true to all applications of phage materials, the manufacturing advantage of phage derived particles is relevant. In the case of gene therapy particles, the phage particle production is particularly relevant due to the simplicity of the genetically encoded cssDNA and shell assembly process. Phage particles completely avoid the manufacturing complexities associated with gene delivery platforms such as virus like particles, lipid nanoparticles, and exosomes where the both the capsule and the DNA cargo are process insensitive. The advent of phage usage in antimicrobial applications have paved the way for facilities of 10,000 L bioreactors specifically for the bacterial replication and purification of phage particles. PDPs which are produced no differently from traditional M13 bacteriophages can also be manufactured at high volumes with minimal production concerns in this way. Furthermore, unlike mammalian viral vectors, bacterial phage vector production is not constrained by expensive cell media and nutrient requirements, mutable cell lines, and in some cases, large adherent surface areas requirements[107,108]. Much like large-scale secreted protein production, PDPs can be harvested by simply gathering the supernatant from the infected bacterial media growth. And due to the intrinsic biology of the PDP particles, the system is unlikely to suffer from empty capsids and risk of gene integration.

Unlike AAVs, PDPs cargoes are closed-ended with low risks of homologous recombination events. And empty but complete shell formation for M13 is considered to be extremely rare due to the extrusion assembly mechanism of the filamentous phage. The phage capsid proteins are assembled around the cssDNA cargo as the structure is pushed out of the bacterial membrane (unlike icosahedral particles where the genomic cargo is injected post capsid assembly). Hence, filamentous phage assembly cannot take place without cssDNA present to provide an axis for stacked helical p8 formation. It is possible that we have assembly around off-target ssDNA present in the bacterial cell[109,110] but such particle contamination would be easily identifiable due the observance size differential (Section 2).

The particles proposed by Hajitou et al. (2007) introduce the AAV transgene cassette into the body of a filamentous phage. To do so, the transgene cassette flanked by the necessary ITR repeats are inserted in addition to the full ~7000 base pair genome of the M13 bacteriophage[4,17,20]. Slightly cleaner, f1 phagemid systems can also be employed to produce phage vector products that carry DNA cargoes with a full f1 origin and the transgene cassette.

However, such systems will also carry along the plasmid production elements such as the antibiotic selection marker and bacterial origin of replication like colE1[5,22,111]. Using the novel inho system, we know that PDP products that consist of only (a) ~200 phage derived base pairs and (b) the AAV transgene cassette, are possible. With this modification to the original AAVP research, the vector gains at least 20 kilobases of real estate for transgene integration as demonstrated in Section 2. This expands the possible library of gene treatments and the diseases that may be considered with PDP therapy. At 20 kb of cargo capacity, the system is more than capable of encoding even the largest known human gene, dystrophin, where the full-length cDNA measures ~14 kb[112]. Moreover, the ability to produce such clean cargo for PDP products enhances the regulatory advantage and clinical safety of phage gene vector administration. In this Section, we additionally explore the capsid engineering range of PDPs, creating an RM13-f1 helper that is equipped for display of minimally four functional moieties.

d. RM13-f1 Helper Plasmid Based Phage Gene Delivery Vector

A phage particle containing an AAV ITR-flanked cassette can be quickly assembled with a phagemid system consisting of a package-able target phagemid containing an f1 phage origin of replication and a secondary helper plasmid (such as the previously described RM13-f1) or helper phage (such as the commercial M13K07). The advantage to the use of a helper plasmid such as RM13-f1 is the homogeneity of the final phage vector batches, which is particularly relevant in the case of the clinical gene therapy applications. The DNA cargo from PDP vector administration must meet purity of content, which cannot be supported by a helper phage system. For instance, with M13K07, every 1 in 9 particles produced is the original helper M13K07 product (FIG. 42). While the likelihood of negative effect or gene integration from helper phage contamination is negligibly low, it is an important risk to mitigate for a gene replacement type technology, especially when intracellular trafficking coat modifications (naturally integrated to the helper gene sequence) may be present on the produced phages. Helper phage presence is also a concern due to the possibility for microbiome interactions as helper phages are still replication competent.

As a sanity check for the transduction of phage delivered genetic material, we produced phages carrying ITR-flanked mCherry reporter gene cassettes. In a positive delivery and translation case, we expected our cells to read out red fluorescence as measure through flow cytometry. Using our GBM22 model and chlorotoxin (CTX) targeting peptide (Section 3), we produced ITRmCherry phages with and without p3 CTX fusion. The RM13-f1 (w/ and w/o CTX) helper plasmid was co-transformed with the commercially available pAAV-minCMV-mCherry addgene phagemid (#27970). The pAAV-minCMV-mCherry flanks the mCherry sequence under CMV promoter with AAV2 derived ITRs and has ampicillin plasmid selection which works well in combination with the kanamycin RM13-f1 selection. The full f1 phagemid sequence is packaged(4887 base length) making phages of ~620 nm in size (FIG. 42).

The GBM22 cell line was seeded in six well plates at 3e5 cells per well and settled overnight. The cells were then treated the next day with ITRmCherry PDPs at MOI of 1e5 particle/cell under serum free media conditions for 4 hrs. At the end of treatment, the phage media is aspirated and replaced with complete growth media. 72 hrs and 120 hrs post treatment, the cells can be trypsin harvested and prepared for FACS readout. Our targeted CTX-phage is able to achieve around 9% transduction rates in GBM22 cells by 120 hrs (FIG. 43). This is on par with early efforts (4% to 10% in-vitro gene expression) reported in the field for a phage encapsulated genetic cassette across multiple groups[2,29,37,39,40,113]. Additionally, due to the complete lack of mammalian cell tropism of M13 phage particles, we can be certain that without appropriate cell surface engagement and directed internalization, phage derived particles are not able to transduce non-targeted cells. Non-targeted ITRmCherry phages minimal red fluorescence readout at ~1% over no-treatment groups. Of note here is our modeling of gene transduction in rapidly growing cancer cell lines. Due the speedy doubling time of GBM22, the dilution of the episomal cssDNA presence and the mcherry signal is likely to be extremely rapid.

i. Cationic Polymer Enhanced Phage Gene Delivery

The major hurdle to mammalian cell transduction for PDPs is the endolysosomal degradation pathway. Internalized phage particles are unable to escape the endosomal pocket and quickly degraded before DNA delivery can be achieved. Treatment of cells with proteasome inhibiting or genotoxic agents may be employed to demonstrate improved transduction efficiencies with targeted phages. Generally, up to 4-fold transduction is observed, reaching 20% to 60% depending on the cell line, and lower the multiplicity of infection is required, as low as 1-10 PDPs/cell[39,114,115]. The body of evidence suggest that the intracellular trafficking from the endosomal vesicle to the nucleus is a major barrier for the natural phage particle. A strategy employed to confer endosomal pocket escape ability to the phage is the wrapping of the phage in cationic polymer material. Highly positively charged polymers (such as PEI, DEAE.Dextran) are well characterized for their ability to build osmotic swelling within endosomal pocket in a phenomenon referred to as the sponge effect[116-121]. Cationic polymers will also confer attraction to the generally negatively charged lipid membranes of cells and endosomal pockets. As a result, transfection reagent formulations often take advantage of such charged polymers.

To demonstrate the importance of endosomal escape to the transduction efficiency of our PDP particles, we chose the quick surface modification of our phage particles with cationic agents in the PEI (70 kDa/branched), DEAE.Dextran (500 kDa), and CPTA ([3-carboxypropyl]trimethylammonium chloride) group. In the case of polymer wrapping, ITRmCherry phages were purified and incubated for 15 min with PEI or DEAE.Dextran at ratios of 120 ng/μg and 160 ng/μg[18,19,21] respectively to produce polymer-phage complexes. Small molecule CPTA was conjugated to the lysine-primary amine residues of phage particle capsids through sulfo-NHS-ester chemistry and covalent conjugation was verified with MALDI mass spectrometry of p8 capsid proteins (WTp8: 5238 Da, CPTAp8: 5366 Da, Figure M1). The cationically modified PDPs were then incubated as previously described with GBM22 cells and FACS readout for mCherry expression was performed 72 hrs post treatment.

From the flow cytometry profile (FIG. 45), we see that PEI wrapped phages achieved up to 30% transduction of GBM22 cells by 72 hrs post transduction, owing to the endosomal escape and membrane interaction made possible by the cationic polymer. The lack of signal from DEAE. Dextran phage treated cells and CPTA-conjugate phage treated cells underlines the optimization necessary for polymer wrapping of PDPs and the strength of charge required to ensure positive outcome. DEAE.Dextran wrapped phages characterized by AFM reveal that the polymer addition resulted in phage aggregates that inhibited internalization by cells. On the other hand, CPTA-conjugate phages are well distributed but failed to initiate a strong enough sponge/membrane disruption effect to allow for relevant endosomal escape and cytoplasmic localization of the phage particles.

e. Inho Type Transgene Cassettes

In addition to the benefit of the RM13-f1 helper plasmid in the production of homogeneous gene delivery phages, the inho phagemid system is highly applicable to the optimization of current PDP transgene cassettes. Phage gene delivery modalities recorded to date have all encoded not only the transgene cassette of interest but additional plasmid regulatory sequences such as the bacterial origin, f1 origin, antibiotic selection sequences, and in some cases, phage genes. An inho packaged cassettes vastly reduces the prokaryotic sequence burden of phage derived particles. To this end, an AAV2 ITR-flanked basic inho construct was cloned. The construct is designed to allow for easy enzymatic break and insertion of the desired transgene package to be placed within the ITR, f1-ori/f1-term/PS flanks.

The mCherry sequence (FIG. 46) under a minimal CMV promoter was placed within the newly assembled inhoITR construct to produce cssDNA of 2782 bases long that could be packaged with our RM13-f1 helper. This eliminates over 2105 bases from the original 620 nm phagemid design (4887 bp, FIG. 42), which could be directed towards more functional cssDNAelements such as self-complementing regions, promoter optimization, and nuclear import DNA sequences. With the minimal inho product, the ITRmCherry cassette produce phages of approximately 400 nm in length (FIG. 47).

The cssDNA from our inho-ITRmCherry design can extracted using standard commercial kits (Qiagen or E.Z.N.A.) or phage cssDNA precipitation protocols[122]. The cssDNA produces is transcriptionally active and can be combined with desired transfection reagents, LNPs, and VLPs to induce reporter gene or transgene expression (FIG. 53).

4-3-1 Inho PDP capsid modification and expanded RM13-f1-p88-p9 construct

Endosomal escape and cytoplasmic localization of phage particles can be enhanced through a number of avenues taking inspiration from across mechanism employment by mammalian, bacterial, viral, plant, and toxin systems. Synthetic peptides and chemical agents are possible as well. Generally, the endosomal escape is facilitated by a peptide or chemical agents that is capable of osmotic rupture, pore formation, membrane fusion or budding, or membrane destabilization in these systems[116,118-120]. Hence, the strength of an endosomal escape peptide (EEP) is highly dependent on driving interactions with endosomal pocket lipid bilayer. As a result, popular EEPs are generally rich in histidine, lysine, and arginine residues for their charge interaction potential with negative membrane surfaces[123]. Histidine residues, with its change in protonation state as the endosome acidifies, are sometimes hypothesized to drive sponge effect, however, it remains disputed if short peptide series are able to drive the level of osmotic pressure necessary to disrupt the pocket as PEI and other such polymers can. Besides electrostatic fusion of peptides with the pocket membrane, EEPs with hydrophobic stretches and cyclization or stereochemistry modifications are also reported for their lipophilic integration to membranes and subsequent endosome disruption efficiencies[118]. Anionic amphiphilic peptides (i.e. INF1-4, INF7, E5, E5WYG) are also used, where under acidic endosomal conditions, protonation results in a conformation change that likely initiate membrane disturbance.

In the case of phage surface display of such EEPs, cationic residues are most likely to succeed in driving membrane phage interactions. The natural phage surface has been reported for low zeta potential near −20 at physiological pH[22,124]. As demonstrated, cationic polymer wrapping of phages is able to overcome this electrostatic barrier (FIG. 45). To mimic the endosomal escape properties conferred by cationic transfection agent, the major coat of the PDP scan be engineered for display of sequences rich in histidine, arginine, and lysine residues. The choice of cationic amino acid sequence and capsid placement may, however, of particular importance as highly positive sequence can be disruptive to the assembly of the particle resulting in extremely low yields or simply no phage production.

As a simple test for the ability of histidine or lysine on the phage surface to enhance transduction ability, inho-ITRmCherry PDPs were chemically modified through EDC chemistry and SMCC linker chemistry to covalent append poly-histidine or poly-lysine residues and the hepatocyte ASGR receptor targeting β-GalNAc moieties. HepG2 hepatocyte cell lines were incubated with these targeted inho PDPs and flow cytometry readout for expression of the reporter mCherry gene was performed 72 hours post the transduction protocol. 15-20% transduction efficiencies were observed with difficulty resulting from the aggregation of the phage materials during the conjugation protocols. The poly-1-lysine (4-20 kDa) and poly-1-histine(5-15 kDa) range in lengths from 30 to 100 amino acid stretches. If available, shorter poly amino acid formulations (10-30AA) are likely to result in better dispersion. Alternatively, the poly conjugate per phage ratio (50 per phage used here) may be lowered to achieve better stability during the EDC reaction window. It is also important to note that particularly strong membrane lysing activity can be cytotoxic and that overall gene expression may not necessary benefit from overloading with cationic charge.

Rational design of phage capsid variants to drive endosomal escape and transduction will benefit from high histidine and lysine content. Polyhistidine tags of 10×His (SEQ ID NO: 30) and 20×His (SEQ ID NO: 31) are reported to increase the endosomal escape and ultimate gene expression by 7000-fold in the literature[118,125]. Polylysines also have a strong recorded history of increasing cytosolic delivery[117]. It is very likely that f88 type phage display of his-tags would be of particular interest for future gene delivery variant discovery. Additionally, EEP sequences identified from highly efficient mammalian viral systems may be employed on the phage surface. Recent work has demonstrated that the influenza derived, histidine-rich H5WYG [GLFHAIAH-FIHGGWHGLIHGWYG (SEQ ID NO: 32)][116,117,121,126] sequence to be particularly effective for PDP based delivery. The p8 display of the H5WYG sequences in a f88 system can drive transduction efficiencies of PDPs to 60%, while others such as INF7 and PC1 are observed to be less efficient with phage particles.[22] Other known viral sequences for future trails include the HIV derived GP41, TAT, FP23, HGP, and PEP1[74] or the AAV derived VPI-$PLA_2$[127-130] type sequences.

Another variety of fusion peptides to consider are the cell-penetrating peptides that bypass the endosome to lysosome pathway completely. In this way, phages may directly enter the cytosol and has already been shown with M13 p3 display of a light chain variable domain 3D8-VL transbody. 3D8-VL-phages were shown to internalize in caveosomes and directly release to the cytosol with substantial phage observed in the cell cytoplasm even 18 hours post uptake[78]. More complex mechanisms of action for endosomal escape are also possible in the realm of bacteriophages (such as DNA injection) but will require extensive investigation as outlined in Section 5. The avenue of directed mutation is of significant interest for high efficiency variants, as has recently been done in the AAV field for systemic capsid evolution[131-133]. The PDPs are naturally amenable to library type searching for p8/p3/p9 variants that pass the endosomal escape/transduction efficiency assay. Small scale, early work for M13 12-mer library based endosomal escape peptide enrichment has already yielded some sequences used in nanocarrier formulations today[62,123]. These libraries can be curated for histidine or lysine rich sequences, rationally inspired sequences, and cyclic sequences and much more. A specific advantage of capsid fusion of the EEP sequences over the surface conjugation method employed here will be the simplicity of processing that will inherently ensure well dispersed phage particles. A major bottleneck to the efficacy of phage poly-amine decoration noticed here has been the need to optimize conjugation conditions to ensure well dispersed, non-aggregated final material.

To facilitate the assay of PDP variants for enhanced cytosolic and nuclear trafficking, an RM13-f1 construct of the f88 type was built which also includes a p9 display option. An recombinant p8 (rp8) sequence was introduced to the helper sequence in the region following gene 4, similar to the f88 vectors (GenBank Accession AF218363) originally described by Scott& Smith[134]. The secondary rp8 sequence differs in nucleotide makeup than the wildtype to reduce recombination. The rp8 and p8 combo produce a mosaic type phage were the rp8 displayed peptide can be very large and the mix of with p8 ensures the phage capsid assembly is still viable. The rp8 is under a tac promoter and is fully expressed with an IPTG (1 mM) inducer. Sequence dependent, the rp8 allows for 1-300 copies of mosaic display. It is also feasible that display on rp8 may be combined with a shorter (<8AA) compatible display on p8.

The RM13-f1-p88 was further modified for display on p9 by separating the overlapping genetic regions of the p7 and p9 sequence as previously described[42]. In the refactored p9, a pelB leader sequence is also presented ahead of the n-terminal display region. The pelB leader ensures the incorporation of the protein fused p9 into the phage coat during assembly. Much like the natural leader sequences of p8, rp8, and p3, the pelB when attached to the p9 mature capsid, directs the protein to the bacterial periplasm, where the leader sequence is removed by a signal peptidase[135,136]. The p9 display option is engineered such to allow for future optimization of the PDP cellular or systemic trafficking profile. In combination with cell penetrating display on p3 and transduction enhancing display on rp8, the p9 functionalization can serve a variety of purposes from circulation enhancement[80,137], BBB or mucosal barrier crossing ability[56,60,65,75,138-140], to nuclear localization of the phages[63,64], to display of enzymes or other active proteins to enhance therapeutic purpose once at the disease site. Specifically, the efficacy of NLS has been demonstrated with lambda phage[63], and such NLS moieties can easily be adapted to the additional p9 capsid handle to drive nuclear trafficking of PDPs and enhance delivery efficiency following release to the cytoplasm. The nuclear transport of a filamentous PDP is especially interesting since the unique geometry (~5 nm diameter) of the phage could allow for easy passage through the nuclear pore structure (9 nm pores capable of expanding to 37 nm). In addition, it is also possible that the optimal PDP gene delivery vehicle benefits from p9 display of EEPs, rp8 display of targeting, and p3 display of NLS or any other combination thereof. As display valency differs across the various capsids, it will be important to consider the balance across the multiple functions of the PDP. Increased valency of p3-targeting has already been shown to play a role in enhancing transduction efficiency[34].

The RM13-f1-p88-p9 provides maximally four sites for peptide integration (FIG. 49). Yet, due to the double vector system of inho, capsid display options can be extended to the inho phagemid. Additional copies of the capsid genes with the desired display sequence may be placed on the inho phagemid without disruptions to the minimal cssDNA production process (FIG. 50). Extension options include the addition of a f33 or f99 type element by incorporating a secondary rp3 or rp9 on the accompanying inho vector. It is equally possible to place a rp7 or rp6. The five-copy-per phage-capsids (p3, p6, p, p9) are able to sustain only up to 2 variants per phage due to the limited copy number. On the other hand, as the p8 capsids number in the hundreds to thousands per phage (depending on size), a 2$^{nd}$ or 3$^{rd}$ rp8 gene on the accompanying inho vector will likely lead to seamless incorporation of the p8 variants onto the phage body during assembly. We know that a mosaic of f88 can produce up to ~300 rp8 inserts, but greater than two p8 display variants at one time is yet to be tested at this time. The possible capsid combinations are many in the two vector inho system and incorporation efficiencies and yields will need to be tested to acquire the highest producing capsid permutations.

Ultimately, the RM13-f1-p88-p9 construct is ideal for testing lead designs for gene expression. It is, however, suggested that for library type enrichment in cell assays or animal models, classic phage display variants (either helper phage or helper phagemid systems) be employed for their simplicity of genetic barcoding. Selected enriched capsid variants should then be placed on the RM13-f1-p88-p9 vector for final inho type products. Testing minus and plus strand delivery to drive double strand synthesis design of the transgene encapsulated by the phage is an area of potential optimization. While the inho type cssDNA enables particularly clean genetic cargo, additional functional elements such as strategic repeat units and hairpins could play a significant role in the nuclear localization and double strand synthesis efficiency of the DNA construct. In incorporating designer elements in to the topology of our PDP cssDNA cargo, we would drive higher transduction levels by enhancing the cellular trafficking events that follow the uncoating of the DNA from the phage capsid shell. Work with T4 and M13 phage gene delivery vectors have shown, that upon successful internalization, the phage particles are found in the cytoplasm and nuclear localization of whole phage particles is likely not the pathway behind the DNA delivery event[1,22,38,39,115]. (Of course, this can look different if phage transport to the nucleus is being engineered through NLS peptides). Generally, following uncoating of the phage cssDNA in the cytoplasm, we expect nuclear localization of the cssDNA to be driven by interactions with regulatory proteins that are transported into the nucleus following their cytoplasmic translation. ITRs, hairpins, and double strand stretches are hypothesized to promote transcription factors binding of DNA and allows the exogenous DNA cargo to piggy-back with transcription factors into the nucleus[141-144].

Other proposed strategies for promoting transcriptionally active double stranded form of delivered genetic cargo include self-complementing and dual plus-minus strand delivery. Self-complementing sequences could half the genetic information delivered by the construct but ensures that the delivered DNA is immediately readable. Dual plus-minus strand requires that phage particles of both cargo+/− types are able to infect a target cell and that the subsequent uncoating of the enclosed cssDNAs results in the two strands meeting to quickly form active double stranded stretches. In the cytoplasm, double strand formation would drive nuclear localization, and in the nucleus, the pairing would ensure that the genetic cassette is transcriptionally active.

To test the potential for dual minus-plus strand delivery, we produced inho type phages carrying GFP reporter gene under CMV promoter in the minus and plus orientation. The sequences align to enable complementing if the two strands were to meet. No ITRs were used with these constructs, confirming that changes in transduction would be solely attributed to the new dual design. GFP+ and GFP− phages were harvested from CsCl gradient ultracentrifugation and treated overnight with DNaseI to eliminate any potential DNA contamination. E.N.Z.A. M13DNA mini kits were then used to extract the plus and minus cssDNA constructs. Using a commercial transfection agent, the TransIT-X2 (Mirus), we tested GFP transduction in the GBM22 cell line.

72 hrs post treatment with plus, minus, dual minus/plus, and double stranded plasmid DNA, we see that the plus and minus strands alone are not as efficient as double stranded plasmids and surprisingly, the dual minus/plus group is only as efficient as the individual plus and minus strands even with twice the DNA content and the complementary sequences (FIG. 53A). This suggests that double strand formation is not enhanced by the annealing of the two strands in the cell. To test that complementation would promote enhanced expressed, we also introduced a transduction group where the dual plus and minus strand were first treated in an annealing temperature reaction (at 95° C.). Here, we see that the extra annealing step gives the cargo similar efficiencies as double stranded plasmid (FIG. 53B). This verifies that dual delivery of phage derived cssDNA is unable to overcome energy or trafficking barriers to allow for the complementing event. Additionally, the phage packaged cssDNA are known to be in super-coiled form which may be limiting the success of the two strand complementation upon internalization.

Phage extracted ITR-flanked mCherry cssDNA (4887 nts) and double stranded pAAV-minCMV-mCherry (4887 pb) plasmids were also tested for expression efficiencies with TransIT-X2. Again, single strand DNA transduction percentage is slightly lesser than the double strand plasmid equivalent. Interestingly, the 72 hr transduction competence of the ITR-flanked mCherry cssDNA and the inhoGFP plus or minus cssDNA strands are very similar near 45% (FIG. 53A). Most likely, the benefits of ITR integration are better characterized over longer periods of observation as they are noted for augmenting stability of expression. In terms of potential nuclear localization enhancement, we may also consider that the hairpin structures prevalent in the f1-origin and packaging signal could be serving as ITR-similar handles for nuclear transport through regulatory element associations. Hence, in the immediate term, the inho derived cssDNA and ITR-flanked cssDNA report similar transduction efficiencies.

f. Conclusions

Overall, the phage extracted inho cssDNA and ITR cssDNA are both shown to be equally active in transduction of cells in-vitro. A combined inhoITR cssDNA design is also shown to be possible that can easily integrate a transgene sequence and can be used to produced phage particles with the RM13-f1 helpers. The inhoITR cssDNA vector produces gene cargoes with less than 200 bases of prokaryotic sequence and is amenable to introduction of at least 20 kb of transgene information (See Section 5, FIG. 56). While additional DNA structures are yet to be tested for gene expression improvements when placed in combination with the phage extracted inho cssDNA, the space is available for any number of interesting functional DNA elements.

Aiming for maximal episomal expression and stability desired in therapeutic models, we can consider various DNA topology based approaches taking inspiration from DNA doggy-bone structures (self-complementing), and incorporation of nuclear localization DNA sequences like SV40-DTS (transcription factors binding sites) or nuclear persistence sequences like S/MAR (scaffold/matrix attachment regions). The inho cssDNA is an elegant and highly efficient closed-ended gene cassette technology which benefits from phage manufacturing, high fidelity and length of sequence, and low likelihood of genomic integration. Congruently, the phage derived particle shell can be engineered towards high mammalian cell transduction by considering the primary hurdles to access to the cell nucleus. In engineering the M13 coat for efficient mammalian cell penetration, the highest priority barrier to cargo delivery is the degradation of the phage by the proteasome. Endosomal escape strategies such as cationic charge on the phage surface is shown to drive reporter gene transduction (20-30%) and suggests that directed or rational mutagenesis of the phage capsids will yield transducing variants. This is confirmed by the recent success (60%) of the influenza virus inspired H5WYG display on phage gene delivery vehicles. Given inhoITR cassettes within an effective PDP shell design, we can expect to achieve transduction efficiencies that are equivalent to mammalian vector types (in the 80-90% range).

To facilitate the production of new inhoITR gene therapy particles for future testing, an RM13-f1 helper design is produced which can encode up to four different capsid functions with a BAP-enabled p3 for easy target switching (FIG. 51). Additional functional capsid genes are cloned into the non-packaged region of the inho vector to further expand the capsid combinatorial possibilities. It is also suggested that quiescent or slow dividing cell lines be used in accessing future platforms.

Phage therapeutic application in humans has its roots dating to the pre-antibiotic era and benefits from established safety in human subjects. Engineered phage platforms therefore are poised to enter the arena of therapeutic nanocarriers as powerful protein nanoparticles. The malleable capsid of phages allows highly selective trafficking of phage particles in the body organ systems as well as at the cellular compartment level. The simplicity of the phage replication mechanism and the many biological tools we have developed in the study of prokaryotic cells also allows for fine control over the genetic makeup of phage particles. The application of the inho phage to mammalian gene expression underlines the many advantages of a phage derived gene delivery system: cargo size, targeting/trafficking specificity, high titers, and clinical safety.

g. Materials and Methods

Vector Cloning

The f1-ori, f1-term, DomainB and PS sequences were cloned into standard ampicillin selection/colE1 origin plasmid vectors such as pUC19 or pUC57. Commercially available helper phage templates M13KE, M13K07, and R408 were used to create RM13-f1 constructs where the intergenic region is reassembled to disrupt the origin for packageable cssDNA replication (the f1 nicking/p2 complexation sites, in particular, was removed). Kanamycin resistance site was added to the constructs for selection purposes and p15a-ori plasmid replication site is included to achieve optimal copy numbers during *E. coli* growth. Additional functionalization (peptide display on p3, p8, or refactored p9, and the required p5[Cys21] and p2[Met40] mutations) of the inho helper is easily also achieved through standard cloning methods. Briefly, plasmid cloning with restriction enzymes or gibson master assembly techniques were used to create constructs from fragments of interest, to add display insertions, and to change the length of the inho-phage constructs. All oligos and small DNA inserts (i.e. SV40NLS) were purchased through IDT. Large insertion sequences such as ITRmCherry, GFP transgene were sourced from Addgene vectors. AAV2 ITR fragments were enzyme cut from the Addgene pAAV-minCMV-mCherry vector #27970 for inho integration. Full capsid protein sequences templates such as rp8-H10 and rp8-H5WYG was fulfilled by Genscript and enzyme cut or PCR amplified for RM13-f1 site integration. rp9 and BAP capsid variants were sourced from the laboratory stores[42]. PCR reactions were performed (KAPA HiFi Kit) to amplify inserts and vectors with enzyme cut sites or gibson overlapping overhangs. PCR products were purified through a 1.2% agarose gel run and extraction (QIAquick Gel Extraction) or DNA spin columns. Fragments products were processed for enzyme digestion (NEB) followed by ligation using T4 DNA (NEB) ligase if ends were restriction designed or fragments were processed for standard Gibson (NEB) if end were designed with overhangs. Cloning products were transformed and plated for single colony picks. Full length sequencing of the mini-prep (Qiagen) purified plasmids were verified for desired final RM13-f1 and inho construct clones. Complete sequences of RM13-f1 and its p2/p5 assembly or p8/p3/p9 display variants and inhoGFP, inhoITRmCherry, inhoITRmCherry and others are presented in Appendix D.

Phage Culture

XL1-Blue *E. coli* strains (Agilent) and Difco LB Broth cultures were used in all amplification and cloning of inho/RM13-f1 phagemids at 37° C. with continuous 215 rpm shaking. Bacterial dual vector co-transformations or colony swabs were cultured overnight in 5 ml volumes under appropriate antibiotic restrictions (100 μg/mL ampicillin, 50 μg/mL kanamycin). The overnight growths were then used to culture 0.8 L LB medium batches with appropriate antibiotic restrictions and allowed to amplify overnight prior to phage purification.

Phage Purification 0.8 L bacterial phage growths were spun at 8000 rpm (Beckman Coulter JLA 8.1000) for 1 hr to pellet out bacterial cell bodies. The phage supernatant was collected and phage precipitation was facilitated through the addition of 200 mL 50% w/v PEG-8000, 100 ml 5M NaCl (final 10%/PEG/0.5M NaCl for inho-phage) and incubation at 4° C. overnight. Post precipitation, phage supernatants were spun at 8000 rpm (Beckman Coulter, JLA 8.1000) for 1 hr to pellet out the phage particles. The phage pellets were resuspended in 1×TBS/$MgCl_2$/DNaseI (final 5 $\mu g/mL_{DNAse}$, 10 mM Tris-HCl, 2.5 mM MgCl2; 25° C.) and incubated overnight on a benchtop shaker to facilitate digestion of DNA contaminants. Post digestion, the phage suspension was separated under CsCl gradient ultracentrifugation (1.2 g/mL to 1.6 g/mL gradient, SW32, 30,000 rmp, 4° C. for 4 hours) where the extracted phage band was further purified of salts via dialysis or TFF: 12-14 kDa or 100 kDa cutoff dialysis against 1×PBS over 72 hrs with frequent buffer changes or 10 kDa to 100 kDa tangential flow filtration against PBS for 5× volumes (MicroKros MPES columns, Repligen). Finally, purified and concentrated phage samples were filtered through 0.45 μm syringe filters (Pall, 4614) prior to use with cell culture.

Polymer Wrapping of Phage

1e12 purified phage was suspended per 1 mL PBS samples. 3 μg of DEAE.Dextran (500 kDa) or 4 μg of PEI (70 kDa, branched) polymer was added to each 1e12 phage sample and incubated for 15-30 minutes. The polymer wrapped phage was further diluted for cell transduction or AFM imaging of complexation morphology.

Click Chemistry Conjugation onto Phage Surface

CPTA: 225 μL of 1M CPTA, 225 μL of 1M Sulfo-NHS (Thermo 24510), 225 μL 1M EDC (Thermo 22980), and 3.075 mL of 1M MES buffer (pH 5.6) was prepared and allowed to react for 40 min benchtop. Upon completion of CPTA small molecule activation, 0.747 mL of 5M NaCl, 5e13 phages particles, and 0.25 mL of 10M NaOH was added to the reaction mixture to a total volume of 5 mL and the EDC chemistry to phage amines was run overnight. The final reaction mixture was purified and concentrated using 10 kDa to 100 kDa tangential flow filtration against milliQ water adjusted to pH10 for 5× volumes (MicroKros MPES columns, Repligen).

β-GalNAc: 10× molar excess (10×p8 capsid count) Sulfo-SMCC (Thermo 22322) was added to 4e13 phage particles in 2 mL PBS suspension. The primary amine reaction was incubated at room temperature for 30 mins, at which time the sample was washed through a 3000 kDa Amicon Ultra-15 filter for 5×PBS volumes to remove the excess Sulfo-SMCC content. p3-GalNAc-PEG3-thiol (Sussex Reseach PE135010) was added to the washed phage concentrate (2 mL) at Ix molar ratio to p8 capsid count of sample. The maleimide-thiol β-GalNAc-phage conjugation reaction was incubated at room temperature for 2 hrs. The final sample was washed again through a 3000 kDa Amicon Ultra-15 filter for 5×PBS volumes to remove excess β-GalNAc.

Poly-L-Histidine (Sigma 386901) & Poly-L-Lysine (MP Biomedicals 0210269125): 10× molar excess of Sulfo-NHS (Thermo 24510) and of EDC (Thermo 22980) were incubated with poly-amino acid chains in milliQ water (pH 5.3) for 30 min. The activated poly-amino acid chain was added to phage samples in PBS at 50 count per phage. EDC conjugation of PLL and PLH to phage primary amines was run for 2 hrs at room temperature. Excess materials were cleaned from final reaction sample through 100 kDa cutoff tangential flow filtration against PBS for 5× volumes (MicroKros MPES columns, Repligen).

MALDI-TOF Confirmation

MALDI-TOF analysis of phage was performed to confirm that the observed p8 mass was as expected for each sample (this was added confirmation on top of sequencing data).

Analysis was performed by the MIT Koch Institute Swanson Biotechnology Center using a Bruker MicroFlex instrument. For samples with a p8 concentration greater than 140 uM, 1 uL of each sample was mixed with 2 uL matrix solution (sinapinic acid), and 1 uL was then spotted and analyzed. For samples with a p8 concentration less than 140 uM, 1 uL of each sample was mixed with 1 uL matrix solution (sinapinic acid), and 1 uL was then spotted and analyzed. Only p8 masses may be read with full phage samples, other capsids are too dilute and must be purified and concentrated from denatured phage particles prior to MALDI reading.

GBM22, HepG2 Cell Transduction

Human GBM22 (HyClone DMEM SH30022.01, 10% Sigma FBS) or HepG2 (ATCC DMEM 30-2002, 10% Sigma FBS) cells were grown in 6 well plates to 60% confluence. Prepared reporter gene carrying phage particles were diluted in serum free cell media at 1e5 phage per cell MOI. Wells are aspirated from complete media and treated with phage media at 2 ml per well for 4 hrs-6 hrs. The phage transduction media is then replaced by complete media and cells are incubated for 72 to 120 hours before proceeding to flow cytometry reading of gene expression.

Extraction and TransIT X2 Transduction of Phage cssDNA

5e12 to 1e13 purified phages were suspended in 1 ml PBS. The samples were processed using the E.Z.N.A M13 DNA Mini Kit (D6900-01) according to manufacturer's instruction, with 40%-60% recovery of phage cssDNA. cssDNA or double stranded plasmid DNA samples were incubated with TransIT X2 transfection reagent (Mirus) according to manufacturer's instruction(750 ng to 1500 ng of cssDNA was allotted for each well of 6-well plate cell preparations). The reagent treated cssDNA was dropped into complete media of confluent cells grown in 6-well plates and incubated for 72 hrs prior to FACS reading.

FACS Gene Expression Reading

Transduced and untreated control cell (n=3) groups were treated with trypsin resuspension media. The collected cells were spun and re-suspended in 1 mL PBS and pipetted through the cell strainer cap of 5 ml (Falcon 353325) flow tubes. Tubes were maintained on ice for flow cytometry readings on FACS Celesta HTS-1 machine with BD FacsDiva software. Acquired data was analyzed using FlowJo package.

Atomic Force Microscopy Imaging of Phage

Purified phage particles were dispersed in 100 μL milliQ water to a total count of 1e11 phages. AFM sample discs were prepared with mica sheets and sticky tape was used to peel a fresh mica surface for sample deposition. 100 μL phage preparation was deposited on the mica for 30 min to an hour. Prior to AFM visualization, the phage sample was wicked from the mica surface and the mice surface was then quick dried with nitrogen or argon has stream. To quantify phage length, the AFM images were analyzed using Gwyddion software. For each phage the line was manually drawn along the phage, and then the ruler command was used to measure the line length.

Agarose Gel Electrophoresis of cssDNA 1.2% agarose gel with 1× SYBRSafe DNA stain (Thermo S33102) was prepared in 1×TAE buffer in 8 well molds. 50 μl DNA samples with 10 μl NEB Purple gel loading dye (B7024S) was distributed to each well and gel was run at 100Volt (Biorad PowerPac) for 1 hour. (Thermo 100 bp, 1 kb DNA ladders were included as needed). In case of poor cssDNA band visibility, gels were incubated in TAE buffer with 1× SYBRGold DNA stain (Thermo S11494) for 30 mins and visualized.

Section 5—Expansions and Future Work h. Inho Phage Assembly System

The inho phage system has been instrumental in the design of the phage-nanofoam cathodes, the glioma targeting mini-phages, and the cssDNA transgene constructs for phage-based gene therapy described in the preceding Sections of the thesis work. The current tested limits for the inho system ranges from inho135 at ~25 nm in length and inho19800 at 2500 nm in length. The maximum tested here (~20 kb) has been defined as the cargo capacity of our phage derived particles (PDPs), however, it is very likely that the upper limit on this length is much greater. Similarly, the lowest cssDNA of 135 may also be challenged in future.

i. Testing Inho cssDNA and Particle Maximal Length

The Inoviridae phage family (of which M13 is a member) include a host of filamentous phage types that are reported to range in length from ~800 nm to 4 μm[1]. This suggests that longer length (>2500 nm) filament production may be supported by the assembly machinery of the in virus group. It is frequently reported that disruptions in the p3 capping protein of the M13 phage results in very long filaments that are unable to terminate and extrude from the bacterial cell body[2]. These filaments were identified to contain many copies of the cssDNA products.

These polyphages of M13 can be over six times in length (containing over six cssDNA copies).

Hence the extrusion machinery of the M13 is able to handle at least ~42 kb cssDNA without breakdown of production. Similarly, fd multimers of over 10 μm (close to ~80 kb cssDNA content) is a common observance[3]. The multimer length of polyphages suggest that inho40000 and even inho80000 may be tested for packaging with likely positive results. It is noted that plasmid of those lengths may require special processing. Additionally, while the wildtype assembly machinery may be sufficient for wrapping of such ultra long phage particles, this process may be aided by enhancing or weakening the translation of the specific capsid proteins involved. For ultra-long phages, the p8 capsid promoter and ribosomal binding regions may be enhanced and the same may be weakened for the p3 capsid in order to balance the p8 body to p3 capping protein ratio required for the phage particle length in question. Ultra-long phages in the 5 to 10 micron range and more may be ideal for bulk materials work such as gel templates, tissue scaffolding, and filtration devices. Ultra long cssDNA production is also enabled by such phages. Finally, rather than ultra-long genes, the ability to drive the multimeric property of a phage particle can be exploited simply for the purpose of delivering multiple cssDNA copies per phage as well. In the case of gene delivery, such polyphage particles could drive higher transduction efficiency with multiple transgene cassettes packaged within a single phage particle. However, aspolyphage particles would be multiples in length, in correlation to the number of cassettes packaged, it is important to consider the size impact on the in-vivo trafficking and endocytosis profile of the gene delivery platform.

In the Inoviridae family, Ff familiars like the fd, f1, and M13 filamentous phages share ~98%[1] sequence identity and ~55%[4] sequence identity with structurally similar Ike and If1[5]. Hence it is likely that many single stranded filamentous phages other than M13 may be amenable to inho-similar genomic manipulations. The filamentous phage types all have unique structures and natural tropism that may be harnessed for applications in their natural environment. Some motivating strains include the Pf phages (implicated in the biofilm matrices of *Pseudomonas* infections), Xf and Lf phages (*Xanthomonas* phages used in plant pathogen models), and SW1 phages (induced by low temperature and high pressure, isolated from deep-sea *Shewanella piezotolerans*) [1]. Given the large body of work that describe phage regulatory genes and the exponential acquisition of sequencing data from newly isolated strains, we can expect novel and useful PDP types to rapidly emerge in the research landscape.

ii. Testing Minimal Inho and Inho cdsDNA Production

Essential to inho cssDNA production, we report a 79 base length f1-ori and 87 base length f1-term sequences required in the current iteration of inho products. As described, the morphological signal, the packaging hairpin, may be removed. However, the absolute minimum sequence of the f1-ori and f1-term is yet to be tested. Specifically, for the region that is packaged within the inho phage, the 44 bp fragment from the f1 hairpin [C] associated with the f1-term is yet to be tested for removal. Inho constructs with lesser and lesser inclusion of the [C] hairpin may be tried for homogenous and high yield batches where the (+) strand circularization is uncompromised. There are no indications in the literature that the [C] hairpin is particularly crucial to the p2 protein recognition and nicking of the (+) strand. However, there is no current work done to elucidate the mechanism of inho cssDNA self-replication in a helper infected cell. The circularized (+) strand inho ssDNA could act as an infective type DNA and form its own minicircle type replicative form plasmids, from which rolling circle replication can be initiated (FIG. 58). In the current inho scheme, we do not yet know if inho cssDNA originate only from the phagemid templates within the cell or if replicative form double stranded inho's, that are created as a result of the first inho (+) products, also contribute to the production of inho cssDNAs. In the second case, (−) strand recognition sites such as the [B][C] hairpins would be important for generating the replicative form. It is suggested that the bacterial host be tested for inho rfDNA presence during inho culturing. Understanding if inho rfDNA can be formed and propagated will be highly interesting for optimizing the cultures of inho production and for characterizing the infectivity potential of inho particles. To this end, helper cells, created from transformation with RM13-f1 helpers, can be incubated with inho particles and the resulting culture may be characterized for amplification of the inho phages. Phage production from f-pilus injection of a mini inho cssDNA would suggest that the inho cssDNA do have a replicative form and that this inho rfDNA can induce daughter inhophage production if the assembly machinery is available.

As we have discovered, cssDNA products from phage extraction are transcriptionally active and can serve as transgene cassettes for gene transduction. However, preliminary work has revealed that double stranded forms are generally more efficient. While the single stranded inho DNA make self-complementing designs easy, it may also be possible that driving rfDNA formation from inho constructs during bacterial cell infection gives us an option for inho closed ended double stranded DNA (cdsDNA) production. rfDNA is usually found at about a 100 copies per cell similar to many plasmid copy numbers. Hence an inho phagemid that intentionally contain the (−) strand origin elements ([B][C]) may be crucial to discovery of cdsDNA products. While such dsDNA cannot be packaged within a phage shell, these products would be equally clean and engineerable as the inho cssDNA discussed so far in Section 4 (the only difference being the double stranded nature and an additional hairpin sequence). These cdsDNA would be amenable to delivery to target cells in a host of formulations from LNPs to VLPs to exosomes.

iii. Functional Elements for Inho cssDNA Transgene Cassettes

Design of transgene cassettes with inho cssDNA is yet to be explored extensively. Not much outside the use of ITRs and promoter specificity has been discussed in the production of phage DNA cassettes. Once unwrapped in the cytoplasm of a target cell host, the DNA cargo will need to travel to the nucleus and facilitate double strand synthesis for efficient translation. A number of strategies are proposed to improve the double strand formation and nuclear localization of a naked cssDNA cassette including DTS regions (transcription factors binding sites) and hairpin and other repeats that can initialize protein binding and second strand synthesis. Much like phage libraries, a library of DNA sequences can also be designed on the inho cssDNA and the cssDNA clones may be selected from the nucleus to identify efficient transport variants. Driving the transduction efficiency of naked inho cssDNA will be applicable to the use of the DNA technology in phage based gene therapy as explored in Section 4. In the near term, however, a highly efficient inho cssDNA will be interesting for vaccination and microbiome modulating applications. The phage shell requires minimal engineering for production of dual DNA and protein vaccination particles. Given a known antigen or epitope for vaccination, the inho cssDNA can simply be designed with the antigenic sequence and the phage body can be used to the display the antigen itself at high copy numbers. Equally painless, the phage wildtype phage capping p3 capsid is naturally tropic to the *E. coli* microbiome populations, where a delivered cassettes may serve as templates for local production of medicinal proteins, enzymes and so on.

iv. Expansion of Short Phages to Phage Libraries and Hierarchical Nanostructures As demonstrated by 50 nm, 100 nm, and 300 nm phage interaction with cells and accumulation to tumor xenograft, the length of phage particles can play a dramatic role in the cellular and tissue trafficking of phage particles and can amplify the targeting of surface displayed moieties. The prevailing application of phage particles is in the building of phage display libraries for panning and peptide discovery where the power of the library can be vulnerable to the extravasation limits of the phage size. An inho type phage library is proposed as a way to enhance the particle distribution during enrichment panning. Here crucial consideration is in the capsid barcoding of the phage particles. A phagemid can be designed that encodes the recombinant display capsid sequence within the packaged cssDNA region of the inho construct. Here the packaged cssDNA will encode for the capsid variant of the inho phage product (FIG. 59). The RM13-f1 helper plasmid may be used as is in to conjunction with the inho library phagemid, either co-transformed or pre-transformed to the host cells to create helper cells[6-9]. The RM13-f1 capsid content may also be altered to drive greater valency of the recombinant capsid display by either weakening or completely removing the target capsid gene on the helper sequence[6]. For such refactoring of capsids across the inho and helper vectors, it is highly recommended to be cautious of promoter and ribosome binding positions and overlappinggene[10-12]. Finally, an issue often cited for phage libraries is the exponential growth of infective phage clones that can skew the library in favor of fast growers. The growth advantage here is nota result from any differences in the total number of phage produced per bacteria (~1000/cell), but rather the serial infection of cells by the fast clones in a culture with excess uninfected bacterial cells[13]. As the inho phage products are thought to be non-replicating and unable to amplify, one advantage of an inho phage library is the preservation of diversity. The library population is unlikely to be outgrown or skewed towards rapid growing clones, drowning out the slow growers that could harbor interesting display ligands. At the same time, due to the difficulty of amplifying inho phages, these libraries are amenable to only a single round of panning, which is a common technique employed when prioritizing the diversity of binders. This removal of the amplification step has been successfully deployed in a number of cases, discovering binders for cancer cells, pluripotent cells, and tissue targets in a human patient[13,14].

We have seen the morphological control that phage units of varying lengths can exert in the formation of aerogels and nanofoams. This genetic control over the porosity and surface area of phage-based foams is only just being explored and will benefit from protocol optimizations that will enhance the gelation of ultra-short phages. While general bulk materials synthesis methods are likely to be non-specific and worked well with the floppy, long, full-length phage filaments, the short phages are uniquely rod-like and could serve us an interesting sub-unit for highly structured formations. The shorter, more rigid phage struts are much more likely to be useful in the construction of self-assembled protein structures ranging from rings, tessellated sheets or layers, tubules, vesicles, cages, and 3D frameworks (FIG. 60)[15]. The specific capsid interactions of phage nano-rod units can be driven by functionalizing the surface with various assembly nodes. These nodes can be coordinated by electrostatic interaction, metal-ligand coordination, receptor-ligand pairs, covalent chemistry pairing, enzymatic pairing and so on. As phage particles are so easily manipulated for cap and head end display of functional moieties, it is very possible to influence the particle directionality in nano-assembly. The valency of the assembly nodes along the body or at either end of the phage can also be manipulated by tuning the display type and optimizing post production processing. With fine tuning of the valency, we can achieve the desired number of linkages at each phage node. Protein architectures like the phage lamp-brush has already been demonstrated using sortase enzyme mediated labeling of full-length phages with streptavidin and biotin pairs[16]. More complex and compact structures are likely to be possible with phage rods of less than 300 nm in length.

i. Tumor Targeted CTX-Phages

Chlorotoxin display on phage is shown to target phage particles specifically to the glioma tumor mass in an orthotopic mouse model. SWIR imaging of CTX-phage-ICG nanoprobes demonstrated the diagnostic potential of the targeted phage shuttle. The power of the phage nanocarrier could additionally be enhanced by the ideal choice of an NIR-II imaging probe.

Imaging agents having a higher excitation and emission wavelength and an overall stronger signal should allow us to better challenge tumor detection at earlier (submillimeter) states. Moreover, chlorotoxin as a targeting moiety has been validated for its ability to home to gliomas of highly heterogenous cellular profiles[17] as well as bind other solid tumors (lung, breast, prostate, melanoma, colorectal) and hematologic tumor cells (leukemia, lymphoma, myeloma)[18]. Due to this ubiquitous nature of CTX tumor homing, chlorotoxin phages are likely useful nanocarriers to a number of cancer models and may be tested in animal models for diagnostic and therapeutic purposes. Finally, due to the its homing to the (matrix metalloproteinase) MMP membrane complexes, chlorotoxin is also reported as being able to inhibit the proliferation of cancerous cell lines, hinting at the potential for CTX as a new therapy for blockage of tumor metastasis. The degradation of the ECM is a major component of tumor invasion and growth process, and chemical inhibitors of MMPs currently in clinical trials suffer from toxicity and specificity issues that are not apparent in CTX phase III trials[19]. Therefore, CTX phages should be tested as a combination tumor diagnosis and tumor growth halting nanomaterial.

i. Brighter SWIR Carbon Nanotubes for Chlorotoxin Phage Targeted Imaging

While ICG dyes are active in the second window near infrared and is FDA approved for human clinical application, imaging agents with higher excitation and emission in the far 900 nm to 1700 nm second window near infrared (NIR-II) range are better able to overcome tissue autofluorescence and provide contrast enhancement. This would be ideal for in-vivo characterization of smaller, early-stage tumors and detailing of local structures such as the satellite lymph nodes that may be relevant to patient diagnosis and treatment plan.

Particularly for brain tumors, effective detection of tumor growth in-vivo requires an optimization for the signal delivered per CTX-phage as well as percentage of the initial dosage (ID) that reach the tumor site to overcome the scattering and signal attenuation resulting from the skull and scalp tissue. In order to improve on the signal from each nanoprobe, we have explored a variety of imaging agents for their strength in the NIR-II regime, including IR1050 (Nirmidas)[20] as well as density gradient ultracentrifuge (DGU) sorted and O-doped single walled carbon nanotubes (SWNT). While IR1050 and ICG dye are both excited at 808 nm and emit mostly in the 1000-1400 nm range, carbon nanotubes can be engineered for far red 980 nm excitation and emissions over 1400 nm. With excitation at 808 nm, greater autofluorescence detected from the bones, particularly skull tissue, hinder in-vivo signal detection.

Autofluorescence of tissue is better avoided with excitation at 980 nm or capturing of emissions above 1300 nm.

The Belcher Lab had previously demonstrated that the M13 bacteriophage can be used as a molecular shuttle for the delivery of SWNT for detection of tumors[21-24]. The ability to complex carbon nanotubes to the surface of the phage using the DSPHTELP (SEQ ID NO: 4) 8-mer p8 insertion can be utilized to test SWNT formulations for strong SWIR target detection (FIG. 61C).

NanoIntegris HiPCO raw SWNTs were first complexed with CTX-phage as previously described (See Appendix A)[25]. While the excitation requirement of the HiPCO SNWT population is at the lower 808 nm wavelength, the HiPCO SWNT population is expected to have diameters which fluoresce at the far range up to 1,600 nm[23]. Preliminary testing revealed that HiPCO SWNT accumulation and local fluorescence to be too low for detection through the skull (FIG. 62A), though explant of the U87MG tumor xenograft and brain show some tumor signal. To improve on the SWNT fluorescent population, density gradient ultracentrifugation sorting of the HiPCO SWNTs was conducted as previously described[26]. DGU separation allows for selection of those chiralities with the highest fluorescence (the HiPCO population of semi-conducting and metallic nanotubes proved to consist largely of defective CNTs, FIG. 63A). The colored, semi-conducting species (FIG. 63A) of SWNT chiralities were extracted from the DGU layers and complexed as before with CTX-phages.

While the DGU sorting of the SWNT highly improved the fluorescence of our carbon nanotubes (2.6× increase in signal, FIG. 63B), the DGU sorted SWNT complexes likewise did not produce sufficiently high signals for imaging through the skull. Often the signals from the tumor site is overwhelmed by bone fluorescence (FIG. 63C). Finally, a highly successful enhancement of imaging signal from SWNTs was achieved through the doping of a single chirality population of 6,5 SWNT[27]. This work by Lin et al. resulted in a 98-fold increase in signal over HiPCO SWNT. By controlled treatment of SWNT with NaClO, Lin et al. are able to create a quantum defect on the SWNT which shift the excitation and emission wavelength of the nanotube to the far 980 nm/1100 nm and above ranges (FIG. 64B).

The O-doped 6,5 SWNTs fluorescence parameters allow for greater contrast and resolution in tissue. Not only do we have an incredibly high level of signal but as the doped 6,5 SWNT excites at 980 nm, the autofluorescence of the mouse tissue is vastly reduced. The preliminary results of the O-doped SWNT and CTX-phage nanoprobes show promise with high level of detail attainable from the brain ex-vivo (FIG. 65A). However, the circulation time, or the accumulation time, of the O-doped SWNT phages complexes will need to be improved to see clear in-vivo localization signals. Surface exposure of the O-doped SWNT in circulation reduces the CTX-phage-SWNT complex half-life to a few minutes. The rapid clearance of O-doped SWNTs is shown to be prevented by the wrapping of the SWNTs in a biocompatible surfactant coating like DSPE-PEG-5K (Laysan Bio)[27], with half-life extended to over 30 minutes (FIG. 65B). These wrapped O-doped SWNTs are able to show fine vasculature features, lymph nodes, and clearance organs in-vivo[27]. It is suggested a similar wrapping strategy be employed to ensure surface coverage of the doped SWNTs prior to phage loading. CTX-phage loaded with such bright imaging material are certain to improve the resolution and detection size limit of solid tumors and further testing should be pursued.

ii. Therapeutic Potential of CTX-Phages

As described, the CTX moiety displayed on the glioma targeting phage confer the phage with therapeutic potential. The inhibition of extracellular matrix degrading MMP complexes on the surface of glioma tumor cells has been observed for CTX molecules. Likewise, CTX expression phage should exhibit such inhibitory activity. In-vitro assays of cell or spheroid proliferation[28] or in-situ gel zymography[29] of cells treated with CTX-phages may be studied for effective tumor growth halting indicators. Additionally, the CTX-phage-ICG nanoprobe established in Section 3 can be employed to mark tumor suppression and monitoring of tumor size with serial treatment of the mice group with the probe. The CTX-phage-ICG serves as a dual purpose therapeutic and monitoring tool in such a study. Tumor bearing mice treated with CTX-phage probes may be tracked for prolonged survival and slower tumor invasion compared to control groups. Due to the broad tumor specificity of CTX, such evaluation of the tumor suppressive ability of CTX-phages may be conducted with a variety of cancer models (lung, breast, prostate, melanoma, colorectal).

An advantage of the CTX-phage system is the capacity for multi-functional loading. Not only can the phage shuttle direct imaging agents such as IGC, but can also simultaneously deliver active agents such as chemotherapies. In the case of toxic chemical agents, the directed delivery on phage shuttles vastly reduces the systemic toxicities associated with bolus treatment and drives localized accumulation to the tumor site. Furthermore, a clear gain of nanocarriers is the possibility to try combinational treatment with more than one drug. Combinations such as temozolomide and bevacizumab[30], temozolomide and siRNA MGMT silencing[31], or temozolomide and bromodomain inhibitor[32] have demonstrated the enhanced efficacy of mixed treatments. Loading of CTX-phages with ICG and drug combinations is suggested for a glioma bearing mouse treatment course. An additional mode of therapy through the delivery of transgene cassette packaged within a CTX-phage may also be considered (FIG. 66). Previous efforts, utilizing αvβ3 integrin specific RGD4C-phages, have been shown to effectively deliver tumor killing genes such as TNF-alpha[33-36] and HSVtk[36-41] to the tumor site, induce expression, and suppress tumor growth. Gene therapy cargoes delivered within CTX-phages loaded with multiple chemotherapeutics such as temozolomide/bevacizumab/capecitabine/paclitaxel is likely to be highly effective in treatment of aggressive glioma types and is a multi-modal system that could overcome tumor chemoresistance issues. Addition of ICG load to the proposed system would then enable immediate monitoring of the tumor bearing mouse groups with each therapy infusion.

j. Additional Phage Particle Engineering for Mammalian Gene Therapy

As discussed in Section 4, the phage delivered particles and their cssDNA cargoes are amenable to engineering towards transduction of mammalian cells. Over 20 years of exploration in engineering the M13 capsid for gene delivery has resulted in 60% transduction rates achieved in-vitro and successful suicide gene treatment of cancer in mouse and dog models[35,38,40].

Expanding on this work, we have explored the potential of inho type PDP production optimized for gene delivery through PDP coat surface conjugates. However, the development of the next generation PDPs will require a number of key studies that explodes the phage particle engineering space. Of particular impact will be the directed of evolution of phage coat proteins towards the cellular trafficking goals outlined for mammalian cell transduction (FIG. 67). In example, phage libraries have been used to enrich for peptide sequences that drive cellular penetration or endosomal escape, leading to the discovery of PC1, CHL8, phylomer-CPPs and others[42-46]. M13 libraries are also employed in searching for organelle specific trafficking peptides[47]. There is enough evidence to suggest that a curated library of phages may be enriched for variants suited for nuclear delivery of DNA cargo. Directed evolution of AAV capsids have recently been tremendously successful in generating mutants with extremely high efficiencies[48-50]. While M13 phages would be starting from a completely non-tropic position, phage libraries are highly diverse and much more complex sequences are possible to present on the filamentous surface than on AAV's icosahedral surface. There is high likelihood of driving the 60% efficiency of phage based transduction to over 90% efficiencies at low MOI (<1e4) by designing and enriching from comprehensive coat libraries.

i. Trafficking of Gene Delivery Phages

In-vivo trafficking of PDP vector variants discovered for their mammalian transduction efficiency also need to be characterized. It will be essential to consider the effect of the peptide display that enhance endosomal escape or nuclear import on the immunogenicity and tissue interactions of systemically administered phages. If rapid clearance or off-target tissues become sink for phage variants, therapeutics levels of particle localization may be compromised. Any new surface modified PDP clones (CPPs, EEPs, NLSs, etc.) will need to be profiled for circulation and tissue target accumulation changes. As we have extensively explored, the length of the filamentous phage derived particles is determined by the size of the cssDNA therapeutic cargo. Additionally, we know that enhanced trafficking profiles can be achieved from smaller sized phages. Hence, in the case of genetic cargoes that will require many kilobases of real estate, it will be important to optimize for the cargo capacity versus tissue loading potential of PDPs. Not only may the in-vivo administration and target tissue loading be affected by longer length PDPs, but the physical profile of the phage particles will become significant to the mechanisms driving the cellular trafficking of the PDP. Specifically, the internalization efficiency of the phage platform will need to be characterized for sizes much greater than wildtype (900 nm). Studies demonstrate the clathrin-mediated endocytosis of wildtype length phage particles upon surface receptor engagement[47,51-54], but we will need to consider the possibility that at sizes over a micron, the phage particle will be internalized through cell membrane pinocytosis or phagocytosis like events. The hydrodynamic diameter of wildtype 900 nm phage is often measured between 200-300 nm which is at the threshold of endocytic envelope sizes. It will be imperative understand the impact of longer lengths on the mechanism of internalization and characterize any rate differential that may result.

ii. Identifying Dynamic Cell Surface Receptors

One of the key difficulties in targeted delivery to specific cell population is that very few cell surface receptors have been identified for their recycling biology. Even if highly specific to the target cell type, most surface receptors do not exhibit sufficient turnover rates to ensure rapid internalization of the receptor engaged vectors. Much of the current success in targeted therapy has been centered around two known receptors, the ASGPR and the TfR. Both have been well characterized for their high internalization biology and a number of ligands have been discovered that bind these receptors at high specificity for cargo internalization. Ideally, to expand beyond the limited repertoire of high rate receptors, phage library variants enriched for certain cell types will also be selected for their internalization dynamic. Hence, library panning with diversely populated phage clones could ensure that both the specificity and internalization rate criteria are met.

On the other hand, to solve for therapeutic levels of internalization, the field has begun to explore active transport mechanisms such as fusogens to drive cargo entry to the cytoplasm.

Virus-like-particles (VLPs) and lipid nanoparticles (LNPs) frequently take inspiration from fusogenic proteins present on natural virus structures[55-57]. Such active transporter drivers, however, suffer from a lack of specificity that is yet to be convincingly solved. We may consider the possibility of fusogenic or cell penetrating peptide display on PDPs that will ensure active internalization to mammalian cells, but we would also face the same specificity dilemma. It is possible that fusogenic or cell-penetrating peptide and a cell surface specific peptide may be presented in combination to guarantee a certain level of specificity. We know that the p3 tail capsid of the M13 can be engineered to present 2-3 copies each of two different peptides and that the p8, p9, p6, and p7 are all additional options. In this scenario, optimization for the capsid locations and ratios of the two ligand types (one for specificity and one for internalization) is required to ensure variants with minimal off-target internalization potential. Finally, the need for rapid internalization and specificity of the gene delivery may also be divided between the phage capsid design and the transgene cassette design. Here PDP capsids may be optimized for cell penetration and a promoter specific to the cell type of interest can be incorporated on the genetic cargo. However, risks of off-target consequences and loss of particles to off-target tissues are high in such a design.

iii. Evading Proteasomal Degradation

Incubation of phage particles in mammalian cell culture has demonstrated the number one hurdle for phage gene delivery is achieving endosomal escape following internalization[54,58-61]. The efficiency of phage particles from degradation as the endosome matures is critical to driving up the transduction efficiencies of phage shuttles. As discussed in Section 4, rationale design as well as directed mutation of the phage surface for endosomal escape could be particularly successful towards this goal. An alternative strategy, that has also been explored in the engineering of AAV capsids[48], is mutagenesis guided by the directive of evading the degradation mechanism. As opposed to endosomal pocket breakout, capsids here are cloned such that the exposed terminals of the phage shells are reduced in lysine (K), tyrosine (Y), serine (S), and threonine (T) content. The surface exposed K are easily ubiquitinated, tagging the phage surface for degradation. Surface exposed Y, S, and T residues can be phosphorylated which is a signal for ubiquitination. Y to F, S to V, T to V, and K to E mutations have been successfully described for AAVs to reduce the proteolytic degradation and poly-ubiquitination events[48]. The densely repeated p8 coat and the more surface exposed p9 and p3 coats of the phage for instance may be easily tested to mutate away potential handles for proteasomal break down signaling.

Methods for bypassing the endolysosomal pockets to directly transport the PDP to the cell cytosol are exciting alternatives to the EEP display strategy. In addition to cell penetrating or fusion peptides, an interesting mechanism inspired by phage infection biology is the use of protein complexes capable of actively injecting DNA material through the cellular membrane.

While such phage tail injection complexes are best understood in the context of the bacterial host[62-67], the varieties still being explored point to the likely engineer ability of such systems towards mammalian cells. While target specificity is always difficult to regulate for technologies with such broad invasiveness, chimeric PDPs with injection complexes or phage based transgene cassettes complexed with injection systems is an unexplored area of technology development that could be highly effective for gene transfer.

iv. Concluding Remarks

The incredibly engineerable nature of the filamentous phage type has made M13 famous as a biological protein template and have lent the system to the creation of bio-inspired nanoparticles and bulk nanomaterials. The range of uses described in the field for the engineered M13 filament spans templated electronics, optical sensors, energy harvesting cells and catalysts, aerogels and hydrogels, hierarchical nanostructures and cssDNA origami, filtration and bioremediation devices, to antimicrobials, vaccines, gene therapy vectors, and targeted nanocarriers. In this thesis, we have explored extensively the filament length parameter of the M13 phage nanoparticle design. Size control is yet to be widely described in the field for its potential impact across the many application of phage. In learning to adapt the phage particle length, we have introduced to the field a new phagemid system, the inho vectors, that exclusively packages sequences flanked by refashioned f1 replication origin and termination sequences. The usefulness of ultra-short and ultra-long phages produced with such tight control over the genetic cargo is discussed in the context of phage templated metal nanofoams, targeted phage nanocarriers, and phage derived transgene cassettes and gene delivery.

The morphological differences noted for phage templated cathode materials demonstrated the ability of the phage strut lengths to influence the ion transport and surface area access of metal nanofoams. These properties translated directly to the performance of $MnO_x$ batteries produced from inho phages ranging in lengths of 320 nm, 430 nm, 550 nm, 750 nm, 900 nm, and 1400 nm phages. Peak battery capacity is achieved with 750 nm phage-based metal nanofoams where the highest porosity is observed with our crosslinking protocols.

For the first time, the scorpion venom derived small peptide, chlorotoxin, is used to direct a phage particle to glioblastoma masses in the brain. Well characterized for its receptor mediated BBB crossing activity and its ability to home to the heterogeneous CNS tumor populations, chlorotoxin is able to drive the healthy brain tissue retention of M13 phage nanocarriers by 4-fold with ~3% of total dosed phage particles reaching the brain parenchyma. In glioma bearing mice, the chlorotoxin-phage particle concentration at the tumor site is 5 times that of the surrounding normal brain tissue. However, with inho derived phage shuttles of 300 nm, 100 nm, and 50 nm lengths, this tumor/normal tissue concentration ratio can be driven to ~10, ~25, and ~80 respectively. The unusual rod-like geometry of the phage particles and the ability to miniaturize the phage enables improved extravasation and tissue interaction of a targeted phage nanocarrier. This is evidenced by the drop in circulation time exhibited by 50 nm phages and the increase in cellular internalization rates with shorter phages. Ultimately, chlorotoxin targeted phage carrying indocyanine green dye demonstrated the delivery of the ICG molecules to the glioma site with clear SWIR visualization and strong signal at dosages 250 times lower than needed with free molecules. The chlorotoxin phage nanoplatform is a solid contender in the space of targeted therapeutic and diagnostic materials delivery. The phage shuttle ensures longer half-life for small molecules and grants differential accumulation to disease versus normal tissue, at low dosages with vastly reduced systemic exposure.

With the level of sequence control granted by the inho system, the phage cssDNA was engineered for AAV-like, ITR-glanked transgene cassettes. These cassettes comprise less than 200 bases of prokaryotic sequence and can be produced with gene lengths as high as 20 kilobases. Such transgene carrying inho phages illustrated the possibility to transduce mammalian cells within phage capsids re-engineered for cellular trafficking. Cationic polymer and poly-amino acid decoration of the phage particle capsids enable transduction of 20-30% in human liver and brain cancer cells. The body of work in the field for internalizing and transducing phage shell types suggests that mutagenesis of the inho capsids may be exercised for highly efficient and precise, ligand-directed delivery of inho type cassettes to host cells. To this end a highly versatile RM13-f1 helper was designed with display options to enhance nuclear transport.

The engineering solutions explored in this thesis took advantage of a variety of chemical and biological methodologies, with techniques borrowed from synthetic biology, nanoparticle science, optical science, cancer biology, electrochemistry and genetic engineering. This speaks to the wide applicability of M13 phage derived nanoplatforms. And, given the long history of chemical and genetic techniques already developed for the capsid and gene modification of M13 phages, phage derived nanoparticles are easily re-designed for the problems at hand. Similarly, as the field continues to discover new phage variants and elucidate their biology, we can expect many more phage derived particle types to emerge in future.

APPENDIX A

A1 Engineering Phage Particle Rigidity

Point Mutations in RM13f5

Various clones containing point mutations (at position 21 or 48 in the p8 major coat protein) were generated using standard Quikchange (Agilent Technologies) protocols. Templates and primers are outlined in Table A1-1. The RM13-f1 construct containing three glutamic acid residues (EEE) at the N-terminus of the p8 major coat protein was also created using Quikchange mutagenesis (see Table A1-1 for details). For plasmids containing an antibiotic resistance gene, the DNA from a single colony was isolated and sequence verified (Quintara Biosciences). For plasmids derived from RF DNA, 10 uL of transformation outgrowth was used to infect healthy XLIBlue cells, which were then grown overnight in top agarose. Viral plaques were selected and amplified, and the resulting RF DNA was isolated and sequence verified (Quintara Biosciences).

TABLE A1-1

Templates and primers used for Quikehange site-directed mutagenesis.

| | | Primers | | SEQ ID |
|---|---|---|---|---|
| Construct | Template | Name | Sequence | NO: |
| RM13_E3 | RM13_f1 | E3_QC_N | 5'-TCTTTCGCTGCTGAGGAGGAGGATCCCGCAAAAGCG-3' | 33 |
| | | E3_QC_C | 5'-CGCTTTTGCGGGATCCTCCTCCTCAGCAGCGAAAGA-3' | 34 |
| E3_K48A M13KE_K48A P89_K48A | E3 RF M13KE P8#9 RF | K48A_N | 5'-GCTGTTTAAGAAATTCACCTCGGCAGCA AGCTGATAAACCGATACA-3' | 35 |
| | | K48A_C | 5'-TGTATCGGTTTATCAGCTTGCTGCCGAG GTGAATTTCTTAAACAGC-3' | 36 |
| RM13_Y21A | RM13_f1 | Y21A_N | 5'-AAGCCTCAGCGACCGAAGCTATCGGTTATGCGTGGG-3' | 37 |
| | | Y21A_C | 5'-CCCACGCATAACCGATAGCTTCGGTCGCTGAGGCTT-3' | 38 |
| RM13_Y21C | RM13_f1 | Y21C_N | 5'-GCAAGCCTCAGCGACCGAATGTATCGGTTATGC-3' | 39 |
| | | Y21C_C | 5'-GCATAACCGATACATTCGGTCGCTGAGGCTTGC-3' | 40 |
| RM13_Y21D | RM13_f1 | Y21D_N | 5'-AGCCTCAGCGACCGAAGATATCGGTTATGCGTG-3' | 41 |
| | | Y21D C | 5'-CACGCATAACCGATATCTTCGGTCGCTGAGGCT-3' | 42 |
| RM13_Y213 | RM13_f1 | Y21E_N | 5'-CCTGCAAGCCTCAGCGACCGAAGAGATCGGTTATGCG-3' | 43 |
| | | Y21E_C | 5'-CGCATAACCGATCTCTTCGGTCGCTGAGGCTTGCAGG-3' | 44 |
| RM13_Y21F | RM13_f1 | Y21F_N | 5'-GCAAGCCTCAGCGACCGAATTTATCGGTTATGC-3' | 45 |
| | | Y21F_C | 5'-GCATAACCGATAAATTCGGTCGCTGAGGCTTGC-3' | 46 |
| RM13_Y21G | RM13_f1 | Y21G_N | 5'-AAGCCTCAGCGACCGAAGGTATCGGTTATGCGTGGG-3' | 47 |
| | | Y21G_C | 5'-CCCACGCATAACCGATACCTTCGGTCGCTGAGGCTT-3' | 48 |
| RM13_Y21H | RM13_f1 | Y21H_N | 5'-AGCCTCAGCGACCGAACATATCGGTTATGCGTG-3' | 49 |
| | | Y21H_C | 5'-CACGCATAACCGATATGTTCGGTCGCTGAGGCT-3' | 50 |
| RM13_Y21I | RM13_f1 | Y21I_N | 5'- AAGCCTCAGCGACCGAAATTATCGGTTAT GCGTGGG-3' | 51 |
| | | Y21I_C | 5'-CCCACGCATAACCGATAATTTCGGTCGCTGAGGCTT-3' | 52 |
| RM13_Y21K | RM13_f1 | Y21K_N | 5'-CCTGCAAGCCTCAGCGACCGAAAAGATCGGTTATGCG-3' | 53 |
| | | Y21K_C | 5'-CGCATAACCGATCTTTTCGGTCGCTGAGGCTTGCAGG-3' | 54 |
| RM13_Y21L | RM13_f1 | Y21L_N | 5'-CAAGCCTCAGCGACCGAATTAATCGGTTATGCGTGG-3' | 55 |
| | | Y21L_C | 5'-CCACGCATAACCGATTAATTCGGTCGCTGAGGCTTG-3' | 56 |
| RM13_Y21N | RM13_f1 | Y21M_N | 5'- TCCCTGCAAGCCTCAGCGACCGAAATGATC GGTTATGCGT-3' | 57 |
| | | Y21M_C | 5'- ACGCATAACCGATCATTTCGGTCGCTGAG GCTTGCAGGGA-3' | 58 |

TABLE A1-1-continued

Templates and primers used for Quikehange site-directed mutagenesis.

| Construct | Template | Primers Name | Primers Sequence | SEQ ID NO: |
|---|---|---|---|---|
| RM13_Y21N | RM13_f1 | Y21N_N | 5'-AGCCTCAGCGACCGAAAATATCGGTTATGCGTG-3' | 59 |
| | | Y21N_C | 5'- CACGCATAACCGATATTTTCGGTCGCTGAGGCT-3' | 60 |
| RM13_Y21P | RM13_f1 | Y21P_N | 5'-AAGCCTCAGCGACCGAACCTATCGGTTATGCGTGGG-3' | 61 |
| | | Y21P_C | 5'-CCCACGCATAACCGATAGGTTCGGTCGCTGAGGCTT-3' | 62 |
| RM13-Y21Q | RM13_f1 | Y21Q_N | 5'-CCTGCAAGCCTCAGCGACCGAACAGATCGGTTATGCG-3' | 63 |
| | | Y21Q_C | 5'-CGCATAACCGATCTGTTCGGTCGCTGAGGCTTGCAGG-3' | 64 |
| RM13_Y21R | RM13_f1 | Y21R_N | 5'-AAGCCTCAGCGACCGAACGTATCGGTTATGCGTGGG-3' | 65 |
| | | Y21R_C | 5'-CCCACGCATAACCGATACGTTCGGTCGCTGAGGCTT-3' | 66 |
| RM13_Y21S | RM13_f1 | Y21S_N | 5'-AAGCCTCAGCGACCGAAAGTATCGGTTATGCGTGGG-3' | 67 |
| | | Y21S_C | 5'-CCCACGCATAACCGATACTTTCGGTCGCTGAGGCTT-3' | 68 |
| RM13Y21T | RM13_f1 | Y21T_N | 5'-AAGCCTCAGCGACCGAAACTATCGGTTATGCGTGGG-3' | 69 |
| | | Y21T_C | 5'-CCCACGCATAACCGATAGTTTCGGTCGCTGAGGCTT-3' | 70 |
| RM13Y21V | RM13_f1 | Y21V_N | 5'-AAGCCTCAGCGACCGAAGTTATCGGTTATGCGTGGG-3' | 71 |
| | | Y21V_C | 5'-CCCACGCATAACCGATAACTTCGGTCGCTGAGGCTT-3' | 72 |
| RM13_Y21W | RM13_f1 | Y21W_N | 5'-CAAGCCTCAGCGACCGAATGGATCGGTTATGCGTGG-3' | 73 |
| | | Y21W_C | 5'-CCACGCATAACCGATCCATTCGGTCGCTGAGGCTTG-3' | 74 |

Calculation of Persistence Length Change in 100 nm Y21× Mutant Phages

Inho475 and RM13-f1_Y21 mutants were co-transformed to obtain 100 nm phage batches with varying stiffness. Dynamic light scattering was performed using a cuvette-based DLS instrument (Wyatt Technology Corporation, DynaPro NanoStar) to calculate the hydrodynamic radius of the 100 nm phage variants. A 450 μL aliquot of phage solution was pipetted into a plastic cuvette (Eppendorf, 952010069) and the hydrodynamic radius $\langle R^2\rangle$ of phage was measured. The persistence length P was calculated considering $\langle R^2\rangle$ and the phage length L, according to $\langle R^2\rangle=2LP-2P^2(1-e^{-L/P})$.

Circulation Modeling for Phage-ICG Conjugates

TABLE A2-1

Exponential decay fits for phage variants (from normalized vasculature signal intensity over time).

| Exponential Decay Equation | | | y = A1*exp(−x/t1) + y0 | | | |
|---|---|---|---|---|---|---|
| Sample | A1 | t1 | y0 | R^2 | t1 | half-life |
| free | 1 | 6.97 ± 0.54 | 0 | 0.996 | 6.97 | 4.831236 |
| 900 WT | 1 | 189.86 ± 22.57 | 0 | 0.945 | 189.86 | 131.6009 |
| 900 WT | 1 | 193.63 ± 33.68 | 0 | 0.856 | 193.63 | 134.2141 |
| 900 WT | 1 | 155.17 ± 56.525 | 0 | 0.883 | 155.17 | 107.5556 |
| 1400 CTX | 1 | 179.51 ± 25.085 | 0 | 0.871 | 179.51 | 124.4269 |
| 1400 CTX | 1 | 170.51 ± 38.280 | 0 | 0.859 | 170.51 | 118.1885 |
| 1400 CTX | 1 | 219.74 ± 50.340 | 0 | 0.904 | 219.74 | 152.3122 |
| 900 CTX | 1 | 175.36 ± 62.237 | 0 | 0.797 | 175.36 | 121.5503 |
| 900 CTX | 1 | 207.2 ± 23.329 | 0 | 0.9 | 207.2 | 143.6201 |
| 990CTX | 1 | 180.69 ± 28.278 | 0 | 0.856 | 180.69 | 125.2448 |
| 300 CTX | I | 219.561 ± 31.602 | 0 | 0.904 | 219.561 | 152.1881 |
| 300 CTX | 1 | 161.952 ± 23.086 | 0 | 0.969 | 161.952 | 112.2566 |
| 300 CTX | 1 | 152.884 ± 25.967 | 0 | 0.925 | 152.884 | 105.9711 |
| 100 CTX | 1 | 168.31 ± 18.348 | 0 | 0.865 | 168.31 | 116.6636 |
| 100 CTX | 1 | 129.36 ± 38.399 | 0 | 0.842 | 129.36 | 89.66552 |
| 100 CTX | 1 | 133.28 ± 14.32 | 0 | 0.929 | 133.28 | 92.38266 |
| 100 CTX | 1 | 146.753 ± 20.34 | 0 | 0.913 | 146.753 | 101.7214 |
| 50 CTX | 1 | 123.99 ± 9.89 | 0 | 0.974 | 123.99 | 85.94332 |
| 50 CTX | 1 | 93.218 ± 5.679 | 0 | 0.971 | 93.218 | 64.61379 |
| 50 CTX | 1 | 98.94 ± 15.14 | 0 | 0.973 | 98.94 | 68.57998 |
| 50 CTX | 1 | 126.76 ± 34.46 | 0 | 0.865 | 126.76 | 87.86334 |
| 50 CTX | 1 | 75.388 ± 8.44 | 0 | 0.961 | 75.388 | 52.25498 |
| 50 CTX | 1 | 119.531 ± 8.8 | 0 | 0.973 | 119.531 | 82.85258 |
| 50 CTX | 1 | 113.338 ± 7.137 | 0 | 0.981 | 113.338 | 78.55992 |
| 50 CTX | 1 | 95.95 ± 16.98 | 0 | 0.887 | 95.95 | 66.50747 |

TABLE A2-2

ANOVA one-way analysis of IGC-phage half-lives across groups.
ANOVA

| Source of Variation | SS | df | MS | F | P-value | F crit |
|---|---|---|---|---|---|---|
| Between Groups | 14269.94 | 5 | 2853.988 | 12.37485 | 2.63E−05 | 2.772853 |
| WithinGroups | 4151.307 | 18 | 230.6282 | | | |

*statistically significant difference in average half-life according to phage size (f(5) = 12, p < 2.63e−5)

TABLE A3-1 cssDNA weights and dilutions for standard curves.

| ITR-mCherry 1508315 | inho-ITR-mCherry 857911 | cssDNA calculate d weight(Da) numberof vg | M13KE-DSPH 2228064 | GTX-M13KE-DSPH 2262374 | inho1960 604798 | inho475 146128 | inho285 87558 |
|---|---|---|---|---|---|---|---|
| | | | pg content of standard curve dilutions (10 µl into 90 µl serial dilutions) | | | | |
| | | 1.00E+07 | 36.99874 | 37.56848 | 10.04314 | 2.426569 | 1.453969 |
| | | 1.00E+06 | 3.699874 | 3.756848 | 1.004314 | 0.242657 | 0.145397 |
| | | 1.00E+05 | 0.369987 | 0.375685 | 0.100431 | 0.024266 | 0.01454 |
| | | 1.00E+04 | 0.036999 | 0.037568 | 0.010043 | 0.002427 | 0.001454 |
| | | 1.00E+03 | 0.0037 | 0.003757 | 0.001004 | 0.000243 | 0.000145 |
| | | 1.00E+02 | 0.00037 | 0.000376 | 0.0001 | 2.43E−05 | 1.45E−05 |
| | | 1.00E+01 | 3.7E−05 | 3.76E−05 | 1E−05 | 2.43E−06 | 1.45E−06 |
| | | 1.00E+00 | 3.7E−06 | 3.76E−06 | 1E−06 | 2.43E−07 | 1.45E−07 |

TABLE A3-2 gDNA qPCR reaction mix.

| S¥BR mix per well | |
|---|---|
| SYBR-Green | 10 µl |
| for primer (5µM) | 2 µl |
| rev primer (5µM) | 2 µl |
| sample DNA extract | 100 ng (up to 6 µl volume) |
| ddH20 | . . . µl |
| total | 20 µl rxn |

A4 SWNT Phage Complexation

Complexation of SWNT to Phage

Add SWNT binding phage DSPHTELP clones (SEQ ID NO: 4) suspended in water to SWNTs dispersed by 2 wt % sodium cholate, ensure that the resulting dilution does not drop the sample sodium cholate concentration below the critical micelle concentration of 0.5 wt %. The mixed solution was dialyzed (12-14 kDa membrane, Spectrum) against milliQ water adjusted to 10 mM NaCl, pH=5.3 for 10 hrs days, with frequent solution changes. At 10 hrs, the dialysis solution was switched to 10 mM NaCl, pH=10 milliQ water to increase the colloidal stability of the complex. Upon another 24 hrs of dialysis, the buffer is changed once again to 30 mM NaCl, pH=10 milliQwater and run for 3 hrs. The dialyzed sample is then removed from the dialysis bag and 10×PBS is added final 1× concentration. The final sample is spun at 6,000 rpm for 5 min to remove any large aggregations.

APPENDIX B

B1 Relevant Filamentous Bacteriophage Values and Equations

TABLE B1-1

Phage proteins.

| Phage Protein | Function | # of Amino Acids | Molecular Weight |
|---|---|---|---|
| p2 | DNA replication | 410 | 46,137 |
| p10 | DNA replication | 111 | 12,672 |
| p5 | binding of ssDNA | 87 | 9,682 |
| p8 | major coat capsid | 50 | 5,235 |
| p3 | minor tail capsid | 406 | 42,522 |
| p6 | minor tail capsid | 112 | 12,342 |
| p7 | minor head capsid | 33 | 3,599 |
| p9 | minor head capsid | 32 | 3,650 |
| p1 | assembly | 348 | 39,502 |
| p4 | assembly | 405 | 43,502 |
| p11 | assembly | 108 | 12,424 |

Phage Quantification

Phage concentrations are given by the absorbance peak at 269 nm with correction at 320 nm (read by NanoDrop) and the number of nucleotides in the given phage genome:

$$\text{Phage Concentration} = \frac{(A269 - A320)(6\times 10^{17})}{\text{number of } nts \text{ of phage genome}}\ \text{particles/ml}$$

Givens: 330 daltons per base and molar extinction coefficient of $1.006\times10^{4}\ M^{-1}cm^{-1}10^{4}$

APPENDIX C

C1 Cloning of Vector Variants

Insertion or Restriction Sites into the RM13-f1 Plasmid

Restriction sites were inserted into the p3 (KpnT/EagI) and p8 (PstI/BamHI) DNA sequences using two-fragment Gibson assembly reactions. Specifically, fragments were PCR-amplified using the primers outlined in Table C1-1 and RM13-f1 as the template. Fragments were gel extracted using the Qiaquick Gel Extraction Kit (Qiagen) and 100 ng of each was used in a standard Gibson assembly reaction. 2 uL of each reaction was then transformed into 50 μL C2987 or XL1Blue chemically competent cells. Individual colonies were selected and DNA was purified using a QiaPrep Spin Miniprep Kit (Qiagen) or a Monarch Plasmid Miniprep Kit (New England Biolabs). All plasmids were sequence verified (Quintara Biosciences).

TABLE C1-1

Primers used for Gibson Assemblies of restriction sites.

| Fragment | Primers Name | Primers Sequence | SEQ ID NO: |
|---|---|---|---|
| KpnI_EagI_Fragment1 | KpnI_EagI_N | 5'-GCAATTCCTTTAGTGGTACCTTTCTATTCTCACTCGGCCGAAACTGTTGAAAGT-3' | 75 |
| | RM13_Assembly_C | 5'-CTTCCTGGCATCTTCCAGGAAATCTCCG-3' | 76 |
| KpnI_EagI_Fragment2 | KpnI_EagI_C | 5'-ACTTTCAACAGTTTCGGCCGAGTGAGAATAGAAAGGTACCACTAAAGGAATTGC-3' | 77 |
| | RM13_Assembly_N | 5'-CGGAGATTTCCTGGAAGATGCCAGGAAG-3' | 78 |
| PstI_BamHI_Fragment1 | PstI_BamHI_N | 5'-TGTCTTTCGCTGCAGAGGGTGAGGATCCCGCAAAAG-3' | 79 |
| | RM13_Assembly_C | 5'-CTTCCTGGCATCTTCCAGGAAATCTCCG-3' | 76 |
| PstI_BamHI_Fragment2 | PstI_BamHI_C | 5'-CTTTTGCGGGATCCTCACCCTCTGCAGCGAAAGACA-3' | 80 |
| | RM13_Assembly_N | 5'-CGGAGATTTCCTGGAAGATGCCAGGAAG-3' | 78 |

8-Mer Insertions in the n-Terminus of p8

The DNA corresponding to the desired 8mers were inserted between the PstI and BamHI restriction sites found near the N-terminus of the p8 protein. 5'-phosphorylated DNA oligos (Integrated DNA Technologies, Inc.) containing the 8mer flanked by the appropriate restriction enzyme overhangs were annealed to create inserts for ligation. Oligos are outlined in Table C1-2. The RM13_PstI_BamHI construct described above was used as a template for insertion. This plasmid was digested with PstI and BamHI and dephosphorylated using shrimp alkaline phosphatase before ligation to the inserts using T4 DNA ligase. The resulting plasmids were then transformed into chemically competent XL1Blue *E. coli* cells. DNA was purified and all plasmids were sequence verified (Quintara Biosciences).

TABLE C1-2

8-mer sequences for oligo design with enzyme overhangs.

| Construct | Oligos Name | Oligos Sequence | SEQ ID NO: |
|---|---|---|---|
| RM13_p89 | P89_Insert_N | 5'-GTGTCGGGGTCGTCGCCGGATTCG-3' | 81 |
| | P89_Insert_C | 5'-CGAATCCGGCGACGACCCCGACAC-3' | 82 |

TABLE C1-2-continued 8-mer sequences for oligo design with enzyme overhangs.

| Construct | Oligos Name | Oligos Sequence | SEQ ID NO: |
|---|---|---|---|
| RM_13_DDAH | DDAH_Insert_N | 5'-GATGATGCGCACGTGCACTGGGAG-3' | 83 |
| | DDAH_Insert_C | 5'-CTCCCAGTGCACGTGCGCATCATC-3' | 84 |
| RM_13_DSPH | DSPH_Insert_N | 5'-GATTCGCCGCATACTGAGTTGCCG-3' | 85 |
| | DSPH_Insert_C | 5'-CGGCAACTCAGTATGCGGCGAATC-3' | 86 |

Insertion of p5 and p2 Mutations into the RM13-f1 Plasmid

Single mutation sites were inserted into the p5[21Cys] and p2[40Met] DNA sequences using two-fragment Gibson assembly reactions. Specifically, fragments were PCR-amplified using the primers outlined in Table C1-3 and RM13-f1 as the template. Fragments were gel extracted using the Qiaquick Gel Extraction Kit (Qiagen) and 100 ng of each was used in a standard Gibson assembly reaction. 2 uL of each reaction was then transformed into 50 μL C2987 or XL1Blue chemically competent cells. Individual colonies were selected and DNA was purified using a QiaPrep Spin Miniprep Kit (Qiagen) or a Monarch Plasmid Miniprep Kit (New EnglandBiolabs). All plasmids were sequence verified (Quintara Biosciences).

TABLE C1-3

Primers used for Gibson Assemblies.

| Fragment | Primers Name | Primers Sequence | SEQ ID NO: |
|---|---|---|---|
| P2_ Fragment1 | P2-for_N | 5'- CCGGCATGAATTTATCAGCTAGAACGGTTG-3' | 87 |
| | RM13_PacI-rev_C | 5'- CTTCTGTAAATCGTCGCTATTAATTAATTTTC CCTTAGAA-3* | 88 |
| P2_ Fragment2 | P2-rev_C | 5'- AAATTCATGCCGGAGAGGGTAGCTATTTTT-3' | 89 |
| | RM13_PacI-for_N | 5'- TTCTAAGGGAAAATTAATTAATAGCGACGA TTTACAGAAG-3' | 90 |
| P5_ Fragment1 | P5-for_N | 5'- GTTCTGGTGTTTCTTGTCAGGGCAAGCCT-3' | 91 |
| | RM13_5900-rev_C | 5'- ACGGCTTTGCCGCGGCCCTCTCACT -3' | 92 |
| P5_ Fragment2 | P5-rev_C | 5'- AGGCTTGCCCTGACAAGAAACACCAGAAC-3' | 93 |
| | RM13_5900-for_N | 5'- AGTGAGAGGGCCGCGGCAAAGCCGT -3' | 94 |

TABLE C1-4

Sequencing primers for full plasmid verification of RM13-f1 clones.

| Primer (by kb location) | Sequence | SEQ ID NO: |
|---|---|---|
| M13-f1-seq-0K | 5'-AACGCTACTACTATTAGTAGAA-3' | 95 |
| M13-f1-seq-1K | 5'-GCCAGCCTATGCGCCTGGTCTG-3' | 96 |
| M13-f1-seq-2K | 5'-TTCTCTTGAGGAGTCTCAGCCT-3' | 97 |
| M13-f1-seq-3K | 5'-GGCTTAACTCAATTCTTGTGGG-3' | 98 |
| M13-f1-seq-4K | 5'-ATATAACCCAACCTAAGCCGGA-3' | 99 |
| M13-f1-seq-5K | 5'-TAAAGACTAATAGCCATTCAAA-3' | 100 |
| M13-f1-seq-6K | 5'-AAAAGCACCACTGGCAGCAGCC-3' | 101 |
| M13-f1-seq-7K | 5'-AATCACCATGAGTGACGACTGA-3' | 102 |
| M13-f1-seq-8K | 5'-TCTCACCCTTTTGAATCTTTAC-3' | 103 |
| M13-f1-seq700 | 5'-ATCTGCATTAGTTGAATGTG-3' | 104 |
| M13-f1-seq1400 | 5'-CGATCCCGCAAAAGCGGCCT-3' | 105 |
| M13-f1-seq-2100 | 5'-TTTATACGGGCACTGTTACT-3' | 106 |
| M13-f1-seq-2800 | 5'-TCTTTTATATGTTGCCACCT-3' | 107 |
| M13-f1-seq-3500 | 5'-TACCCGTTCTTGGAATGATAA-3' | 108 |
| M13-f1-seq-4200 | 5'-TTGATTTATGTACTGTTTCC-3' | 109 |
| M13-f1-seq-4900 | 5'-CTCAGCGTGGCACTGTTGCA-3' | 110 |
| M13-f1-seq-5600 | 5'-TCGCTTTCTTCCCTTCCTTT-3' | 111 |
| M13-f1-seq-6300 | 5'-TACCTCGGTTCAAAGAGTTGG-3' | 112 |
| M13-f1-seq-7700 | 5'-CCCATATAAATCAGCATCCAT-3' | 113 |

TABLE C1-5

Sequencing primers for sequence verification of inhoITR clones.

| Primer (by kb location) | Sequence | SEQ ID NO: |
|---|---|---|
| f1-ori-for | 5'- ATTTCCCCGAAAAGTGCCACCTGACGTC-3' | 114 |
| f1-term-rev | 5'-TTTTTACGGTTCCTGGCCTTTTGCTGG-3' | 115 |
| transgene-for | 5'-CCGCACGCGAAAGCTTCAAAATAT-3' | 116 |
| transgene-rev | 5'-ACATGAAGCAAATATTTAAATTGT-3' | 117 |

TABLE C1-6

Sequencing primers for sequence verification of inho clones.

| Primer (by kb location) | Sequence | SEQ ID NO: |
|---|---|---|
| EcoRI-for | 5'- CCCTTTCGTCTTCAAGAATTCTGGGC-3' | 118 |
| HindIII-rev | 5'- TGTGATAAACTACCGCATTAAAGCT-3' | 119 |

Insertion of Large, Whole Regions into the RM13-f1 and Inho Vectors

Recombinant capsid sequences (i.e. p9-pelB, p3-BAP, SV40NLS, rp8-H5WYG, rp8-H10) and stuffer DNA (i.e. 1960) were introduced to the inho and RM13-f1 vector DNA sequences using multi-fragment Gibson assembly reactions. Specifically, up to 6 kb fragments were PCR-amplified using the appropriate primers designed from the inho and RM13-f1 sequences (complete sequence outlined in Appendix D) as the template. Insert fragments were PCR-amplified off available vectors procured from the lab bank or fulfilled by Genscript. Fragments were gel extracted using the Qiaquick Gel Extraction Kit (Qiagen) or PCR purified using spin columns and 100 ng of each was used in a standard Gibson assembly reaction. 2 uL of each reaction was then transformed into 50 μL C2987 or XL 1Blue chemically competent cells.

Individual colonies were selected and DNA was purified using a QiaPrep Spin Miniprep Kit(Qiagen) or a Monarch Plasmid Miniprep Kit (New England Biolabs). All plasmids were sequence verified (Quintara Biosciences).

Transgene Insertions in ITR Flanked Inho Vector

Transgene sequences were PCR-amplified with primers designed for overlap with the HindIII, EcoRI, or SwaI enzyme cut ends of the linearized inhoITR vector. To obtain the linearized inhoITR fragment, 500 ng of the vector was restriction digested for 3 hours and dephosphorylated using shrimp alkaline phosphatase overnight and spin column purified. The inhoITR fragment and the transgene insert fragment was used in a standard Gibson Assembly reaction. 2 uL of each reaction was then transformed into 50 μL C2987 or XL1Blue chemically competent cells.

Individual colonies were selected and DNA was purified using a QiaPrep Spin Miniprep Kit(Qiagen) or a Monarch Plasmid Miniprep Kit (New England Biolabs). All plasmids were sequence verified (Quintara Biosciences).

Culturing with IPTG Inducible Capsids

Individual co-transformed colonies are grown overnight in 5 ml LB supplemented with 100 μg/ml ampicillin and 50 μg/ml of kanamycin in 15 ml culture tubes shaken at 230 rpms at 37° C. The following day, the cultures were diluted to an O.D.600 of 0.05 in 800 ml LB supplemented with 100 μg/ml ampicillin and 50 μg/ml of kanamycin and grown between 3 h to 5 hrs, when 1 mM IPTG is introduced to the culture. The culture is then left to grow another 15-20 hrs at 230 rpms at 37° C. Following overnight growth under 1 mM IPTG induction, the culture is spun to remove the bacterial pellet and we proceed to PEG/nacl precipitation of phage from the supernatant and further purification steps (these include 0.45 um filtration, cscl density gradient ultracentrifugation, and TFF buffer exchange at 10-100 kd cutoff).

APPENDIX D

D1 Select RM13-f1 Helper Sequences

RM13-f1

(SEQ ID NO: 120)

AACGCTACTACTATTAGTAGAATTGATGCCACCTTTTCAGCTCGCGCCCCAAATGAAAATATAGCTA

AACAGGTTATTGACCATTTGCGAAATGTATCTAATGGTCAAACTAAATCTACTCGTTCGCAGAATTG

GGAATCAACTGTTACATGGAATGAAACTTCCAGACACCGTACTTTAGTTGCATATTTAAAACATGTT

GAGCTACAGCACCAGATCCAGCAATTAAGCTCTAAGCCATCCGCAAAAATGACCTCTTATCAAAAG

GAGCAATTAAAGGTACTCTCTAATCCTGACCTGTTGGAGTTTGCTTCCGGTCTGGTTCGCTTTGAAG

CTCGAATTAAAACGCGATATTTGAAGTCTTTCGGGCTTCCTCTTAATCTTTTTGATGCAATCCGCTTT

GCTTCTGACTATAATAGTCAGGGTAAAGACCTGATTTTTGATTTATGGTCATTCTCGTTTTCTGAACT

GTTTAAAGCATTTGAGGGGGATTCAATGAATATTTATGACGATTCCGCAGTATTGGACGCTATCCAG

TCTAAACATTTTACTATTACCCCCTCTGGCAAAACTTCTTTTGCAAAAGCCTCTCGCTATTTTGTTTT

TATCGTCGTCTGGTAAACGAGGGTTATGATAGTGTTGCTCTTACTATGCCTCGTAATTCCTTTTGGCG

TTATGTATCTGCATTAGTTGAATGTGGTATTCCTAAATCTCAACTGATGAATCTTTCTACCTGTAATA

ATGTTGTTCCGTTAGTTCGTTTTATTAACGTAGATTTTTCTTCCCAACGTCCTGACTGGTATAATGAG

CCAGTTCTTAAAATCGCATAAGGTAATTCACAATGATTAAAGTTGAAATTAAACCATCTCAAGCGCA

ATTCACTACCCGTTCTGGTGTTTCTCGTCAGGGCAAGCCTTATTCACTGAATGAGCAGCTTTGTTACG

TTGATTTGGGTAATGAATATCCGGTGCTTGTCAAGATTACTCTTGATGACGGTCAGCCAGCCTATGC

GCCTGGTCTGTACACCGTTCATCTGTCCTCGTTCAAAGTTGGTCAGTTCGGTTCCCTTATGATTGACC

GTCTGCGCCTCGTTCCGGCTAAGTAACATGGAGCAGGTCGCGGATTTCGACACAATTTATCAGGCGA

TGATACAAATCTCCGTTGTACTTTGTTTCGCGCTTGGTATAATCGCTGGGGGTCAAAGATGAGTGTT

TTAGTGTATTCTTTCGCCTCTTTCGTTTTAGGTTGGTGCCTTCGTAGTGGCATTACGTATTTTACCCGT

TTAATGGAAGCTTCCTCATGAAAAAGTCTTTAGTCCTCAAAGCCTCTGTAGCCGTTGCTACCCTCGTT

CCGATGCTGTCTTTCGCTGCTGAGGGTGACGATCCCGCAAAAGCGGCCTTTGACTCCCTGCAAGCCT

CAGCGACCGAATATATCGGTTATGCGTGGGCGATGGTTGTTGTCATTGTCGGCGCAACTATCGGTAT

CAAGCTGTTTAAGAAATTCACCTCGAAAGCAAGCTGATAAACCGATACAATTAAAGGCTCCTTTTG

GAGCCTTTTTTTTTGGAGATTTTCAACGTGAAAAAATTATTATTCGCAATTCCTTTAGTTGTTCCTTTC

TATTCTCACTCCGCTGAAACTGTTGAAAGTTGTTTAGCAAAACCCCATACAGAAAATTCATTTACTA

ACGTCTGGAAAGACGACAAAACTTTAGATCGTTACGCTAACTATGAGGGCTGTCTGTGGAATGCTA

-continued

CAGGCGTTGTAGTTTGTACTGGTGACGAAACTCAGTGTTACGGTACATGGGTTCCTATTGGGCTTGC

TATCCCTGAAAATGAGGGTGGTGGCTCTGAGGGTGGCGGTTCTGAGGGTGGCGGCTCTGAGGGTGG

CGGTACTAAACCTCCTGAGTACGGTGATACACCTATTCCGGGCTATACTTATATCAACCCTCTCGAC

GGCACTTATCCGCCTGGTACTGAGCAAAACCCCGCTAATCCTAATCCTTCTCTTGAGGAGTCTCAGC

CTCTTAATACTTTCATGTTTCAGAATAATAGGTTCCGAAATAGGCAGGGGGCATTAACTGTTTATAC

GGGCACTGTTACTCAAGGCACTGACCCCGTTAAAACTTATTACCAGTACACTCCTGTATCATCAAAA

GCCATGTATGACGCTTACTGGAACGGTAAATTCAGAGACTGCGCTTTCCATTCTGGCTTTAATGAGG

ATCCATTCGTTTGTGAATATCAAGGCCAATCGTCTGACCTGCCTCAACCTCCTGTTAATGCTGGCGG

CGGCTCTGGTGGTGGTTCTGGTGGCGGCTCTGAGGGTGGTGGCTCTGAGGGTGGCGGTTCTGAGGGT

GGCGGCTCTGAGGGTGGCGGTTCCGGTGGTGGCTCTGGTTCCGGTGATTTTGATTATGAAAAGATGG

CAAACGCTAATAAGGGGGCTATGACCGAAAATGCCGATGAAAACGCGCTACAGTCTGACGCTAAA

GGCAAACTTGATTCTGTCGCTACTGATTACGGTGCTGCTATCGACGGTTTCATTGGTGACGTTTCCG

GCCTTGCTAATGGTAATGGTGCTACTGGTGATTTTGCTGGCTCTAATTCCCAAATGGCTCAAGTCGG

TGACGGTGATAATTCACCTTTAATGAATAATTTCCGTCAATATTTACCTTCCCTCCCTCAATCGGTTG

AATGTCGCCCTTTTGTCTTTGGCGCTGGTAAACCATATGAATTTTCTATTGATTGTGACAAAATAAAC

TTATTCCGTGGTGTCTTTGCGTTTCTTTTATATGTTGCCACCTTTATGTATGTATTTTCTACGTTTGCT

AACATACTGCGTAATAAGGAGTCTTAATCATGCCAGTTCTTTTGGGTATTCCGTTATTATTGCGTTTC

CTCGGTTTCCTTCTGGTAACTTTGTTCGGCTATCTGCTTACTTTTCTTAAAAAGGGCTTCGGTAAGAT

AGCTATTGCTATTTCATTGTTTCTTGCTCTTATTATTGGGCTTAACTCAATTCTTGTGGGTTATCTCTC

TGATATTAGCGCTCAATTACCCTCTGACTTTGTTCAGGGTGTTCAGTTAATTCTCCCGTCTAATGCGC

TTCCCTGTTTTTATGTTATTCTCTCTGTAAAGGCTGCTATTTTCATTTTTGACGTTAAACAAAAAATC

GTTTCTTATTTGGATTGGGATAAATAATATGGCTGTTTATTTTGTAACTGGCAAATTAGGCTCTGGAA

AGACGCTCGTTAGCGTTGGTAAGATTCAGGATAAAATTGTAGCTGGGTGCAAAATAGCAACTAATC

TTGATTTAAGGCTTCAAAACCTCCCGCAAGTCGGGAGGTTCGCTAAAACGCCTCGCGTTCTTAGAAT

ACCGGATAAGCCTTCTATATCTGATTTGCTTGCTATTGGGCGCGGTAATGATTCCTACGATGAAAAT

AAAAACGGCTTGCTTGTTCTCGATGAGTGCGGTACTTGGTTTAATACCCGTTCTTGGAATGATAAGG

AAAGACAGCCGATTATTGATTGGTTTCTACATGCTCGTAAATTAGGATGGGATATTATTTTTCTTGTT

CAGGACTTATCTATTGTTGATAAACAGGCGCGTTCTGCATTAGCTGAACATGTTGTTTATTGTCGTCG

TCTGGACAGAATTACTTTACCTTTGTCGGTACTTTATATTCTCTTATTACTGGCTCGAAAATGCCTC

TGCCTAAATTACATGTTGGCGTTGTTAAATATGGCGATTCTCAATTAAGCCCTACTGTTGAGCGTTG

GCTTTATACTGGTAAGAATTTGTATAACGCATATGATACTAAACAGGCTTTTTCTAGTAATTATGATT

CCGGTGTTTATTCTTATTTAACGCCTTATTTATCACACGGTCGGTATTTCAAACCATTAAATTTAGGT

CAGAAGATGAAATTAACTAAAATATATTTGAAAAAGTTTTCTCGCGTTCTTTGTCTTGCGATTGGAT

TTGCATCAGCATTTACATATAGTTATATAACCCAACCTAAGCCGGAGGTTAAAAAGGTAGTCTCTCA

GACCTATGATTTTGATAAATTCACTATTGACTCTTCTCAGCGTCTTAATCTAAGCTATCGCTATGTTT

TCAAGGATTCTAAGGGAAAATTAATTAATAGCGACGATTTACAGAAGCAAGGTTATTCACTCACAT

ATATTGATTTATGTACTGTTTCCATTAAAAAAGGTAATTCAAATGAAATTGTTAAATGTAATTAATTT

TGTTTTCTTGATGTTTGTTTCATCATCTTCTTTTGCTCAGGTAATTGAAATGAATAATTCGCCTCTGCG

CGATTTTGTAACTTGGTATTCAAAGCAATCAGGCGAATCCGTTATTGTTTCTCCCGATGTAAAAGGT

ACTGTTACTGTATATTCATCTGACGTTAAACCTGAAAATCTACGCAATTTCTTTATTTCTGTTTTACG

TGCAAATAATTTTGATATGGTAGGTTCTAACCCTTCCATTATTCAGAAGTATAATCCAAACAATCAG

-continued

```
GATTATATTGATGAATTGCCATCATCTGATAATCAGGAATATGATGATAATTCCGCTCCTTCTGGTG
GTTTCTTTGTTCCGCAAAATGATAATGTTACTCAAACTTTAAAATTAATAACGTTCGGGCAAAGGA
TTTAATACGAGTTGTCGAATTGTTTGTAAAGTCTAATACTTCTAAATCCTCAAATGTATTATCTATTG
ACGGCTCTAATCTATTAGTTGTTAGTGCTCCTAAAGATATTTTAGATAACCTTCCTCAATTCCTTTCA
ACTGTTGATTTGCCAACTGACCAGATATTGATTGAGGGTTTGATATTTGAGGTTCAGCAAGGTGATG
CTTTAGATTTTTCATTTGCTGCTGGCTCTCAGCGTGGCACTGTTGCAGGCGGTGTTAATACTGACCGC
CTCACCTCTGTTTTATCTTCTGCTGGTGGTTCGTTCGGTATTTTTAATGGCGATGTTTTAGGGCTATCA
GTTCGCGCATTAAAGACTAATAGCCATTCAAAAATATTGTCTGTGCCACGTATTCTTACGCTTTCAG
GTCAGAAGGGTTCTATCTCTGTTGGCCAGAATGTCCCTTTTATTACTGGTCGTGTGACTGGTGAATCT
GCCAATGTAAATAATCCATTTCAGACGATTGAGCGTCAAAATGTAGGTATTTCCATGAGCGTTTTTC
CTGTTGCAATGGCTGGCGGTAATATTGTTCTGGATATTACCAGCAAGGCCGATAGTTTGAGTTCTTC
TACTCAGGCAAGTGATGTTATTACTAATCAAAGAAGTATTGCTACAACGGTTAATTTGCGTGATGGA
CAGACTCTTTTACTCGGTGGCCTCACTGATTATAAAAACACTTCTCAGGATTCTGGCGTACCGTTCCT
GTCTAAAATCCCTTTAATCGGCCTCCTGTTTAGCTCCCGCTCTGATTCTAACGAGGAAAGCACGTTA
TACGTGCTCGTCAAAGCAACCATAGTACGCGCCCTGTAGCGGCGCATTAAGCGCGGCGGGTGTGGT
GGTTACGCGCAGCGTGACCGCTACACTTGCCAGCGCCCTAGCGCCCGCTCCTTTCGCTTTCTTCCCTT
CCTTTCTCGCCACGTTCGCCGGCTTTCTGCAGAGAACATGGCTTCATGTGGCAGGAGAAAAAAGGCT
GCACCGGTGCGTCAGCAGAATATGTGATACAGGATATATTCCGCTTCCTCGCTCACTGACTCGCTAC
GCTCGGTCGTTCGACTGCGGCGAGCGGAAATGGCTTACGAACGGGGCGGAGATTTCCTGGAAGATG
CCAGGAAGATACTTAACAGGGAAGTGAGAGGGCCGCGGCAAAGCCGTTTTTCCATAGGCTCCGCCC
CCCTGACAAGCATCACGAAATCTGACGCTCAAATCAGTGGTGGCGAAACCCGACAGGACTATAAAG
ATACCAGGCGTTTCCCCCTGGCGGCTCCCTCGTGCGCTCTCCTGTTCCTGCCTTTCGGTTTACCGGTG
TCATTCCGCTGTTATGGCCGCGTTTGTCTCATTCCACGCCTGACACTCAGTTCCGGGTAGGCAGTTCG
CTCCAAGCTGGACTGTATGCACGAACCCCCCGTTCAGTCCGACCGCTGCGCCTTATCCGGTAACTAT
CGTCTTGAGTCCAACCCGGAAAGACATGCAAAAGCACCACTGGCAGCAGCCACTGGTAATTGATTT
AGAGGAGTTAGTCTTGAAGTCATGCGCCGGTTAAGGCTAAACTGAAAGGACAAGTTTTGGTGACTG
CGCTCCTCCAAGCCAGTTACCTCGGTTCAAAGAGTTGGTAGCTCAGAGAACCTTCGAAAAACCGCC
CTGCAAGGCGGTTTTTTCGTTTTCAGAGCAAGAGATTACGCGCAGACCAAAACGATCTCAAGAAGA
TCATCTTATTAAGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGGCTTA
CCATCTGGCCCCAGTGCTGCAATGATACCGCGAGACCCACGCTCACCGGCTCCAGATTTATCAGCAA
TAAACCAGCCAGCCGATTCGAGCTCGCCCGGGGATCGACCAGTTGGTGATTTTGAACTTTTGCTTTG
CCACGGAACGGTCTGCGTTGTCGGGAAGATGCGTGATCTGATCCTTCAACTCAGCAAAAGTTCGATT
TATTCAACAAAGCCGCCGTCCCGTCAAGTCAGCGTAATGCTCTGCCAGTGTTACAACCAATTAACCA
ATTCTGATTAGAAAAACTCATCGAGCATCAAATGAAACTGCAATTTATTCATATCAGGATTATCAAT
ACCATATTTTTGAAAAAGCCGTTTCTGTAATGAAGGAGAAAACTCACCGAGGCAGTTCCATAGGAT
GGCAAGATCCTGGTATCGGTCTGCGATTCCGACTCGTCCAACATCAATACAACCTATTAATTTCCCC
TCGTCAAAAATAAGGTTATCAAGTGAGAAATCACCATGAGTGACGACTGAATCCGGTGAGAATGGC
```

-continued

AAAAGCTTATGCATTTCTTTCCAGACTTGTTCAACAGGCCAGCCATTACGCTCGTCATCAAAATCAC

TCGCATCAACCAAACCGTTATTCATTCGTGATTGCGCCTGAGCGAGACGAAATACGCGATCGCTGTT

AAAAGGACAATTACAAACAGGAATCGAATGCAACCGGCGCAGGAACACTGCCAGCGCATCAACAA

TATTTTCACCTGAATCAGGATATTCTTCTAATACCTGGAATGCTGTTTTCCCGGGGATCGCAGTGGTG

AGTAACCATGCATCATCAGGAGTACGGATAAAATGCTTGATGGTCGGAAGAGGCATAAATTCCGTC

AGCCAGTTTAGTCTGACCATCTCATCTGTAACATCATTGGCAACGCTACCTTTGCCATGTTTCAGAA

ACAACTCTGGCGCATCGGGCTTCCCATACAATCGATAGATTGTCGCACCTGATTGCCCGACATTATC

GCGAGCCCATTTATACCCATATAAATCAGCATCCATGTTGGAATTTAATCGCGGCCTCGAGCAAGAC

GTTTCCCGTTGAATATGGCTCATAACACCCCTTGTATTACTGTTTATGTAAGNAGACAGTTTTATTGT

TCATGATGATATATTTTTATCTTGTGCAATGTAACATCAGAGACCTATTGGTTAAAAAATGAGCTGA

TTTAACAAAAATTTAACGCGAATTTTAACAAAATATTAACGTTTACAATTTAAATATTTGCTTATAC

AATCTTCCTGTTTTTGGGGCTTTTCTGATTATCAACCGGGGTACATATGATTGACATGCTAGTTTTAC

GATTACCGTTCATCGATTCTCTTGTTTGCTCCAGACTCTCAGGCAATGACCTGATAGCCTTTGTAGAC

CTCTCAAAAATAGCTACCCTCTCCGGCATGAATTTATCAGCTAGAACGGTTGAATATCATATTGATG

GTGATTTGACTGTCTCCGGCCTTTCTCACCCGTTTGAATCTTTACCTACACATTACTCAGGCATTGCA

TTTAAAATATATGAGGGTTCTAAAAATTTTTATCCTTGCGTTGAAATAAAGGCTTCTCCCGCAAAAG

TATTACAGGGTCATAATGTTTTTGGTACAACCGATTTAGCTTTATGCTCTGAGGCTTTATTGCTTAAT

TTTGCTAATTCTTTGCCTTGCCTGTATGATTTATTGGATGTT

RM13-f1-P8DSPH-P3CTX (SEQ ID NO: 121)

AACGCTACTACTATTAGTAGAATTGATGCCACCTTTTCAGCTCGCGCCCCAAATGAAAATATAGCTA

AACAGGTTATTGACCATTTGCGAAATGTATCTAATGGTCAAACTAAATCTACTCGTTCGCAGAATTG

GGAATCAACTGTTACATGGAATGAAACTTCCAGACACCGTACTTTAGTTGCATATTTAAAACATGTT

GAGCTACAGCACCAGATCCAGCAATTAAGCTCTAAGCCATCCGCAAAAATGACCTCTTATCAAAAG

GAGCAATTAAAGGTACTCTCTAATCCTGACCTGTTGGAGTTTGCTTCCGGTCTGGTTCGCTTTGAAG

CTCGAATTAAAACGCGATATTTGAAGTCTTTCGGGCTTCCTCTTAATCTTTTTGATGCAATCCGCTTT

GCTTCTGACTATAATAGTCAGGGTAAAGACCTGATTTTTGATTTATGGTCATTCTCGTTTTCTGAACT

GTTTAAAGCATTTGAGGGGGATTCAATGAATATTTATGACGATTCCGCAGTATTGGACGCTATCCAG

TCTAAACATTTTACTATTACCCCCTCTGGCAAAACTTCTTTTGCAAAAGCCTCTCGCTATTTTTGTTTT

TATCGTCGTCTGGTAAACGAGGGTTATGATAGTGTTGCTCTTACTATGCCTCGTAATTCCTTTTGGCG

TTATGTATCTGCATTAGTTGAATGTGGTATTCCTAAATCTCAACTGATGAATCTTTCTACCTGTAATA

ATGTTGTTCCGTTAGTTCGTTTTATTAACGTAGATTTTTCTTCCCAACGTCCTGACTGGTATAATGAG

CCAGTTCTTAAAATCGCATAAGGTAATTCACAATGATTAAAGTTGAAATTAAACCATCTCAAGCGCA

ATTCACTACCCGTTCTGGTGTTTCTCGTCAGGGCAAGCCTTATTCACTGAATGAGCAGCTTTGTTACG

TTGATTTGGGTAATGAATATCCGGTGCTTGTCAAGATTACTCTTGATGACGGTCAGCCAGCCTATGC

GCCTGGTCTGTACACCGTTCATCTGTCCTCGTTCAAAGTTGGTCAGTTCGGTTCCCTTATGATTGACC

GTCTGCGCCTCGTTCCGGCTAAGTAACATGGAGCAGGTCGCGGATTTCGACACAATTTATCAGGCGA

TGATACAAATCTCCGTTGTACTTTGTTTCGCGCTTGGTATAATCGCTGGGGGTCAAAGATGAGTGTT

TTAGTGTATTCTTTCGCCTCTTTCGTTTTAGGTTGGTGCCTTCGTAGTGGCATTACGTATTTTACCCGT

TTAATGGAAGCTTCCTCATGAAAAAGTCTTTAGTCCTCAAAGCCTCTGTAGCCGTTGCTACCCTCGTT

CCGATGCTGTCTTTCGCTGCAGATTCGCCGCATACTGAGTTGCCGGATCCCGCAAAAGCGGCCTTTG

ACTCCCTGCAAGCCTCAGCGACCGAATATATCGGTTATGCGTGGGCGATGGTTGTTGTCATTGTCGG

-continued

CGCAACTATCGGTATCAAGCTGTTTAAGAAATTCACCTCGAAAGCAAGCTGATAAACCGATACAAT

TAAAGGCTCCTTTTGGAGCCTTTTTTTTTGGAGATTTTCAACGTGAAAAAATTATTATTCGCAATTCC

TTTAGTGGTACCTTTCTATTCTCACTCTATGTGCATGCCGTGCTTTACCACCGATCATCAGATGGCGC

GCAAATGCGATGATTGCTGCGGCGGCAAAGGCCGCGGCAAATGCTATGGCCCGCAGTGCCTGTGCC

GCTCGGCCGAAACTGTTGAAAGTTGTTTAGCAAAACCCCATACAGAAAATTCATTTACTAACGTCTG

GAAAGACGACAAAACTTTAGATCGTTACGCTAACTATGAGGGCTGTCTGTGGAATGCTACAGGCGT

TGTAGTTTGTACTGGTGACGAAACTCAGTGTTACGGTACATGGGTTCCTATTGGGCTTGCTATCCCT

GAAAATGAGGGTGGTGGCTCTGAGGGTGGCGGTTCTGAGGGTGGCGGCTCTGAGGGTGGCGGTACT

AAACCTCCTGAGTACGGTGATACACCTATTCCGGGCTATACTTATATCAACCCTCTCGACGGCACTT

ATCCGCCTGGTACTGAGCAAAACCCCGCTAATCCTAATCCTTCTCTTGAGGAGTCTCAGCCTCTTAA

TACTTTCATGTTTCAGAATAATAGGTTCCGAAATAGGCAGGGGGCATTAACTGTTTATACGGGCACT

GTTACTCAAGGCACTGACCCCGTTAAAACTTATTACCAGTACACTCCTGTATCATCAAAAGCCATGT

ATGACGCTTACTGGAACGGTAAATTCAGAGACTGCGCTTTCCATTCTGGCTTTAATGAGGATCCATT

CGTTTGTGAATATCAAGGCCAATCGTCTGACCTGCCTCAACCTCCTGTTAATGCTGGCGGCGGCTCT

GGTGGTGGTTCTGGTGGCGGCTCTGAGGGTGGTGGCTCTGAGGGTGGCGGTTCTGAGGGTGGCGGC

TCTGAGGGTGGCGGTTCCGGTGGTGGCTCTGGTTCCGGTGATTTTGATTATGAAAAGATGGCAAACG

CTAATAAGGGGGCTATGACCGAAAATGCCGATGAAAACGCGCTACAGTCTGACGCTAAAGGCAAA

CTTGATTCTGTCGCTACTGATTACGGTGCTGCTATCGACGGTTTCATTGGTGACGTTTCCGGCCTTGC

TAATGGTAATGGTGCTACTGGTGATTTTGCTGGCTCTAATTCCCAAATGGCTCAAGTCGGTGACGGT

GATAATTCACCTTTAATGAATAATTTCCGTCAATATTTACCTTCCCTCCCTCAATCGGTTGAATGTCG

CCCTTTTGTCTTTGGCGCTGGTAAACCATATGAATTTTCTATTGATTGTGACAAAATAAACTTATTCC

GTGGTGTCTTTGCGTTTCTTTTATATGTTGCCACCTTTATGTATGTATTTTCTACGTTTGCTAACATAC

TGCGTAATAAGGAGTCTTAATCATGCCAGTTCTTTTGGGTATTCCGTTATTATTGCGTTTCCTCGGTT

TCCTTCTGGTAACTTTGTTCGGCTATCTGCTTACTTTTCTTAAAAAGGGCTTCGGTAAGATAGCTATT

GCTATTTCATTGTTTCTTGCTCTTATTATTGGGCTTAACTCAATTCTTGTGGGTTATCTCTCTGATATT

AGCGCTCAATTACCCTCTGACTTTGTTCAGGGTGTTCAGTTAATTCTCCCGTCTAATGCGCTTCCCTG

TTTTTATGTTATTCTCTCTGTAAAGGCTGCTATTTTCATTTTTGACGTTAAACAAAAAATCGTTTCTTA

TTTGGATTGGGATAAATAATATGGCTGTTTATTTTGTAACTGGCAAATTAGGCTCTGGAAAGACGCT

CGTTAGCGTTGGTAAGATTCAGGATAAAATTGTAGCTGGGTGCAAAATAGCAACTAATCTTGATTTA

AGGCTTCAAAACCTCCCGCAAGTCGGGAGGTTCGCTAAAACGCCTCGCGTTCTTAGAATACCGGAT

AAGCCTTCTATATCTGATTTGCTTGCTATTGGGCGCGGTAATGATTCCTACGATGAAAATAAAAACG

GCTTGCTTGTTCTCGATGAGTGCGGTACTTGGTTTAATACCCGTTCTTGGAATGATAAGGAAAGACA

GCCGATTATTGATTGGTTTCTACATGCTCGTAAATTAGGATGGGATATTATTTTTCTTGTTCAGGACT

TATCTATTGTTGATAAACAGGCGCGTTCTGCATTAGCTGAACATGTTGTTTATTGTCGTCGTCTGGAC

AGAATTACTTTACCTTTTGTCGGTACTTTATATTCTCTTATTACTGGCTCGAAAATGCCTCTGCCTAA

ATTACATGTTGGCGTTGTTAAATATGGCGATTCTCAATTAAGCCCTACTGTTGAGCGTTGGCTTTATA

CTGGTAAGAATTTGTATAACGCATATGATACTAAACAGGCTTTTTCTAGTAATTATGATTCCGGTGT

TTATTCTTATTTAACGCCTTATTTATCACACGGTCGGTATTTCAAACCATTAAATTTAGGTCAGAAGA

TGAAATTAACTAAAATATATTTGAAAAAGTTTTCTCGCGTTCTTTGTCTTGCGATTGGATTTGCATCA

GCATTTACATATAGTTATATAACCCAACCTAAGCCGGAGGTTAAAAAGGTAGTCTCTCAGACCTATG

-continued

ATTTTGATAAATTCACTATTGACTCTTCTCAGCGTCTTAATCTAAGCTATCGCTATGTTTTCAAGGAT

TCTAAGGGAAAATTAATTAATAGCGACGATTTACAGAAGCAAGGTTATTCACTCACATATATTGATT

TATGTACTGTTTCCATTAAAAAAGGTAATTCAAATGAAATTGTTAAATGTAATTAATTTTGTTTTCTT

GATGTTTGTTTCATCATCTTCTTTTGCTCAGGTAATTGAAATGAATAATTCGCCTCTGCGCGATTTTG

TAACTTGGTATTCAAAGCAATCAGGCGAATCCGTTATTGTTTCTCCCGATGTAAAAGGTACTGTTAC

TGTATATTCATCTGACGTTAAACCTGAAAATCTACGCAATTTCTTTATTTCTGTTTTACGTGCAAATA

ATTTTGATATGGTAGGTTCTAACCCTTCCATTATTCAGAAGTATAATCCAAACAATCAGGATTATAT

TGATGAATTGCCATCATCTGATAATCAGGAATATGATGATAATTCCGCTCCTTCTGGTGGTTTCTTTG

TTCCGCAAAATGATAATGTTACTCAAACTTTTAAAATTAATAACGTTCGGGCAAAGGATTTAATACG

AGTTGTCGAATTGTTTGTAAAGTCTAATACTTCTAAATCCTCAAATGTATTATCTATTGACGGCTCTA

ATCTATTAGTTGTTAGTGCTCCTAAAGATATTTTAGATAACCTTCCTCAATTCCTTTCAACTGTTGAT

TTGCCAACTGACCAGATATTGATTGAGGGTTTGATATTTGAGGTTCAGCAAGGTGATGCTTTAGATT

TTTCATTTGCTGCTGGCTCTCAGCGTGGCACTGTTGCAGGCGGTGTTAATACTGACCGCCTCACCTCT

GTTTTATCTTCTGCTGGTGGTTCGTTCGGTATTTTTAATGGCGATGTTTTAGGGCTATCAGTTCGCGC

ATTAAAGACTAATAGCCATTCAAAAATATTGTCTGTGCCACGTATTCTTACGCTTTCAGGTCAGAAG

GGTTCTATCTCTGTTGGCCAGAATGTCCCTTTTATTACTGGTCGTGTGACTGGTGAATCTGCCAATGT

AAATAATCCATTTCAGACGATTGAGCGTCAAAATGTAGGTATTTCCATGAGCGTTTTTCCTGTTGCA

ATGGCTGGCGGTAATATTGTTCTGGATATTACCAGCAAGGCCGATAGTTTGAGTTCTTCTACTCAGG

CAAGTGATGTTATTACTAATCAAAGAAGTATTGCTACAACGGTTAATTTGCGTGATGGACAGACTCT

TTTACTCGGTGGCCTCACTGATTATAAAAACACTTCTCAGGATTCTGGCGTACCGTTCCTGTCTAAA

ATCCCTTTAATCGGCCTCCTGTTTAGCTCCCGCTCTGATTCTAACGAGGAAAGCACGTTATACGTGCT

CGTCAAAGCAACCATAGTACGCGCCCTGTAGCGGCGCATTAAGCGCGGCGGGTGTGGTGGTTACGC

GCAGCGTGACCGCTACACTTGCCAGCGCCCTAGCGCCCGCTCCTTTCGCTTTCTTCCCTTCCTTTCTC

GCCACGTTCGCCGGCTTTCTGCAGAGAACATGGCTTCATGTGGCAGGAGAAAAAAGGCTGCACCGG

TGCGTCAGCAGAATATGTGATACAGGATATATTCCGCTTCCTCGCTCACTGACTCGCTACGCTCGGT

CGTTCGACTGCGGCGAGCGGAAATGGCTTACGAACGGGGCGGAGATTTCCTGGAAGATGCCAGGAA

GATACTTAACAGGGAAGTGAGAGGGCCGCGGCAAAGCCGTTTTTCCATAGGCTCCGCCCCCCTGAC

AAGCATCACGAAATCTGACGCTCAAATCAGTGGTGGCGAAACCCGACAGGACTATAAAGATACCAG

GCGTTTCCCCCTGGCGGCTCCCTCGTGCGCTCTCCTGTTCCTGCCTTTCGGTTTACCGGTGTCATTCC

GCTGTTATGGCCGCGTTTGTCTCATTCCACGCCTGACACTCAGTTCCGGGTAGGCAGTTCGCTCCAA

GCTGGACTGTATGCACGAACCCCCCGTTCAGTCCGACCGCTGCGCCTTATCCGGTAACTATCGTCTT

GAGTCCAACCCGGAAAGACATGCAAAAGCACCACTGGCAGCAGCCACTGGTAATTGATTTAGAGGA

GTTAGTCTTGAAGTCATGCGCCGGTTAAGGCTAAACTGAAAGGACAAGTTTTGGTGACTGCGCTCCT

CCAAGCCAGTTACCTCGGTTCAAAGAGTTGGTAGCTCAGAGAACCTTCGAAAAACCGCCCTGCAAG

GCGGTTTTTTCGTTTTCAGAGCAAGAGATTACGCGCAGACCAAAACGATCTCAAGAAGATCATCTTA

TTAAGGGGTCTGACGCTCAGTGGAACGAAAACTCACGTTAAGGGATTTTGGTCATGAGATTATCAA

AAAGGATCTTCACCTAGATCCTTTTAAATTAAAAATGAAGTTTTAAATCAATCTAAAGTATATATGA

GTAAACTTGGTCTGACAGTTACCAATGCTTAATCAGTGAGGCACCTATCTCAGCGATCTGTCTATTT

CGTTCATCCATAGTTGCCTGACTCCCCGTCGTGTAGATAACTACGATACGGGAGGGCTTACCATCTG

GCCCCAGTGCTGCAATGATACCGCGAGACCCACGCTCACCGGCTCCAGATTTATCAGCAATAAACC

AGCCAGCCGATTCGAGCTCGCCCGGGGATCGACCAGTTGGTGATTTTGAACTTTTGCTTTGCCACGG

-continued

AACGGTCTGCGTTGTCGGGAAGATGCGTGATCTGATCCTTCAACTCAGCAAAAGTTCGATTTATTCA

ACAAAGCCGCCGTCCCGTCAAGTCAGCGTAATGCTCTGCCAGTGTTACAACCAATTAACCAATTCTG

ATTAGAAAAACTCATCGAGCATCAAATGAAACTGCAATTTATTCATATCAGGATTATCAATACCATA

TTTTTGAAAAAGCCGTTTCTGTAATGAAGGAGAAAACTCACCGAGGCAGTTCCATAGGATGGCAAG

ATCCTGGTATCGGTCTGCGATTCCGACTCGTCCAACATCAATACAACCTATTAATTTCCCCTCGTCAA

AAATAAGGTTATCAAGTGAGAAATCACCATGAGTGACGACTGAATCCGGTGAGAATGGCAAAAGCT

TATGCATTTCTTTCCAGACTTGTTCAACAGGCCAGCCATTACGCTCGTCATCAAAATCACTCGCATC

AACCAAACCGTTATTCATTCGTGATTGCGCCTGAGCGAGACGAAATACGCGATCGCTGTTAAAAGG

ACAATTACAAACAGGAATCGAATGCAACCGGCGCAGGAACACTGCCAGCGCATCAACAATATTTTC

ACCTGAATCAGGATATTCTTCTAATACCTGGAATGCTGTTTTCCCGGGGATCGCAGTGGTGAGTAAC

CATGCATCATCAGGAGTACGGATAAAATGCTTGATGGTCGGAAGAGGCATAAATTCCGTCAGCCAG

TTTAGTCTGACCATCTCATCTGTAACATCATTGGCAACGCTACCTTTGCCATGTTTCAGAAACAACTC

TGGCGCATCGGGCTTCCCATACAATCGATAGATTGTCGCACCTGATTGCCCGACATTATCGCGAGCC

CATTTATACCCATATAAATCAGCATCCATGTTGGAATTTAATCGCGGCCTCGAGCAAGACGTTTCCC

GTTGAATATGGCTCATAACACCCCTTGTATTACTGTTTATGTAAGNAGACAGTTTTATTGTTCATGAT

GATATATTTTTATCTTGTGCAATGTAACATCAGAGACCTATTGGTTAAAAAATGAGCTGATTTAACA

AAAATTTAACGCGAATTTTAACAAAATATTAACGTTTACAATTTAAATATTTGCTTATACAATCTTCC

TGTTTTTGGGGCTTTTCTGATTATCAACCGGGGTACATATGATTGACATGCTAGTTTTACGATTACCG

TTCATCGATTCTCTTGTTTGCTCCAGACTCTCAGGCAATGACCTGATAGCCTTTGTAGACCTCTCAAA

AATAGCTACCCTCTCCGGCATGAATTTATCAGCTAGAACGGTTGAATATCATATTGATGGTGATTTG

ACTGTCTCCGGCCTTTCTCACCCGTTTGAATCTTTACCTACACATTACTCAGGCATTGCATTTAAAAT

ATATGAGGGTTCTAAAAATTTTTATCCTTGCGTTGAAATAAAGGCTTCTCCCGCAAAAGTATTACAG

GGTCATAATGTTTTTGGTACAACCGATTTAGCTTTATGCTCTGAGGCTTTATTGCTTAATTTTGCTAA

TTCTTTGCCTTGCCTGTATGATTTATTGGATGTT

RM13-f1-P8H10-P9SV40NLS-P3BAP (SEQ ID NO: 122)

GCCGGCTTTCTGCAGAGAACATGGCTTCATGTGGCAGGAGAAAAAAGGCTGCAGCTCGAGCTTACT

CCCCATCCCCCTGTTGACAATTAATCATCGGCTCGTATAATGTGTGGAATTGTGAGCGGATAACAAT

TTCTTAATGGAAACTTCCTCATGAAAAAGTCTTTAGTTCTTAAAGCATCTGTTGCTGTTGCGACTCTT

GTTCCTATGCTAAGCTTTGCCCACCACCACCACCATCATCATCACCACCACGGTGGAGGTCCTGCAG

AAGGTGATGACCCGGCTAAAGCTGCTTTTGACTCTCTTCAGGCTTCTGCTACTGAATACATCGGCTA

CGCTTGGGCTATGGTGGTTGTTATCGTTGGTGCTACTATTGGCATCAAACTTTTCAAAAAATTCACTT

CTAAAGCGTCTTAATGAACTCAGATACCCAGCCCGCCTAATGAGCGGGCTTTTTTTTAAGCTAGCTT

ACCGGTGCGTCAGCAGAATATGTGATACAGGATATATTCCGCTTCCTCGCTCACTGACTCGCTACGC

TCGGTCGTTCGACTGCGGCGAGCGGAAATGGCTTACGAACGGGGCGGAGATTTCCTGGAAGATGCC

AGGAAGATACTTAACAGGGAAGTGAGAGGGCCGCGGCAAAGCCGTTTTTCCATAGGCTCCGCCCCC

CTGACAAGCATCACGAAATCTGACGCTCAAATCAGTGGTGGCGAAACCCGACAGGACTATAAAGAT

ACCAGGCGTTTCCCCCTGGCGGCTCCCTCGTGCGCTCTCCTGTTCCTGCCTTTCGGTTTACCGGTGTC

ATTCCGCTGTTATGGCCGCGTTTGTCTCATTCCACGCCTGACACTCAGTTCCGGGTAGGCAGTTCGCT

CCAAGCTGGACTGTATGCACGAACCCCCCGTTCAGTCCGACCGCTGCGCCTTATCCGGTAACTATCG

TCTTGAGTCCAACCCGGAAAGACATGCAAAAGCACCACTGGCAGCAGCCACTGGTAATTGATTTAG

-continued

AGGAGTTAGTCTTGAAGTCATGCGCCGGTTAAGGCTAAACTGAAAGGACAAGTTTTGGTGACTGCG

CTCCTCCAAGCCAGTTACCTCGGTTCAAAGAGTTGGTAGCTCAGAGAACCTTCGAAAAACCGCCCTG

CAAGGCGGTTTTTTCGTTTTCAGAGCAAGAGATTACGCGCAGACCAAAACGATCTCAAGAAGATCA

TCTTATTAAGGGGTCTGACGCTCACTGGAACGAAAACTCACGTTAAGGGATTTTGGTCATGAGATTA

TCAAAAAGGATCTTCACCTAGATCCTTTTAAATTAAAAATGAAGTTTTAAATCAATCTAAAGTATAT

ATGAGTAAACTTGGTCTGACAGTTACCAATGCTTAATCAGTGAGGCACCTATCTCAGCGATCTGTCT

ATTTCGTTCATCCATAGTTGCCTGACTCCCCGTCGTGTAGATAACTACGATACGGGAGGGCTTACCA

TCTGGCCCCAGTGCTGCAATGATACCGCGAGACCCACGCTCACCGGCTCCAGATTTATCAGCAATAA

ACCAGCCAGCCGATTCGAGCTCGCCCGGGGATCGACCAGTTGGTGATTTTGAACTTTTGCTTTGCCA

CGGAACGGTCTGCGTTGTCGGGAAGATGCGTGATCTGATCCTTCAACTCAGCAAAAGTTCGATTTAT

TCAACAAAGCCGCCGTCCCGTCAAGTCAGCGTAATGCTCTGCCAGTGTTACAACCAATTAACCAATT

CTGATTAGAAAAACTCATCGAGCATCAAATGAAACTGCAATTTATTCATATCAGGATTATCAATACC

ATATTTTTGAAAAAGCCGTTTCTGTAATGAAGGAGAAAACTCACCGAGGCAGTTCCATAGGATGGC

AAGATCCTGGTATCGGTCTGCGATTCCGACTCGTCCAACATCAATACAACCTATTAATTTCCCCTCG

TCAAAAATAAGGTTATCAAGTGAGAAATCACCATGAGTGACGACTGAATCCGGTGAGAATGGCAAA

AGCTTATGCATTTCTTTCCAGACTTGTTCAACAGGCCAGCCATTACGCTCGTCATCAAAATCACTCG

CATCAACCAAACCGTTATTCATTCGTGATTGCGCCTGAGCGAGACGAAATACGCGATCGCTGTTAAA

AGGACAATTACAAACAGGAATCGAATGCAACCGGCGCAGGAACACTGCCAGCGCATCAACAATAT

TTTCACCTGAATCAGGATATTCTTCTAATACCTGGAATGCTGTTTTCCCGGGGATCGCAGTGGTGAG

TAACCATGCATCATCAGGAGTACGGATAAAATGCTTGATGGTCGGAAGAGGCATAAATTCCGTCAG

CCAGTTTAGTCTGACCATCTCATCTGTAACATCATTGGCAACGCTACCTTTGCCATGTTTCAGAAAC

AACTCTGGCGCATCGGGCTTCCCATACAATCGATAGATTGTCGCACCTGATTGCCCGACATTATCGC

GAGCCCATTTATACCCATATAAATCAGCATCCATGTTGGAATTTAATCGCGGCCTCGAGCAAGACGT

TTCCCGTTGAATATGGCTCATAACACCCCTTGTATTACTGTTTATGTAAGNAGACAGTTTTATTGTTC

ATGATGATATATTTTTATCTTGTGCAATGTAACATCAGAGACCTATTGGTTAAAAAATGAGCTGATT

TAACAAAAATTTAACGCGAATTTTAACAAAATATTAACGTTTACAATTTAAATATTTGCTTATACAA

TCTTCCTGTTTTTGGGGCTTTTCTGATTATCAACCGGGGTACATATGATTGACATGCTAGTTTTACGA

TTACCGTTCATCGATTCTCTTGTTTGCTCCAGACTCTCAGGCAATGACCTGATAGCCTTTGTAGACCT

CTCAAAAATAGCTACCCTCTCCGGCATGAATTTATCAGCTAGAACGGTTGAATATCATATTGATGGT

GATTTGACTGTCTCCGGCCTTTCTCACCCGTTTGAATCTTTACCTACACATTACTCAGGCATTGCATT

TAAAATATATGAGGGTTCTAAAAATTTTTATCCTTGCGTTGAAATAAAGGCTTCTCCCGCAAAAGTA

TTACAGGGTCATAATGTTTTTGGTACAACCGATTTAGCTTTATGCTCTGAGGCTTTATTGCTTAATTT

TGCTAATTCTTTGCCTTGCCTGTATGATTTATTGGATGTTAACGCTACTACTATTAGTAGAATTGATG

CCACCTTTTCAGCTCGCGCCCCAAATGAAAATATAGCTAAACAGGTTATTGACCATTTGCGAAATGT

ATCTAATGGTCAAACTAAATCTACTCGTTCGCAGAATTGGGAATCAACTGTTACATGGAATGAAACT

TCCAGACACCGTACTTTAGTTGCATATTTAAAACATGTTGAGCTACAGCACCAGATCCAGCAATTAA

GCTCTAAGCCATCCGCAAAAATGACCTCTTATCAAAAGGAGCAATTAAAGGTACTCTCTAATCCTGA

CCTGTTGGAGTTTGCTTCCGGTCTGGTTCGCTTTGAAGCTCGAATTAAAACGCGATATTTGAAGTCTT

TCGGGCTTCCTCTTAATCTTTTTGATGCAATCCGCTTTGCTTCTGACTATAATAGTCAGGGTAAAGAC

CTGATTTTTGATTTATGGTCATTCTCGTTTTCTGAACTGTTTAAAGCATTTGAGGGGGATTCAATGAA

TATTTATGACGATTCCGCAGTATTGGACGCTATCCAGTCTAAACATTTTACTATTACCCCCTCTGGCA

-continued

AAACTTCTTTTGCAAAAGCCTCTCGCTATTTTTGTTTTTATCGTCGTCTGGTAAACGAGGGTTATGAT

AGTGTTGCTCTTACTATGCCTCGTAATTCCTTTTGGCGTTATGTATCTGCATTAGTTGAATGTGGTAT

TCCTAAATCTCAACTGATGAATCTTTCTACCTGTAATAATGTTGTTCCGTTAGTTCGTTTTATTAACG

TAGATTTTTCTTCCCAACGTCCTGACTGGTATAATGAGCCAGTTCTTAAAATCGCATAAGGTAATTC

ACAATGATTAAACTTGAAATTAAACCATCTCAAGCGCAATTCACTACCCGTTCTGGTGTTTCTCGTC

AGGGCAAGCCTTATTCACTGAATGAGCAGCTTTGTTACGTTGATTTGGGTAATGAATATCCGGTGCT

TGTCAAGATTACTCTTGATGACGGTCAGCCAGCCTATGCGCCTGGTCTGTACACCGTTCATCTGTCCT

CGTTCAAAGTTGGTCAGTTCGGTTCCCTTATGATTGACCGTCTGCGCCTCGTTCCGGCTAAGTAACAT

GGAGCAGGTCGCGGATTTCGACACAATTTATCAGGCGATGATACAAATCTCCGTTGTACTTTGTTTC

GCGCTTGGTATAATCGCAGGCGGCCAGAGGTGAGACGTGCTGACGGCCAGCTGATAAACCGATTAC

TGTTCGCTGGGGGTCAAAGAATGAAATCCCTATTGCCTACGGCAGCCGCTGGATTGTTATTACTCGC

GGCCCAGCCGGCCATGGCGAAAAGGACAGCTGATGGATCAGAATTTGAGAGCCCGAAAAAGAAAC

GTAAGGTGGGCCAGGGCGGCCAGGGTGTCGACATGAGTGTTTTAGTGTATTCTTTCGCTAGCTTCGT

TTTAGGTTGGTGCCTTCGTAGTGGCATTACGTATTTTACCCGTTTAATGGAAACTTCCTCATGAAAAA

GTCTTTAGTCCTCAAAGCCTCTGTAGCCGTTGCTACCCTCGTTCCGATGCTGTCTTTCGCTGCTGAGG

GTGACGATCCCGCAAAAGCGGCCTTTGACTCCCTGCAAGCCTCAGCGACCGAATATATCGGTTATGC

GTGGGCGATGGTTGTTGTCATTGTCGGCGCAACTATCGGTATCAAGCTGTTTAAGAAATTCACCTCG

AAAGCAAGCTGATAAACCGATACAATAAAGGCTCCTTTTGGAGCCTTTTTTTTTGGAGATTTTCAA

CGTGAAAAAATTATTATTCGCAATTCCTTTAGTGGTACCTTTCTATTCTCACTCTGGCCTGAACGACA

TCTTCGAGGCTCAGAAAATCGAATGGCACGAGTCGGCCGAAACTGTTGAAAGTTGTTTAGCAAAAC

CCCATACAGAAAATTCATTTACTAACGTCTGGAAAGACGACAAAACTTTAGATCGTTACGCTAACTA

TGAGGGCTGTCTGTGGAATGCTACAGGCGTTGTAGTTTGTACTGGTGACGAAACTCAGTGTTACGGT

ACATGGGTTCCTATTGGGCTTGCTATCCCTGAAAATGAGGGTGGTGGCTCTGAGGGTGGCGGTTCTG

AGGGTGGCGGCTCTGAGGGTGGCGGTACTAAACCTCCTGAGTACGGTGATACACCTATTCCGGGCT

ATACTTATATCAACCCTCTCGACGGCACTTATCCGCCTGGTACTGAGCAAAACCCCGCTAATCCTAA

TCCTTCTCTTGAGGAGTCTCAGCCTCTTAATACTTTCATGTTTCAGAATAATAGGTTCCGAAATAGGC

AGGGGGCATTAACTGTTTATACGGGCACTGTTACTCAAGGCACTGACCCCGTTAAAACTTATTACCA

GTACACTCCTGTATCATCAAAAGCCATGTATGACGCTTACTGGAACGGTAAATTCAGAGACTGCGCT

TTCCATTCTGGCTTTAATGAGGATCCATTCGTTTGTGAATATCAAGGCCAATCGTCTGACCTGCCTCA

ACCTCCTGTTAATGCTGGCGGCGGCTCTGGTGGTGGTTCTGGTGGCGGCTCTGAGGGTGGTGGCTCT

GAGGGTGGCGGTTCTGAGGGTGGCGGCTCTGAGGGTGGCGGTTCCGGTGGTGGCTCTGGTTCCGGT

GATTTTGATTATGAAAAGATGGCAAACGCTAATAAGGGGGCTATGACCGAAAATGCCGATGAAAAC

GCGCTACAGTCTGACGCTAAAGGCAAACTTGATTCTGTCGCTACTGATTACGGTGCTGCTATCGACG

GTTTCATTGGTGACGTTTCCGGCCTTGCTAATGGTAATGGTGCTACTGGTGATTTTGCTGGCTCTAAT

TCCCAAATGGCTCAAGTCGGTGACGGTGATAATTCACCTTTAATGAATAATTTCCGTCAATATTTAC

CTTCCCTCCCTCAATCGGTTGAATGTCGCCCTTTTGTCTTTGGCGCTGGTAAACCATATGAATTTTCT

ATTGATTGTGACAAAATAAACTTATTCCGTGGTGTCTTTGCGTTTCTTTTATATGTTGCCACCTTTAT

GTATGTATTTTCTACGTTTGCTAACATACTGCGTAATAAGGAGTCTTAATCATGCCAGTTCTTTTGGG

TATTCCGTTATTATTGCGTTTCCTCGGTTTCCTTCTGGTAACTTTGTTCGGCTATCTGCTTACTTTTCTT

AAAAAGGGCTTCGGTAAGATAGCTATTGCTATTTCATTGTTTCTTGCTCTTATTATTGGGCTTAACTC

-continued
AATTCTTGTGGGTTATCTCTCTGATATTAGCGCTCAATTACCCTCTGACTTTGTTCAGGGTGTTCAGT

TAATTCTCCCGTCTAATGCGCTTCCCTGTTTTTATGTTATTCTCTCTGTAAAGGCTGCTATTTTCATTT

TTGACGTTAAACAAAAAATCGTTTCTTATTTGGATTGGGATAAATAATATGGCTGTTTATTTTGTAAC

TGGCAAATTAGGCTCTGGAAAGACGCTCGTTAGCGTTGGTAAGATTCAGGATAAAATTGTAGCTGG

GTGCAAAATAGCAACTAATCTTGATTTAAGGCTTCAAAACCTCCCGCAAGTCGGGAGGTTCGCTAA

AACGCCTCGCGTTCTTAGAATACCGGATAAGCCTTCTATATCTGATTTGCTTGCTATTGGGCGCGGT

AATGATTCCTACGATGAAAATAAAAACGGCTTGCTTGTTCTCGATGAGTGCGGTACTTGGTTTAATA

CCCGTTCTTGGAATGATAAGGAAAGACAGCCGATTATTGATTGGTTTCTACATGCTCGTAAATTAGG

ATGGGATATTATTTTTCTTGTTCAGGACTTATCTATTGTTGATAAACAGGCGCGTTCTGCATTAGCTG

AACATGTTGTTTATTGTCGTCGTCTGGACAGAATTACTTTACCTTTTGTCGGTACTTTATATTCTCTTA

TTACTGGCTCGAAAATGCCTCTGCCTAAATTACATGTTGGCGTTGTTAAATATGGCGATTCTCAATT

AAGCCCTACTGTTGAGCGTTGGCTTTATACTGGTAAGAATTTGTATAACGCATATGATACTAAACAG

GCTTTTTCTAGTAATTATGATTCCGGTGTTTATTCTTATTTAACGCCTTATTTATCACACGGTCGGTAT

TTCAAACCATTAAATTTAGGTCAGAAGATGAAATTAACTAAAATATATTTGAAAAAGTTTTCTCGCG

TTCTTTGTCTTGCGATTGGATTTGCATCAGCATTTACATATAGTTATATAACCCAACCTAAGCCGGAG

GTTAAAAAGGTAGTCTCTCAGACCTATGATTTTGATAAATTCACTATTGACTCTTCTCAGCGTCTTAA

TCTAAGCTATCGCTATGTTTTCAAGGATTCTAAGGGAAAATTAATTAATAGCGACGATTTACAGAAG

CAAGGTTATTCACTCACATATATTGATTTATGTACTGTTTCCATTAAAAAAGGTAATTCAAATGAAA

TTGTTAAATGTAATTAATTTTGTTTTCTTGATGTTTGTTTCATCATCTTCTTTTGCTCAGGTAATTGAA

ATGAATAATTCGCCTCTGCGCGATTTTGTAACTTGGTATTCAAAGCAATCAGGCGAATCCGTTATTG

TTTCTCCCGATGTAAAAGGTACTGTTACTGTATATTCATCTGACGTTAAACCTGAAAATCTACGCAA

TTTCTTTATTTCTGTTTTACGTGCAAATAATTTTGATATGGTAGGTTCTAACCCTTCCATTATTCAGAA

GTATAATCCAAACAATCAGGATTATATTGATGAATTGCCATCATCTGATAATCAGGAATATGATGAT

AATTCCGCTCCTTCTGGTGGTTTCTTTGTTCCGCAAAATGATAATGTTACTCAAACTTTTAAAATTAA

TAACGTTCGGGCAAAGGATTTAATACGAGTTGTCGAATTGTTTGTAAAGTCTAATACTTCTAAATCC

TCAAATGTATTATCTATTGACGGCTCTAATCTATTAGTTGTTAGTGCTCCTAAAGATATTTTAGATAA

CCTTCCTCAATTCCTTTCAACTGTTGATTTGCCAACTGACCAGATATTGATTGAGGGTTTGATATTTG

AGGTTCAGCAAGGTGATGCTTTAGATTTTTCATTTGCTGCTGGCTCTCAGCGTGGCACTGTTGCAGG

CGGTGTTAATACTGACCGCCTCACCTCTGTTTTATCTTCTGCTGGTGGTTCGTTCGGTATTTTTAATG

GCGATGTTTTAGGGCTATCAGTTCGCGCATTAAAGACTAATAGCCATTCAAAAATATTGTCTGTGCC

ACGTATTCTTACGCTTTCAGGTCAGAAGGGTTCTATCTCTGTTGGCCAGAATGTCCCTTTTATTACTG

GTCGTGTGACTGGTGAATCTGCCAATGTAAATAATCCATTTCAGACGATTGAGCGTCAAAATGTAGG

TATTTCCATGAGCGTTTTTCCTGTTGCAATGGCTGGCGGTAATATTGTTCTGGATATTACCAGCAAGG

CCGATAGTTTGAGTTCTTCTACTCAGGCAAGTGATGTTATTACTAATCAAAGAAGTATTGCTACAAC

GGTTAATTTGCGTGATGGACAGACTCTTTTACTCGGTGGCCTCACTGATTATAAAAACACTTCTCAG

GATTCTGGCGTACCGTTCCTGTCTAAAATCCCTTTAATCGGCCTCCTGTTTAGCTCCCGCTCTGATTC

TAACGAGGAAAGCACGTTATACGTGCTCGTCAAAGCAACCATAGTACGCGCCCTGTAGCGGCGCAT

TAAGCGCGGCGGGTGTGGTGGTTACGCGCAGCGTGACCGCTACACTTGCCAGCGCCCTAGCGCCCG

CTCCTTTCGCTTTCTTCCCTTCCTTTCTCGCCACGTTC

-continued

Chlorotoxin (SEQ ID NO: 123)

ATGTGCATGCCGTGCTTTACCACCGATCATCAGATGGCGCGCAAATGCGATGATTGCTGCGGCGGC

AAAGGCCGCGGCAAATGCTATGGCCCGCAGTGCCTGTGCCGC

BAP (SEQ ID NO: 124)

GGCCTGAACGACATCTTCGAGGCTCAGAAAATCGAATGGCACGAG

BPSV40NLS (SEQ ID NO: 125)

AAAAGGACAGCTGATGGATCAGAATTTGAGAGCCCGAAAAAGAAACGTAAGGTGGGCCAGGGCGG

CCAGGGTGTCGAC

D2 Select Inho Sequences inho475

(SEQ ID NO: 126)

TTCTGGGCCATCGCCCTGATAGACGGTTTTTCGCCCTTTGACGTTGGCTTTAATAGTGGACTCTTGTT

CCAAACTGGAACAACACTCAACCCTATCTCGGGCTATTCTTTTGATTTATAAGGGATTTTGCCGATTT

CGGCCTATTGGTTAAAAAATGAGCTGATTTAACAAAAATTTAACGCGAATTTTAACAAAATATTAAC

GTTTACAATTTAAATATTTGCTTATACAATCCGCGCCCTGTAGCGGCGCATTAAGCGCGGCGGGTGT

GGTGGTTACGCGCAGCGTGACCGCTACACTTGCCAGCGCCCTAGCGCCCGCTCCTTTCGCTTTCTTC

CCTTCCTTTCTCGCCACGTTCGCCGGCTTTCCCCGTCAAGCTCTAAATCGGGGGCTCCCTTTAGGGTT

CCGATTTAGTGCTTTACGGCACCTCGACCCCAAAAAACTTGATTTGGGTGATGGTTCACGTAGTGGG

CCATCGCCCTGATAGACGGTTTTTCGCCCTTTGACGTTGGAGTCCACGTTCTTTAATAGTGGACTCTT

GTTCCAAACAACACTAAGCTTTAATGCGGTAGTTTATCACAGTTAAATTGCTAACGCAGTCAGGCAC

CGTGTATGAAATCTAACAATGCGCTCATCGTCATCCTCGGCACCGTCACCCTGGATGCTGTAGGCAT

AGGCTTGGTTATGCCGGTACTGCCGGGCCTCTTGCGGGATATCGTCCATTCCGACAGCATCGCCAGT

CACTATGGCGTGCTGCTAGCGCTATATGCGTTGATGCAATTTCTATGCGCACCCGTTCTCGGAGCAC

TGTCCGACCGCTTTGGCCGCCGCCCAGTCCTGCTCGCTTCGCTACTTGGAGCCACTATCGACTACGC

GATCATGGCGACCACACCCGTCCTGTGGATCCTCTACGCCGGACGCATCGTGGCCGGCATCACCGG

CGCCACAGGTGCGGTTGCTGGCGCCTATATCGCCGACATCACCGATGGGGAAGATCGGGCTCGCCA

CTTCGGGCTCATGAGCGCTTGTTTCGGCGTGGGTATGGTGGCAGGCCCCGTGGCCGGGGGACTGTTG

GGCGCCATCTCCTTGCATGCACCATTCCTTGCGGCGGCGGTGCTCAACGGCCTCAACCTACTACTGG

GCTGCTTCCTAATGCAGGAGTCGCATAAGGGAGAGCGTCGACCGATGCCCTTGAGAGCCTTCAACC

CAGTCAGCTCCTTCCGGTGGGCGCGGGGCATGACTATCGTCGCCGCACTTATGACTGTCTTCTTTAT

CATGCAACTCGTAGGACAGGTGCCGGCAGCGCTCTGGGTCATTTTCGGCGAGGACCGCTTTCGCTGG

AGCGCGACGATGATCGGCCTGTCGCTTGCGGTATTCGGAATCTTGCACGCCCTCGCTCAAGCCTTCG

TCACTGGTCCCGCCACCAAACGTTTCGGCGAGAAGCAGGCCATTATCGCCGGCATGGCGGCCGACG

CGCTGGGCTACGTCTTGCTGGCGTTCGCGACGCGAGGCTGGATGGCCTTCCCCATTATGATTCTTCT

CGCTTCCGGCGGCATCGGGATGCCCGCGTTGCAGGCCATGCTGTCCAGGCAGGTAGATGACGACCA

TCAGGGACAGCTTCAAGGATCGCTCGCGGCTCTTACCAGCCTAACTTCGATCATTGGACCGCTGATC

GTCACGGCGATTTATGCCGCCTCGGCGAGCACATGGAACGGGTTGGCATGGATTGTAGGCGCCGCC

CTATACCTTGTCTGCCTCCCCGCGTTGCGTCGCGGTGCATGGAGCCGGGCCACCTCGACCTGAATGG

AAGCCGGCGGCACCTCGCTAACGGATTCACCACTCCAAGAATTGGAGCCAATCAATTCTTGCGGAG

AACTGTGAATGCGCAAACCAACCCTTGGCAGAACATATCCATCGCGTCCGCCATCTCCAGCAGCCG

-continued

CACGCGGCGCATCTCGGGCAGCGTTGGGTCCTGGCCACGGGTGCGCATGATCGTGCTCCTGTCGTTG

AGGACCCGGCTAGGCTGGCGGGGTTGCCTTACTGGTTAGCAGAATGAATCACCGATACGCGAGCGA

ACGTGAAGCGACTGCTGCTGCAAAACGTCTGCGACCTGAGCAACAACATGAATGGTCTTCGGTTTC

CGTGTTTCGTAAAGTCTGGAAACGCGGAAGTCAGCGCCCTGCACCATTATGTTCCGGATCTGCATCG

CAGGATGCTGCTGGCTACCCTGTGGAACACCTACATCTGTATTAACGAAGCGCTGGCATTGACCCTG

AGTGATTTTTCTCTGGTCCCGCCGCATCCATACCGCCAGTTGTTTACCCTCACAACCTTCCAGTAACC

GGGCATGTTCATCATCAGTAACCCGTATCGTGAGCATCCTCTCTCGTTTCATCGGTATCATTACCCCC

ATGAACAGAAATCCCCCTTACACGGAGGCATCAGTGACCAAACAGGAAAAAACCGCCCTTAACATG

GCCCGCTTTATCAGAAGCCAGACATTAACGCTTCTGGAGAAACTCAACGAGCTGGACGCGGATGAA

CAGGCAGACATCTGTGAATCGCTTCACGACCACGCTGATGAGCTTTACCGCAGCTGCCTCGCGCGTT

TCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCGCA

GCCATGACCCAGTCACGTAGCGATAGCGGAGTGTATACTGGCTTAACTATGCGGCATCAGAGCAGA

TTGTACTGAGAGTGCACCATATGCGGTGTGAAATACCGCACAGATGCGTAAGGAGAAAATACCGCA

TCAGGCGCTCTTCCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGCAGGAAAGAACAT

GTGAGCAAAAGGCCAGCAAAAGGCCAGGAACCGTAAAAAGGCCGCGTTGCTGGCGTTTTTCCATAG

GCTCCGCCCCCCTGACGAGCATCACAAAAATCGACGCTCAAGTCAGAGGTGGCGAAACCCGACAGG

ACTATAAAGATACCAGGCGTTTCCCCCTGGAAGCTCCCTCGTGCGCTCTCCTGTTCCGACCCTGCCG

CTTACCGGATACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCCCGTTCAGCCC

GACCGCTGCGCCTTATCCGGTAACTATCGTCTTGAGTCCAACCCGGTAAGACACGACTTATCGCCAC

TGGCAGCAGCCACTGGTAACAGGATTAGCAGAGCGAGGTATGTAGGCGGTGCTACAGAGTTCTTGA

AGTGGTGGCCTAACTACGGCTACACTAGAAGGACAGTATTTGGTATCTGCGCTCTGCTGAAGCCAGT

TACCTTCGGAAAAAGAGTTGGTAGCTCTTGATCCGGCAAACAAACCACCGCTGGTAGCGGTGGTTTT

TTTGTTTGCAAGCAGCAGATTACGCGCAGAAAAAAAGGATCTCAAGAAGATCCTTTGATCTTTTCTA

CGGGGTCTGACGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTGTCTATTTCGTT

CATCCATAGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAAACCAGCC

AGCCGGAAGGGCCGAGCGCAGAAGTGGTCCTGCAACTTTATCCGCCTCCATCCAGTCTATTAATTGT

TGCCGGGAAGCTAGAGTAAGTAGTTCGCCAGTTAATAGTTTGCGCAACGTTGTTGCCATTGCTGCAG

GCATCGTGGTGTCACGCTCGTCGTTTGGTATGGCTTCATTCAGCTCCGGTTCCCAACGATCAAGGCG

AGTTACATGATCCCCCATGTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAATAGTGTATGCG

GCGACCGAGTTGCTCTTGCCCGGCGTCAACACGGGATAATACCGCGCCACATAGCAGAACTTTAAA

AGTGCTCATCATTGGAAAACGTTCTTCGGGGCGAAAACTCTCAAGGATCTTACCGCTGTTGAGATCC

AGTTCGATGTAACCCACTCGTGCACCCAACTGATCTTCAGCATCTTTTACTTTCACCAGCGTTTCTGG

GTGAGCAAAAACAGGAAGGCAAAATGCCGCAAAAAAGGGAATAAGGGCGACACGGAAATGTTGA

-continued

ATACTCATACTCTTCCTTTTTCAATATTATTGAAGCATTTATCAGGGTTATTGTCTCATGAGCGGATA

CATATTTGAATGTATTTAGAAAAATAAACAAATAGGGGTTCCGCGCACATTTCCCCGAAAAGTGCC

ACCTGACGTCTAAGAAACCATTATTATCATGACATTAACCTATAAAAATAGGCGTATCACGAGGCC

CTTTCGTCTTCAAGAA inho1960

(SEQ ID NO: 127)

TTCTGGGCCATCGCCCTGATAGACGGTTTTTCGCCCTTTGACGTTGGCTTTAATAGTGGACTCTTGTT

CCAAACTGGAACAACACTCAACCCTATCTCGGGCTATTCTTTTGATTTATAAGGGATTTTGCCGATTT

CGGCCTATTGGTTAAAAAATGAGCTGATTTAACAAAAATTTAACGCGAATTTTAACAAAATATTAAC

GTTTACAATTTGATGTACGGGCCAGATATACGCGTTGACATTGATTATTGACTAGTTATTAATAGTA

ATCAATTACGGGGTCATTAGTTCATAGCCCATATATGGAGTTCCGCGTTACATAACTTACGGTAAAT

GGCCCGCCTGGCTGACCGCCCAACGACCCCCGCCCATTGACGTCAATAATGACGTATGTTCCCATAG

TAACGCCAATAGGGACTTTCCATTGACGTCAATGGGTGGACTATTTACGGTAAACTGCCCACTTGGC

AGTACATCAAGTGTATCATATGCCAAGTACGCCCCCTATTGACGTCAATGACGGTAAATGGCCCGCC

TGGCATTATGCCCAGTACATGACCTTATGGGACTTTCCTACTTGGCAGTACATCTACGTATTAGTCAT

CGCTATTACCATGGTGATGCGGTTTTGGCAGTACATCAATGGGCGTGGATAGCGGTTTGACTCACGG

GGATTTCCAAGTCTCCACCCCATTGACGTCAATGGGAGTTTGTTTTGGCACCAAAATCAACGGGACT

TTCCAAAATGTCGTAACAACTCCGCCCCATTGACGCAAATGGGCGGTAGGCGTGTACGGTGGGAGG

TCTATATAAGCAGAGCTCTCTGGCTAACTAGAGAACCCACTGCTTACTGGCTTATCGAAATTAATAC

GACTCACTATAGGGAGACCCAAGCTTGGTACCGAGCTCGGATCCAGCCACCATGGGAGTCAAAGTT

CTGTTTGCCCTGATCTGCATCGCTGTGGCCGAGGCCAAGCCCACCGAGAACAACGAAGACTTCAAC

ATCGTGGCCGTGGCCAGCAACTTCGCGACCACGGATCTCGATGCTGACCGCGGGAAGTTGCCCGGC

AAGAAGCTGCCGCTGGAGGTGCTCAAAGAGATGGAAGCCAATGCCCGGAAAGCTGGCTGCACCAG

GGGCTGTCTGATCTGCCTGTCCCACATCAAGTGCACGCCCAAGATGAAGAAGTTCATCCCAGGACG

CTGCCACACCTACGAAGGCGACAAAGAGTCCGCACAGGGCGGCATAGGCGAGGCGATCGTCGACA

TTCCTGAGATTCCTGGGTTCAAGGACTTGGAGCCCATGGAGCAGTTCATCGCACAGGTCGATCTGTG

TGTGGACTGCACAACTGGCTGCCTCAAAGGGCTTGCCAACGTGCAGTGTTCTGACCTGCTCAAGAA

GTGGCTGCCGCAACGCTGTGCGACCTTTGCCAGCAAGATCCAGGGCCAGGTGGACAAGATCAAGGG

GGCCGGTGGTGACTAAGCGGCCGCAATAAAATATCTTTATTTTCATTACATCTGTGTGTTGGTTTTTT

GTGTGTCTAGAAATAATTCTTACTGTCATATCCCGCCCCTAACTCCGCCCAGTTCCGCCCATTCTCCG

CCCCATGGCTGACTAATTTTTTTTATTTATGCAGAGGCCGAGGCCGCCTCTGCCTCTGAGCTATTCCA

GAAGTAGTGAGGAGGCTTTTTTGGAGGCCAAATATTTGCTTATACAATCCGCGCCCTGTAGCGGCGC

ATTAAGCGCGGCGGGTGTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTCCCCGTCAAGCTCTAAATCG

GGGGCTCCCTTTAGGGTTCCGATTTAGTGCTTTACGGCACCTCGACCCCAAAAAACTTGATTTGGGT

GATGGTTCACGTAGTGGGCCATCGCCCTGATAGACGGTTTTTCGCCCTTTGACGTTGGAGTCCACGT

TCTTTAATAGTGGACTCTTGTTCCAAACAACACTAAGCTTTAATGCGGTAGTTTATCACAGTTAAATT

GCTAACGCAGTCAGGCACCGTGTATGAAATCTAACAATGCGCTCATCGTCATCCTCGGCACCGTCAC

CCTGGATGCTGTAGGCATAGGCTTGGTTATGCCGGTACTGCCGGGCCTCTTGCGGGATATCGTCCAT

TCCGACAGCATCGCCAGTCACTATGGCGTGCTGCTAGCGCTATATGCGTTGATGCAATTTCTATGCG

CACCCGTTCTCGGAGCACTGTCCGACCGCTTTGGCCGCCGCCCAGTCCTGCTCGCTTCGCTACTTGG

-continued

AGCCACTATCGACTACGCGATCATGGCGACCACACCCGTCCTGTGGATCCTCTACGCCGGACGCATC

GTGGCCGGCATCACCGGCGCCACAGGTGCGGTTGCTGGCGCCTATATCGCCGACATCACCGATGGG

GAAGATCGGGCTCGCCACTTCGGGCTCATGAGCGCTTGTTTCGGCGTGGGTATGGTGGCAGGCCCC

GTGGCCGGGGGACTGTTGGGCGCCATCTCCTTGCATGCACCATTCCTTGCGGCGGCGGTGCTCAACG

GCCTCAACCTACTACTGGGCTGCTTCCTAATGCAGGAGTCGCATAAGGGAGAGCGTCGACCGATGC

CCTTGAGAGCCTTCAACCCAGTCAGCTCCTTCCGGTGGGCGCGGGGCATGACTATCGTCGCCGCACT

TATGACTGTCTTCTTTATCATGCAACTCGTAGGACAGGTGCCGGCAGCGCTCTGGGTCATTTTCGGC

GAGGACCGCTTTCGCTGGAGCGCGACGATGATCGGCCTGTCGCTTGCGGTATTCGGAATCTTGCACG

CCCTCGCTCAAGCCTTCGTCACTGGTCCCGCCACCAAACGTTTCGGCGAGAAGCAGGCCATTATCGC

CGGCATGGCGGCCGACGCGCTGGGCTACGTCTTGCTGGCGTTCGCGACGCGAGGCTGGATGGCCTT

CCCCATTATGATTCTTCTCGCTTCCGGCGGCATCGGGATGCCCGCGTTGCAGGCCATGCTGTCCAGG

CAGGTAGATGACGACCATCAGGGACAGCTTCAAGGATCGCTCGCGGCTCTTACCAGCCTAACTTCG

ATCATTGGACCGCTGATCGTCACGGCGATTTATGCCGCCTCGGCGAGCACATGGAACGGGTTGGCA

TGGATTGTAGGCGCCGCCCTATACCTTGTCTGCCTCCCCGCGTTGCGTCGCGGTGCATGGAGCCGGG

CCACCTCGACCTGAATGGAAGCCGGCGGCACCTCGCTAACGGATTCACCACTCCAAGAATTGGAGC

CAATCAATTCTTGCGGAGAACTGTGAATGCGCAAACCAACCCTTGGCAGAACATATCCATCGCGTC

CGCCATCTCCAGCAGCCGCACGCGGCGCATCTCGGGCAGCGTTGGGTCCTGGCCACGGGTGCGCAT

GATCCTGCTCCTGTCGTTGAGGACCCGGCTAGGCTGGCGGGGTTGCCTTACTGGTTAGCAGAATGAA

TCACCGATACGCGAGCGAACGTGAAGCGACTGCTGCTGCAAAACGTCTGCGACCTGAGCAACAACA

TGAATGGTCTTCGGTTTCCGTGTTTCGTAAAGTCTGGAAACGCGGAAGTCAGCGCCCTGCACCATTA

TGTTCCGGATCTGCATCGCAGGATGCTGCTGGCTACCCTGTGGAACACCTACATCTGTATTAACGAA

GCGCTGGCATTGACCCTGAGTGATTTTTCTCTGGTCCCGCCGCATCCATACCGCCAGTTGTTTACCCT

CACAACGTTCCAGTAACCGGGCATGTTCATCATCAGTAACCCGTATCGTGAGCATCCTCTCTCGTTT

CATCGGTATCATTACCCCCATGAACAGAAATCCCCCTTACACGGAGGCATCAGTGACCAAACAGGA

AAAAACCGCCCTTAACATGGCCCGCTTTATCAGAAGCCAGACATTAACGCTTCTGGAGAAACTCAA

CGAGCTGGACGCGGATGAACAGGCAGACATCTGTGAATCGCTTCACGACCACGCTGATGAGCTTTA

CCGCAGCTGCCTCGCGCGTTTCGGTGATGACGGTGAAAACCTCTGACACATGCAGCTCCCGGAGAC

GGTCACAGCTTGTCTGTAAGCGGATGCCGGGAGCAGACAAGCCCGTCAGGGCGCGTCAGCGGGTGT

TGGCGGGTGTCGGGGCGCAGCCATGACCCAGTCACGTAGCGATAGCGGAGTGTATACTGGCTTAAC

TATGCGGCATCAGAGCAGATTGTACTGAGAGTGCACCATATGCGGTGTGAAATACCGCACAGATGC

GTAAGGAGAAAATACCGCATCAGGCGCTCTTCCGCTTCCTCGCTCACTGACTCGCTGCGCTCGGTCG

TTCGGCTGCGGCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAAATCGACGCTCAAGTCAG

AGGTGGCGAAACCCGACAGGACTATAAAGATACCAGGCGTTTCCCCCTGGAAGCTCCCTCGTGCGC

TCTCCTGTTCCGACCCTGCCGCTTACCGGATACCTGTCCGCCTTTCTCCCTTCGGGAAGCGTGGCGCT

TTCTCATAGCTCACGCTGTAGGTATCTCAGTTCGGTGTAGGTCGTTCGCTCCAAGCTGGGCTGTGTG

CACGAACCCCCCGTTCAGCCCGACCGCTGCGCCTTATCCGGTAACTATCGTCTTGAGTCCAACCCGG

TAAGACACGACTTATCGCCACTGGCAGCAGCCACTGGTAACAGGATTAGCAGAGCGAGGTATGTAG

GCGGTGCTACAGAGTTCTTGAAGTGGTGGCCTAACTACGGCTACACTAGAAGGACAGTATTTGGTA

TCTGCGCTCTGCTGAAGCCAGTTACCTTCGGAAAAAGAGTTGGTAGCTCTTGATCCGGCAAACAAAC

-continued

CACCGCTGGTAGCGGTGGTTTTTTTGTTTGCAAGCAGCAGATTACGCGCAGAAAAAAAGGATCTCA

AGAAGATCCTTTGATCTTTTCTACGGGGTCTGACGCTCAGTGGAACGAAAACTCACGTTAAGGGATT

TTGGTCATGAGATTATCAAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTGAGGCACCTAT

CTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAG

ATTTATCAGCAATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTAATAGTTTGCG

CAACGTTGTTGCCATTGCTGCAGGCATCGTGGTGTCACGCTCGTCGTTTGGTATGGCTTCATTCAGCT

CCGGTTCCCAACGATCAAGGCGAGTTACATGATCCCCCATGTTGTGCAAAAAAGCGGTTAGCTCCTT

CGGTCCTCCGATCGTTGTCAGAAGTAAGTTGGCCGCAGTGTTATCACTCATGGTTATGGCAGCACTG

CATAATTCTCTTACTGTCATGCCATCCGTAAGATGCTTTTCTGTGACTGGTGAGTACTCAACCAAGTC

ATTCTGAGAATAGTGTATGCGGCGACCGAGTTGCTCTTGCCCGGCGTCAACACGGGATAATACCGC

GCCACATAGCAGAACTTTAAAAGTGCTCATCATTGGAAAACGTTCTTCGGGGCGAAAACTCTCAAG

GATCTTACCGCTGTTGAGATCCAGTTCGATGTAACCCACTCGTGCACCCAACTGATCTTCAGCATCT

TTTACTTTCACCAGCGTTTCTGGGTGAGCAAAAACAGGAAGGCAAAATGCCGCAAAAAAGGGAATA

AGGGCGACACGGAAATGTTGAATACTCATACTCTTCCTTTTTCAATATTATTGAAGCATTTATCAGG

GTTATTGTCTCATGAGCGGATACATATTTGAATGTATTTAGAAAAATAAACAAATAGGGGTTCCGCG

CACATTTCCCCGAAAAGTGCCACCTGACGTCTAAGAAACCATTATTATCATGACATTAACCTATAAA

AATAGGCGTATCACGAGGCCCTTTCGTCTTCAAGAA inhoITR (SEQ ID NO: 128)

CCAATGATTGGGCCATCGCCCTGATAGACGGTTTTTCGCCCTTTGACGTTGGCTTTAATAGTGGACT

CTTGTTCCAAACTGGAACAACACTCAACCCTATCTCGGGCTATTCTTTTGATTTATAAGGGATTTTGC

CGATTTCGGCCTATTGGTTAAAAAATGAGCTGATTTAACAAAAATTTAACGCGACATGTCCTGCAGG

CAGCTGCGCGCTCGCTCGCTCACTGAGGCCGCCCGGGCAAAGCCCGGGCGTCGGGCGACCTTTGGT

CGCCCGGCCTCAGTGAGCGAGCGAGCGCGCAGAGAGGGAGTGGCCAACTCCATCACTAGGGGTTCC

TGCGGCCGCACGCGAAAGCTTCAAAATATTAGAATTCACGTTTACAATTTAAATATTTGCTTCATGT

CCTGCAGGCAGCTGCGCGCTCGCTCGCTCACTGAGGCCGCCCGGGCAAAGCCCGGGCGTCGGGCGA

CCTTTGGTCGCCCGGCCTCAGTGAGCGAGCGAGCGCGCAGAGAGGGAGTGGCCAACTCCATCACTA

GGGGTTCCTGCGGCCGCACGCGATACAATCCGCGCCCTGTAGCGGCGCATTAAGCGCGGCGGGTGT

GGTGGTTACGCGCAGCGTGACCGCTACACTTGCCAGCGCCCTAGCGCCCGCTCCTTTCGCTTTCTTC

CCTTCCTTTCTCGCCACGTTCGCCGGCTTTCCCCGTCAAGCTCTAAATCGGGGGCTCCCTTTAGGGTT

CCGATTTAGTGCTTTACGGCACCTCGACCCCAAAAAACTTGATTTGGGTGATGGTTCACGTAGTGGG

CCATCGCCCTGATAGACGGTTTTTCGCCCTTTGACGTTGGAGTCCACGTTCTTTAATAGTGGACTCTT

GTTCCAAACAACACTATCGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAAAAATCGACGC

TCAAGTCAGAGGTGGCGAAACCCGACAGGACTATAAAGATACCAGGCGTTTCCCCCTGGAAGCTCC

CTCGTGCGCTCTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGCTCCAAGCTG

GGCTGTGTGCACGAACCCCCCGTTCAGCCCGACCGCTGCGCCTTATCCGGTAACTATCGTCTTGAGT

-continued

CCAACCCGGTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGAAAACTCACGT

TAAGGGATTTTGGTCATGAGATTATCAAAAAGGATCTTCACCTAGATCCTTTTAAATTAAAAATGAA

GTTTTAAATCAATCTAAAGTATATATGAGTAAACTTGGTCTGACAGTTACCAATGCTTAATCAGTGA

GGCACCTATCTCAGCGATCTGTCTATTTCGTTCATCCATAGTTGCCTGACTCCCCGTCGTGTAGATAA

CTACGATACGGGAGGGCTTACCATCTGGCCCCAGTGCTGCAATGATACCGCGAGACCCACGCTCAC

CGGCTCCAGATTTATCAGCAATAAACCAGCCAGCCGGAAGGGCCGAGCGCAGAAGTGGTCCTGCAA

CTTTATCCGCCTCCATCCAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCTCGTCGTTTGGTATGGCTT

CATTCAGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGACTGGTGAGTACTC

AACCAAGTCATTCTGAGAATAGTGTATGCGGCGACCGAGTTGCTCTTGCCCGGCGTCAATACGGGA

TAATACCGCGCCACATAGCAGAACTTTAAAAGTGCTCATCATTGGAAAACGTTCTTCGGGGCGAAA

ACTCTCAAGGATCTTACCGCTGTTGAGATCCAGTTCGATGTAACCCACTCGTGCACCCAACTGATCT

TCAGCATCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAATAAACAAATAGG

GGTTCCGCGCACATTTCCCCGAAAAGTGCCACCTGACGTC inhoITR-m Cherry (SEQ ID NO: 129)

CCAATGATTGGGCCATCGCCCTGATAGACGGTTTTTCGCCCTTTGACGTTGGCTTTAATAGTGGACT

CTTGTTCCAAACTGGAACAACACTCAACCCTATCTCGGGCTATTCTTTTGATTTATAAGGGATTTTGC

CGATTTCGGCCTATTGGTTAAAAAATGAGCTGATTTAACAAAAATTTAACGCGACATGTCCTGCAGG

CAGCTGCGCGCTCGCTCGCTCACTGAGGCCGCCCGGGCAAAGCCCGGGCGTCGGGCGACCTTTGGT

CGCCCGGCCTCAGTGAGCGAGCGAGCGCGCAGAGAGGGAGTGGCCAACTCCATCACTAGGGGTTCC

TGCGGCCGCACGCGAAAGCTTCAAAATATTAGAATTCACGTTTACAATTTGATAATACGACTCACTA

TAGGGGGATCCACGTATGTCGAGGTAGGCGTGTACGGTGGGAGGCCTATATAAGCAGAGCTCGTTT

AGTGAACCGTCAGATCGCCTGGAGGTACCGCCACCATGGTGAGCAAGGGCGAGGAGGATAACATG

GCCATCATCAAGGAGTTCATGCGCTTCAAGGTGCACATGGAGGGCTCCGTGAACGGCCACGAGTTC

GAGATCGAGGGCGAGGGCGAGGGCCGCCCCTACGAGGGCACCCAGACCGCCAAGCTGAAGGTGAC

CAAGGGTGGCCCCCTGCCCTTCGCCTGGGACATCCTGTCCCCTCAGTTCATGTACGGCTCCAAGGCC

TACGTGAAGCACCCCGCCGACATCCCCGACTACTTGAAGCTGTCCTTCCCCGAGGGCTTCAAGTGGG

AGCGCGTGATGAACTTCGAGGACGGCGGCGTGGTGACCGTGACCCAGGACTCCTCCCTGCAGGACG

GCGAGTTCATCTACAAGGTGAAGCTGCGCGGCACCAACTTCCCCTCCGACGGCCCCGTAATGCAGA

AGAAGACCATGGGCTGGGAGGCCTCCTCCGAGCGGATGTACCCCGAGGACGGCGCCCTGAAGGGC

GAGATCAAGCAGAGGCTGAAGCTGAAGGACGGCGGCCACTACGACGCTGAGGTCAAGACCACCTA

CAAGGCCAAGAAGCCCGTGCAGCTGCCCGGCGCCTACAACGTCAACATCAAGTTGGACATCACCTC

CCACAACGAGGACTACACCATCGTGGAACAGTACGAACGCGCCGAGGGCCGCCACTCCACCGGCG

-continued

GCATGGACGAGCTGTACAAGTAAGAATTCGATATCAAGCTTATCGATAATCAACCTCTGGATTACA

AAATTTGTGAAAGATTGACTGGTATTCTTAACTATGTTGCTCCTTTTACGCTATGTGGATACGCTGCT

TTAATGCCTTTGTATCATGCTATTGCTTCCCGTATGGCTTTCATTTTCTCCTCCTTGTATAAATCCTGG

TTGCTGTCTCTTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGACTTTCGCTTTC

CCCCTCCCTATTGCCACGGCGGAACTCATCGCCGCCTGCCTTGCCCGCTGCTGGACAGGGGCTCGGC

TGTTGGGCACTGACAATTCCGTGGTGTTGTCGGGGAAATCATCGTCCTTTCCTTGGCTGCTCGCCTAT

GTTGCCACCTGGATTCTGCGCGGGACGTCCTTCTGCTACGTCCCTTCGGCCCTCAATCCAGCGGACC

TTCCTTCCCGCGGCCTGCTGCCGGCTCTGCGGCCTCTTCCGCGTCTTCGCCTTCGCCCTCAGACGAGT

CGGATCTCCCTTTGGGCCGCCTCCCCGCATCGATACCGAGCGCTGCTCGAGAGATCTACGGGTGGCA

TCCCTGTGACCCCTCCCCAGTGCCTCTCCTGGCCCTGGAAGTTGCCACTCCAGTGCCCACCAGCCTT

GTCCTAATAAAATTAAGTTGCATCATTTTGTCTGACTAGGTGTCCTTCTATAATATTATGGGGTGGA

GGGGGGTGGTATGGAGCAAGGGGCAAGTTGGGAAGACAACCTGTAGGGCCTGCGGGGTCTATTGG

GAACCAAGCTGGAGTGCAGTGGCACAATCTTGGCTCACTGCAATCTCCGCCTCCTGGGTTCAAGCG

ATTCTCCTGCCTCAGCCTCCCGAGTTGTTGGGATTCCAGGCATGCATGACCAGGCTCAGCTAATTTTT

GTTTTTTTGGTAGAGACGGGGTTTCACCATATTGGCCAGGCTGGTCTCCAACTCCTAATCTCAGGTG

ATCTACCCACCTTGGCCTCCCAAATTGCTGGGATTACAGGCGTGAACCACTGCTCCCTTCCCTGTCCT

TCTGATTTTGTAGGTAACCACGTGCGGACCGAGCAAATATTTGCTTCATGTCCTGCAGGCAGCTGCG

CGCTCGCTCGCTCACTGAGGCCGCCCGGGCAAAGCCCGGGCGTCGGGCGACCTTTGGTCGCCCGGC

CTCAGTGAGCGAGCGAGCGCGCAGAGAGGGAGTGGCCAACTCCATCACTAGGGGTTCCTGCGGCCG

CACGCGATACAATCCGCGCCCTGTAGCGGCGCATTAAGCGCGGCGGGTGTGGTGGTTACGCGCAGC

GTGACCGCTACACTTGCCAGCGCCCTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGTTCCGATTTAGTGCTTTAC

GGCACCTCGACCCCAAAAAACTTGATTTGGGTGATGGTTCACGTAGTGGGCCATCGCCCTGATAGA

CGGTTTTTCGCCCTTTGACGTTGGAGTCCACGTTCTTTAATAGTGGACTCTTGTTCCAAACAACACTA

TCGGAAAGAACATGTGAGCAAAAGGCCAGCAAAAGGCCAGGAACCGTAAAAAGGCCGCGTTGCTG

GCGTTTTTCCATAGGCTCCGCCCCCCTGACGAGCATCACAAAAATCGACGCTCAAGTCAGAGGTGG

CGAAACCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTTTCTCAT

AGCTCACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTAAGACA

CGACTTATCGCCACTGGCAGCAGCCACTGGTAACAGGATTAGCAGAGCGAGGTATGTAGGCGGTGC

TACAGAGTTCTTGAAGTGGTGGCCTAACTACGGCTACACTAGAAGAACAGTATTTGGTATCTGCGCT

CTGCTGAAGCCAGTTACCTTCGGAAAAAGAGTTGGTAGCTCTTGATCCGGCAAACAAACCACCGCT

GGTAGCGGTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGATTTTGGTCA

TGAGATTATCAAAAAGGATCTTCACCTAGATCCTTTTAAATTAAAAATGAAGTTTTAAATCAATCTA

AAGTATATATGAGTAAACTTGGTCTGACAGTTACCAATGCTTAATCAGTGAGGCACCTATCTCAGCG

ATCTGTCTATTTCGTTCATCCATAGTTGCCTGACTCCCCGTCGTGTAGATAACTACGATACGGGAGG

GCTTACCATCTGGCCCCAGTGCTGCAATGATACCGCGAGACCCACGCTCACCGGCTCCAGATTTATC

-continued

AGCAATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCAACGTT

GTTGCCATTGCTACAGGCATCGTGGTGTCACGCTCGTCGTTTGGTATGGCTTCATTCAGCTCCGGTTC

CCAACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATAATT

CTCTTACTGTCATGCCATCCGTAAGATGCTTTTCTGTGACTGGTGAGTACTCAACCAAGTCATTCTGA

GAATAGTGTATGCGGCGACCGAGTTGCTCTTGCCCGGCGTCAATACGGGATAATACCGCGCCACAT

AGCAGAACTTTAAAAGTGCTCATCATTGGAAAACGTTCTTCGGGGCGAAAACTCTCAAGGATCTTA

CCGCTGTTGAGATCCAGTTCGATGTAACCCACTCGTGCACCCAACTGATCTTCAGCATCTTTTACTTT

CACCAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGTTATTGT

CTCATGAGCGGATACATATTTGAATGTATTTAGAAAAATAAACAAATAGGGGTTCCGCGCACATTTC

CCCGAAAAGTGCCACCTGACGTC

Domain B (SEQ ID NO: 130)

CACTCAACCCTATCTCGGGCTATTCTTTTGATTTATAAGGGATTTTGCCGATTTCGGCCTATTGGTTA

AAAAATGAGCTGATTTAACAAAAATTTAACGCG

Packaging Signal (SEQ ID NO: 131)

CGCGCCCTGTAGCGGCGCATTAAGCGCGGCGGGTGTGGTGGTTACGCGCAGCGTGACCGCTACACT

TGCCAGCGCCCTAGCGCCCGCTCC

F1-ori (SEQ ID NO: 132)

TGGGCCATCGCCCTGATAGACGGTTTTTCGCCCTTTGACGTTGGCTTTAATAGTGGACTCTTGTTCCA

AACTGGAACAA

F1-term (SEQ ID NO: 133)

TGGGCCATCGCCCTGATAGACGGTTTTTCGCCCTTTGACGTTGGAGTCCACGTTCTTTAATAGTGGA

CTCTTGTTCCAAACAACACT

AAV2 ITR (SEQ ID NO: 134)

CCTGCAGGCAGCTGCGCGCTCGCTCGCTCACTGAGGCCGCCCGGGCAAAGCCCGGGCGTCGGGCGA

CCTTTGGTCGCCCGGCCTCAGTGAGCGAGCGAGCGCGCAGAGAGGGAGTGGCCAACTCCATCACTA

GGGGTTCCT

The following references are incorporated by reference herein:

REFERENCES

Section 1 References

1. Clokie, M. R., *Bacteriophage* 1, 31-45 (2011).
2. *Bacteriophages*. vol. 501 (Humana Press, 2009).
3. Heckmann, C. M. *ChemCatChem* 12, 6082-6102 (2020).
4. Sioud, M. *Mol. Biotechnol.* 61, 286-303 (2019).
5. Krumpe, L. R. H. & Mori, T. *Int. J. Pept. Res. Ther.* 12, 79-91(2006).
6. Ebrahimizadeh, W. & Rajabibazl, M. *Curr. Microbiol.* 69, 109-120 (2014).
7. Velappan, N. et al. *Nucleic Acids Res.* 38, e22 (2010).
8. Scott, J. K. & Smith, *Science* 249, 386-390 (1990).
9. Cwirla, S. E., *Proc. Natl. Acad. Sci.* 87, 6378-6382 (1990).
10. Huovinen, T. et al. *BMC Res. Notes* 7, 661 (2014).
11. Enshell-Seijffers, D. *Nucleic Acids Res.* 29, 50e–550 (2001).
12. Gao, C. et al. *Proc. Natl. Acad. Sci. U.S.A* 96, 6025-6030 (1999).
13. Jespers, L S. et al. *Biotechnol. Nat. Publ. Co.* 13, 378-382 (1995).
14. Fransen, M., *Biochem. J.* 340, 561-568 (1999).
15. Hufton, S. E. et al. *J. Immunol. Methods* 231, 39-51 (1999).
16. Barbas, C. F. *Phage display: a laboratory manual*. (Cold Spring Harbor Laboratory Press, 2001).
17. Çelik, E. et al. *Biotechnol. J.* 10, 199-209 (2015).
18. Çelik, E. *Protein Sci. Publ. Protein Soc.* 19, 2006-2013 (2010).
19. Hess, G. T. et al. *Bioconjug. Chem.* 23, 1478-1487 (2012).
20. Ghosh, D., *ACS Synth. Biol.* 1, 576-582 (2012).

21. Henry, K. A., *Front. Microbiol.* 6, (2015).
22. Paczesny, J. & Bielec, K. *Nanomaterials* 10, 1944 (2020).
23. Yang, S. H., *Chem. Rec.* 13, 43-59 (2013).
24. Moon, J.-S. et al. *Mini-Rev. Org. Chem.* 12, 271-281 (2015).
25. Vilona, D. et al. *J. Mater. Chem. B* 3, 6718-6730 (2015).
26. Ohmura, J. F. et al. *Nanoscale* 11, 1091-1102 (2019).
27. Nam, K. T. et al. *Science* 312, 885-888 (2006).
28. Records, W. C., Wei, S. & Belcher, A. M. *Small* 15, 1903166 (2019).
29. Courchesne, N.-M. D. et al. *Adv. Mater.* 26, 3398-3404 (2014).
30. Jung, S. M., *Adv. Funct. Mater.* 27, 1603203 (2017).
31. Ghosh, D. et al. *Nat. Nanotechnol.* 7, 677-682 (2012).
32. Oh, D. et al. *Small* 8, 1006-1011 (2012).
33. Ghosh, D. et al. *Proc. Natl. Acad. Sci.* 111, 13948-13953 (2014).
34. H, Y. et al. *Nano Lett.* 12, 1176-1183 (2012).
35. Lee, Y. J. et al. *Science* 324, 1051-1055 (2009).
36. Oh, D. et al. *Nat. Commun.* 4, 2756 (2013).
37. Dang, X. et al. *Nat. Nanotechnol.* 6, 377-384 (2011).
38. Mohan, K. & Weiss, G. A. *ACS Chem. Biol.* 11, 1167-1179 (2016).
39. Kim, K.-P. et al. *Microb. Biotechnol.* 1, 247-257 (2008).
40. Peng, H., *Proc. Natl. Acad. Sci.* 117, 1951-1961 (2020).
41. Ju, Z. & Sun, W. *Drug Deliv.* 24, 1898-1908 (2017).
42. DePorter, S. M., *Bioconjug. Chem.* 25, 1620-1625 (2014).
43. Xu, J., *Proc. Natl. Acad. Sci.* 116, 5493-5498 (2019).
44. Chung, W.-J., *Int. J. Nanomedicine* 9, 5825-5836 (2014).
45. Lee, B. Y. et al. *Nat. Nanotechnol.* 7, 351-356 (2012).
46. Morag, O., *Proc. Natl. Acad. Sci.* 112, 971-976 (2015).
47. Donnelly, A., *Viruses* 7, 6476-6489 (2015).
48. Yata, T. et al. *Mol. Ther.-Nucleic Acids* 3, e185 (2014).
49. Lamboy, J. A. et al. *J. Am. Chem. Soc.* 131, 16454-16460 (2009).
50. Chung, W.-J., *Soft Matter* 6, 4454-4459 (2010).
51. Bardhan, N. M., *J. Biophotonics* 7, 617-623 (2014).
52. Bio-mimetic Nanostructure Self-assembled from Au@Ag Heterogeneous Nanorods and Phage Fusion Proteins for Targeted Tumor Optical Detection and Photothermal Therapy Scientific Reports. https://www.nature.com/articles/srep06808.
53. Dong, X. et al. *Sci. Adv.* 6, eaba1590 (2020).
54. Bar, H., Yacoby, I. & Benhar, *BMC Biotechnol.* 8, 37 (2008).
55. Karimi, M. et al., *Adv. Drug Deliv. Rev.* 106, 45-62 (2016).
56. Schmelcher, M. & Loessner, M. J. *Bacteriophage* 4, (2014).
57. Sorokulova, I., *Expert Rev. Med. Devices* 11, 175-186 (2014).
58. Li, S. et al. *Biosens. Bioelectron.* 26, 1313-1319 (2010).
59. Moon, J.-S. et al. *Nanomaterials* 9, (2019).
60. Machera, S. J., *Chemosensors* 8, 61(2020).
61. Cruz, V. F. de la., *J. Biol. Chem.* 263, 4318-4322 (1988).
62. Kneissel, S. et al. *J. Mol. Biol.* 288, 21-28 (1999).
63. Hashiguchi, S., *Biochem. Biophys. Res. Commun.* 402, 19-22 (2010).
64. Motti, C. et al. *Gene* 146, 191-198 (1994).
65. Meola, A. et al. *J. Immunol.* 154, 3162-3172 (1995).
66. Henry, K. A., *Bioeng. Bugs* 2, 275-283 (2011).
67. Majewska, J. et al. *Front. Immunol.* 10, (2019).
68. Hess, K. L. & Jewell, C. M. *Bioeng. Transl. Med.* 5, (2019).
69. Murgas, P. et al. *Cancer Immunol. Immunother.* 67, 183-193 (2018).
70. Saggio, I., *Gene* 152, 35-39 (1995).
71. Gram, H., *J. Immunol. Methods* 161, 169-176 (1993).
72. Wang, H. et al. *Nat. Commun.* 11, (2020).
73. Adu-Berchie, K. & Mooney, D. *J. Acc. Chem. Res.* 53, 1749-1760 (2020).
74. The Forgotten Cure—The Past and Future of Phage Therapy|Anna Kuchment|Springer. https://www.springer-.com/gp/book/9781461402503.
75. Wittebole, X., *Virulence* 5, 226-235 (2014).
76. Law, N. et al. *Infection* 47, 665-668 (2019).
77. Patey, O. et al. *Viruses* 11, 18 (2019).
78. Asla m, S. et al., *Open Forum Infect. Dis.* 7, (2020).
79. Chibani-Chennoufi, S. et al. *Antimicrob. Agents Chemother.* 48, 2558-2569 (2004).
80. Bruttin, A. & Brüssow, H. Antimicrob. Agents Chemother. 49, 2874-2878 (2005).
81. Sarker, S. A. et al., *Virology* 434, 222-232 (2012).
82. Barbu, E. M., *Cold Spring Harb. Perspect. Biol.* 8, a023879 (2016).
83. Krag, D. N. et al. *Cancer Res.* 66, 7724-7733 (2006).
84. Shukla, G. S. et al. *Cancer Immunol. Immunother.* 62, 1397-1410 (2013).
85. Bach, M. S. et al. *Filamentous Bacteriophage Delay Healing of Pseudomonas-Infected Wounds*. http://biorxiv.org/lookup/doi/10.1101/2020.03.10.985663 (2020) doi:10.1101/2020.03.10.985663.
86. Sweere, J. M. et al. *Science* 363, (2019).
87. Secor, P. R., *PLOS ONE* 12, e0179659 (2017).
88. Secor, P. R. et al. *Front. Immunol.* 11, (2020).
89. Studies on bacteriophage penetration in patients subjected to phage therapy.—Abstract—Europe PMC. https://europepmc.org/article/med/3332066.
90. Moustafa, A. et al. *PLOS Pathog.* 13, e1006292 (2017).
91. Górski, A. et al. *FEMS Immunol. Med. Microbial.* 46, 313-319 (2006).
92. Thannesberger, J. et al. *FASEB J.* 31, 1987-2000 (2017).
93. Method for discovering novel DNA viruses in blood using viral particle selection and shotgun sequencing|BioTechniques. https://www.future-science.com/doi/10.2144/000112019?url_ver=Z39.88-2003&rfr_id=ori%3Arid%3Acrossref.org&rfr_dat=cr_pub++0pubmed.
94. Nguyen, S. et al. *mBio* 8, (2017).
95. Li, J. et al. *Amino Acids* 42, 2373-2381 (2012).
96. Górski, A. et al. *Future Microbiol.* 12, 905-914 (2017).
97. Krut, O. *J. Immunol.* 200, 3037-3044 (2018).
98. van Houten, N. E., *Vaccine* 28, 2174-2185 (2010).
99. Suwan, K. et al. *Proc. Natl. Acad. Sci.* 116, 18571-18577 (2019).
100. Jin, P. et al. *Nano Lett.* 19, 1467-1478 (2019).
101. Lang, L H. *Gastroenterology* 131, 1370 (2006).
102. A non-chromatographic method for the removal of endotoxins from bacteriophages—Branston—2015—Biotechnology and Bioengineering—Wiley Online Library. https://onlinelibrary.wiley.com/doi/full/10.1002/bit.25571.
103. Boratyński, J. et al. *Cell. Mol. Biol. Lett.* 9, 253-259 (2004).
104. Chasteen, L., *Nucleic Acids Res.* 34, e145-e145 (2006).
105. Larocca, D. et al. *Curr. Pharm. Biotechnol.* 3, 45-57 (2002).
106. Burg, M. A. et al., *Cancer Res.* 62, 977-981 (2002).
107. Chung, Y.-S. A., *BMC Mol. Biol.* 9, 37 (2008).
108. Di Giovine, M. et al. *Virology* 282, 102-112 (2001).

109. Poul, M.-A. & Marks, J. D. *J. Mol. Biol.* 288, 203-211 (1999).
110. Hajitou, A. et al. *Cell* 125, 385-398 (2006).
111. Stoneham, C. A., *J. Biol. Chem.* 287, 35849-35859 (2012).
112. Tsafa, E. et al. *Int. J. Mal. Sci.* 21, 7867 (2020).
113. Przystal, J. M. et al. *Mol. Oncol.* 7, 55-66 (2013).
114. Yokoyamakobayashi, M. *Biochem. Biophys. Res. Commun.* 192, 935-939 (1993).
115. Kia, A. et al. *Mal. Cancer Ther.* 11, 2566-2577 (2012).
116. Trepel, M. et al., *Mol. Cancer Ther.* 8, 2383-2391 (2009).
117. Staquicini, F. I. et al. *Cancer Gene Ther.* 27, 301-310 (2020).
118. Smith, T. L. et al. *Proc. Natl. Acad. Sci.* 113, 2466-2471 (2016).
119. Paoloni, M. C. et al. *PLoS ONE* 4, e4972 (2009).
120. Tandle, A. et al. *Cancer* 115, 128-139 (2009).
121. Ferrara, F. et al. *Proc. Natl. Acad. Sci.* 113, 12786-12791 (2016).
122. Kick, B., *Nano Lett.* 15, 4672-4676 (2015).
123. Shepherd, T. R., *Sci. Rep.* 9, 6121 (2019).

Section 2 References

1. Kick, B., *Nano Lett.* 15, 4672-4676 (2015).
2. Shepherd, T. R., *Sci. Rep.* 9, 6121 (2019).
3. Specthrie, L. et al. *J. Mol. Biol.* 228, 720-724 (1992).
4. Nafisi, P. M., *Synth. Biol.* 3, (2018).
5. Sattar, S. et al. *Front. Microbiol.* 6, (2015).
6. Dotto, G. P., *Proc. Natl. Acad. Sci. U.S.A* 79, 7122-7126 (1982).
7. Dotto, G. P., in *Proteins Involved in DNA Replication* (eds. Hübscher, U. & Spadari, S.) 185-191 (Springer US, 1984). doi:10.1007/978-1-4684-8730-5_18.
8. Dotto, G. P., *J. Mol. Biol.* 172, 507-521 (1984).
9. Horiuchi, K. *Genes Cells* 2, 425-432 (1997).
10. Schaller, H. *Spring Harb. Symp. Quant. Biol.* 43 Pt 1, 401-408 (1979).
11. Suggs, S. V. & Ray, D. S. *Cold Spring Harb. Symp. Quant. Biol* 43, 379-388 (1979).
12. Wezenbeek, P. Nucleotide sequence of the bacteriophage M13 DNA: further studies on its regulatory elements. undefined/paper/Nucleotide-sequence-of-the-bacteriophage-M13—DNA %3A-Wezenbeek/cf21d96d14f25648f84de0cdd9c62a0be7ca095c (1981).
13. Dotto, G. P., *J. Mol. Biol.* 162, 335-343 (1982).
14. Greenstein, D. *J. Mal. Biol.* 197, 157-174 (1987).
15. Higashitani, A., *J. Mol. Biol.* 237, 388-400 (1994).
16. Asano, S., *Nucleic Acids Res.* 27, 1882-1889 (1999).
17. Mazur, B. J. & Model, *J. Mol. Biol.* 78, 285-300 (1973).
18. Mazur, B. J. & Zinder, N. D. *Virology* 68, 490-502 (1975).
19. Michel, B. & Zinder, N. D. *Proc. Natl. Acad. Sci.* 86, 4002-4006 (1989).
20. Model, P., *Cell* 29, 329-335 (1982).
21. Yen, T. S. & Webster, R. E., *Cell* 29, 337-345 (1982).
22. Michel, B. & Zinder, N. D. *Nucleic Acids Res.* 17, 7333-7344 (1989).
23. Greenstein, D. & Horiuchi, K. *J. Mol. Biol.* 211, 91-101 (1990).
24. Johnston, S. & Ray, D. S. *J. Mol. Biol.* 177, 685-700 (1984).
25. Zygiel, E. M. et al. *PLOS ONE* 12, e0176421 (2017).
26. Dotto, G. P. & Zinder, N. D. *Nature* 311, 279-280 (1984).
27. Dotto, G. P. & Zinder, N. D.. *Proc. Natl. Acad. Sci.* 81, 1336-1340 (1984).Zinder, N. D. & Horiuchi, K. *Microbiol. Rev.* 49, 101-106 (1985).
28. Dotto, G. P. & Zinder, N. D. *Virology* 130, 252-256 (1983).
29. Dotto, G. P., *Virology* 114, 463-473 (1981).
30. Cleary, J. M. & Ray, D. S. *Proc. Natl. Acad. Sci. U.S.A* 77, 4638-4642 (1980).
31. Ghosh, D., *ACS Synth. Biol.* 1, 576-582 (2012).
32. Ghosh, D. et al. *Nat. Nanotechnol.* 7, 677-682 (2012).
33. H, Y. et al. *Nano Lett.* 12, 1176-1183 (2012).
34. Bar, H., *BMC Biotechnol.* 8, 37 (2008).
35. DePorter, S. M. *Bioconjug. Chem.* 25, 1620-1625 (2014).
36. Murgas, P. et al. *Cancer Immunol. Immunother.* 67, 183-193 (2018).
37. Champion, J. A., *J. Controlled Release* 121, 3-9 (2007).
38. Geng, Y. et al. *Nat. Nanotechnol.* 2, 249-255 (2007).
39. Gentile, F. et al. *J. Biomech.* 41, 2312-2318 (2008).
40. Hoshyar, N., *Nanomed.* 11, 673-692 (2016).
41. Shukla, S. et al. *Adv. Healthc. Mater.* 4, 874-882 (2015).
42. Smith, B. R. et al. *Nano Lett.* 12, 3369-3377 (2012).
43. Toy, R., *Nanomed.* 9, 121-134 (2013).
44. Improved electrode materials for Li-ion batteries using microscale and sub-micrometer scale porous materials—A review—ScienceDirect. https://www.sciencedirect.com/science/article/pii/S0925838817332164.
45. Tappan, B. C., *Angew. Chem. Int. Ed.* 49, 4544-4565 (2010).
46. Mao, J. et al. *Energy Environ. Sci.* 11, 772-799 (2018).
47. Zankowski, S. P., *J. Mater. Chem.* A 8, 14178-14189 (2020).
48. Barrios, E. et al. *Polymers* 11, 726 (2019).
49. Courchesne, N.-M. D. et al. *Adv. Mater.* 26, 3398-3404 (2014).
50. Dang, X. et al., *Nat. Nanotechnol.* 6, 377-384 (2011).
51. Jung, S. M., *Adv. Funct. Mater.* 27, 1603203 (2017).
52. Lee, Y. J. et al. *Science* 324, 1051-1055 (2009).
53. Nam, K. T. et al *Science* 312, 885-888 (2006).
54. Oh, D. et al., *Small* 8, 1006-1011 (2012).
55. Oh, D. et al. *Nat. Commun.* 4, 2756 (2013).
56. Ohmura, J. F. et al. *Nanoscale* 11, 1091-1102 (2019).
57. Records, W. C., *Small* 15, 1903166 (2019).
58. Jeong, C. K. et al. *ACS Nano* 7, 11016-11025 (2013).
59. Lee, J.-H. et al. *Nano Lett.* 19, 2661-2667 (2019).
60. Ebrahimizadeh, W. *Curr. Microbiol.* 69, 109-120 (2014).
61. Sunbul, M., *ChemBioChem* 12, 380-386 (2011).
62. Shukla, G. S. *Protein Eng.* Des. Set. 23, 431-440 (2010).
63. Chen, M. & Samuelson, J. C. *Biochemistry* 55, 3175-3179 (2016).
64. Moghimian, P., *J. Biomater. Nanobiotechnology* 7, 72-77 (2016).
65. Branston, S. D., *Biotechnol. Bioprocess Eng.* 18, 560-566 (2013).
66. Raeeszadeh-Sarmazdeh, M., *Curr. Opin. Chem. Eng.* 13, 109-118 (2016).
67. Brown, P., *J. Sol-Get Sci. Technol.* 61, 104-111 (2012).
68. Ge, X. et al. *Carbohydr. Polym.* 197, 277-283 (2018).
69. Huang, J. et al. *RSC Adv.* 9, 21155-21163 (2019).
70. Liao, W., *Compos. Part B Eng.* 173, 107036 (2019).
71. Meng, J. et al. *Electrochimica Acta* 176, 1001-1009 (2015).
72. Shanmugam, B., *Appl. Surf. Sci.* 498, 143792 (2019).
73. Tamon, H., *J. Colloid Interface Sci.* 188, 162-167 (1997).
74. Tang, Y., *J. Appl. Polym. Sci.* 137, 49127 (2020).
75. Wang, Y., *J. Appl. Electrochem.* 48, 495-507 (2018).

76. Yin, L. et al. *Adv. Funct. Mater.* 24, 4176-4185 (2014).
77. Zhu, X. et al. *Nanoscale* 12, 4882-4894 (2020).
78. A three-dimensional porous LiFePO4 cathode material modified with a nitrogen-doped graphene aerogel for high-power lithium ion batteries—Energy & Environmental Science (RSC Publishing). https://pubs.rsc.org/en/content/articlelanding/2015/ee/c4ee03825h#!divAbstract.
79. An Easy Way To Prepare Monolithic Inorganic Oxide Aerogels—Ren—2014—Angewandte Chemie—Wiley Online Library. https://onlinelibrary.wiley.com/doi/abs/10.1002/ange.201406387.
80. Ice Templated Free-Standing Hierarchically WS2/CNT-rGO Aerogel for High-Performance Rechargeable Lithium and Sodium Ion Batteries—Wang—2016—Advanced Energy Materials—Wiley Online Library. https://onlinelibrary.wiley.com/doi/full/10.1002/aenm.201601057.
81. Promising Dual-Doped Graphene Aerogel/SnS2 Nanocrystal Building High Performance Sodium Ion Batteries|ACS Applied Materials & Interfaces. https://pubs.acs.org/doi/abs/10.1021/acsami.7b18195.
82. Structural control of silica aerogel fibers for methylene blue removal|SpringerLink. https://link.springer.com/article/10.1007/s11431-018-9389-7.
83. Feng, X.-Q., *Appl. Phys. Lett.* 94, 011916 (2009).
84. Liu, D. et al. *Chem. Mater.* 20, 1376-1380 (2008).
85. Putra, B. R. et al., *ACS Appl. Bio Mater.* 3, 512-521 (2020).
86. Wen, A. M. & Steinmetz, N. F. *Chem. Soc. Rev.* 45, 4074-4126 (2016).
87. Sharma, R. S., *Ecol. Evol.* 9, 2263-2304 (2019).
88. Rizvi, S. A. A. & Saleh, A. M. *J. SPJ* 26, 64-70 (2018).
89. Paczesny, J. & Bielec, K. *Nanomaterials* 10, 1944 (2020).
90. Yang, S. H., Chem. Rec. 13, 43-59 (2013).
91. Henry, K. A., *Front. Microbiol.* 6, (2015).
92. Moon, J.-S. et al., *Mini-Rev. Org. Chem.* 12, 271-281 (2015).
93. Vilona, D. et al. *J. Mater. Chem. B* 3, 6718-6730 (2015).
94. Barry, E., *Soft Matter* 5, 2563-2570 (2009).

Section 3 References

1. Rajotte, D. et al. Molecular heterogeneity of the vascular endothelium revealed by in vivo phage display. https://www.jci.org/articles/view/3008/pdf (1998) doi:10.1172/JC13008.
2. Yip, Y. L., *J. Immunol. Methods* 225, 171-178 (1999).
3. Sartorius, R., *Pharmaceutics* 11, (2019).
4. Dabrowska, K., *J. Appl. Microbiol.* 98, 7-13 (2005).
5. Zou, *J. Mol. Biol. Rep.* 31, 121-129 (2004).
6. Molenaar, T. J. M. et al. *Virology* 293, 182-191(2002).
7. Li, J. et al. *Amino Acids* 42, 2373-2381 (2012).
8. Dubos, R. *J., J. Exp. Med.* 78, 161-168 (1943).
9. Frenkel, D. & Solomon, *Proc. Natl. Acad. Sci.* 99, 5675-5679 (2002).
10. Ksendzovsky, A. et al. *J. Neurosurg.* 117, 197-203 (2012).
11. Papisov, M. I. et al. *Drug Deliv. Transl. Res.* 2, 210-221 (2012).
12. Bakhshinejad, B., *Neural Regen. Res.* 10, 862-865 (2015).
13. Oller-Salvia, B., *Chem. Soc. Rev.* 45, 4690-4707 (2016).
14. Wu, L.-P. et al. *Nat. Commun.* 10, 4635 (2019).
15. Lee, J. H., *Eur. J. Biochem.* 268, 2004-2012 (2001).
16. Diaz-Perlas, C. et al. *Pept. Sci.* 108, e22928 (2017).
17. Identification of nose-to-brain homing peptide through phage display—ScienceDirect. https://www.sciencedirect.com/science/article/abs/pii/S019697810800435X?via %3Dihub.
18. Li, J. et al. *Biomaterials* 32, 4943-4950 (2011).
19. Smith, M. W., *Peptides* 38, 172-180 (2012).
20. Staquicini, F. I. et al. *J. Clin. Invest.* 121, 161-173 (2011).
21. Muruganandam, A., *FASEB J.* 16, 1-22 (2002).
22. Ivanenkov, V. V. & Menon, A. *Biochem. Biophys. Res. Commun.* 276, 251-257 (2000).
23. van Rooy, I. et al. *Pharm. Res.* 27, 673-682 (2010).
24. Wu, M., *Gene Ther.* 10, 1429-1436 (2003).
25. Arap, W. et al. *Nat. Med.* 8, 121-127 (2002).
26. Lee, T.-Y., *Cancer Res.* 67, 10958-10965 (2007).
27. Johanson, C. E., *Pharm. Res.* 22, 1011-1037 (2005).
28. Baird, A. et al. Targeting the Choroid Plexus-CSF-Brain *Nexus* Using Peptides Identified by Phage Display. in *The Blood-Brain and Other Neural Barriers: Reviews and Protocols* (ed. Nag, S.) 483-498 (Humana Press, 2011). doi:10.1007/978-1-60761-938-3_25.
29. Gonzalez, A. M. et al. Targeting choroid plexus epithelia and ventricular ependyma for drug delivery to the central nervous system. *BMC Neurosci.* 12, 4 (2011).
30. Gonzalez, A. M. et al. *Brain Res.* 1359, 1-13 (2010).
31. Sellers, D. L. et al. *Proc. Natl. Acad. Sci.* 113, 2514-2519 (2016).
32. Stroud, M. R., *Curr. Pharm. Des.* 17, 4362-4371 (2011).
33. Dardevet, L et al. *Toxins* 7, 1079-1101 (2015).
34. Westphal, M. et al. *Acta Neurochir.* (Wien) 148, 269-275; discussion 275 (2006).
35. Niewald, M. et al. *Radiat. Oncol.* 6, 141 (2011).
36. New strategies for cancer management: how can temozolomide carrier modifications improve its delivery-?|Therapeutic Delivery. https://www.future-science.com/doi/10.4155/tde–2017-0016.
37. Lee, C. Y. *OncoTargets Ther.* 10, 265-270 (2017).
38. Sarkaria, J. N. et al. Clin. *Cancer Res. Off. J. Am. Assoc. Cancer Res.* 14, 2900-2908 (2008).
39. Karim, R., *J. Controlled Release* 227, 23-37 (2016).
40. Pokorny, J. L. et al. *Clin. Cancer Res. Off. J. Am. Assoc. Cancer Res.* 21, 1916-1924 (2015).
41. Saraiva, C. et al. *J. Control. Release Off. J. Control. Release Soc.* 235, 34-47 (2016).
42. Ds, H. et al. *Curr. Pharm. Des.* 22, 1177-1193 (2016).
43. Challis, R. C. et al. *Nat. Protoc.* 14, 379-414 (2019).
44. Deverman, B. E. et al. *Nat. Biotechnol.* 34, 204-209 (2016).
45. Büning, H. & Srivastava, A. *Mol. Ther. Methods Clin. Dev.* 12, 248-265 (2019).
46. Louveau, A. et al. *Nature* 523, 337-341 (2015).
47. Raivich, G. & Banati, R. *Brain Res. Rev.* 46, 261-281 (2004).
48. Takeshita, Y. & Ransohoff, R. M. *Immunol. Rev.* 248, 228-239 (2012).
49. Johnson, L. A. et al. *Sci. Transl. Med.* 7, 275ra22-275ra22 (2015).
50. O'Rourke, D. M. et al. *Sci. Transl. Med.* 9, (2017).
51. Barbu, E., Molnár, E., Tsibouklis, J. & Górecki, D. C. *Expert Opin. Drug Deliv.* 6, 553-565 (2009).
52. Fang, C. et al. *ACS Appl. Mater. Interfaces* 7, 6674-6682 (2015).
53. Gao, H. et al. *Biomaterials* 33, 5115-5123 (2012).
54. Lockman, P. R., *J. Drug Target.* 12, 635-641(2004).
55. Jain, K. K. *Nanomed.* 7, 1225-1233 (2012).
56. Sonali et al. *Nanotheranostics* 2, 70-86 (2018).

57. Portnow, J. et al. *Clin. Cancer Res. Off. J. Am. Assoc. Cancer Res.* 15, 7092-7098 (2009).
58. Banks, W. A. *BMC Neural.* 9, S3 (2009).
59. Lee, J., In Vivo Measurement of Glioma-Induced Vascular Permeability. in *Permeability Barrier: Methods and Protocols* (ed. Turksen, K.) 417-422 (Humana Press, 2011). doi:10.1007/978-1-61779-191-8_28.
60. Lee, J. et al. *Brain Res.* 1288, 125-134 (2009).
61. Sunderland, K. S., C. Phage-Enabled Nanomedicine: From Probes to Therapeutics in Precision Medicine. *Angew. Chem. Int. Ed Engl.* 56, 1964-1992 (2017).
62. Leal, J. et al. *M13 phage display to identify a permeating peptide against hyperconcentrated mucin.* http://biorxiv.org/lookup/doi/10.1101/659573 (2019) doi: 10.1101/659573.
63. Braathen, R. et al. *J. Biol. Chem.* 281, 7075-7081(2006).
64. Kang, S. K. et al. *J. Biotechnol.* 135, 210-216 (2008).
65. Morris, C. J., Smith, M. W., *J. Controlled Release* 151, 83-94 (2011).
66. Ghosh, D., *ACS Synth. Biol.* 1, 576-582 (2012).
67. H, Y. et al. *Nano Lett.* 12, 1176-1183 (2012).
68. Ghosh, D. et al. *Nat. Nanotechnol.* 7, 677-682 (2012).
69. Ghosh, D. et al. *Proc. Natl. Acad. Sci.* 111, 13948-13953 (2014).
70. Bar, H., *BMC Biotechnol.* 8, 37 (2008).
71. Peng, H., *Proc. Natl. Acad. Sci.* 117, 1951-1961 (2020).
72. Staquicini, F. I. et al. *Cancer Gene Ther.* 27, 301-310 (2020).
73. Smith, T. L. et al. *Proc. Natl. Acad. Sci.* 113, 2466-2471 (2016).
74. Hajitou, A. et al., *Cell* 125, 385-398 (2006).
75. Przystal, J. M. et al. *EMBO Mol. Med.* 11, (2019).
76. Trepel, M. et al. *Mol. Cancer Ther.* 8, 2383-2391(2009).
77. Cohen-Inbar, O. & Zaaroor, M. *J. Clin. Neurosci. Off. J. Neurosurg. Soc. Australas.* 33, 52-58 (2016).
78. Deshane, J., Garner, C. C. & Sontheimer, *J. Biol. Chem.* 278, 4135-4144 (2003).
79. Kasai, T. et al. *J. Drug Deliv.* 2012, e975763 (2012).
80. Ayed, A. S. et al. *Int. J. Pept. Res. Ther.* 27, 659-667 (2021).
81. Wiranowska, M., *Cancer Cell Int.* 11, 27 (2011).
82. Veiseh, O. et al. *Cancer Res.* 69, 6200-6207 (2009).
83. Butte, P. V. et al. *Neurosurg. Focus* 36, E1 (2014).
84. Zhao, L. et al. *J. Nanobiotechnology* 17, 30 (2019).
85. Veiseh, M. et al. *Cancer Res.* 67, 6882-6888 (2007).
86. Wang, D. et al. *Sci. Transl. Med.* 12, (2020).
87. Yoo, B., *Mol. Imaging Biol.* 16, 680-689 (2014).
88. Costa, P. M. et al. *Mol. Ther.-Nucleic Acids* 2, (2013).
89. Kievit, F. M. et al. *ACS Nano* 4, 4587-4594 (2010).
90. Mamelak, A. N. et al., *J. Clin. Oncol. Off. J. Am. Soc. Clin. Oncol.* 24, 3644-3650 (2006).
91. Kim, A. et al. *PLOS ONE* 7, e51813 (2012).
92. Gao, H., *Proc. Natl. Acad. Sci.* 102, 9469-9474 (2005).
93. Stoneham, C. A., *J. Biol. Chem.* 287, 35849-35859 (2012).
94. Ivanenkov, V. V., *Biochim. Biophys. Acta* BBA—Mal. Cell Res. 1448, 450-462 (1999).
95. Suwan, K. et al. *Proc. Natl. Acad. Sci.* 116, 18571-18577 (2019).
96. Przystal, J. M. et al. *Mol. Oncol.* 7, 55-66 (2013).
97. Greenstein, D. & Horiuchi, K. *J. Mol. Biol.* 211, 91-101 (1990).
98. Zygiel, E. M. et al. *PLOS ONE* 12, e0176421 (2017).
99. Dotto, G. P. & Zinder, N. D. *Proc. Natl. Acad. Sci.* 81, 1336-1340 (1984).
100. Dotto, G. P. & Zinder, N. D. *Nature* 311, 279-280 (1984).
101. Zinder, N. D. & Horiuchi, K. *Microbiol. Rev.* 49, 101-106 (1985).
102. The second window ICG technique demonstrates a broad plateau period for near infrared fluorescence tumor contrast in glioblastoma. https://www.ncbi.nlm.nih.gov/pmc/articles/PMC5524327/.
103. Carr, J. A. et al. *Proc. Natl. Acad. Sci.* 115, 4465-4470 (2018).
104. Yuan, B., Chen, N. & Zhu, Q. *J. Biomed. Opt.* 9, 497-503 (2004).
105. Lin, C.-W. et al. *Nat. Commun.* 10, 2874 (2019).
106. Wang, Y.-G., *Quant. Imaging Med. Surg.* 3, 13240-13140 (2013).
107. Teng, C. W. et al. *Neurosurg. Focus* 50, E4 (2021).
108. Longmire, M., *Nanomed.* 3, 703-717 (2008).
109. Caster, J. M. et al., *Nanomedicine Nanotechnol. Biol. Med.* 13, 1673-1683 (2017).
110. McKenzie, M., *Biophys. J.* 114, 1830-1846 (2018).
111. Champion, J. A., *J. Controlled Release* 121, 3-9 (2007).
112. Smith, B. R. et al. *Nano Lett.* 12, 3369-3377 (2012).
113. Toy, R., *Nanomed.* 9, 121-134 (2013).
114. Hoshyar, N., *Nanomed.* 11, 673-692 (2016).
115. Gentile, F. et al. *J. Biomech.* 41, 2312-2318 (2008).
116. Shukla, S. et al. *Adv. Healthc. Mater.* 4, 874-882 (2015).
117. Geng, Y. et al. 2, 249-255 (2007).
118. Schmidt, M. M. *Mol. Cancer Ther.* 8, 2861-2871 (2009).
119. Mechanistic and quantitative insight into cell surface targeted molecular imaging agent design|Scientific Reports. https://www.nature.com/articles/srep25424.
120. Zhou, Y., *Bioconjug. Chem.* 25, 1801-1810 (2014).

References 4

1. Zhu, J. et al. *Sci. Adv.* 5, eaax0064 (2019).
2. Poul, M.-A. *J. Mol. Biol.* 288, 203-211 (1999).
3. Burg, M. A. et al. *Cancer Res.* 62, 977-981(2002).
4. Hajitou, A. et al. *Cell* 125, 385-398 (2006).
5. Smith, T. L. et al. *Proc. Natl. Acad. Sci.* 113, 2466-2471 (2016).
6. Tao, P. et al. *Proc. Natl. Acad. Sci.* 110, 5846-5851 (2013).
7. Zhang, Z. et al. *PLoS Biol.* 9, (2011).
8. Yan, Z., *J. Virol.* 79, 364-379 (2005).
9. Daya, S. *Clin. Microbiol. Rev.* 21, 583-593 (2008).
10. 557. Impact of the Integrity of the ITRs on the Production of rAAV Vectors: Molecular Therapy. https://www.cell.com/molecular-therapy-family/molecular-therapy/comments/51525-0016(16)34166-1.
11. Tandle, A. et al. *Cancer* 115, 128-139 (2009).
12. Hajitou, A. et al. *Proc. Natl. Acad. Sci.* 105, 4471-4476 (2008).
13. Staquicini, F. I. et al. *Cancer Gene Ther.* 27, 301-310 (2020).
14. Trepel, M. et al., *Mol. Cancer Ther.* 8, 2383-2391 (2009).
15. Kia, A. et al., *Mol. Cancer Ther.* 11, 2566-2577 (2012).
16. Przystal, J. M. et al. *EMBO Mol. Med.* 11, (2019).
17. Hajitou, A. et al. *Nat. Protoc.* 2, 523-531 (2007).
18. Yata, T. et al. *Mol. Ther.—Nucleic Acids* 3, e185 (2014).
19. Donnelly, A., *Viruses* 7, 6476-6489 (2015).
20. Yoo, S. Y. et al., *Adv. Healthc. Mater.* 5, 88-93 (2016).
21. Yokoyamakobayashi, M. *Biochem. Biophys. Res. Commun.* 192, 935-939 (1993).
22. Suwan, K. et al. *Proc. Natl. Acad. Sci.* 116, 18571-18577 (2019).
23. Ellis, B. L. et al. *Virol. J.* 10, 74 (2013).
24. Colella, P., *Mol. Ther.—Methods Clin. Dev.* 8, 87-104 (2018).

25. Büning, H. *Mol. Ther*. Methods Clin. Dev. 12, 248-265 (2019).
26. Deverman, B. E. et al. *Nat. Biotechnol.* 34, 204-209 (2016).
27. Sunderland, K. S., *Angew. Chem. Int. Ed Engl.* 56, 1964-1992 (2017).
28. Phage Display In Biotechnology and Drug Discovery. *Routledge & CRC Press* https://www.routledge.com/Phage-Display-In-Biotechnology-and-Drug-Discovery/Sidhu-Geyer/p/book/9781138894679.
29. Baird, A. *Cold Spring Harb. Protoc.* 2011, 950-957 (2011).
30. Gonzalez, A. M. et al. *Endocr. Abstr.* 8, (2004).
31. Kassner, P. D., *Biochem. Biophys. Res. Commun.* 264, 921-928 (1999).
32. Larocca, D., *Hum. Gene Ther.* 9, 2393-2399 (1998).
33. Larocca, D. et al. *Curr. Pharm. Biotechnol.* 3, 45-57 (2002).
34. Larocca, D., *Mol. Ther.* 3, 476-484 (2001).
35. Ebrahimizadeh, W. *Curr. Microbiol.* 69, 109-120 (2014).
36. Shukla, G. S. & Krag, D. N. *Protein Eng. Des. Sel. PEDS* 23, 431-440 (2010).
37. Chung, Y.-S. A., *BMC Mol. Biol.* 9, 37 (2008).
38. Stoneham, C. A., *J. Biol. Chem.* 287, 35849-35859 (2012).
39. Przystal, J. M. et al. *Mol. Oncol.* 7, 55-66 (2013).
40. Di Giovine, M. et al. *Virology* 282, 102-112 (2001).
41. Ferrara, F. et al. *Proc. Natl. Acad. Sci.* 113, 12786-12791 (2016).
42. Ghosh, D., *ACS Synth. Biol.* 1, 576-582 (2012).
43. Ghosh, D. et al. *Proc. Natl. Acad. Sci.* 111, 13948-13953 (2014).
44. Karimi, M. et al. *Adv. Drug Deliv. Rev.* 106, 45-62 (2016).
45. Kim, M. J., *J. Ind. Eng. Chem.* 45, 404-411(2017).
46. Lee, K. J. et al. *Amino Acids* 47, 281-289 (2015).
47. Murgas, P. et al. *Cancer Immunol. Immunother.* 67, 183-193 (2018).
48. Peng, H., *Proc. Natl. Acad. Sci.* 117, 1951-1961 (2020).
49. Yacoby, I. & Benhar, I. *Expert Opin. Drug Deliv.* 5, 321-329 (2008).
50. Henry, K. A., *Front. Microbiol.* 6, (2015).
51. van Houten, N. E., *Vaccine* 28, 2174-2185 (2010).
52. Kanki, S. et al. *J. Mol. Cell. Cardiol.* 50, 841-848 (2011).
53. Samli, K. N., *Diabetes* 54, 2103-2108 (2005).
54. Sellers, D. L. et al. *Proc. Natl. Acad. Sci.* 113, 2514-2519 (2016).
55. Staquicini, F. I. et al. *J. Clin. Invest.* 121, 161-173 (2011).
56. Smith, M. W., *Peptides* 38, 172-180 (2012).
57. Samoylova, T. I. *Muscle Nerve* 22, 460-466 (1999).
58. Yip, Y. L., *J. Immunol. Methods* 225, 171-178 (1999).
59. Zou, J., *Mol. Biol. Rep.* 31, 121-129 (2004).
60. Li, J. et al. *Biomaterials* 32, 4943-4950 (2011).
61. Nicol, C. G. et al. *FEBS Lett.* 583, 2100-2107 (2009).
62. Hirosue, S. & Weber, T. *Biochemistry* 45, 6476-6487 (2006).
63. Akuta, T. et al. *Biochem. Biophys. Res. Commun.* 297, 779-786 (2002).
64. Redrejo-Rodríguez, M. & Salas, M. Virology 468-470, 322-329 (2014).
65. Diaz-Perlas, C. et al. *Pept. Sci.* 108, e22928 (2017).
66. Muruganandam, A., *FASEB J.* 16, 1-22 (2002).
67. Leal, J. et al. *M13 phage display to identify a permeating peptide against hyperconcentrated mucin.* http://biorxiv.org/lookup/doi/10.1101/659573 (2019) doi: 10.1101/659573.
68. Costantini, T. W. et al. *Peptides* 38, 94-99 (2012).
69. Braathen, R. et al. *J. Biol. Chem.* 281, 7075-7081 (2006).
70. Kang, S. K. et al., *J. Biotechnol.* 135, 210-216 (2008).
71. Kim, K.-P. et al. *Microb. Biotechnol.* 1, 247-257 (2008).
72. Mohan, K. & Weiss, G. A. *ACS Chem. Biol.* 11, 1167-1179 (2016).
73. Moon, J.-S. et al. *Mini-Rev. Org. Chem.* 12, 271-281 (2015).
74. Alipour, M., *Sci. Rep.* 7, 41507 (2017).
75. Bakhshinejad, B., *Neural Regen. Res.* 10, 862-865 (2015).
76. DePorter, S. M. *Bioconjug. Chem.* 25, 1620-1625 (2014).
77. Ju, Z. & Sun, W. *Drug Deliv.* 24, 1898-1908 (2017).
78. Kim, A. et al. *PloS One* 7, e51813 (2012).
79. Barbu, E. M., *Cold Spring Harb. Perspect. Biol.* 8, a023879 (2016).
80. Jin, P. et al., *Nano Lett.* 19, 1467-1478 (2019).
81. Krag, D. N. et al. *Cancer Res.* 66, 7724-7733 (2006).
82. Shukla, G. S. et al. *Cancer Immunol. Immunother.* 62, 1397-1410 (2013).
83. Arap, W. et al. *Nat. Med.* 8, 121-127 (2002).
84. Bach, M. S. et al. *Filamentous Bacteriophage Delay Healing of Pseudomonas-Infected Wounds.* http://biorxiv.org/lookup/doi/10.1101/2020.03.10.985663 (2020) doi:10.1101/2020.03.10.985663.
85. Secor, P. R. et al., *Front. Immunol.* 11, (2020).
86. Sweere, J. M. et al. *Science* 363, (2019).
87. Cruz, V. F. de la, *J. Biol. Chem.* 263, 4318-4322 (1988).
88. Gram, H., *J. Immunol. Methods* 161, 169-176 (1993).
89. Henry, K. A., *Bioeng. Bugs* 2, 275-283 (2011).
90. Hess, K. L. & Jewell, *Bioeng. Transt. Med.* 5, (2019).
91. Meola, A. et al. *J. Immunol.* 154, 3162-3172 (1995).
92. Sartorius, R., *Pharmaceutics* 11, (2019).
93. Adu-Berchie, K. & Mooney, D. J. *Acc. Chem. Res.* 53, 1749-1760 (2020).
94. Dąbrowska, K. *Med. Res. Rev.* 39, 2000-2025 (2019).
95. Górski, A. et al. *FEMS Immunol. Med. Microbiol.* 46, 313-319 (2006).
96. Roach, D. R. et al. *Cell Host Microbe* 22, 38-47.e4 (2017).
97. Altamirano, F. L. G. *Clin. Microbiol. Rev.* 32, (2019).
98. The Forgotten Cure—The Past and Future of Phage Therapy|Anna Kuchment|Springer. https://www.springer.com/gp/book/9781461402503.
99. Aslam, S. et al. *Open Forum Infect. Dis.* 7, (2020).
100. Bruttin, A. & Brüssow, H Antimicrob. Agents Chemother. 49, 2874-2878 (2005).
101. Lang, L. H. *Gastroenterology* 131, 1370 (2006).
102. Krut, O. & Bekeredjian-Ding, I. *J. Immunol.* 200, 3037-3044 (2018).
103. usiak-Szelachowska, M. et al. *Viral Immunol.* 27, 295-304 (2014).
104. Górski, A. et al. *Future Microbiol.* 12, 905-914 (2017).
105. Dong, X. et al. *Sci. Adv.* 6, eaba1590 (2020).
106. Nguyen, S. et al., *mBio* 8, (2017).
107. Clément, N. & Grieger, J. C. *Mol. Ther.—Methods Clin. Dev.* 3, (2016).
108. Clément, N. Large-Scale Clinical Manufacturing of AAV Vectors for Systemic Muscle Gene Therapy. in *Muscle Gene Therapy* (eds. Duan, D. & Mendell, J. R.) 253-273 (Springer International Publishing, 2019). doi: 10.1007/978-3-030-03095-7_15.
109. Griffith, J. & Kornberg, A. *Virology* 59, 139-152 (1974).

110. Miniphage—a Class of Satellite Phage to M13|Microbiology Society. https://www.microbiologyresearch.org/content/journal/jgv/10.1099/0022-1317-26-1-87.
111. Yang Zhou, J., *J. Clin. Med.* 9, 1498 (2020).
112. Transfer of the Full-Length Dystrophin-Coding Sequence into Muscle Cells by a Dual High-Capacity Hybrid Viral Vector with Site-Specific Integration Ability|Journal of Virology. https://jvi.asm.org/content/79/5/3146.
113. Liang, Y. et al. *Biotechnol. Prog.* 22, 626-630 (2006).
114. Burg, M. A. et al. *Cancer Res.* 62, 977-981 (2002).
115. Tsafa, E. et al. *Int. J. Mal. Sci.* 21, 7867 (2020).
116. Brock, D. J., *Bioconjug. Chem.* 30, 293-304 (2019).
117. Pichon, C., *Adv. Drug Deliv. Rev.* 53, 75-94 (2001).
118. Nadal-Buff, F. *Pept. Sci.* 112, e24168 (2020).
119. Smith, S. A., *Bioconjug. Chem.* 30, 263-272 (2019).
120. LeCher, J. C., *Biomol. Concepts* 8, 131-141 (2017).
121. Moore, N. M., *J. Gene Med.* 10, 1134-1149 (2008).
122. III, C. F. B., Burton, D. R. & Silverman, G. *J. Phage Display: A Laboratory Manual.* (Cold Spring Harbor Laboratory Press, 2004).
123. Mi, Z., *Mol. Ther.* 2, 339-347 (2000).
124. Niu, Z., *Nano Res.* 1, 235-241 (2008).
125. Lo, S. L. & Wang, S. *Biomaterials* 29, 2408-2414 (2008).
126. Teo, S. L. Y. et al. *Unravelling cytosolic delivery of endosomal escape peptides with a quantitative endosomal escape assay* (*SLEEQ*). http://biorxiv.org/lookup/doi/10.1101/2020.08.20.258350 (2020) doi:10.1101/2020.08.20.258350.
127. Stahnke, S. et al. *Virology* 409, 77-83 (2011).
128. Farr, G. A., *Proc. Natl. Acad. Sci.* 102, 17148-17153 (2005).
129. Girod, A. et al. *J. Gen. Virol.* 83, 973-978.
130. Popa-Wagner, R. et al. *J. Virol.* 86, 9163-9174 (2012).
131. Bartel, M. A., *Gene Ther.* 19, 694-700 (2012).
132. Byrne, L C. et al. *JCI Insight* 5, (2020).
133. Davidsson, M. et al. *Proc. Natl. Acad. Sci.* 116, 27053-27062 (2019).
134. Scott, J. K. & Smith, G. P. *Science* 249, 386-390 (1990).
135. Lei, S. P., *J. Bacteriol.* 169, 4379-4383 (1987).
136. Singh, P. et al. *PLoS ONE* 8, (2013).
137. Merril, C. R. et al. *Proc. Natl. Acad. Sci.* 93, 3188-3192 (1996).
138. Wu, L-P. et al. *Nat. Commun.* 10, 4635 (2019).
139. Identification of nose-to-brain homing peptide through phage display—ScienceDirect. https://www.sciencedirect.com/science/article/abs/pii/S019697810800435X?via %3Dihub.
140. Li, J. et al. *Amino Acids* 42, 2373-2381 (2012).
141. Vaughan, E. E., *Curr. Gene Ther.* 6, 671-681 (2006).
142. Lam, A. P. & Dean, D. A. *Gene Ther.* 17, 439-447 (2010).
143. Yao, J., Fan, Y., Li, Y. & Huang, L *J. Drug Target.* 21, 926-939 (2013).
144. Withers, J. et al. *Proc. Natl. Acad. Sci.* 109, 20148-20153 (2012).

References Section 5

1. Hay, I. D. & Lithgow, T. *EMBO Rep.* 20, (2019).
2. Rakonjac, J. & Model, P. *J. Mol. Biol.* 282, 25-41(1998).
3. Barry, E., *Soft Matter* 5, 2563-2570 (2009).
4. Williams, K. A. & Deber, C. M. *Biochemistry* 35, 10472-10483 (1996).
5. Xu, *J., Proc. Natl. Acad. Sci.* 116, 5493-5498 (2019).
6. Phipps, M. L. et al. *PLoS ONE* 11, (2016).
7. Chasteen, L, *Nucleic Acids Res.* 34, e145-e145 (2006).
8. Shepherd, T. R., *Sci. Rep.* 9, 6121 (2019).
9. Ebrahimizadeh, W *Curr. Microbiol.* 69, 109-120 (2014).
10. Cashman, J. S., *J. Biol. Chem.* 255, 2554-2562 (1980).
11. Smeal, S. W., S *Virology* 500, 259-274 (2017).
12. van Wezenbeek, *Gene* 11, 129-148 (1980).
13. Derda, R. et al., *Molecules* 16, 1776-1803 (2011).
14. Arap, W. et al. *Nat. Med.* 8, 121-127 (2002).
15. Sun, H., *Nano Today* 14, 16-41(2017).
16. Hess, G. T. et al., *Bioconjug. Chem.* 23, 1478-1487 (2012).
17. Wang, D. et al. *Sci. Transl. Med.* 12, (2020).
18. Grimes, C. A., *Cancer Res.* 65, 1300-1300 (2005).
19. El-Ghlban, S. et al. *BioMed Res. Int.* 2014, e152659 (2014).
20. A small-molecule dye for NIR-II imaging|Nature Materials. https://www.nature.com/articles/nmat4476.
21. Ghosh, D. et al. *Proc. Natl. Acad. Sci.* 111, 13948-13953 (2014).
22. Ghosh, D., *ACS Synth. Biol.* 1, 576-582 (2012).
23. H, Y. et al. *Nano Lett.* 12, 1176-1183 (2012).
24. Sunderland, *Angew. Chem. Int. Ed Engl.* 56, 1964-1992 (2017).
25. Dang, X. et al., *Nat. Nanotechnol.* 6, 377-384 (2011).
26. Ghosh, S., *Nat. Nanotechnol.* 5, 443-450 (2010).
27. Lin, C.-W. et al. *Nat. Commun.* 10, 2874 (2019).
28. Xu, T. et al. *Sci. Rep.* 6, 19799 (2016).
29. Deshane, *J., J. Biol. Chem.* 278, 4135-4144 (2003).
30. Johansson, F. et al. *Anticancer Res.* 32, 4001-4006 (2012).
31. Yoo, B., *Mol. Imaging Biol.* 16, 680-689 (2014).
32. Lam, F. C. et al. *Nat. Commun.* 9, 1991 (2018).
33. Paoloni, M. C. et al. *PLoS ONE* 4, e4972 (2009).
34. Smith, T. L. et al. *Proc. Natl. Acad. Sci.* 113, 2466-2471 (2016).
35. Staquicini, F. I. et al. *Cancer Gene Ther.* 27, 301-310 (2020).
36. Trepel, M. et al. *Mol. Cancer Ther.* 8, 2383-2391 (2009).
37. Hajitou, A. et al. *Proc. Natl. Acad. Sci.* 105, 4471-4476 (2008).
38. Ferrara, F. et al. *Proc. Natl. Acad. Sci.* 113, 12786-12791 (2016).
39. Hajitou, A. et al. *Cell* 125, 385-398 (2006).
40. Przystal, J. M. et al *EMBO Mol. Med.* 11, (2019).
41. Kim, A. et al. *PloS One* 7, e51813 (2012).
42. DePorter, S. M. & McNaughton, B. R. *Bioconjug. Chem.* 25, 1620-1625 (2014).
43. Hirosue, S. & Weber, T. *Biochemistry* 45, 6476-6487 (2006).
44. Gao, C. et al. *Bioorg. Med. Chem.* 10, 4057-4065 (2002).
45. Hoffmann, K. et al. *Sci. Rep.* 8, 12538 (2018).
46. Dobroff, A. S. et al. *Curr. Protoc. Protein Sci.* 79, (2015).
47. Büning, H. & Srivastava, *Mol. Ther*. Methods Clin. Dev. 12, 248-265 (2019).
48. Davidsson, M. et al. *Proc. Natl. Acad. Sci.* 116, 27053-27062 (2019).
49. Deverman, B. E. et al. *Nat. Biotechnol.* 34, 204-209 (2016).
50. Ivanenkov, V. V., *Biochim. Biophys. Acta* BBA—Mal. Cell Res. 1448, 450-462 (1999).
51. Kim, A. et al. *PLOS ONE* 7, e51813 (2012).
52. Molenaar, T. J. M. et al. *Virology* 293, 182-191 (2002).
53. Stoneham, C. A., *J. Biol. Chem.* 287, 35849-35859 (2012).
54. Chan, K. M. C., *bioRxiv* 761502 (2019) doi:10.1101/761502.

55. Smurova, K. & *Small GTPases* 8, 177-180 (2016).
56. Yang, J. et al. *ACS Cent. Sci.* 2, 621-630 (2016).
57. Przystal, J. M. et al. *Mol. Oncol.* 7, 55-66 (2013).
58. Suwan, K. et al. *Proc. Natl. Acad. Sci.* 116, 18571-18577 (2019).
59. Burg, M. A. et al. *Cancer Res.* 62, 977-981 (2002).
60. Tsafa, E. et al. *Int. J. Mol. Sci.* 21, 7867 (2020).
61. Zhao, H. et al. *PLoS ONE* 11, (2016).
62. Maghsoodi, A., *Proc. Natl. Acad. Sci.* 116, 25097-25105 (2019).
63. González-Huici, V., *Mol. Microbiol.* 52, 529-540 (2004).
64. Xu, J. &. *J. Virol.* 91, (2017).
65. Hu, B., *Proc. Natl. Acad. Sci.* 112, E4919-E4928 (2015).
66. Grayson, P. *Curr. Opin. Microbiol.* 10, 401-409 (2007).

It should be understood that the subject matter defined in the appended claims is not necessarily limited to the specific implementations described above. The specific implementations described above are disclosed as examples only.

What is claimed is:

1. An engineered phage-derived particle (PDP) for expressing a transgene in a target cell transduced with a bacteriophage, the PDP comprising: (i) less than about 500 bp of DNA from the bacteriophage genome, (ii) an ITR-flanked therapeutic gene up to 20 kb, (iii) an endosomal escape sequence, (iv) a nuclear localization sequence, and (v) a cell-specific targeting moiety, wherein the PDP escapes lysosomal degradation, traffics across the nuclear envelope and expresses a therapeutic gene in a mammalian cell.

2. The PDP of claim 1, comprising between about 25-200 bp of the bacteriophage genome.

3. The PDP of claim 2, wherein the DNA sequences from the bacteriophage genome comprise (i) modified fragments of the f1 origin sequence of the bacteriophage, (ii) modified fragments of the f1 termination of replication sequence of the bacteriophage, and (iii) phage packaging signal.

4. The PDP of claim 3, wherein (i) the modified f1 origin sequence comprises (a) a truncated hairpin C, (b) a truncated hairpin D, and (c) a hairpin E, and does not comprise hairpins A and B, and (ii) the modified f1 termination of replication sequence comprises (a) a truncated hairpin C, (b) a hairpin D, and (c) a truncated hairpin E, and does not comprise hairpins A and B.

5. The PDP of claim 1, further comprising covalent or electrostatic cationic surface decoration with cationic polymer or poly-amino acids.

6. The PDP of claim 1, further comprising covalent surface conjugation with β-GalNAc.

7. The PDP of claim 1, wherein the bacteriophage is selected from the group consisting of M13, fd, f1, and Ff group phages.

8. The PDP of claim 1, wherein the transgene is a gene addition sequence or a gene editing sequence.

9. The PDP of claim 1, wherein the transgene is used to treat a single-gene disorder.

10. The PDP of claim 1, wherein the transgene is used to treat multiple-gene disorders.

11. The PDP of claim 1, wherein the transgene is used to treat an infectious disease.

12. The PDP of claim 1, wherein the transgene is immunotherapeutic.

13. The PDP of claim 1, wherein the cell-specific targeting moiety comprises a peptide, antibody, antibody fragment, non-antibody ligand-binding protein, or non-proteinaceous molecule present on the PDP capsid.

14. The PDP of claim 1, wherein the nucleic acid sequence of the transgene cassettes are codon-optimized for expression in the host cell.

15. The PDP of claim 1, wherein the antibody is attached to the PDP capsid with a solubility-enhancing linker.

16. The PDP of claim 1, wherein the transgene is diagnostic.

17. The PDP of claim 1, wherein a cell-penetrating peptide ligand is present on the PDP capsid.

18. The PDP of claim 1, wherein the transgene further comprises a promoter specific for the cell.

19. A system for producing a recombinant phage particle from a prokaryotic host, the system comprising: (i) the PDP vector of claim 1, and (ii) a helper phagemid.

20. A method for producing a recombinant phage particle from a prokaryotic host, the method comprising: (i) introducing into a prokaryotic host cell the PDP vector of claim 1 and a helper phagemid, and (ii) culturing the host under conditions which result in single-stranded DNA being packaged by the structural proteins to form and extrude a recombinant phage particle from the prokaryotic host.

21. A method of delivering a therapeutic transgene to a mammalian subject by administering to the subject the phage particles produced by the method of claim 20.

22. A pharmaceutical composition comprising the recombinant phage particles produced by the system of claim 19 and a pharmaceutically acceptable vehicle.

23. A pharmaceutical composition comprising the recombinant phage particle produced by the method of claim 20, and a pharmaceutically acceptable vehicle.

24. A composition comprising circular single stranded-DNA (cssDNA) extracted from the phage-derived particles produced by the method of claim 20, wherein the cssDNA encodes the therapeutic transgene.

* * * * *